(12) United States Patent
Ito et al.

(10) Patent No.: US 7,632,783 B2
(45) Date of Patent: Dec. 15, 2009

(54) 3-(DIHYDRO(TETRAHYDRO)ISOQUINOLIN-1-YL)QUINOLINE COMPOUND

(75) Inventors: Hiroyuki Ito, Yasu (JP); Kota Fujiwara, Yasu (JP); Munetsugu Morimoto, Yasu (JP); Harukazu Tanaka, Yasu (JP); Yasushi Tamagawa, Yasu (JP); Hiroyuki Komai, Yasu (JP)

(73) Assignee: Mitsui Chemicals Agro, Inc., Tokyo (JP)

( * ) Notice: Subject to any disclaimer, the term of this patent is extended or adjusted under 35 U.S.C. 154(b) by 686 days.

(21) Appl. No.: 10/587,100

(22) PCT Filed: Jan. 21, 2005

(86) PCT No.: PCT/JP2005/001171

§ 371 (c)(1),
(2), (4) Date: Jul. 21, 2006

(87) PCT Pub. No.: WO2005/070917

PCT Pub. Date: Aug. 4, 2005

(65) Prior Publication Data

US 2008/0275242 A1   Nov. 6, 2008

(30) Foreign Application Priority Data

Jan. 23, 2004   (JP) ............... 2004-015360

(51) Int. Cl.
*A01N 43/42*   (2006.01)
*C07D 215/36*   (2006.01)

(52) U.S. Cl. .......... 504/247; 546/153; 546/159; 546/162; 546/167

(58) Field of Classification Search ............... 504/247; 546/153, 159, 162, 167
See application file for complete search history.

(56) References Cited

U.S. PATENT DOCUMENTS 7,132,428 B2 * 11/2006 Majid et al. ............... 514/293
2004/0038979 A1   2/2004 Schmidt

FOREIGN PATENT DOCUMENTS

| JP | 2003-171381 A | 6/2003 |
|----|----|----|
| WO | WO 00/42019 A1 | 7/2000 |
| WO | WO 02/06270 A1 | 1/2002 |

OTHER PUBLICATIONS

Das, Michael, CA 108:21688, abstract only of Indian Journal of Chemistry, Section B: Organic Chemistry Including Medicinal Chemistry, 1986,. 25B(10), pp. 1072-1078.*

(Continued)

*Primary Examiner*—D. Margaret Seaman
(74) *Attorney, Agent, or Firm*—Frishauf, Holtz, Goodman & Chick, P.C.

(57) ABSTRACT

The invention provides compounds which exert excellent fungicidal activities against various plant diseases and are useful as active ingredients of pesticides permitting the control of rice blast and so on even in low dosages. Compounds represented by the general formulae (1a) to (1d) or salts thereof: (1a) (1b) (1c) (or) (1d) wherein $R^1$ and $R^2$ are each $C_{1-6}$ alkyl or the like; $R^3$ and $R^4$ are each hydrogen, halogeno, or the like; $R^5$ is hydrogen, $C_{1-6}$ alkyl, or the like; X is halogeno, $C_{1-6}$ alkyl, or the like; Y is halogeno, $C_{1-6}$ alkyl, or the like; n is an integer of 0 to 4; and m is an integer of 0 to 6.

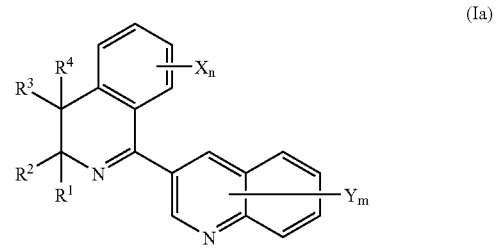

(1a)

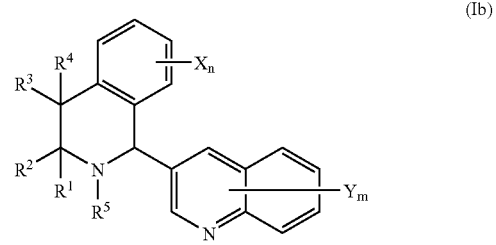

(1b)

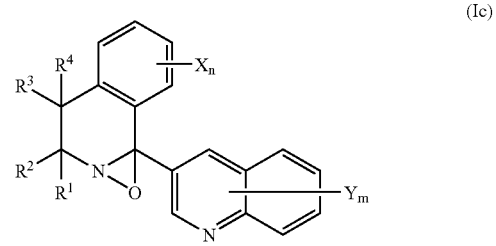

(1c)

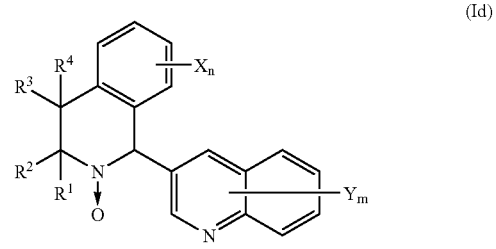

(1d)

12 Claims, No Drawings

OTHER PUBLICATIONS

Chakravorti, S.S. et al., "Isoquinolylquinoline Derivatives: Part III—Synthesis of Some 4-Substituted 3-(3',4'-Dihydro-1'-isoquinolyl) quinoline Derivatives as Possible Antifilarial Agents", *Indian J. Chem.*, Sect. B, 24B(7), pp. 737-746 (Jul. 1985).

Das, M. et al., "Isoquinolylquinoline Derivatives: Part IV—Synthesis of Some 4-Substituted 3-(3',4'-Dihydro-3'methyl-1'-isoquinolyl)-7-chloro-quinoline Derivatives as Possibly Trypanocidal Agents", *Indian J. Chem.*, Sect. B, 25(B) pp. 1072-1078 (Oct. 1986).

Chandra, A. et al., "Isoquinolylquinoline Derivatives: Part II—Synthesis of Some Azaheterocyclic Derivatives as Possible Antispasmodic or Amoebicidal Agents", *Indian J. Chem.*, vol. 8, pp. 505-508 (Jun. 1970).

Sankar, S. et al., "Isoquinolylquinoline Derivatives: Part I—Synthesis of Some 3-(3',4'-Dihydroisoquinolyl-I')-4-subsituted Qunioline Derivatives as Possible Spasmolytic Agents", *Indian J. Chem .*, vol. 7, pp. 1010-1016 (Oct. 1969).

* cited by examiner

3-(DIHYDRO(TETRAHYDRO)ISOQUINOLIN-1-YL)QUINOLINE COMPOUND

This application is the United States national phase application of International Application PCT/JP2005/001171 filed Jan. 21, 2005.

TECHNICAL FIELD

The present invention relates to a 3-(dihydro(tetrahydro)isoquinolin-1-yl)quinoline compound or a salt thereof, and an agricultural chemical containing said compound or salt thereof as an active ingredient.

BACKGROUND ART

Although International Publication WO 00/42019 and International Publication WO 02/06270 describe a 6-arylphenanthridine compound as a PDE4 inhibitor, in which a cyclohexane ring is formed between positions 3 and 4 of a dihydroisoquinoline ring, while Japanese Patent Publication No. 2003-171381 describes a 6-arylfuroisoquinoline compound as an entry inhibitor, in which a dihydrofuran ring is formed between positions 7 and 8 of a dihydroisoquinoline ring, there are no descriptions of a 3-dihydroisoquinolin-1-yl quinoline compound in which the isoquinoline ring is not condensed with another ring, and there are no descriptions relating to an agrohorticultural antimicrobial agent. In addition, although the Indian Journal of Chemistry 1969, 7(10), 1010-1016, ibid 1970, 8(6), 505-508, ibid 1985, 24B(7), 737-746, and ibid 1986, 25B(10), 1072-1078 describe the synthesis of a 3-(dihydro(tetrahydro)isoquinolin-1-yl)quinoline compound, there is no description of a 3-(dihydro(tetrahydro)isoquinolin-1-yl)quinoline compound in which position 3 of the isoquinoline ring is substituted by two substituents, and there are no descriptions relating to an agrohorticultural antimicrobial agent. In this manner, the use of a 3-(dihydro(tetrahydro)isoquinolin-1-yl)quinoline compound, in which position 3 of the isoquinoline ring is substituted by two substituents, as an agrohorticultural antimicrobial agent is not known in the prior art.

As a result of conducting extensive studies on a 3-(dihydro(tetrahydro)isoquinolin-1-yl)quinoline compound, the inventors of the present invention found that a 3-(dihydro(tetrahydro)isoquinolin-1-yl)quinoline compound, in which position 3 of the isoquinoline ring is substituted by two substituents and other rings are not condensed with the isoquinoline ring, has superior antimicrobial activity against various plant diseases and is useful as an active ingredient of an agricultural chemical, and in particular, found that this compound is able to control rice blast (*Pyricularia oryzae*), which is a plant mold that frequently causes serious damage to agrohorticultural crops, as well as gray mold (*Botrytis cinerea*) in tomatoes, cucumbers and green beans, at low doses, thereby leading to completion of the present invention.

DISCLOSURE OF THE INVENTION

The present invention is a compound or salt thereof represented by general formula (Ia), (Ib), (Ic) or (Id):

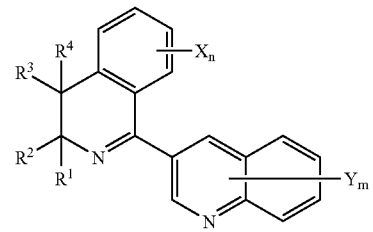
(Ia)

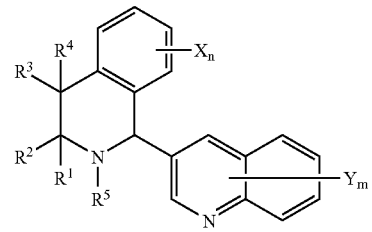
(Ib)

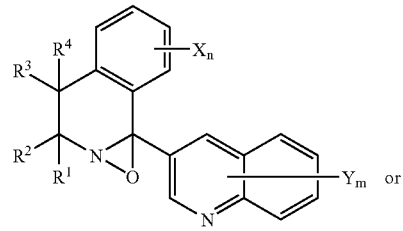
(Ic)

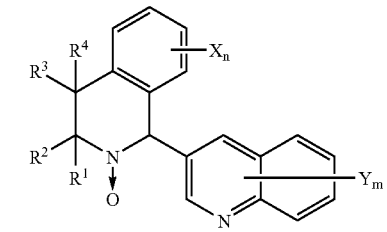
(Id)

(wherein, $R^1$ and $R^2$ may be the same or different, and represent a $C_1$-$C_6$ alkyl group which may be substituted with 1 to 3 substituents, which may be the same or different, selected from the group consisting of a halogen atom, $C_1$-$C_6$ alkoxy group, $C_1$-$C_6$ alkylthio group and phenoxy group;

an aryl group which may be substituted with 1 to 6 substituents, which may the same or different, selected from the group consisting of a halogen atom, $C_1$-$C_6$ alkyl group which may be substituted with 1 to 3 same or different halogen atoms, $C_1$-$C_6$ alkoxy group, amino group which may be substituted with 1 to 2 same or different $C_1$-$C_6$ alkyl groups or acyl groups, nitro group, cyano group, hydroxyl group, mercapto group, and $C_1$-$C_6$ alkylthio group;

a heteroaryl group which may be substituted with 1 to 6 substituents, which may be the same or different, selected from the group consisting of a halogen atom, $C_1$-$C_6$ alkyl group which may be substituted with 1 to 3 same or different halogen atoms, and $C_1$-$C_6$ alkoxy group;

an aralkyl group which may be substituted with 1 to 6 substituents, which may be the same or different, selected from the group consisting of a halogen atom, $C_1$-$C_6$ alkyl group which may be substituted with 1 to 3 same or different halogen atoms, $C_1$-$C_6$ alkoxy group, amino group which may be substituted with 1 to 2 same or different $C_1$-$C_6$ alkyl groups or acyl groups, nitro group, cyano group, hydroxyl group, mercapto group and $C_1$-$C_6$ alkylthio group; or $R^1$ and $R^2$ together represent a $C_3$-$C_{10}$ cycloalkyl group, which may be substituted with 1 to 3 substituents, which may be the same or different, selected from the group consisting of a halogen atom, $C_1$-$C_6$ alkyl group, $C_1$-$C_6$ alkoxy group and phenoxy group;

$R^3$ and $R^4$ may be the same or different, and represent a hydrogen atom;

a $C_1$-$C_6$ alkyl group which may be substituted with 1 to 3 substituents, which may be the same or different, selected from the group consisting of a halogen atom, $C_1$-$C_6$ alkoxy group, $C_1$-$C_6$ alkylthio group and phenoxy group;

a halogen atom;

a $C_1$-$C_6$ alkylene group;

a $C_1$-$C_6$ alkoxy group;

a hydroxyl group; or, $R^3$ and $R^4$ together represent a $C_3$-$C_{10}$ cycloalkyl group which may be substituted with 1 to 3 substituents, which may the same or different, selected from the group consisting of a halogen atom, $C_1$-$C_6$ alkyl group, $C_1$-$C_6$ alkoxy group and phenoxy group;

$R^5$ represents a hydrogen atom, acyl group; or a $C_1$-$C_6$ alkyl group which may be substituted with 1 to 3 substituents, which may be the same or different, selected from the group consisting of a halogen atom, $C_1$-$C_6$ alkoxy group, $C_1$-$C_6$ alkylthio group and phenoxy group;

X represents a halogen atom;

a $C_1$-$C_6$ alkyl group which may be substituted with 1 to 3 substituents, which may be the same or different, selected from the group consisting of a halogen atom, $C_1$-$C_6$ alkoxy group, hydroxyl group, $C_1$-$C_6$ alkoxycarbonyl group and phenoxy group;

a $C_2$-$C_6$ alkenyl group which may be substituted with 1 to 3 substituents, which may be the same or different, selected from the group consisting of a halogen atom, $C_1$-$C_6$ alkoxy group, $C_1$-$C_6$ alkoxycarbonyl group, phenyl group and phenoxy group;

a $C_2$-$C_6$ alkynyl group which may be substituted with 1 to 3 substituents, which may be the same or different, selected from the group consisting of a halogen atom, $C_1$-$C_6$ alkoxy group and phenoxy group;

an aryl group which may be substituted with 1 to 6 substituents, which may be the same or different, selected from the group consisting of a halogen atom, $C_1$-$C_6$ alkyl group which may be substituted with 1 to 3 same or different halogen atoms, $C_1$-$C_6$ alkoxy group, amino group which may be substituted with 1 to 2 same or different $C_1$-$C_6$ alkyl groups or acyl groups, nitro group, cyano group, hydroxyl group, mercapto group and $C_1$-$C_6$ alkylthio group;

a heteroaryl group which may be substituted with 1 to 6 substituents, which may be the same or different, selected from the group consisting of a halogen atom, $C_1$-$C_6$ alkyl group which may be substituted with 1 to 3 same or different halogen atoms, and $C_1$-$C_6$ alkoxy group;

a $C_1$-$C_6$ alkoxy group;

an amino group which may be substituted with 1 to 2 $C_1$-$C_6$ alkyl groups or acyl groups, which may be the same or different;

an acyl group;

a cyano group; or an N-hydroxyalkaneimidoyl group in which a hydrogen atom of the hydroxyl group may be substituted with a substituent selected from the group consisting of a $C_1$-$C_6$ alkyl group, $C_2$-$C_6$ alkenyl group, $C_2$-$C_6$ alkynyl group, aralkyl group, aryl group and heteroaryl group;

Y represents a substituent selected from the group consisting of a halogen atom, $C_1$-$C_6$ alkyl group, $C_1$-$C_6$ alkoxy group and hydroxyl group;

n represents an integer of 0 to 4; and, m represents an integer of 0 to 6.

BEST MODE FOR CARRYING OUT THE INVENTION

In the present invention, a "$C_1$-$C_6$ alkyl group" is a linear or branched alkyl group having 1 to 6 carbon atoms such as a methyl group, ethyl group, propyl group, isopropyl group, butyl group, isobutyl group, s-butyl group, t-butyl group, pentyl group, isopentyl group, 2-methylbutyl group, neopentyl group, 1-ethylpropyl group, hexyl group, 4-methylpentyl group, 3-methylpentyl group, 2-methylpentyl group, 1-methylpentyl group, 3,3-dimethylbutyl group, 2,2-dimethylbutyl group, 1,1-dimethylbutyl group, 1,2-dimethylbutyl group, 1,3-dimethylbutyl group, 2,3-dimethylbutyl group or 2-ethylbutyl group, preferably a linear or branched alkyl group having 1 to 5 carbon atoms ($C_1$-$C_5$ alkyl group), more preferably a linear or branched alkyl group having 1 to 4 carbon atoms ($C_1$-$C_4$ alkyl group), even more preferably a linear or branched alkyl group having 1 to 3 carbon atoms ($C_1$-$C_3$ alkyl group), particularly preferably a methyl group, ethyl group or propyl group, and most preferably a methyl group or ethyl group.

In the present invention, a "$C_2$-$C_6$ alkenyl group" may be linear or branched, and can contain one or an arbitrary number of double bonds, examples of which include a vinyl group, prop-1-en-1-yl group, allyl group, isopropenyl group, but-1-en-1-yl group, but-2-en-1-yl group, but-3-en-1-yl group, 2-methylprop-2-en-1-yl group, 1-methylprop-2-en-1-yl group, pent-1-en-1-yl group, pent-2-en-1-yl group, pent-3-en-1-yl group, pent-4-en-1-yl group, 3-methylbut-2-en-1-yl group, 3-methylbut-3-en-1-yl group, hex-1-en-1-yl group, hex-2-en-1-yl group, hex-3-en-1-yl group, hex-4-en-1-yl group, hex-5-en-1-yl group and 4-methylpent-3-en-1-yl group.

In the present invention, a "$C_2$-$C_6$ alkynyl group" may be linear or branched, and can contain one or an arbitrary number of triple bonds, examples of which include an ethynyl group, prop-1-yn-1-yl group, prop-2-yn-1-yl group, but-1-yn-1-yl group, but-3-yn-1-yl group, 1-methylprop-2-yn-1-yl group, pent-1-yn-1-yl group, pent-4-yn-1-yl group, hex-1-yn-1-yl group and hex-5-yn-1-yl group.

In the present invention, examples of an "aryl group" include a phenyl group, 1-naphthyl group, 2-naphthyl group, anthracenyl group, phenanthracenyl group and acenaphthylenyl group.

In the present invention, a "heteroaryl group" may have a single ring or multiple rings, and a heteroaryl group can be used which contains one or two or more same or different ring-composing heteroatoms. There are no particular limitations on the type of heteroatom, and examples include a nitrogen atom, oxygen atom and sulfur atom. Examples of heteroaryl groups include 5- to 7-member monocyclic heteroaryl groups such as a furyl group, thienyl group, pyrrolyl group, oxazolyl group, isoxazolyl group, dihydroisoxazolyl group, thiazolyl group, isothiazolyl group, imidazolyl group, pyrazolyl group, oxadiazolyl group, thiadiazolyl group, triazolyl group, tetrazolyl group, pyridyl group, azepinyl group and oxazepinyl group. Examples of polycyclic heteroaryl groups which compose a heteroarylalkyl group include 8- to 14-member polycyclic heteroaryl groups such as a benzofuranyl group, isobenzofuranyl group, benzothienyl group, indolyl group, isoindolyl group, indazolyl group, benzoxazolyl group, benzoisoxazolyl group, benzothiazolyl group, benzoisothiazolyl group, benzoxadiazolyl group, benzothiadiazolyl group, benzotriazolyl group, quinolyl group, isoquinolyl group, cinnolinyl group, quinazolinyl group, quinoxalinyl group, phthalazinyl group, naphthilizinyl group, purinyl group, pteridinyl group, carbozolyl group, carbolinyl group, acridinyl group, 2-acridinyl group, 3-acridinyl group, 4-acridinyl group, 9-acridinyl group, phenoxadinyl group, phenothiadinyl group and phenadinyl group.

In the present invention, examples of an "aralkyl group" include groups in which one or two or more hydrogen atoms of the aforementioned "$C_1$-$C_6$ alkyl group" is substituted with an "aryl group", examples of which include a benzyl group, 1-naphthylmethyl group, 2-naphthylmethyl group, anthracenylmethyl group, phenanthranylmethyl group, acenaphthylenylmethyl group, diphenylmethyl group, 1-phenethyl group, 2-phenethyl group, 1-(1-naphthyl)ethyl group, 1-(2-naphthyl)ethyl group, 2-(1-naphthyl)ethyl group, 2-(2-naphthyl)ethyl group, 3-phenylpropyl group, 3-(1-naphthyl)propyl group, 3-(2-naphthyl)propyl group, 4-phenylbutyl group, 4-(1-naphthyl)butyl group, 4-(2-naphthyl)butyl group, 5-phenylpentyl group, 5-(1-naphthyl)pentyl group, 5-(2-naphthyl)pentyl group, 6-phenylhexyl group, 6-(1-naphthyl)hexyl group and 6-(2-naphthyl)hexyl group.

In the present invention, examples of a "$C_3$-$C_{10}$ cycloalkyl group" include monocyclic or polycyclic cycloalkyl groups having 3 to 10 carbon atoms such as a cyclobutyl group, cyclopentyl group, cyclohexyl group, cycloheptyl group or norbornyl group, preferably a cyclopentyl group, cyclohexyl group or cycloheptyl group, and more preferably a cyclopentyl group.

In the present invention, a "halogen atom" is a fluorine atom, chlorine atom, bromine atom or iodine atom, preferably a fluorine atom, chlorine atom or bromine atom, more preferably a fluorine atom or chlorine atom, and most preferably a fluorine atom.

In the present invention, examples of a "$C_1$-$C_6$ alkoxy group" include linear or branched alkoxy groups having 1 to 6 carbon atoms such as a methoxy group, ethoxy group, propoxy group, isopropoxy group, butoxy group, isobutoxy group, s-butoxy group, t-butoxy group, pentyloxy group, isopentyloxy group, 2-methylbutoxy group, neopentyloxy group, 1-ethylpropoxy group, hexyloxy group, (4-methylpentyl)oxy group, (3-methylpentyl)oxy group, (2-methylpentyl)oxy group, (1-methylpentyl)oxy group, 3,3-dimethylbutoxy group, 2,2-dimethylbutoxy group, 1,1-dimethylbutoxy group, 1,2-dimethylbutoxy group, 1,3-dimethylbutoxy group, 2,3-dimethylbutoxy group and 2-ethylbutoxy group, preferably linear or branched alkoxy groups having 1 to 4 carbon atoms ($C_1$-$C_4$ alkoxy groups), more preferably a methoxy group, ethoxy group or isopropoxy group, even more preferably a methoxy group or ethoxy group, and most preferably a methoxy group.

In the present invention, examples of a "$C_1$-$C_6$ alkylthio group" include linear or branched alkylthio groups having 1 to 6 carbon atoms such as a methylthio group, ethylthio group, propylthio group, isopropylthio group, butylthio group, isopentylthio group, neopentylthio group, 3,3-dimethylbutylthio group or 2-ethylbutylthio group, preferably linear or branched alkylthio groups having 1 to 4 carbon atoms, and more preferably a methylthio group.

In the present invention, examples of an "acyl group" include a formyl group, carbonyl group bound to the aforementioned "$C_1$-$C_6$ alkyl group" ($C_2$-$C_7$ alkylcarbonyl group), carbonyl group bound to the aforementioned "$C_2$-$C_6$ alkenyl group" ($C_3$-$C_7$ alkenylcarbonyl group), carbonyl group bound to the aforementioned "aryl group" ("arylcarbonyl group"), carbonyl group bound to the aforementioned "$C_1$-$C_6$ alkoxy group" ($C_2$-$C_7$ alkoxycarbonyl group) or carbonyl group bound to the aforementioned "amino group which may be substituted with 1 to 2 same or different $C_1$-$C_6$ alkyl groups" ($C_2$-$C_7$ alkylaminocarbonyl group), preferably linear or branched alkylcarbonyl groups having 2 to 5 carbon atoms ($C_2$-$C_5$ alkylcarbonyl groups) or alkylaminocarbonyl groups having 2 to 7 carbon atoms ($C_2$-$C_7$ alkylaminocarbonyl groups), and more preferably an acetyl group or methylaminocarbonyl group.

In the present invention, examples of a "$C_1$-$C_6$ alkyl group which may be substituted with 1 to 3 same or different halogen atoms" include the aforementioned "$C_1$-$C_6$ alkyl groups" as well as "$C_1$-$C_6$ alkyl groups" substituted with 1 to 3 of the aforementioned same or different "halogen atoms" such as a trifluoromethyl group, trichloromethyl group, difluoromethyl group, dichloromethyl group, dibromomethyl group, fluoromethyl group, chloromethyl group, bromomethyl group, iodomethyl group, 2,2,2-trichloroethyl group, 2,2,2-trifluoroethyl group, 2-bromoethyl group, 2-chloroethyl group, 2-fluoroethyl group, 3-chloropropyl group, 3,3,3-trifluoropropyl group, 4-fluorobutyl group, 3-fluoro-2-methylpropyl group, 3,3,3-trifluoro-2-methylpropyl group and 6,6,6-trichlorohexyl group, preferably the aforementioned "$C_1$-$C_4$ alkyl groups" which may be substituted with 1 to 3 of the aforementioned same or different "halogen atoms", more preferably the aforementioned "$C_1$-$C_3$ alkyl groups" which may be substituted with 1 to 3 of the aforementioned same or different "fluorine atoms or chlorine atoms", even more preferably a methyl group, ethyl group, propyl group, chloromethyl group or trifluoromethyl group, and particularly preferably a methyl group, ethyl group or trifluoromethyl group.

In the present invention, examples of a "N-hydroxyalkaneimidoyl group in which a hydrogen atom of the hydroxyl group may be substituted with a substituent selected from the group consisting of a $C_1$-$C_6$ alkyl group, $C_2$-$C_6$ alkenyl group, $C_2$-$C_6$ alkynyl group, aralkyl group, aryl group and heteroaryl group" include groups in which the hydroxyl group of a N-hydroxyalkaneimidoyl group having 1 to 6 carbon atoms, such as a hydroxyiminomethyl group, N-hydroxyethaneimidoyl group, N-hydroxypropaneimidoyl group or N-hydroxybutaneimidoyl group, is substituted with the aforementioned "$C_1$-$C_6$ alkyl group", the aforementioned "$C_2$-$C_6$ alkenyl group", the aforementioned "$C_2$-$C_6$ alkynyl group", the aforementioned "aralkyl group", the aforementioned "aryl group" or the aforementioned "heteroaryl group", examples of which include a methoxyiminomethyl group, N-methoxyethaneimidoyl group, N-ethoxyethaneimidoyl group, N-butoxyalkaneimidoyl group, N-aryloxyethaneimidoyl group, N-phenoxyethaneimidoyl group, N-methoxypropaneimidoyl group, N-methoxybutaneimidoyl group and N-methoxypropaneimidoyl group.

In the present invention, a "$C_1$-$C_6$ alkyl group which may be substituted with 1 to 3 substituents, which may be the same or different, selected from the group consisting of a halogen atom, $C_1$-$C_6$ alkoxy group and phenoxy group" includes the aforementioned "$C_1$-$C_6$ alkyl groups", the aforementioned "$C_1$-$C_6$ alkyl groups which may be substituted with 1 to 3 same or different halogen atoms", the aforementioned "$C_1$-$C_6$ alkyl groups" substituted with 1 to 3 of the same or different "$C_1$-$C_6$ alkyl groups", such as a methoxymethyl group, ethoxymethyl group, ethoxyethyl group or propoxymethyl group, the aforementioned "$C_1$-$C_6$ alkyl groups" substituted with a phenoxy group such as a phenoxymethyl group or phenoxyethyl group, and the aforementioned "$C_1$-$C_6$ alkyl groups" substituted with 2 or more substituents selected from the group consisting of a halogen atom, the aforementioned $C_1$-$C_6$ alkoxy groups and a phenoxy group, such as a 2-methoxy-1-chloromethyl group or a 3-phenoxy-2-bromo-2-methoxypropyl group.

In the present invention, a "$C_2$-$C_6$ alkenyl group which may be substituted with 1 to 3 substituents, which may be the same or different, selected from the group consisting of a halogen atom, $C_1$-$C_6$ alkoxy group, phenyl group and phenoxy group" includes the aforementioned "$C_2$-$C_6$ alkenyl groups", the aforementioned "$C_2$-$C_6$ alkenyl groups" substituted with 1 to 3 same or different halogen atoms, such as a 3-chloroallyl group or 4-bromo-2-butenyl group, the aforementioned "$C_2$-$C_6$ alkenyl groups" substituted with 1 to 3 of the same or different "$C_1$-$C_6$ alkoxy groups", such as a 3-methoxy-2-propenyl group or 4-ethoxy-3-butenyl group, the aforementioned "$C_2$-$C_6$ alkenyl groups" substituted with a phenyl group, such as a 1-phenylvinyl group, styryl group or cinnamyl group, the aforementioned "$C_2$-$C_6$ alkenyl groups" substituted with a phenoxy group, such as a 3-phenoxy-2-butenyl group, and the aforementioned "$C_2$-$C_6$ alkenyl groups" substituted with two or more types of substituents selected from the group consisting of a halogen atom, the aforementioned $C_1$-$C_6$ alkoxy group and a phenoxy group, such as a 4-methoxy-3-chloro-2-butenyl group.

In the present invention, a "$C_2$-$C_6$ alkynyl group which may be substituted with 1 to 3 substituents, which may be the same or different, selected from the group consisting of a halogen atom, $C_1$-$C_6$ alkoxy group and phenoxy group" includes the aforementioned "$C_2$-$C_6$ alkynyl groups", the aforementioned "$C_2$-$C_6$ alkynyl groups" substituted with 1 to 3 same or different halogen atoms, such as a 3-chloro-2-propynyl group or 4-bromo-2-butynyl group, the aforementioned "$C_2$-$C_6$ alkynyl groups" substituted with 1 to 3 of the same or different "$C_1$-$C_6$ alkoxy groups", such as a 3-methoxy-2-propynyl group or 4-ethoxy-3-butynyl group, the aforementioned "$C_2$-$C_6$ alkynyl groups" substituted with a phenoxy group, such as a 3-phenoxy-2-butynyl group, and the aforementioned "$C_2$-$C_6$ alkynyl groups" substituted with two or more types of substituents selected from the group consisting of a halogen atom, the aforementioned $C_1$-$C_6$ alkoxy group and a phenoxy group, such as a 4-methoxy-4-chloro-2-butynyl group.

In the present invention, examples of an "amino group which may be substituted with 1 to 2 same or different $C_1$-$C_6$ alkyl groups or acyl groups" include an amino group, and an amino group where 1 to 2 of the aforementioned same or different "$C_1$-$C_6$ alkyl groups" or 1 to 2 of the aforementioned same or different "acyl groups" are substituted, preferably an amino group where 1 to 2 of aforementioned same or different "$C_1$-$C_4$ alkyl groups" or 1 to 2 of the aforementioned same or different "acyl groups" are substituted, and more preferably a dimethylamino group, diethylamino group or acetylamino group.

In the present invention, an "aryl group which may be substituted with 1 to 6 substituents, which may the same or different, selected from the group consisting of a halogen atom, $C_1$-$C_6$ alkoxy group which may be substituted with 1 to 3 same or different halogen atoms, $C_1$-$C_6$ alkoxy group, amino group which may be substituted with 1 to 2 same or different $C_1$-$C_6$ alkyl groups or acyl groups, nitro group, cyano group, hydroxyl group mercapto group, and $C_1$-$C_6$ alkylthio group" includes the aforementioned "aryl groups", the aforementioned "aryl groups" substituted with 1 to 6 same or different halogen atoms, the aforementioned "aryl groups" substituted with 1 to 6 of the aforementioned same or different "$C_1$-$C_6$ alkyl groups which may be substituted with 1 to 3 same or different halogen atoms", the aforementioned "aryl groups" substituted with 1 to 6 of the aforementioned same or different "$C_1$-$C_6$ alkoxy groups", the aforementioned "aryl groups" substituted with 1 to 6 of the aforementioned same or different "amino groups which may be substituted with 1 to 2 same or different $C_1$-$C_6$ alkyl groups or acyl groups", the aforementioned "aryl groups" substituted with 1 to 6 nitro groups, the aforementioned "aryl groups" substituted with 1 to 6 cyano groups, the aforementioned "aryl groups" substituted with 1 to 6 hydroxyl groups, the aforementioned "aryl groups" substituted with 1 to 6 mercapto groups, the aforementioned "aryl groups" substituted with 1 to 6 of the aforementioned same or different "$C_1$-$C_6$ alkylthio groups", and the aforementioned "aryl groups" substituted with two or more types of substituents selected from the group consisting of a halogen atom, the aforementioned "$C_1$-$C_6$ alkyl group which may be substituted with 1 to 3 same or different halogen atoms", the aforementioned "$C_1$-$C_6$ alkoxy group", the aforementioned "amino group which may be substituted with 1 to 2 same or different $C_1$-$C_6$ alkyl groups or acyl groups", nitro group, cyano group, hydroxyl group, mercapto group and the aforementioned "$C_1$-$C_6$ alkylthio group".

In the present invention, a "heteroaryl group which may be substituted with 1 to 6 substituents, which may be the same or different, selected from the group consisting of a halogen atom, $C_1$-$C_6$ alkyl group which may be substituted with 1 to 3 same or different halogen atoms, and $C_1$-$C_6$ alkoxy group" includes the aforementioned "heteroaryl groups", the aforementioned "heteroaryl groups" substituted with 1 to 6 same or different halogen atoms, the above-mentioned "heteroaryl groups" substituted with 1 to 6 of the same or different "$C_1$-$C_6$ alkyl groups which may be substituted with 1 to 3 same or different halogen atoms", the aforementioned "heteroaryl groups" substituted with 1 to 6 of the aforementioned same or different "$C_1$-$C_6$ alkoxy groups", the aforementioned "heteroaryl groups" substituted with 1 to 6 hydroxyl groups, and the aforementioned "heteroaryl groups" substituted with two or more types of substituents selected from the group consisting of a halogen atom, the aforementioned "$C_1$-$C_6$ alkyl group", the aforementioned "$C_1$-$C_6$ alkoxy group" and a hydroxyl group.

In the present invention, an "aralkyl group which may be substituted with 1 to 6 substituents, which may be the same or different, selected from the group consisting of a halogen atom, $C_1$-$C_6$ alkyl group which may be substituted with 1 to 3 same or different halogen atoms, $C_1$-$C_6$ alkoxy group, amino group which may be substituted with 1 to 2 same or different $C_1$-$C_6$ alkyl groups or acyl groups, nitro group, cyano group, hydroxyl group, mercapto group and $C_1$-$C_6$ alkylthio group" includes the aforementioned "aralkyl groups", the aforementioned "aralkyl groups" substituted with 1 to 6 same or different halogen atoms, the aforementioned "aralkyl groups" substituted with 1 to 6 of the aforementioned same or different "$C_1$-$C_6$ alkyl groups which may be substituted with 1 to 3 same or different halogen atoms", the aforementioned "aralkyl groups" substituted with 1 to 6 of the aforementioned same or different "$C_1$-$C_6$ alkoxy groups", the aforementioned "aralkyl groups" substituted with 1 to 6 of the aforementioned same or different "amino groups which may be substituted with 1 to 2 same or different $C_1$-$C_6$ alkyl groups or acyl groups", the aforementioned "aralkyl groups" substituted with 1 to 6 nitro groups, the aforementioned "aralkyl groups" substituted with 1 to 6 cyano groups, the aforementioned "aralkyl groups" substituted with 1 to 6 hydroxyl groups, the aforementioned "aralkyl groups" substituted with 1 to 6 mercapto groups, the aforementioned "aralkyl groups" substituted with 1 to 6 of the aforementioned same or different "$C_1$-$C_6$ alkylthio groups", and the aforementioned "aralkyl groups" substituted with two or more types of substituents selected from the group consisting of a halogen atom, the aforementioned "$C_1$-$C_6$ alkyl group which may be substituted with 1 to 3 same or different halogen atoms", the aforementioned "$C_1$-$C_6$ alkoxy group", the aforementioned "amino group which may be substituted with 1 to 2 same or different $C_1$-$C_6$ alkyl groups or acyl groups", nitro group, cyano group, hydroxyl group, mercapto group and the aforementioned "$C_1$-$C_6$ alkylthio group". In the case an aralkyl group has a substituent, said substituent may be substituted on the aryl ring which composes the aralkyl group and/or on the alkyl group.

X can be substituted at 1 to 4 arbitrary substitutable locations on the isoquinoline ring, and in the case there are two or more X present, they may be the same or different.

Y can be substituted at 1 to 6 arbitrary substitutable locations on the quinoline ring, and in the case two or more Y are present, they may be the same or different.

In compounds (Ia), (Ib), (Ic) or (Id) of the present invention:

(1) $R^1$ and $R^2$ are preferably a $C_1$-$C_6$ alkyl group which may be substituted with 1 to 3 same or different substituents selected from the group consisting of a halogen atom, $C_1$-$C_6$ alkoxy group and phenoxy group; or an aryl group which may be substituted with 1 to 6 same or different substituents selected from the group consisting of a halogen atom, $C_1$-$C_6$ alkyl group, $C_1$-$C_6$ alkoxy group and hydroxyl group, more preferably a $C_1$-$C_6$ alkyl group which may be substituted with 1 to 3 same or different halogen atoms, or a phenyl group which may be substituted with 1 to 6 same or different halogen atoms, and even more preferably a methyl group, ethyl group, propyl group, trifluoromethyl group, trifluoroethyl group, phenyl group, fluorophenyl group or chlorophenyl group, (2) $R^3$ and $R^4$ are preferably a hydrogen atom, halogen atom or $C_1$-$C_6$ alkyl group, and $R^5$ is preferably a hydrogen atom, (3) $X_n$ is preferably such that X is a halogen atom; $C_1$-$C_6$ alkyl group; $C_2$-$C_6$ alkynyl group; aryl group which may be substituted with 1 to 6 same or different substituents selected from the group consisting of a halogen atom, $C_1$-$C_6$ alkyl group which substituted with 1 to 3 same or different halogen atoms and $C_1$-$C_6$ alkoxy group; heteroaryl group which may be substituted with 1 to 6 same or different substituents selected from the group consisting of a halogen atom, $C_1$-$C_6$ alkyl group which may be substituted with 1 to 3 same or different halogen atoms and $C_1$-$C_6$ alkoxy group; cyano group; or, N-hydroxyalkaneimidoyl in which the hydrogen atom of a hydroxyl group which may be substituted with a substituent selected from the group consisting of a $C_1$-$C_6$ alkyl group and phenyl group, and n is an integer of 0 to 2, more preferably X is a halogen atom; $C_1$-$C_6$ alkyl group; $C_2$-$C_6$ alkynyl group; heteroaryl group which may be substituted with 1 to 6 same or different substituents selected from the group consisting of a halogen atom, $C_1$-$C_6$ alkyl group which may be substituted with 1 to 3 same or different halogen atoms and $C_1$-$C_6$ alkoxy group; cyano group; or N-hydroxyalkaneimidoyl group in which a hydrogen atom of the hydroxyl group may be substituted with a substituent selected from the group consisting of a $C_1$-$C_6$ alkyl group and a phenyl group, and n is an integer of 0 to 2, and even more preferably X is a fluorine atom, chlorine atom, bromine atom, methyl group, ethynyl group, furyl group, thienyl group, cyano group, methoxyethaneimidoyl group, ethoxyethaneimidoyl group or phenoxyethaneimidoyl group, and n is 0 or 1, and (4) $Y_m$ is preferably such that Y is a fluorine atom, chlorine atom or methyl group, and m is 0 or 1, and more preferably Y is a methyl group and m is 0 or 1.

In compounds (Ia), (Ib), (Ic) or (Id) of the present invention, preferably:

(a1) $R^1$ and $R^2$ are a $C_1$-$C_6$ alkyl group which may be substituted with 1 to 3 same or different substituents selected from the group consisting of a halogen atom, $C_1$-$C_6$ alkoxy group and phenoxy group; or, an aryl group which may be substituted with 1 to 6 same or different substituents selected from the group consisting of a halogen atom, $C_1$-$C_6$ alkyl group, $C_1$-$C_6$ alkoxy group and hydroxyl group, (a2) $R^3$ and $R^4$ are a hydrogen atom, halogen atom or $C_1$-$C_6$ alkyl group, and $R^5$ is a hydrogen atom, (a3) $X_n$ is preferably such that X is a halogen atom; $C_1$-$C_6$ alkyl group; aryl group which may be substituted with 1 to 6 same or different substituents selected from the group consisting of a halogen atom, $C_1$-$C_6$ alkyl group which may be substituted with 1 to 3 same or different halogen atoms and $C_1$-$C_6$ alkoxy group; heteroaryl group which may be substituted with 1 to 6 same or different substituents selected from the group consisting of a halogen atom, $C_1$-$C_6$ alkyl group which may be substituted with 1 to 3 same or different halogen atoms and $C_1$-$C_6$ alkoxy group; cyano group; or, N-hydroxyalkaneimidoyl in which the hydrogen atom of a hydroxyl group is which may be substituted with a substituent selected from the group consisting of a $C_1$-$C_6$ alkyl group and phenyl group, and n is an integer of 0 to 2, and (a4) $Y_m$ is such that Y is a fluorine atom, chlorine atom or methyl group, and m is 0 or 1, more preferably:

(b1) $R^1$ and $R^2$ are a $C_1$-$C_6$ alkyl group which may be substituted with 1 to 3 same or different halogen atoms, or a phenyl group which may be substituted with 1 to 6 same or different halogen atoms, (b2) $R^3$ and $R^4$ are a halogen atom or a $C_1$-$C_6$ alkyl group, and $R^5$ is a hydrogen atom, (b3) $X_n$ is such that X is a halogen atom; $C_1$-$C_6$ alkyl group; $C_2$-$C_6$ alkynyl group; heteroaryl group which may be substituted with 1 to 6 same or different substituents selected from the group consisting of a halogen atom, $C_1$-$C_6$ alkyl group which may be substituted with 1 to 3 same or different halogen atoms and $C_1$-$C_6$ alkoxy group; cyano group; or N-hydroxyalkaneimidoyl in which the hydrogen atom of a hydroxyl group may be substituted with a substituent selected from the group consisting of a $C_1$-$C_6$ alkyl group and phenyl group, and n is an integer of 0 to 2, and (b4) $Y_m$ is such that Y is a fluorine atom, chlorine atom or methyl group, and m is 0 or 1, even more preferably:

(c1) $R^1$ and $R^2$ are a methyl group, ethyl group, propyl group, trifluoromethyl group, trifluoroethyl group, phenyl group, fluorophenyl group or chlorophenyl group, (c2) $R^3$ and $R^4$ are a fluorine atom or methyl group, and $R^5$ is a hydrogen atom, (c3) $X_n$ is such that X is a fluorine atom, chlorine atom, bromine atom, methyl group, ethynyl group, furyl group, thienyl group, cyano group, methoxyethaneimidoyl group, ethoxyethaneimidoyl group or phenoxyethaneimidoyl group, and n is 0 or 1, and (c4) $Y_m$ is such that Y is a methyl group and m is 0 or 1, and most preferably:

(d) compound (Ia), (Ib), (Ic) or (Id) is:
3-(5-fluoro-3,3-dimethyl-3,4-dihydroisoquinolin-1-yl) quinoline,
3-(5-chloro-3,3-dimethyl-3,4-dihydroisoquinolin-1-yl) quinoline,
3-(5-bromo-3,3-dimethyl-3,4-dihydroisoquinolin-1-yl) quinoline, 3-(5-ethynyl-3,3-dimethyl-3,4-dihydroisoquinolin-1-yl)quinoline,
3-(5,6-difluoro-3,3-dimethyl-3,4-dihydroisoquinolin-1-yl)quinoline,
3-(3-ethyl-5-fluoro-3-methyl-3,4-dihydroisoquinolin-1-yl)quinoline,
3-(5-fluoro-3-methyl-3-propyl-3,4-dihydroisoquinolin-1-yl)quinoline,
3-(3-methyl-3-trifluoromethyl-3,4-dihydroisoquinolin-1-yl)quinoline,
3-[3-methyl-3-(2,2,2-trifluoroethyl)-3,4-dihydroisoquinolin-1-yl]quinoline,
3-(3-methyl-3-phenyl-3,4-dihydroisoquinolin-1-yl)quinoline,
3-[3-methyl-3-(4-fluorophenyl)-3,4-dihydroisoquinolin-1-yl]quinoline,
3-[3-methyl-3-(4-chlorophenyl)-3,4-dihydroisoquinolin-1-yl]quinoline,
3-(5-fluoro-3,3,4,4-tetramethyl-3,4-dihydroisoquinolin-1-yl)-6-fluoroquinoline,
3-(5-fluoro-3,3,4,4-tetramethyl-3,4-dihydroisoquinolin-1-yl)-8-fluoroquinoline,
3-(5-fluoro-3,3,4,4-tetramethyl-3,4-dihydroisoquinolin-1-yl)-8-methylquinoline,
3-(4,5-difluoro-3,3-dimethyl-3,4-dihydroisoquinolin-1-yl)quinoline,
3-(4,4-difluoro-3,3-dimethyl-3,4-dihydroisoquinolin-1-yl)quinoline,
3-(4,4,5-trifluoro-3,3-dimethyl-3,4-dihydroisoquinolin-1-yl)quinoline,
5-fluoro-3,3,4,4-tetramethyl-8b-quinolin-3-yl-4,8b-dihydro-3H-oxazileno[3,2-a]isoquinoline,
3,3,4,4-tetramethyl-8b-quinolin-3-yl-4,8b-dihydro-3H-oxazileno[3,2-a]isoquinoline,
5-fluoro-3,3-dimethyl-8b-quinolin-3-yl-4,8b-dihydro-3H-oxazileno[3,2-a]isoquinoline,
6-fluoro-3,3,4,4-tetramethyl-8b-quinolin-3-yl-4,8b-dihydro-3H-oxazileno[3,2-a]isoquinoline,
4',4'-dimethyl-8b'-quinolin-3-yl-4',8b'-dihydrospiro[cyclopentane-1,3'-oxazileno[3,2-a]isoquinoline],
4,4,5-trifluoro-3,3-dimethyl-8b-quinolin-3-yl-4,8b-dihydro-3H-oxazileno[3,2-a]isoquinoline,
3-(5-fluoro-3,3,4,4-tetramethyl-2-oxide-3,4-dihydroisoquinolin-1-yl)quinoline,
3-(3,3,4,4-tetramethyl-2-oxide-3,4-dihydroisoquinolin-1-yl)quinoline,
3-(6-fluoro-3,3,4,4-tetramethyl-2-oxide-3,4-dihydroisoquinolin-1-yl)quinoline,
3-(6-chloro-3,3,4,4-tetramethyl-2-oxide-3,4-dihydroisoquinolin-1-yl)quinoline,
3-(4,4-difluoro-3,3-dimethyl-2-oxide-3,4-dihydroisoquinolin-1-yl)quinoline,
3-(4,4,5-trifluoro-3,3-dimethyl-2-oxide-3,4-dihydroisoquinolin-1-yl)quinoline or
3-(5-fluoro-3,3,4,4-tetramethyl-3,4-dihydroisoquinolin-1-yl)quinoline.

Compound (Ia), (Ib), (Ic) or (Id) of the present invention can be converted to a salt in the manner of, for example, a sulfate, hydrochloride, nitrate or phosphate, and these salts are included in the present invention provided they can be used as agrohorticultural antimicrobial agents.

Compound (Ia), (Ib), (Ic) or (Id) of the present invention or salts thereof can be converted to a solvent hydrate, and these solvent hydrates are also included in the present invention. A solvent hydrate is preferably a hydrate.

Compounds having asymmetric carbons are also included in compound (Ia), (Ib), (Ic) or (Id) of the present invention, and in such cases, the invention of the present application also includes mixtures containing arbitrary ratios of one species of optically active form or several species of optically active forms.

Although representative compounds of the present invention are indicated in the following tables, the present invention is not limited to these compounds.

In the following tables, "Me" indicates a methyl group, "Et" an ethyl group, "Pr" a propyl group, "iPr" an isopropyl group, "Bu" a butyl group, "iBu" an isobutyl group, "tBu" a t-butyl group, "iPen" an isopentyl group, "Vinyl" a vinyl group, "Allyl" an allyl group, "Ethynyl" and ethynyl group, "Ph" a phenyl group, "FUR" a furyl group, "2THI" a 2-thienyl group, "OXA" an oxazolyl group, "Ac" an acetyl group, "EtIMD" an N-hydroxyethaneimidoyl group, "3PYD" a 3-pyridyl group, "Bn" a benzyl group, "cPen" a cyclopentyl group in which $R^1$ and $R^2$ or $R^3$ and $R^4$ form a ring, "cHex" a cyclohexyl group in which $R^1$ and $R^2$ or $R^3$ and $R^4$ form a ring, "cHep" a cycloheptyl group in which $R^1$ and $R^2$ or $R^3$ and $R^4$ form a ring, and in "$X_n$" and "$Y_m$", "H" indicates that n=0 and m=0.

TABLE 1

(Ia)

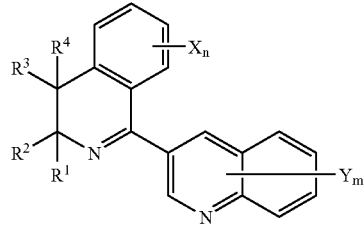

| Compound No. | R1, R2 | R3, R4 | Xn | Ym |
|---|---|---|---|---|
| 1-1 | Me, Me | H, H | H | H |
| 1-2 | Me, Me | H, H | H | 2-F |
| 1-3 | Me, Me | H, H | H | 4-F |
| 1-4 | Me, Me | H, H | H | 5-F |
| 1-5 | Me, Me | H, H | H | 6-F |
| 1-6 | Me, Me | H, H | H | 7-F |
| 1-7 | Me, Me | H, H | H | 8-F |

TABLE 1-continued (Ia)

| Compound No. | R1, R2 | R3, R4 | Xn | Ym |
|---|---|---|---|---|
| 1-8 | Me, Me | H, H | H | 2-Cl |
| 1-9 | Me, Me | H, H | H | 4-Cl |
| 1-10 | Me, Me | H, H | H | 5-Cl |
| 1-11 | Me, Me | H, H | H | 6-Cl |
| 1-12 | Me, Me | H, H | H | 7-Cl |
| 1-13 | Me, Me | H, H | H | 8-Cl |
| 1-14 | Me, Me | H, H | H | 2-Me |
| 1-15 | Me, Me | H, H | H | 4-Me |
| 1-16 | Me, Me | H, H | H | 5-Me |
| 1-17 | Me, Me | H, H | H | 6-Me |
| 1-18 | Me, Me | H, H | H | 7-Me |
| 1-19 | Me, Me | H, H | H | 8-Me |
| 1-20 | Me, Me | H, H | H | 2-MeO |
| 1-21 | Me, Me | H, H | H | 4-MeO |
| 1-22 | Me, Me | H, H | H | 5-MeO |
| 1-23 | Me, Me | H, H | H | 6-MeO |
| 1-24 | Me, Me | H, H | H | 7-MeO |
| 1-25 | Me, Me | H, H | H | 8-MeO |
| 1-26 | Me, Me | H, H | H | 2-OH |
| 1-27 | Me, Me | H, H | H | 4-OH |
| 1-28 | Me, Me | H, H | H | 5-OH |
| 1-29 | Me, Me | H, H | H | 6-OH |
| 1-30 | Me, Me | H, H | H | 7-OH |
| 1-31 | Me, Me | H, H | H | 8-OH |
| 1-32 | Me, Me | H, H | 5-F | H |
| 1-33 | Me, Me | H, H | 5-F | 4-F |
| 1-34 | Me, Me | H, H | 5-F | 8-F |
| 1-35 | Me, Me | H, H | 5-F | 4-Cl |
| 1-36 | Me, Me | H, H | 5-F | 6-Cl |
| 1-37 | Me, Me | H, H | 5-F | 4-MeO |
| 1-38 | Me, Me | H, H | 5-F | 8-Me |
| 1-39 | Me, Me | H, H | 5-F | 8-MeO |
| 1-40 | Me, Me | H, H | 5-F | 8-OH |
| 1-41 | Me, Me | H, H | 6-F | H |
| 1-42 | Me, Me | H, H | 7-F | H |
| 1-43 | Me, Me | H, H | 8-F | H |
| 1-44 | Me, Me | H, H | 5-Cl | H |
| 1-45 | Me, Me | H, H | 5-Cl | 4-F |
| 1-46 | Me, Me | H, H | 5-Cl | 8-F |
| 1-47 | Me, Me | H, H | 5-Cl | 4-Cl |
| 1-48 | Me, Me | H, H | 5-Cl | 6-Cl |
| 1-49 | Me, Me | H, H | 5-Cl | 4-Me |
| 1-50 | Me, Me | H, H | 5-Cl | 8-Me |
| 1-51 | Me, Me | H, H | 5-Cl | 8-MeO |
| 1-52 | Me, Me | H, H | 5-Cl | 8-OH |
| 1-53 | Me, Me | H, H | 6-Cl | H |
| 1-54 | Me, Me | H, H | 7-Cl | H |
| 1-55 | Me, Me | H, H | 8-Cl | H |
| 1-56 | Me, Me | H, H | 5-Br | H |
| 1-57 | Me, Me | H, H | 5-Br | 4-F |
| 1-58 | Me, Me | H, H | 5-Br | 8-F |
| 1-59 | Me, Me | H, H | 5-Br | 4-Cl |
| 1-60 | Me, Me | H, H | 5-Br | 6-Cl |
| 1-61 | Me, Me | H, H | 5-Br | 4-Me |
| 1-62 | Me, Me | H, H | 5-Br | 8-Me |
| 1-63 | Me, Me | H, H | 5-Br | 8-MeO |
| 1-64 | Me, Me | H, H | 5-Br | 8-OH |
| 1-65 | Me, Me | H, H | 6-Br | H |
| 1-66 | Me, Me | H, H | 7-Br | H |
| 1-67 | Me, Me | H, H | 8-Br | H |
| 1-68 | Me, Me | H, H | 5-I | H |
| 1-69 | Me, Me | H, H | 5-Me | H |
| 1-70 | Me, Me | H, H | 6-Me | H |

TABLE 1-continued (Ia)

| Compound No. | R1, R2 | R3, R4 | Xn | Ym |
|---|---|---|---|---|
| 1-71 | Me, Me | H, H | 7-Me | H |
| 1-72 | Me, Me | H, H | 8-Me | H |
| 1-73 | Me, Me | H, H | 5-Et | H |
| 1-74 | Me, Me | H, H | 6-Et | H |
| 1-75 | Me, Me | H, H | 7-Et | H |
| 1-76 | Me, Me | H, H | 8-Et | H |
| 1-77 | Me, Me | H, H | 5-Pr | H |
| 1-78 | Me, Me | H, H | 6-Pr | H |
| 1-79 | Me, Me | H, H | 7-Pr | H |
| 1-80 | Me, Me | H, H | 8-Pr | H |
| 1-81 | Me, Me | H, H | 5-Vinyl | H |
| 1-82 | Me, Me | H, H | 6-Vinyl | H |
| 1-83 | Me, Me | H, H | 7-Vinyl | H |
| 1-84 | Me, Me | H, H | 8-Vinyl | H |
| 1-85 | Me, Me | H, H | 5-Etynyl | H |
| 1-86 | Me, Me | H, H | 6-Etynyl | H |
| 1-87 | Me, Me | H, H | 7-Etynyl | H |
| 1-88 | Me, Me | H, H | 8-Etynyl | H |
| 1-89 | Me, Me | H, H | 5-Ph | H |
| 1-90 | Me, Me | H, H | 6-Ph | H |
| 1-91 | Me, Me | H, H | 7-Ph | H |
| 1-92 | Me, Me | H, H | 8-Ph | H |
| 1-93 | Me, Me | H, H | 5-FUR | H |
| 1-94 | Me, Me | H, H | 5-2THI | H |
| 1-95 | Me, Me | H, H | 5-3THI | H |
| 1-96 | Me, Me | H, H | 5-(2-Cl-2THI) | H |
| 1-97 | Me, Me | H, H | OXA | H |
| 1-98 | Me, Me | H, H | 5-HEtIMD | H |
| 1-99 | Me, Me | H, H | 5-MeMeIMD | H |
| 1-100 | Me, Me | H, H | 5-MeEtIMD | H |
| 1-101 | Me, Me | H, H | 5-EtEtIMD | H |
| 1-102 | Me, Me | H, H | 5-PrEtIMD | H |
| 1-103 | Me, Me | H, H | 5-tBuEtIMD | H |
| 1-104 | Me, Me | H, H | 5-AllylEtIMD | H |
| 1-105 | Me, Me | H, H | 5-BnEtIMD | H |
| 1-106 | Me, Me | H, H | 5-PhEtIMD | H |
| 1-107 | Me, Me | H, H | 5-MeO | H |
| 1-108 | Me, Me | H, H | 6-MeO | H |
| 1-109 | Me, Me | H, H | 7-MeO | H |
| 1-110 | Me, Me | H, H | 8-MeO | H |
| 1-111 | Me, Me | H, H | 5-NH2 | H |
| 1-112 | Me, Me | H, H | 5-NHAc | H |
| 1-113 | Me, Me | H, H | 5-CHO | H |
| 1-114 | Me, Me | H, H | 5-Ac | H |
| 1-115 | Me, Me | H, H | 5-CONHMe | H |
| 1-116 | Me, Me | H, H | 5-CN | H |
| 1-117 | Me, Me | H, H | 5,6-F2 | H |
| 1-118 | Me, Me | H, H | 5,6-F2 | 4-F |
| 1-119 | Me, Me | H, H | 5,6-F2 | 8-F |
| 1-120 | Me, Me | H, H | 5,6-F2 | 4-Cl |
| 1-121 | Me, Me | H, H | 5,6-F2 | 6-Cl |
| 1-122 | Me, Me | H, H | 5,6-F2 | 4-Me |
| 1-123 | Me, Me | H, H | 5,6-F2 | 8-Me |
| 1-124 | Me, Me | H, H | 5,6-F2 | 8-MeO |
| 1-125 | Me, Me | H, H | 5,6-F2 | 8-OH |
| 1-126 | Me, Me | H, H | 5,6-Cl2 | H |
| 1-127 | Me, Me | H, H | 5,6-Cl2 | 4-F |
| 1-128 | Me, Me | H, H | 5,6-Cl2 | 8-F |
| 1-129 | Me, Me | H, H | 5,6-Cl2 | 4-Cl |
| 1-130 | Me, Me | H, H | 5,6-Cl2 | 6-Cl |
| 1-131 | Me, Me | H, H | 5,6-Cl2 | 4-Me |
| 1-132 | Me, Me | H, H | 5,6-Cl2 | 8-Me |
| 1-133 | Me, Me | H, H | 5,6-Cl2 | 8-MeO |

TABLE 1-continued (Ia)

| Compound No. | R1, R2 | R3, R4 | Xn | Ym |
|---|---|---|---|---|
| 1-134 | Me, Me | H, H | 5,6-Cl2 | 8-OH |
| 1-135 | Me, Me | H, H | 5-F,7-Me | H |
| 1-136 | Me, Me | H, H | 6-F,7-Me | H |
| 1-137 | Me, Et | H, H | H | H |
| 1-138 | Me, Et | H, H | H | 4-F |
| 1-139 | Me, Et | H, H | H | 8-F |
| 1-140 | Me, Et | H, H | H | 4-Cl |
| 1-141 | Me, Et | H, H | H | 6-Cl |
| 1-142 | Me, Et | H, H | H | 8-Cl |
| 1-143 | Me, Et | H, H | H | 4-Me |
| 1-144 | Me, Et | H, H | H | 8-Me |
| 1-145 | Me, Et | H, H | H | 8-MeO |
| 1-146 | Me, Et | H, H | H | 8-OH |
| 1-147 | Me, Et | H, H | 5-F | H |
| 1-148 | Me, Et | H, H | 6-F | H |
| 1-149 | Me, Et | H, H | 7-F | H |
| 1-150 | Me, Et | H, H | 5-Cl | H |
| 1-151 | Me, Et | H, H | 6-Cl | H |
| 1-152 | Me, Et | H, H | 7-Cl | H |
| 1-153 | Me, Et | H, H | 5-Br | H |
| 1-154 | Me, Et | H, H | 6-Br | H |
| 1-155 | Me, Et | H, H | 7-Br | H |
| 1-156 | Me, Et | H, H | 5-I | H |
| 1-157 | Me, Et | H, H | 5-Me | H |
| 1-158 | Me, Et | H, H | 5-Vinyl | H |
| 1-159 | Me, Et | H, H | 5-Etynyl | H |
| 1-160 | Me, Et | H, H | 5-Ph | H |
| 1-161 | Me, Et | H, H | 5-FUR | H |
| 1-162 | Me, Et | H, H | 5-2THI | H |
| 1-163 | Me, Et | H, H | 5-3THI | H |
| 1-164 | Me, Et | H, H | 5-(2-Cl-2THI) | H |
| 1-165 | Me, Et | H, H | OXA | H |
| 1-166 | Me, Et | H, H | 5-MeMeIMD | H |
| 1-167 | Me, Et | H, H | 5-MeEtIMD | H |
| 1-168 | Me, Et | H, H | 5-EtEtIMD | H |
| 1-169 | Me, Et | H, H | 5-AllylEtIMD | H |
| 1-170 | Me, Et | H, H | 5-BnEtIMD | H |
| 1-171 | Me, Et | H, H | 5-PhEtIMD | H |
| 1-172 | Me, Et | H, H | 5-CN | H |
| 1-173 | Me, Et | H, H | 5,6-F2 | H |
| 1-174 | Me, Et | H, H | 5,6-Cl2 | H |
| 1-175 | Me, Pr | H, H | H | H |
| 1-176 | Me, Pr | H, H | H | 4-F |
| 1-177 | Me, Pr | H, H | H | 8-F |
| 1-178 | Me, Pr | H, H | H | 4-Cl |
| 1-179 | Me, Pr | H, H | H | 6-Cl |
| 1-180 | Me, Pr | H, H | H | 8-Cl |
| 1-181 | Me, Pr | H, H | H | 4-Me |
| 1-182 | Me, Pr | H, H | H | 8-Me |
| 1-183 | Me, Pr | H, H | H | 8-MeO |
| 1-184 | Me, Pr | H, H | H | 8-OH |
| 1-185 | Me, Pr | H, H | 5-F | H |
| 1-186 | Me, Pr | H, H | 6-F | H |
| 1-187 | Me, Pr | H, H | 7-F | H |
| 1-188 | Me, Pr | H, H | 5-Cl | H |
| 1-189 | Me, Pr | H, H | 6-Cl | H |
| 1-190 | Me, Pr | H, H | 7-Cl | H |
| 1-191 | Me, Pr | H, H | 5-Br | H |
| 1-192 | Me, Pr | H, H | 6-Br | H |
| 1-193 | Me, Pr | H, H | 7-Br | H |
| 1-194 | Me, Pr | H, H | 5-I | H |
| 1-195 | Me, Pr | H, H | 5-Me | H |
| 1-196 | Me, Pr | H, H | 5-Vinyl | H |

TABLE 1-continued (Ia)

| Compound No. | R1, R2 | R3, R4 | Xn | Ym |
|---|---|---|---|---|
| 1-197 | Me, Pr | H, H | 5-Etynyl | H |
| 1-198 | Me, Pr | H, H | 5-Ph | H |
| 1-199 | Me, Pr | H, H | 5-FUR | H |
| 1-200 | Me, Pr | H, H | 5-2THI | H |
| 1-201 | Me, Pr | H, H | 5-3THI | H |
| 1-202 | Me, Pr | H, H | 5-(2-Cl-2THI) | H |
| 1-203 | Me, Pr | H, H | OXA | H |
| 1-204 | Me, Pr | H, H | 5-MeMeIMD | H |
| 1-205 | Me, Pr | H, H | 5-MeEtIMD | H |
| 1-206 | Me, Pr | H, H | 5-EtEtIMD | H |
| 1-207 | Me, Pr | H, H | 5-AllylEtIMD | H |
| 1-208 | Me, Pr | H, H | 5-BnEtIMD | H |
| 1-209 | Me, Pr | H, H | 5-PhEtIMD | H |
| 1-210 | Me, Pr | H, H | 5-CN | H |
| 1-211 | Me, Pr | H, H | 5,6-F2 | H |
| 1-212 | Me, Pr | H, H | 5,6-Cl2 | H |
| 1-213 | Me, iPr | H, H | H | H |
| 1-214 | Me, iPr | H, H | H | 4-F |
| 1-215 | Me, iPr | H, H | H | 8-F |
| 1-216 | Me, iPr | H, H | H | 4-Cl |
| 1-217 | Me, iPr | H, H | H | 6-Cl |
| 1-218 | Me, iPr | H, H | H | 8-Cl |
| 1-219 | Me, iPr | H, H | H | 4-Me |
| 1-220 | Me, iPr | H, H | H | 8-Me |
| 1-221 | Me, iPr | H, H | H | 8-MeO |
| 1-222 | Me, iPr | H, H | H | 8-OH |
| 1-223 | Me, iPr | H, H | 5-F | H |
| 1-224 | Me, iPr | H, H | 6-F | H |
| 1-225 | Me, iPr | H, H | 7-F | H |
| 1-226 | Me, iPr | H, H | 5-Cl | H |
| 1-227 | Me, iPr | H, H | 6-Cl | H |
| 1-228 | Me, iPr | H, H | 7-Cl | H |
| 1-229 | Me, iPr | H, H | 5-Br | H |
| 1-230 | Me, iPr | H, H | 6-Br | H |
| 1-231 | Me, iPr | H, H | 7-Br | H |
| 1-232 | Me, iPr | H, H | 5-I | H |
| 1-233 | Me, iPr | H, H | 5-Me | H |
| 1-234 | Me, iPr | H, H | 5-Vinyl | H |
| 1-235 | Me, iPr | H, H | 5-Etynyl | H |
| 1-236 | Me, iPr | H, H | 5-Ph | H |
| 1-237 | Me, iPr | H, H | 5-FUR | H |
| 1-238 | Me, iPr | H, H | 5-2THI | H |
| 1-239 | Me, iPr | H, H | 5-3THI | H |
| 1-240 | Me, iPr | H, H | 5-(2-Cl-2THI) | H |
| 1-241 | Me, iPr | H, H | OXA | H |
| 1-242 | Me, iPr | H, H | 5-MeMeIMD | H |
| 1-243 | Me, iPr | H, H | 5-MeEtIMD | H |
| 1-244 | Me, iPr | H, H | 5-EtEtIMD | H |
| 1-245 | Me, iPr | H, H | 5-AllylEtIMD | H |
| 1-246 | Me, iPr | H, H | 5-BnEtIMD | H |
| 1-247 | Me, iPr | H, H | 5-PhEtIMD | H |
| 1-248 | Me, iPr | H, H | 5-CN | H |
| 1-249 | Me, iPr | H, H | 5,6-F2 | H |
| 1-250 | Me, iPr | H, H | 5,6-Cl2 | H |
| 1-251 | Me, iBu | H, H | H | H |
| 1-252 | Me, iBu | H, H | H | 4-F |
| 1-253 | Me, iBu | H, H | H | 8-F |
| 1-254 | Me, iBu | H, H | H | 4-Cl |
| 1-255 | Me, iBu | H, H | H | 6-Cl |
| 1-256 | Me, iBu | H, H | H | 8-Cl |
| 1-257 | Me, iBu | H, H | H | 4-Me |
| 1-258 | Me, iBu | H, H | H | 8-Me |
| 1-259 | Me, iBu | H, H | H | 8-MeO |

TABLE 1-continued

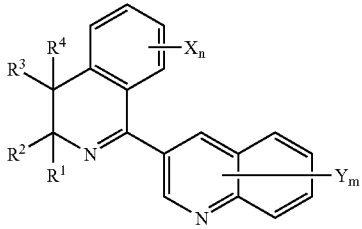

(Ia)

| Compound No. | R1, R2 | R3, R4 | Xn | Ym |
|---|---|---|---|---|
| 1-260 | Me, iBu | H, H | H | 8-OH |
| 1-261 | Me, iBu | H, H | 5-F | H |
| 1-262 | Me, iBu | H, H | 6-F | H |
| 1-263 | Me, iBu | H, H | 7-F | H |
| 1-264 | Me, iBu | H, H | 5-Cl | H |
| 1-265 | Me, iBu | H, H | 6-Cl | H |
| 1-266 | Me, iBu | H, H | 7-Cl | H |
| 1-267 | Me, iBu | H, H | 5-Br | H |
| 1-268 | Me, iBu | H, H | 6-Br | H |
| 1-269 | Me, iBu | H, H | 7-Br | H |
| 1-270 | Me, iBu | H, H | 5-I | H |
| 1-271 | Me, iBu | H, H | 5-Me | H |
| 1-272 | Me, iBu | H, H | 5-Vinyl | H |
| 1-273 | Me, iBu | H, H | 5-Etynyl | H |
| 1-274 | Me, iBu | H, H | 5-Ph | H |
| 1-275 | Me, iBu | H, H | 5-FUR | H |
| 1-276 | Me, iBu | H, H | 5-2THI | H |
| 1-277 | Me, iBu | H, H | 5-3THI | H |
| 1-278 | Me, iBu | H, H | 5-(2-Cl-2THI) | H |
| 1-279 | Me, iBu | H, H | OXA | H |
| 1-280 | Me, iBu | H, H | 5-MeMeIMD | H |
| 1-281 | Me, iBu | H, H | 5-MeEtIMD | H |
| 1-282 | Me, iBu | H, H | 5-EtEtIMD | H |
| 1-283 | Me, iBu | H, H | 5-AllylEtIMD | H |
| 1-284 | Me, iBu | H, H | 5-BnEtIMD | H |
| 1-285 | Me, iBu | H, H | 5-PhEtIMD | H |
| 1-286 | Me, iBu | H, H | 5-CN | H |
| 1-287 | Me, iBu | H, H | 5,6-F2 | H |
| 1-288 | Me, iBu | H, H | 5,6-Cl2 | H |
| 1-289 | Me, tBu | H, H | H | H |
| 1-290 | Me, tBu | H, H | 5-F | H |
| 1-291 | Me, tBu | H, H | 5-Cl | H |
| 1-292 | Me, tBu | H, H | 5-Br | H |
| 1-293 | Me, tBu | H, H | 5-I | H |
| 1-294 | Me, tBu | H, H | 5-Me | H |
| 1-295 | Me, tBu | H, H | 5-Vinyl | H |
| 1-296 | Me, tBu | H, H | 5-Etynyl | H |
| 1-297 | Me, tBu | H, H | 5-Ph | H |
| 1-298 | Me, tBu | H, H | 5-FUR | H |
| 1-299 | Me, tBu | H, H | 5-2THI | H |
| 1-300 | Me, tBu | H, H | 5-3THI | H |
| 1-301 | Me, tBu | H, H | 5-MeEtIMD | H |
| 1-302 | Me, tBu | H, H | 5-EtEtIMD | H |
| 1-303 | Me, tBu | H, H | 5-PhEtIMD | H |
| 1-304 | Me, tBu | H, H | 5-CN | H |
| 1-305 | Me, tBu | H, H | 5,6-F2 | H |
| 1-306 | Me, tBu | H, H | 5,6-Cl2 | H |
| 1-307 | Me, iPen | H, H | H | H |
| 1-308 | Me, iPen | H, H | H | 4-F |
| 1-309 | Me, iPen | H, H | H | 8-F |
| 1-310 | Me, iPen | H, H | H | 4-Cl |
| 1-311 | Me, iPen | H, H | H | 6-Cl |
| 1-312 | Me, iPen | H, H | H | 8-Cl |
| 1-313 | Me, iPen | H, H | H | 4-Me |
| 1-314 | Me, iPen | H, H | H | 8-Me |
| 1-315 | Me, iPen | H, H | H | 8-MeO |
| 1-316 | Me, iPen | H, H | H | 8-OH |
| 1-317 | Me, iPen | H, H | 5-F | H |
| 1-318 | Me, iPen | H, H | 6-F | H |
| 1-319 | Me, iPen | H, H | 7-F | H |
| 1-320 | Me, iPen | H, H | 5-Cl | H |
| 1-321 | Me, iPen | H, H | 6-Cl | H |
| 1-322 | Me, iPen | H, H | 7-Cl | H |

TABLE 1-continued (Ia)

| Compound No. | R1, R2 | R3, R4 | Xn | Ym |
|---|---|---|---|---|
| 1-323 | Me, iPen | H, H | 5-Br | H |
| 1-324 | Me, iPen | H, H | 6-Br | H |
| 1-325 | Me, iPen | H, H | 7-Br | H |
| 1-326 | Me, iPen | H, H | 5-I | H |
| 1-327 | Me, iPen | H, H | 5-Me | H |
| 1-328 | Me, iPen | H, H | 5-Vinyl | H |
| 1-329 | Me, iPen | H, H | 5-Etynyl | H |
| 1-330 | Me, iPen | H, H | 5-Ph | H |
| 1-331 | Me, iPen | H, H | 5-FUR | H |
| 1-332 | Me, iPen | H, H | 5-2THI | H |
| 1-333 | Me, iPen | H, H | 5-3THI | H |
| 1-334 | Me, iPen | H, H | 5-(2-Cl-2THI) | H |
| 1-335 | Me, iPen | H, H | OXA | H |
| 1-336 | Me, iPen | H, H | 5-MeMeIMD | H |
| 1-337 | Me, iPen | H, H | 5-MeEtIMD | H |
| 1-338 | Me, iPen | H, H | 5-EtEtIMD | H |
| 1-339 | Me, iPen | H, H | 5-AllylEtIMD | H |
| 1-340 | Me, iPen | H, H | 5-BnEtIMD | H |
| 1-341 | Me, iPen | H, H | 5-PhEtIMD | H |
| 1-342 | Me, iPen | H, H | 5-CN | H |
| 1-343 | Me, iPen | H, H | 5,6-F2 | H |
| 1-344 | Me, iPen | H, H | 5,6-Cl2 | H |
| 1-345 | Et, Et | H, H | H | H |
| 1-346 | Et, Et | H, H | H | 4-F |
| 1-347 | Et, Et | H, H | H | 8-F |
| 1-348 | Et, Et | H, H | H | 4-Cl |
| 1-349 | Et, Et | H, H | H | 6-Cl |
| 1-350 | Et, Et | H, H | H | 8-Cl |
| 1-351 | Et, Et | H, H | H | 4-Me |
| 1-352 | Et, Et | H, H | H | 8-Me |
| 1-353 | Et, Et | H, H | H | 8-MeO |
| 1-354 | Et, Et | H, H | H | 8-OH |
| 1-355 | Et, Et | H, H | 5-F | H |
| 1-356 | Et, Et | H, H | 6-F | H |
| 1-357 | Et, Et | H, H | 7-F | H |
| 1-358 | Et, Et | H, H | 5-Cl | H |
| 1-359 | Et, Et | H, H | 6-Cl | H |
| 1-360 | Et, Et | H, H | 7-Cl | H |
| 1-361 | Et, Et | H, H | 5-Br | H |
| 1-362 | Et, Et | H, H | 6-Br | H |
| 1-363 | Et, Et | H, H | 7-Br | H |
| 1-364 | Et, Et | H, H | 5-I | H |
| 1-365 | Et, Et | H, H | 5-Me | H |
| 1-366 | Et, Et | H, H | 5-Vinyl | H |
| 1-367 | Et, Et | H, H | 5-Etynyl | H |
| 1-368 | Et, Et | H, H | 5-Ph | H |
| 1-369 | Et, Et | H, H | 5-FUR | H |
| 1-370 | Et, Et | H, H | 5-2THI | H |
| 1-371 | Et, Et | H, H | 5-3THI | H |
| 1-372 | Et, Et | H, H | 5-(2-Cl-2THI) | H |
| 1-373 | Et, Et | H, H | OXA | H |
| 1-374 | Et, Et | H, H | 5-MeMeIMD | H |
| 1-375 | Et, Et | H, H | 5-MeEtIMD | H |
| 1-376 | Et, Et | H, H | 5-EtEtIMD | H |
| 1-377 | Et, Et | H, H | 5-AllylEtIMD | H |
| 1-378 | Et, Et | H, H | 5-BnEtIMD | H |
| 1-379 | Et, Et | H, H | 5-PhEtIMD | H |
| 1-380 | Et, Et | H, H | 5-CN | H |
| 1-381 | Et, Et | H, H | 5,6-F2 | H |
| 1-382 | Et, Et | H, H | 5,6-Cl2 | H |
| 1-383 | Et, iBu | H, H | H | H |
| 1-384 | Pr, Pr | H, H | H | H |
| 1-385 | Me, ClCH2 | H, H | H | H |

TABLE 1-continued (Ia)

| Compound No. | R1, R2 | R3, R4 | Xn | Ym |
|---|---|---|---|---|
| 1-386 | Me, Cl2CH | H, H | H | H |
| 1-387 | Me, CF3 | H, H | H | H |
| 1-388 | Me, CF3 | H, H | H | 4-F |
| 1-389 | Me, CF3 | H, H | H | 8-F |
| 1-390 | Me, CF3 | H, H | H | 4-Cl |
| 1-391 | Me, CF3 | H, H | H | 6-Cl |
| 1-392 | Me, CF3 | H, H | H | 8-Cl |
| 1-393 | Me, CF3 | H, H | H | 4-Me |
| 1-394 | Me, CF3 | H, H | H | 8-Me |
| 1-395 | Me, CF3 | H, H | H | 8-MeO |
| 1-396 | Me, CF3 | H, H | H | 8-OH |
| 1-397 | Me, CF3 | H, H | 5-F | H |
| 1-398 | Me, CF3 | H, H | 6-F | H |
| 1-399 | Me, CF3 | H, H | 7-F | H |
| 1-400 | Me, CF3 | H, H | 5-Cl | H |
| 1-401 | Me, CF3 | H, H | 6-Cl | H |
| 1-402 | Me, CF3 | H, H | 7-Cl | H |
| 1-403 | Me, CF3 | H, H | 5-Br | H |
| 1-404 | Me, CF3 | H, H | 6-Br | H |
| 1-405 | Me, CF3 | H, H | 7-Br | H |
| 1-406 | Me, CF3 | H, H | 5-I | H |
| 1-407 | Me, CF3 | H, H | 5-Me | H |
| 1-408 | Me, CF3 | H, H | 5-Vinyl | H |
| 1-409 | Me, CF3 | H, H | 5-Etynyl | H |
| 1-410 | Me, CF3 | H, H | 5-Ph | H |
| 1-411 | Me, CF3 | H, H | 5-FUR | H |
| 1-412 | Me, CF3 | H, H | 5-2THI | H |
| 1-413 | Me, CF3 | H, H | 5-3THI | H |
| 1-414 | Me, CF3 | H, H | 5(2-Cl-2THI) | H |
| 1-415 | Me, CF3 | H, H | OXA | H |
| 1-416 | Me, CF3 | H, H | 5-MeMeIMD | H |
| 1-417 | Me, CF3 | H, H | 5-MeEtIMD | H |
| 1-418 | Me, CF3 | H, H | 5-EtEtIMD | H |
| 1-419 | Me, CF3 | H, H | 5-AllylEtIMD | H |
| 1-420 | Me, CF3 | H, H | 5-BnEtIMD | H |
| 1-421 | Me, CF3 | H, H | 5-PhEtIMD | H |
| 1-422 | Me, CF3 | H, H | 5-CN | H |
| 1-423 | Me, CF3 | H, H | 5,6-F2 | H |
| 1-424 | Me, CF3CH2 | H, H | 5,6-Cl2 | H |
| 1-425 | Me, CF3CH2 | H, H | H | H |
| 1-426 | Me, CF3CH2 | H, H | H | 4-F |
| 1-427 | Me, CF3CH2 | H, H | H | 8-F |
| 1-428 | Me, CF3CH2 | H, H | H | 4-Cl |
| 1-429 | Me, CF3CH2 | H, H | H | 6-Cl |
| 1-430 | Me, CF3CH2 | H, H | H | 8-Cl |
| 1-431 | Me, CF3CH2 | H, H | H | 4-Me |
| 1-432 | Me, CF3CH2 | H, H | H | 8-Me |
| 1-433 | Me, CF3CH2 | H, H | H | 8-MeO |
| 1-434 | Me, CF3CH2 | H, H | H | 8-OH |
| 1-435 | Me, CF3CH2 | H, H | 5-F | H |
| 1-436 | Me, CF3CH2 | H, H | 6-F | H |
| 1-437 | Me, CF3CH2 | H, H | 7-F | H |
| 1-438 | Me, CF3CH2 | H, H | 5-Cl | H |
| 1-439 | Me, CF3CH2 | H, H | 6-Cl | H |
| 1-440 | Me, CF3CH2 | H, H | 7-Cl | H |
| 1-441 | Me, CF3CH2 | H, H | 5-Br | H |
| 1-442 | Me, CF3CH2 | H, H | 6-Br | H |
| 1-443 | Me, CF3CH2 | H, H | 7-Br | H |
| 1-444 | Me, CF3CH2 | H, H | 5-I | H |
| 1-445 | Me, CF3CH2 | H, H | 5-Me | H |
| 1-446 | Me, CF3CH2 | H, H | 5-Vinyl | H |
| 1-447 | Me, CF3CH2 | H, H | 5-Etynyl | H |
| 1-448 | Me, CF3CH2 | H, H | 5-Ph | H |

TABLE 1-continued

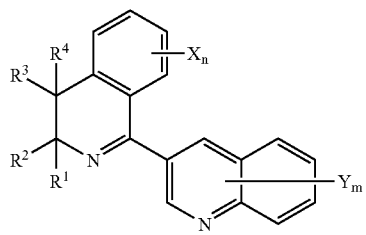

(Ia)

| Compound No. | R1, R2 | R3, R4 | Xn | Ym |
|---|---|---|---|---|
| 1-449 | Me, CF3CH2 | H, H | 5-FUR | H |
| 1-450 | Me, CF3CH2 | H, H | 5-2THI | H |
| 1-451 | Me, CF3CH2 | H, H | 5-3THI | H |
| 1-452 | Me, CF3CH2 | H, H | 5-(2-Cl-2THI) | H |
| 1-453 | Me, CF3CH2 | H, H | OXA | H |
| 1-454 | Me, CF3CH2 | H, H | 5-MeMeIMD | H |
| 1-455 | Me, CF3CH2 | H, H | 5-MeEtIMD | H |
| 1-456 | Me, CF3CH2 | H, H | 5-EtEtIMD | H |
| 1-457 | Me, CF3CH2 | H, H | 5-AllylEtIMD | H |
| 1-458 | Me, CF3CH2 | H, H | 5-BnEtIMD | H |
| 1-459 | Me, CF3CH2 | H, H | 5-PhEtIMD | H |
| 1-460 | Me, CF3CH2 | H, H | 5-CN | H |
| 1-461 | Me, CF3CH2 | H, H | 5,6-F2 | H |
| 1-462 | Me, CF3CH2 | H, H | 5,6-Cl2 | H |
| 1-463 | ClCH2, ClCH2 | H, H | H | H |
| 1-464 | Me, Ph | H, H | H | H |
| 1-465 | Me, Ph | H, H | H | 4-F |
| 1-466 | Me, Ph | H, H | H | 8-F |
| 1-467 | Me, Ph | H, H | H | 4-Cl |
| 1-468 | Me, Ph | H, H | H | 6-Cl |
| 1-469 | Me, Ph | H, H | H | 8-Cl |
| 1-470 | Me, Ph | H, H | H | 4-Me |
| 1-471 | Me, Ph | H, H | H | 8-Me |
| 1-472 | Me, Ph | H, H | H | 8-MeO |
| 1-473 | Me, Ph | H, H | H | 8-OH |
| 1-474 | Me, Ph | H, H | 5-F | H |
| 1-475 | Me, Ph | H, H | 6-F | H |
| 1-476 | Me, Ph | H, H | 7-F | H |
| 1-477 | Me, Ph | H, H | 5-Cl | H |
| 1-478 | Me, Ph | H, H | 6-Cl | H |
| 1-479 | Me, Ph | H, H | 7-Cl | H |
| 1-480 | Me, Ph | H, H | 5-Br | H |
| 1-481 | Me, Ph | H, H | 6-Br | H |
| 1-482 | Me, Ph | H, H | 7-Br | H |
| 1-483 | Me, Ph | H, H | 5-I | H |
| 1-484 | Me, Ph | H, H | 5-Me | H |
| 1-485 | Me, Ph | H, H | 5-Vinyl | H |
| 1-486 | Me, Ph | H, H | 5-Etynyl | H |
| 1-487 | Me, Ph | H, H | 5-Ph | H |
| 1-488 | Me, Ph | H, H | 5-FUR | H |
| 1-489 | Me, Ph | H, H | 5-2THI | H |
| 1-490 | Me, Ph | H, H | 5-3THI | H |
| 1-491 | Me, Ph | H, H | 5-(2-Cl-2THI) | H |
| 1-492 | Me, Ph | H, H | OXA | H |
| 1-493 | Me, Ph | H, H | 5-MeMeIMD | H |
| 1-494 | Me, Ph | H, H | 5-MeEtIMD | H |
| 1-495 | Me, Ph | H, H | 5-EtEtIMD | H |
| 1-496 | Me, Ph | H, H | 5-AllylEtIMD | H |
| 1-497 | Me, Ph | H, H | 5-BnEtIMD | H |
| 1-498 | Me, Ph | H, H | 5-PhEtIMD | H |
| 1-499 | Me, Ph | H, H | 5-CN | H |
| 1-500 | Me, Ph | H, H | 5,6-F2 | H |
| 1-501 | Me, Ph | H, H | 5,6-Cl2 | H |
| 1-502 | Me, FPh | H, H | H | H |
| 1-503 | Me, FPh | H, H | H | 4-F |
| 1-504 | Me, FPh | H, H | H | 8-F |
| 1-505 | Me, FPh | H, H | H | 4-Cl |
| 1-506 | Me, FPh | H, H | H | 6-Cl |
| 1-507 | Me, FPh | H, H | H | 8-Cl |
| 1-508 | Me, FPh | H, H | H | 4-Me |
| 1-509 | Me, FPh | H, H | H | 8-Me |
| 1-510 | Me, FPh | H, H | H | 8-MeO |
| 1-511 | Me, FPh | H, H | H | 8-OH |

TABLE 1-continued (Ia)

| Compound No. | R1, R2 | R3, R4 | Xn | Ym |
|---|---|---|---|---|
| 1-512 | Me, FPh | H, H | 5-F | H |
| 1-513 | Me, FPh | H, H | 6-F | H |
| 1-514 | Me, FPh | H, H | 7-F | H |
| 1-515 | Me, FPh | H, H | 5-Cl | H |
| 1-516 | Me, FPh | H, H | 6-Cl | H |
| 1-517 | Me, FPh | H, H | 7-Cl | H |
| 1-518 | Me, FPh | H, H | 5-Br | H |
| 1-519 | Me, FPh | H, H | 6-Br | H |
| 1-520 | Me, FPh | H, H | 7-Br | H |
| 1-521 | Me, FPh | H, H | 5-I | H |
| 1-522 | Me, FPh | H, H | 5-Me | H |
| 1-523 | Me, FPh | H, H | 5-Vinyl | H |
| 1-524 | Me, FPh | H, H | 5-Etynyl | H |
| 1-525 | Me, FPh | H, H | 5-Ph | H |
| 1-526 | Me, FPh | H, H | 5-FUR | H |
| 1-527 | Me, FPh | H, H | 5-2THI | H |
| 1-528 | Me, FPh | H, H | 5-3THI | H |
| 1-529 | Me, FPh | H, H | 5-(2-Cl-2THI) | H |
| 1-530 | Me, FPh | H, H | OXA | H |
| 1-531 | Me, FPh | H, H | 5-MeMeIMD | H |
| 1-532 | Me, FPh | H, H | 5-MeEtIMD | H |
| 1-533 | Me, FPh | H, H | 5-EtEtIMD | H |
| 1-534 | Me, FPh | H, H | 5-AllylEtIMD | H |
| 1-535 | Me, FPh | H, H | 5-BnEtIMD | H |
| 1-536 | Me, FPh | H, H | 5-PhEtIMD | H |
| 1-537 | Me, FPh | H, H | 5-CN | H |
| 1-538 | Me, FPh | H, H | 5,6-F2 | H |
| 1-539 | Me, FPh | H, H | 5,6-Cl2 | H |
| 1-540 | Me, ClPh | H, H | H | H |
| 1-541 | Me, ClPh | H, H | H | 4-F |
| 1-542 | Me, ClPh | H, H | H | 8-F |
| 1-543 | Me, ClPh | H, H | H | 4-Cl |
| 1-544 | Me, ClPh | H, H | H | 6-Cl |
| 1-545 | Me, ClPh | H, H | H | 8-Cl |
| 1-546 | Me, ClPh | H, H | H | 4-Me |
| 1-547 | Me, ClPh | H, H | H | 8-Me |
| 1-548 | Me, ClPh | H, H | H | 8-MeO |
| 1-549 | Me, ClPh | H, H | H | 8-OH |
| 1-550 | Me, ClPh | H, H | 5-F | H |
| 1-551 | Me, ClPh | H, H | 6-F | H |
| 1-552 | Me, ClPh | H, H | 7-F | H |
| 1-553 | Me, ClPh | H, H | 5-Cl | H |
| 1-554 | Me, ClPh | H, H | 6-Cl | H |
| 1-555 | Me, ClPh | H, H | 7-Cl | H |
| 1-556 | Me, ClPh | H, H | 5-Br | H |
| 1-557 | Me, ClPh | H, H | 6-Br | H |
| 1-558 | Me, ClPh | H, H | 7-Br | H |
| 1-559 | Me, ClPh | H, H | 5-I | H |
| 1-560 | Me, ClPh | H, H | 5-Me | H |
| 1-561 | Me, ClPh | H, H | 5-Vinyl | H |
| 1-562 | Me, ClPh | H, H | 5-Etynyl | H |
| 1-563 | Me, ClPh | H, H | 5-Ph | H |
| 1-564 | Me, ClPh | H, H | 5-FUR | H |
| 1-565 | Me, ClPh | H, H | 5-2THI | H |
| 1-566 | Me, ClPh | H, H | 5-3THI | H |
| 1-567 | Me, ClPh | H, H | 5-(2-Cl-2THI) | H |
| 1-568 | Me, ClPh | H, H | OXA | H |
| 1-569 | Me, ClPh | H, H | 5-MeMeIMD | H |
| 1-570 | Me, ClPh | H, H | 5-MeEtIMD | H |
| 1-571 | Me, ClPh | H, H | 5-EtEtIMD | H |
| 1-572 | Me, ClPh | H, H | 5-AllylEtIMD | H |
| 1-573 | Me, ClPh | H, H | 5-BnEtIMD | H |
| 1-574 | Me, ClPh | H, H | 5-PhEtIMD | H |

TABLE 1-continued (Ia)

| Compound No. | R1, R2 | R3, R4 | Xn | Ym |
|---|---|---|---|---|
| 1-575 | Me, ClPh | H, H | 5-CN | H |
| 1-576 | Me, ClPh | H, H | 5,6-F2 | H |
| 1-577 | Me, ClPh | H, H | 5,6-Cl2 | H |
| 1-578 | Ph, CF3 | H, H | H | H |
| 1-579 | Ph, CF3 | H, H | 5-F | H |
| 1-580 | Ph, CF3 | H, H | 5-Cl | H |
| 1-581 | Ph, CF3 | H, H | 5-Br | H |
| 1-582 | Ph, CF3 | H, H | 5-I | H |
| 1-583 | Ph, CF3 | H, H | 5-Me | H |
| 1-584 | Ph, CF3 | H, H | 5-Vinyl | H |
| 1-585 | Ph, CF3 | H, H | 5-Etynyl | H |
| 1-586 | Ph, CF3 | H, H | 5-Ph | H |
| 1-587 | Ph, CF3 | H, H | 5-FUR | H |
| 1-588 | Ph, CF3 | H, H | 5-2THI | H |
| 1-589 | Ph, CF3 | H, H | 5-3THI | H |
| 1-590 | Ph, CF3 | H, H | 5-MeEtIMD | H |
| 1-591 | Ph, CF3 | H, H | 5-EtEtIMD | H |
| 1-592 | Ph, CF3 | H, H | 5-PhEtIMD | H |
| 1-593 | Ph, CF3 | H, H | 5-CN | H |
| 1-594 | ClCH2, FPh | H, H | H | H |
| 1-595 | ClCH2, FPh | H, H | H | 4-F |
| 1-596 | ClCH2, FPh | H, H | H | 8-F |
| 1-597 | ClCH2, FPh | H, H | H | 4-Cl |
| 1-598 | ClCH2, FPh | H, H | H | 6-Cl |
| 1-599 | ClCH2, FPh | H, H | H | 8-Cl |
| 1-600 | ClCH2, FPh | H, H | H | 4-Me |
| 1-601 | ClCH2, FPh | H, H | H | 8-Me |
| 1-602 | ClCH2, FPh | H, H | H | 8-MeO |
| 1-603 | ClCH2, FPh | H, H | H | 8-OH |
| 1-604 | ClCH2, FPh | H, H | 5-F | H |
| 1-605 | ClCH2, FPh | H, H | 6-F | H |
| 1-606 | ClCH2, FPh | H, H | 7-F | H |
| 1-607 | ClCH2, FPh | H, H | 5-Cl | H |
| 1-608 | ClCH2, FPh | H, H | 6-Cl | H |
| 1-609 | ClCH2, FPh | H, H | 7-Cl | H |
| 1-610 | ClCH2, FPh | H, H | 5-Br | H |
| 1-611 | ClCH2, FPh | H, H | 6-Br | H |
| 1-612 | ClCH2, FPh | H, H | 7-Br | H |
| 1-613 | ClCH2, FPh | H, H | 5-I | H |
| 1-614 | ClCH2, FPh | H, H | 5-Me | H |
| 1-615 | ClCH2, FPh | H, H | 5-Vinyl | H |
| 1-616 | ClCH2, FPh | H, H | 5-Etynyl | H |
| 1-617 | ClCH2, FPh | H, H | 5-Ph | H |
| 1-618 | ClCH2, FPh | H, H | 5-FUR | H |
| 1-619 | ClCH2, FPh | H, H | 5-2THI | H |
| 1-620 | ClCH2, FPh | H, H | 5-3THI | H |
| 1-621 | ClCH2, FPh | H, H | 5-(2-Cl-2THI) | H |
| 1-622 | ClCH2, FPh | H, H | OXA | H |
| 1-623 | ClCH2, FPh | H, H | 5-MeMeIMD | H |
| 1-624 | ClCH2, FPh | H, H | 5-MeEtIMD | H |
| 1-625 | ClCH2, FPh | H, H | 5-EtEtIMD | H |
| 1-626 | ClCH2, FPh | H, H | 5-AllylEtIMD | H |
| 1-627 | ClCH2, FPh | H, H | 5-BnEtIMD | H |
| 1-628 | ClCH2, FPh | H, H | 5-PhEtIMD | H |
| 1-629 | ClCH2, FPh | H, H | 5-CN | H |
| 1-630 | ClCH2, FPh | H, H | 5,6-F2 | H |
| 1-631 | ClCH2, FPh | H, H | 5,6-Cl2 | H |
| 1-632 | ClCH2, ClPh | H, H | H | H |
| 1-633 | ClCH2, ClPh | H, H | H | 4-F |
| 1-634 | ClCH2, ClPh | H, H | H | 8-F |
| 1-635 | ClCH2, ClPh | H, H | H | 4-Cl |
| 1-636 | ClCH2, ClPh | H, H | H | 6-Cl |
| 1-637 | ClCH2, ClPh | H, H | H | 8-Cl |

TABLE 1-continued (Ia)

| Compound No. | R1, R2 | R3, R4 | Xn | Ym |
|---|---|---|---|---|
| 1-638 | ClCH2, ClPh | H, H | H | 4-Me |
| 1-639 | ClCH2, ClPh | H, H | H | 8-Me |
| 1-640 | ClCH2, ClPh | H, H | H | 8-MeO |
| 1-641 | ClCH2, ClPh | H, H | H | 8-OH |
| 1-642 | ClCH2, ClPh | H, H | 5-F | H |
| 1-643 | ClCH2, ClPh | H, H | 6-F | H |
| 1-644 | ClCH2, ClPh | H, H | 7-F | H |
| 1-645 | ClCH2, ClPh | H, H | 5-Cl | H |
| 1-646 | ClCH2, ClPh | H, H | 6-Cl | H |
| 1-647 | ClCH2, ClPh | H, H | 7-Cl | H |
| 1-648 | ClCH2, ClPh | H, H | 5-Br | H |
| 1-649 | ClCH2, ClPh | H, H | 6-Br | H |
| 1-650 | ClCH2, ClPh | H, H | 7-Br | H |
| 1-651 | ClCH2, ClPh | H, H | 5-I | H |
| 1-652 | ClCH2, ClPh | H, H | 5-Me | H |
| 1-653 | ClCH2, ClPh | H, H | 5-Vinyl | H |
| 1-654 | ClCH2, ClPh | H, H | 5-Etynyl | H |
| 1-655 | ClCH2, ClPh | H, H | 5-Ph | H |
| 1-656 | ClCH2, ClPh | H, H | 5-FUR | H |
| 1-657 | ClCH2, ClPh | H, H | 5-2THI | H |
| 1-658 | ClCH2, ClPh | H, H | 5-3THI | H |
| 1-659 | ClCH2, ClPh | H, H | 5(2-Cl-2THI) | H |
| 1-660 | ClCH2, ClPh | H, H | OXA | H |
| 1-661 | ClCH2, ClPh | H, H | 5-MeMeIMD | H |
| 1-662 | ClCH2, ClPh | H, H | 5-MeEtIMD | H |
| 1-663 | ClCH2, ClPh | H, H | 5-EtEtIMD | H |
| 1-664 | ClCH2, ClPh | H, H | 5-AllylEtIMD | H |
| 1-665 | ClCH2, ClPh | H, H | 5-BnEtIMD | H |
| 1-666 | ClCH2, ClPh | H, H | 5-PhEtIMD | H |
| 1-667 | ClCH2, ClPh | H, H | 5-CN | H |
| 1-668 | ClCH2, ClPh | H, H | 5,6-F2 | H |
| 1-669 | ClCH2, ClPh | H, H | 5,6-Cl2 | H |
| 1-670 | Me, 3PYD | H, H | H | H |
| 1-671 | Me, 4PYD | H, H | H | H |
| 1-672 | Me, Bn | H, H | H | H |
| 1-673 | Me, Bn | H, H | H | 4-F |
| 1-674 | Me, Bn | H, H | H | 8-F |
| 1-675 | Me, Bn | H, H | H | 4-Cl |
| 1-676 | Me, Bn | H, H | H | 6-Cl |
| 1-677 | Me, Bn | H, H | H | 8-Cl |
| 1-678 | Me, Bn | H, H | H | 4-Me |
| 1-679 | Me, Bn | H, H | H | 8-Me |
| 1-680 | Me, Bn | H, H | H | 8-MeO |
| 1-681 | Me, Bn | H, H | H | 8-OH |
| 1-682 | Me, Bn | H, H | 5-F | H |
| 1-683 | Me, Bn | H, H | 6-F | H |
| 1-684 | Me, Bn | H, H | 7-F | H |
| 1-685 | Me, Bn | H, H | 5-Cl | H |
| 1-686 | Me, Bn | H, H | 6-Cl | H |
| 1-687 | Me, Bn | H, H | 7-Cl | H |
| 1-688 | Me, Bn | H, H | 5-Br | H |
| 1-689 | Me, Bn | H, H | 6-Br | H |
| 1-690 | Me, Bn | H, H | 7-Br | H |
| 1-691 | Me, Bn | H, H | 5-I | H |
| 1-692 | Me, Bn | H, H | 5-Me | H |
| 1-693 | Me, Bn | H, H | 5-Vinyl | H |
| 1-694 | Me, Bn | H, H | 5-Etynyl | H |
| 1-695 | Me, Bn | H, H | 5-Ph | H |
| 1-696 | Me, Bn | H, H | 5-FUR | H |
| 1-697 | Me, Bn | H, H | 5-2THI | H |
| 1-698 | Me, Bn | H, H | 5-3THI | H |
| 1-699 | Me, Bn | H, H | 5-(2-Cl-2THI) | H |
| 1-700 | Me, Bn | H, H | OXA | H |

TABLE 1-continued (Ia)

| Compound No. | R1, R2 | R3, R4 | Xn | Ym |
|---|---|---|---|---|
| 1-701 | Me, Bn | H, H | 5-MeMeIMD | H |
| 1-702 | Me, Bn | H, H | 5-MeEtIMD | H |
| 1-703 | Me, Bn | H, H | 5-EtEtIMD | H |
| 1-704 | Me, Bn | H, H | 5-AllylEtIMD | H |
| 1-705 | Me, Bn | H, H | 5-BnEtIMD | H |
| 1-706 | Me, Bn | H, H | 5-PhEtIMD | H |
| 1-707 | Me, Bn | H, H | 5-CN | H |
| 1-708 | Me, Bn | H, H | 5,6-F2 | H |
| 1-709 | Me, Bn | H, H | 5,6-Cl2 | H |
| 1-710 | cPen | H, H | H | H |
| 1-711 | cPen | H, H | H | 4-F |
| 1-712 | cPen | H, H | H | 8-F |
| 1-713 | cPen | H, H | H | 4-Cl |
| 1-714 | cPen | H, H | H | 6-Cl |
| 1-715 | cPen | H, H | H | 8-Cl |
| 1-716 | cPen | H, H | H | 4-Me |
| 1-717 | cPen | H, H | H | 8-Me |
| 1-718 | cPen | H, H | H | 8-MeO |
| 1-719 | cPen | H, H | H | 8-OH |
| 1-720 | cPen | H, H | 5-F | H |
| 1-721 | cPen | H, H | 6-F | H |
| 1-722 | cPen | H, H | 7-F | H |
| 1-723 | cPen | H, H | 6-F | 4-Me |
| 1-724 | cPen | H, H | 5-Cl | H |
| 1-725 | cPen | H, H | 6-Cl | H |
| 1-726 | cPen | H, H | 7-Cl | H |
| 1-727 | cPen | H, H | 5-Br | H |
| 1-728 | cPen | H, H | 6-Br | H |
| 1-729 | cPen | H, H | 7-Br | H |
| 1-730 | cPen | H, H | 5-I | H |
| 1-731 | cPen | H, H | 5-Me | H |
| 1-732 | cPen | H, H | 5-Vinyl | H |
| 1-733 | cPen | H, H | 5-Etynyl | H |
| 1-734 | cPen | H, H | 5-Ph | H |
| 1-735 | cPen | H, H | 5-FUR | H |
| 1-736 | cPen | H, H | 5-2THI | H |
| 1-737 | cPen | H, H | 5-3THI | H |
| 1-738 | cPen | H, H | 5-(2-Cl-2THI) | H |
| 1-739 | cPen | H, H | OXA | H |
| 1-740 | cPen | H, H | 5-MeMeIMD | H |
| 1-741 | cPen | H, H | 5-MeEtIMD | H |
| 1-742 | cPen | H, H | 5-EtEtIMD | H |
| 1-743 | cPen | H, H | 5-AllylEtIMD | H |
| 1-744 | cPen | H, H | 5-BnEtIMD | H |
| 1-745 | cPen | H, H | 5-PhEtIMD | H |
| 1-746 | cPen | H, H | 5-CN | H |
| 1-747 | cPen | H, H | 5,6-F2 | H |
| 1-748 | cPen | H, H | 5,6-Cl2 | H |
| 1-749 | cHex | H, H | H | H |
| 1-750 | cHex | H, H | H | 4F |
| 1-751 | cHex | H, H | H | 8F |
| 1-752 | cHex | H, H | H | 4-Cl |
| 1-753 | cHex | H, H | H | 6-Cl |
| 1-754 | cHex | H, H | H | 8-Cl |
| 1-755 | cHex | H, H | H | 4-Me |
| 1-756 | cHex | H, H | H | 8-Me |
| 1-757 | cHex | H, H | H | 8-MeO |
| 1-758 | cHex | H, H | H | 8-OH |
| 1-759 | cHex | H, H | 5-F | H |
| 1-760 | cHex | H, H | 6-F | H |
| 1-761 | cHex | H, H | 7-F | H |
| 1-762 | cHex | H, H | 5-F | 4-Me |
| 1-763 | cHex | H, H | 5-Cl | H |

TABLE 1-continued (Ia)

| Compound No. | R1, R2 | R3, R4 | Xn | Ym | |
|---|---|---|---|---|---|
| 1-764 | cHex | H, H | 6-Cl | H | |
| 1-765 | cHex | H, H | 7-Cl | H | |
| 1-766 | cHex | H, H | 5-Cl | 4-Me | |
| 1-767 | cHex | H, H | 5-Br | H | |
| 1-768 | cHex | H, H | 6-Br | H | |
| 1-769 | cHex | H, H | 7-Br | H | |
| 1-770 | cHex | H, H | 5-I | H | |
| 1-771 | cHex | H, H | 5-Me | H | |
| 1-772 | cHex | H, H | 6-Me | H | |
| 1-773 | cHex | H, H | 7-Me | H | |
| 1-774 | cHex | H, H | 6-Me | 4-Me | |
| 1-775 | cHex | H, H | 5-FUR | H | |
| 1-776 | cHex | H, H | 5-2THI | H | |
| 1-777 | cHex | H, H | 5-3THI | H | |
| 1-778 | cHex | H, H | 5-(2-Cl-2THI) | H | |
| 1-779 | cHex | H, H | OXA | H | |
| 1-780 | cHex | H, H | 5-MeMeIMD | H | |
| 1-781 | cHex | H, H | 5-MeEtIMD | H | |
| 1-782 | cHex | H, H | 5-EtEtIMD | H | |
| 1-783 | cHex | H, H | 5-AllylEtIMD | H | |
| 1-784 | cHex | H, H | 5-BnEtIMD | H | |
| 1-785 | cHex | H, H | 5-PhEtIMD | H | |
| 1-786 | cHex | H, H | 6-CN | H | |
| 1-787 | cHex | H, H | 5,6-F2 | H | |
| 1-788 | cHex | H, H | 5,6-Cl2 | H | |
| 1-789 | cHep | H, H | H | H | |
| 1-790 | MecPen | H, H | H | H | |
| 1-791 | Pyran | H, H | H | H | |
| 1-792 | Me, Me | H, H | H | H | HCl Salt |
| 1-793 | Me, Me | H, H | 5-F | H | HCl Salt |
| 1-794 | Me, Me | H, H | 5-Cl | H | HCl Salt |
| 1-795 | Me, Me | H, H | H | H | $H_2SO_4$ Salt |
| 1-796 | Me, Me | H, H | 5-F | H | $H_2SO_4$ Salt |
| 1-797 | Me, Me | H, H | 5-Cl | H | $H_2SO_4$ Salt |
| 1-798 | Me, Me | H, H | H | H | $HNO_3$ Salt |
| 1-799 | Me, Me | H, H | 5-F | H | $HNO_3$ Salt |
| 1-800 | Me, Me | H, H | 5-Cl | H | $HNO_3$ Salt |
| 1-801 | Me, Me | H, H | H | H | $(COOH)_2$ Salt |
| 1-802 | Me, Me | H, H | 5-F | H | $(COOH)_2$ Salt |
| 1-803 | Me, Me | H, H | H | H | MsOH Salt |
| 1-804 | Me, Me | H, H | 5-F | H | MsOH Salt |
| 1-805 | Me, Me | H, H | H | H | Salicylate |
| 1-806 | Me, Me | H, H | 5-F | H | Salicylate |
| 1-807 | Me, Me | H, H | 5-F | H | fumarate |
| 1-808 | Me, Et | H, H | H | H | HCl Salt |
| 1-809 | Me, Et | H, H | 5-F | H | HCl Salt |
| 1-810 | Me, Et | H, H | 5-Cl | H | HCl Salt |
| 1-811 | Me, Et | H, H | H | H | $H_2SO_4$ Salt |
| 1-812 | Me, Et | H, H | 5-F | H | $H_2SO_4$ Salt |
| 1-813 | Me, Et | H, H | 5-Cl | H | $H_2SO_4$ Salt |
| 1-814 | Me, Et | H, H | H | H | $HNO_3$ Salt |
| 1-815 | Me, Et | H, H | 5-F | H | $HNO_3$ Salt |
| 1-816 | Me, Et | H, H | 5-Cl | H | $HNO_3$ Salt |
| 1-817 | Me, Et | H, H | H | H | $(COOH)_2$ Salt |
| 1-818 | Me, Et | H, H | 5-F | H | $(COOH)_2$ Salt |
| 1-819 | Me, Et | H, H | H | H | MsOH Salt |
| 1-820 | Me, Et | H, H | 5-F | H | MsOH Salt |
| 1-821 | Me, Et | H, H | H | H | Salicylate |
| 1-822 | Me, Et | H, H | 5-F | H | Salicylate |
| 1-823 | Me, Et | H, H | 5-F | H | fumarate |
| 1-824 | Me, Pr | H, H | H | H | HCl Salt |
| 1-825 | Me, Pr | H, H | 5-F | H | HCl Salt |
| 1-826 | Me, Pr | H, H | 5-Cl | H | HCl Salt |

TABLE 1-continued (Ia)

| Compound No. | R1, R2 | R3, R4 | Xn | Ym | |
|---|---|---|---|---|---|
| 1-827 | Me, Pr | H, H | H | H | H$_2$SO$_4$ Salt |
| 1-828 | Me, Pr | H, H | 5-F | H | H$_2$SO$_4$ Salt |
| 1-829 | Me, Pr | H, H | 5-Cl | H | H$_2$SO$_4$ Salt |
| 1-830 | Me, Pr | H, H | H | H | HNO$_3$ Salt |
| 1-831 | Me, Pr | H, H | 5-F | H | HNO$_3$ Salt |
| 1-832 | Me, Pr | H, H | 5-Cl | H | HNO$_3$ Salt |
| 1-833 | Me, Pr | H, H | H | H | (COOH)$_2$ Salt |
| 1-834 | Me, Pr | H, H | 5-F | H | (COOH)$_2$ Salt |
| 1-835 | Me, Pr | H, H | H | H | MsOH Salt |
| 1-836 | Me, Pr | H, H | 5-F | H | MsOH Salt |
| 1-837 | Me, Pr | H, H | H | H | Salicylate |
| 1-838 | Me, Pr | H, H | 5-F | H | Salicylate |
| 1-839 | Me, Pr | H, H | 5-F | H | fumarate |
| 1-840 | Me, Ph | H, H | H | H | HCl Salt |
| 1-841 | Me, Ph | H, H | 5-F | H | HCl Salt |
| 1-842 | Me, Ph | H, H | 5-Cl | H | HCl Salt |
| 1-843 | Me, Ph | H, H | H | H | H$_2$SO$_4$ Salt |
| 1-844 | Me, Ph | H, H | 5-F | H | H$_2$SO$_4$ Salt |
| 1-845 | Me, Ph | H, H | 5-Cl | H | H$_2$SO$_4$ Salt |
| 1-846 | Me, Ph | H, H | H | H | HNO$_3$ Salt |
| 1-847 | Me, Ph | H, H | 5-F | H | HNO$_3$ Salt |
| 1-848 | Me, Ph | H, H | 5-Cl | H | HNO$_3$ Salt |
| 1-849 | Me, Ph | H, H | H | H | (COOH)$_2$ Salt |
| 1-850 | Me, Ph | H, H | 5-F | H | (COOH)$_2$ Salt |
| 1-851 | Me, Ph | H, H | H | H | MsOH Salt |
| 1-852 | Me, Ph | H, H | 5-F | H | MsOH Salt |
| 1-853 | Me, Ph | H, H | H | H | Salicylate |
| 1-854 | Me, Ph | H, H | 5-F | H | Salicylate |
| 1-855 | Me, Ph | H, H | 5-F | H | fumarate |
| 1-856 | Me, Me | H, Me | H | H | |
| 1-857 | Me, Me | H, Me | 5-F | H | |
| 1-858 | Me, Me | H, Me | 5-Cl | H | |
| 1-859 | Me, Me | H, Et | H | H | |
| 1-860 | Me, Me | H, Et | 5-F | H | |
| 1-861 | Me, Me | H, Et | 5-Cl | H | |
| 1-862 | Me, Me | H, Pr | H | H | |
| 1-863 | Me, Me | H, Pr | 5-F | H | |
| 1-864 | Me, Me | H, Pr | 5-Cl | H | |
| 1-865 | Me, Me | Me, Me | H | H | |
| 1-866 | Me, Me | Me, Me | 5-F | H | |
| 1-867 | Me, Me | Me, Me | 5-Cl | H | |
| 1-868 | Me, Et | H, Me | H | H | |
| 1-869 | Me, Et | H, Me | 5-F | H | |
| 1-870 | Me, Et | H, Me | 5-Cl | H | |
| 1-871 | Me, Pr | H, Me | H | H | |
| 1-872 | Me, Pr | H, Me | 5-F | H | |
| 1-873 | Me, Pr | H, Me | 5-Cl | H | |
| 1-874 | Me, Ph | H, Me | H | H | |
| 1-875 | Me, Ph | H, Me | 5-F | H | |
| 1-876 | Me, Ph | H, Me | 5-Cl | H | |
| 1-877 | Me, Ph | Me, Me | H | H | |
| 1-878 | Me, Ph | Me, Me | 5-F | H | |
| 1-879 | Me, Ph | Me, Me | 5-Cl | H | |
| 1-880 | Me, Me | H, H | 5-iPr | H | |
| 1-881 | Me, Me | H, H | 5-CH(Me)CH$_2$CH$_3$ | H | |
| 1-882 | Me, Me | H, H | 5-C(Me)=CH$_2$ | H | |
| 1-883 | Me, Me | H, H | 5-CH=CHCO$_2$Me | H | |
| 1-884 | Me, Me | H, H | 5-CH$_2$F | H | |
| 1-885 | Me, Me | H, H | 5-CH$_2$Cl | H | |
| 1-886 | Me, Me | H, H | 5-CHF$_2$ | H | |
| 1-887 | Me, Me | H, H | 5-CH$_2$OH | H | |
| 1-888 | Me, Me | H, H | 5-C(Me)$_2$OH | H | |
| 1-889 | Me, Me | H, H | 5-CH$_2$OMe | H | |

TABLE 1-continued (Ia)

| Compound No. | R1, R2 | R3, R4 | Xn | Ym | |
|---|---|---|---|---|---|
| 1-890 | Me, Me | H, H | 5-CH$_2$CO$_2$Me | H | |
| 1-891 | Me, Me | H, H | 5-NHCOPh | H | |
| 1-892 | Me, Me | H, H | 5-NHCO(2-FPh) | H | |
| 1-893 | Me, Me | H, H | 5-NHCO(3-FPh) | H | |
| 1-894 | Me, Me | H, H | 5-NHCO(4-FPh) | H | |
| 1-895 | Me, Me | H, H | 5-CO$_2$H | H | |
| 1-896 | Me, Me | H, H | 5-CO$_2$Me | H | |
| 1-897 | Me, Me | H, H | 5-CO$_2$Et | H | |
| 1-898 | Me, Me | H, H | 5-CONH$_2$ | H | |
| 1-899 | Me, Me | H, H | 5-F | 2-Me | |
| 1-900 | Me, Me | H, H | 5-F | 4-Me | |
| 1-901 | Me, Me | H, Me | 5-F | 2-Me | |
| 1-902 | Me, Me | H, Me | 5-F | 8-Me | |
| 1-903 | Me, Me | H, Me | 5-F | 8-MeO | |
| 1-904 | Me, Me | Me, Me | 6-F | H | |
| 1-905 | Me, Me | Me, Me | 7-F | H | |
| 1-906 | Me, Me | Me, Me | 5-F | 2-Me | |
| 1-907 | Me, Me | Me, Me | 5-F | 4-Me | |
| 1-908 | Me, Me | Me, Me | 6-Cl | H | |
| 1-909 | Me, Me | Me, Me | 7-Cl | H | |
| 1-910 | Me, Me | Me, Me | 5-F | H | HCl Salt |
| 1-911 | Me, Me | Me, Me | 5-F | H | H$_2$SO$_4$ Salt |
| 1-912 | Me, Me | Me, Me | 5-F | H | HNO$_3$ Salt |
| 1-913 | Me, Me | Me, Me | 5-F | H | MsOH Salt |
| 1-914 | Me, Me | Me, Me | 5-Me | H | |
| 1-915 | Me, Me | Me, Me | 6-Me | H | |
| 1-916 | Me, Me | Me, Me | 7-Me | H | |
| 1-917 | Me, Me | Me, Me | 5-F | 6-F | |
| 1-918 | Me, Me | Me, Me | 5-F | 8-F | |
| 1-919 | Me, Me | Me, Me | 5-F | 8-Me | |
| 1-920 | Me, Me | Me, Me | 5-F | 8-MeO | |
| 1-921 | Me, Me | cPen | H | H | |
| 1-922 | cPen | Me, Me | H | H | |
| 1-923 | Me, Me | cHex | H | H | |
| 1-924 | cHex | Me, Me | H | H | |
| 1-925 | cBu | H, H | 5-F | H | |
| 1-926 | Me, Me | CH$_2$= | 5-F | H | |
| 1-927 | Me, Me | H, F | 5-F | H | |
| 1-928 | Me, Me | H, Cl | 5-F | H | |
| 1-929 | Me, Me | F, F | H | H | |
| 1-930 | Me, Me | F, F | 5-F | H | |
| 1-931 | Me, Me | H, OH | 5-F | H | |
| 1-932 | Me, Me | H, OMe | 5-F | H | |
| 1-933 | Me, Me | O= | H | H | |
| 1-934 | Me, Me | O= | 5-F | H | |
| 1-935 | Me, Me | Me, OH | 5-F | H | |
| 1-936 | Me, Me | Et, OH | 5-F | H | |
| 1-937 | Me, Me | Me, OMe | 5-F | H | |
| 1-938 | Me, Me | Me, OEt | 5-F | H | |
| 1-939 | Me, Me | Et, OMe | 5-F | H | |
| 1-940 | Me, Me | F, F | 6-F | H | |
| 1-941 | Me, Me | F, F | 7-F | H | |
| 1-942 | Me, Me | F, F | 5-Cl | H | |
| 1-943 | Me, Me | F, F | 6-Cl | H | |
| 1-944 | Me, Me | F, F | 7-Cl | H | |
| 1-945 | Me, Me | F, F | 5-Br | H | |
| 1-946 | Me, Me | F, F | 6-Br | H | |
| 1-947 | Me, Me | F, F | 7-Br | H | |
| 1-948 | Me, Me | F, F | 5-Me | H | |
| 1-949 | Me, Me | F, F | 6-Me | H | |
| 1-950 | Me, Me | F, F | 6-MeO | H | |
| 1-951 | Me, Me | F, F | 5,7-Cl$_2$ | H | |
| 1-952 | Me, Me | F, F | 6-F,7-Me | H | |

TABLE 1-continued (Ia)

| Compound No. | R1, R2 | R3, R4 | Xn | Ym |
|---|---|---|---|---|
| 1-953 | Me, Me | O= | 6-F | H |
| 1-954 | Me, Me | O= | 7-F | H |
| 1-955 | Me, Me | O= | 5-Cl | H |
| 1-956 | Me, Me | O= | 6-Cl | H |
| 1-957 | Me, Me | O= | 7-Cl | H |
| 1-958 | Me, Me | O= | 5-Br | H |
| 1-959 | Me, Me | O= | 6-Br | H |
| 1-960 | Me, Me | O= | 7-Br | H |

TABLE 2

(Ib)

| Compound No. | R1, R2 | R3, R4 | R5 | Xn | Ym |
|---|---|---|---|---|---|
| 2-1 | Me, Me | H, H | H | H | H |
| 2-2 | Me, Me | H, H | H | H | 2-F |
| 2-3 | Me, Me | H, H | H | H | 4-F |
| 2-4 | Me, Me | H, H | H | H | 5-F |
| 2-5 | Me, Me | H, H | H | H | 6-F |
| 2-6 | Me, Me | H, H | H | H | 7-F |
| 2-7 | Me, Me | H, H | H | H | 8-F |
| 2-8 | Me, Me | H, H | H | H | 2-Cl |
| 2-9 | Me, Me | H, H | H | H | 4-Cl |
| 2-10 | Me, Me | H, H | H | H | 5-Cl |
| 2-11 | Me, Me | H, H | H | H | 6-Cl |
| 2-12 | Me, Me | H, H | H | H | 7-Cl |
| 2-13 | Me, Me | H, H | H | H | 8-Cl |
| 2-14 | Me, Me | H, H | H | H | 2-Me |
| 2-15 | Me, Me | H, H | H | H | 4-Me |
| 2-16 | Me, Me | H, H | H | H | 5-Me |
| 2-17 | Me, Me | H, H | H | H | 6-Me |
| 2-18 | Me, Me | H, H | H | H | 7-Me |
| 2-19 | Me, Me | H, H | H | H | 8-Me |
| 2-20 | Me, Me | H, H | H | H | 2-MeO |
| 2-21 | Me, Me | H, H | H | H | 4-MeO |
| 2-22 | Me, Me | H, H | H | H | 5-MeO |
| 2-23 | Me, Me | H, H | H | H | 6-MeO |
| 2-24 | Me, Me | H, H | H | H | 7-MeO |
| 2-25 | Me, Me | H, H | H | H | 8-MeO |
| 2-26 | Me, Me | H, H | H | H | 2-OH |
| 2-27 | Me, Me | H, H | H | H | 4-OH |
| 2-28 | Me, Me | H, H | H | H | 5-OH |
| 2-29 | Me, Me | H, H | H | H | 6-OH |
| 2-30 | Me, Me | H, H | H | H | 7-OH |
| 2-31 | Me, Me | H, H | H | H | 8-OH |
| 2-32 | Me, Me | H, H | H | H | H |
| 2-33 | Me, Me | H, H | Me | H | H |
| 2-34 | Me, Me | H, H | Et | H | H |
| 2-35 | Me, Me | H, H | Pr | H | H |

TABLE 2-continued (Ib)

| Compound No. | R1, R2 | R3, R4 | R5 | Xn | Ym |
|---|---|---|---|---|---|
| 2-36 | Me, Me | H, H | H | 5-F | H |
| 2-37 | Me, Me | H, H | Me | 5-F | H |
| 2-38 | Me, Me | H, H | Et | 5-F | H |
| 2-39 | Me, Me | H, H | Pr | 5-F | H |
| 2-40 | Me, Me | H, H | H | 5-Cl | H |
| 2-41 | Me, Me | H, H | Me | 5-Cl | H |
| 2-42 | Me, Me | H, H | Et | 5-Cl | H |
| 2-43 | Me, Me | H, H | Pr | 5-Cl | H |
| 2-44 | Me, Me | H, H | H | 5-Br | H |
| 2-45 | Me, Me | H, H | Me | 5-Br | H |
| 2-46 | Me, Me | H, H | Et | 5-Br | H |
| 2-47 | Me, Me | H, H | Pr | 5-Br | H |
| 2-48 | Me, Me | H, H | H | 5-I | H |
| 2-49 | Me, Me | H, H | Me | 5-I | H |
| 2-50 | Me, Me | H, H | Et | 5-I | H |
| 2-51 | Me, Me | H, H | Pr | 5-I | H |
| 2-52 | Me, Me | H, H | H | 5-MeEtIMD | H |
| 2-53 | Me, Me | H, H | Me | 5-MeEtIMD | H |
| 2-54 | Me, Me | H, H | Et | 5-MeEtIMD | H |
| 2-55 | Me, Me | H, H | Pr | 5-MeEtIMD | H |
| 2-56 | Me, Me | H, H | H | 5-EtEtIMD | H |
| 2-57 | Me, Me | H, H | Me | 5-EtEtIMD | H |
| 2-58 | Me, Me | H, H | Et | 5-EtEtIMD | H |
| 2-59 | Me, Me | H, H | Pr | 5-EtEtIMD | H |
| 2-60 | Me, Me | H, H | H | 5-PrEtIMD | H |
| 2-61 | Me, Me | H, H | Me | 5-PrEtIMD | H |
| 2-62 | Me, Me | H, H | Et | 5-PrEtIMD | H |
| 2-63 | Me, Me | H, H | Pr | 5-PrEtIMD | H |
| 2-64 | Me, Me | H, H | H | 5,6-F2 | H |
| 2-65 | Me, Me | H, H | Me | 5,6-F2 | H |
| 2-66 | Me, Me | H, H | Et | 5,6-F2 | H |
| 2-67 | Me, Me | H, H | Pr | 5,6-F2 | H |
| 2-68 | Me, Me | H, H | H | 5,6-Cl2 | H |
| 2-69 | Me, Me | H, H | Me | 5,6-Cl2 | H |
| 2-70 | Me, Me | H, H | Et | 5,6-Cl2 | H |
| 2-71 | Me, Me | H, H | Pr | 5,6-Cl2 | H |
| 2-72 | Me, Et | H, H | H | H | H |
| 2-73 | Me, Et | H, H | H | 5-F | H |
| 2-74 | Me, Et | H, H | H | 5-Cl | H |
| 2-75 | Me, Et | H, H | H | 5-Br | H |
| 2-76 | Me, Et | H, H | H | 5-I | H |
| 2-77 | Me, Et | H, H | H | 5-MeMeIMD | H |
| 2-78 | Me, Et | H, H | H | 5-MeEtIMD | H |
| 2-79 | Me, Et | H, H | H | 5-EtEtIMD | H |
| 2-80 | Me, Et | H, H | H | 5,6-F2 | H |
| 2-81 | Me, Et | H, H | H | 5,6-Cl2 | H |
| 2-82 | Me, Pr | H, H | H | H | H |
| 2-83 | Me, Pr | H, H | H | 5-F | H |
| 2-84 | Me, Pr | H, H | H | 5-Cl | H |
| 2-85 | Me, Pr | H, H | H | 5-Br | H |
| 2-86 | Me, Pr | H, H | H | 5-I | H |
| 2-87 | Me, Pr | H, H | H | 5-MeMeIMD | H |
| 2-88 | Me, Pr | H, H | H | 5-MeEtIMD | H |
| 2-89 | Me, Pr | H, H | H | 5-EtEtIMD | H |
| 2-90 | Me, Pr | H, H | H | 5,6-F2 | H |
| 2-91 | Me, Pr | H, H | H | 5,6-Cl2 | H |
| 2-92 | Me, iPr | H, H | H | H | H |
| 2-93 | Me, iPr | H, H | H | 5-F | H |
| 2-94 | Me, iPr | H, H | H | 5-Cl | H |
| 2-95 | Me, iPr | H, H | H | 5-Br | H |
| 2-96 | Me, iPr | H, H | H | 5-I | H |
| 2-97 | Me, iPr | H, H | H | 5-MeMeIMD | H |
| 2-98 | Me, iPr | H, H | H | 5-MeEtIMD | H |
| 2-99 | Me, iPr | H, H | H | 5-EtEtIMD | H |

TABLE 2-continued (Ib)

| Compound No. | R1, R2 | R3, R4 | R5 | Xn | Ym |
|---|---|---|---|---|---|
| 2-100 | Me, iPr | H, H | H | 5,6-F2 | H |
| 2-101 | Me, iPr | H, H | H | 5,6-Cl2 | H |
| 2-102 | Me, iBu | H, H | H | H | H |
| 2-103 | Me, iBu | H, H | H | 5-F | H |
| 2-104 | Me, iBu | H, H | H | 5-Cl | H |
| 2-105 | Me, iBu | H, H | H | 5-Br | H |
| 2-106 | Me, iBu | H, H | H | 5-I | H |
| 2-107 | Me, iBu | H, H | H | 5-MeMeIMD | H |
| 2-108 | Me, iBu | H, H | H | 5-MeEtIMD | H |
| 2-109 | Me, iBu | H, H | H | 5-EtEtIMD | H |
| 2-110 | Me, iBu | H, H | H | 5,6-F2 | H |
| 2-111 | Me, iBu | H, H | H | 5,6-Cl2 | H |
| 2-112 | Me, tBu | H, H | H | H | H |
| 2-113 | Me, tBu | H, H | H | 5-F | H |
| 2-114 | Me, tBu | H, H | H | 5-Cl | H |
| 2-115 | Me, tBu | H, H | H | 5-Br | H |
| 2-116 | Me, tBu | H, H | H | 5-MeEtIMD | H |
| 2-117 | Me, tBu | H, H | H | 5-EtEtIMD | H |
| 2-118 | Me, iPen | H, H | H | H | H |
| 2-119 | Me, iPen | H, H | H | 5-F | H |
| 2-120 | Me, iPen | H, H | H | 5-Cl | H |
| 2-121 | Me, iPen | H, H | H | 5-Br | H |
| 2-122 | Me, iPen | H, H | H | 5-I | H |
| 2-123 | Me, iPen | H, H | H | 5-MeMeIMD | H |
| 2-124 | Me, iPen | H, H | H | 5-MeEtIMD | H |
| 2-125 | Me, iPen | H, H | H | 5-EtEtIMD | H |
| 2-126 | Me, iPen | H, H | H | 5,6-F2 | H |
| 2-127 | Me, iPen | H, H | H | 5,6-Cl2 | H |
| 2-128 | Et, Et | H, H | H | H | H |
| 2-129 | Et, Et | H, H | H | 5-F | H |
| 2-130 | Et, Et | H, H | H | 5-Cl | H |
| 2-131 | Et, Et | H, H | H | 5-Br | H |
| 2-132 | Et, Et | H, H | H | 5-I | H |
| 2-133 | Et, Et | H, H | H | 5-MeMeIMD | H |
| 2-134 | Et, Et | H, H | H | 5-MeEtIMD | H |
| 2-135 | Et, Et | H, H | H | 5-EtEtIMD | H |
| 2-136 | Et, Et | H, H | H | 5,6-F2 | H |
| 2-137 | Et, Et | H, H | H | 5,6-Cl2 | H |
| 2-138 | Me, CF3 | H, H | H | H | H |
| 2-139 | Me, CF3 | H, H | H | 5-F | H |
| 2-140 | Me, CF3 | H, H | H | 5-Cl | H |
| 2-141 | Me, CF3 | H, H | H | 5-Br | H |
| 2-142 | Me, CF3 | H, H | H | 5-I | H |
| 2-143 | Me, CF3 | H, H | H | 5-MeMeIMD | H |
| 2-144 | Me, CF3 | H, H | H | 5-MeEtIMD | H |
| 2-145 | Me, CF3 | H, H | H | 5-EtEtIMD | H |
| 2-146 | Me, CF3 | H, H | H | 5,6-F2 | H |
| 2-147 | Me, CF3 | H, H | H | 5,6-Cl2 | H |
| 2-148 | Me, CF3CH2 | H, H | H | H | H |
| 2-149 | Me, CF3CH2 | H, H | H | 5-F | H |
| 2-150 | Me, CF3CH2 | H, H | H | 5-Cl | H |
| 2-151 | Me, CF3CH2 | H, H | H | 5-Br | H |
| 2-152 | Me, CF3CH2 | H, H | H | 5-I | H |
| 2-153 | Me, CF3CH2 | H, H | H | 5-MeMeIMD | H |
| 2-154 | Me, CF3CH2 | H, H | H | 5-MeEtIMD | H |
| 2-155 | Me, CF3CH2 | H, H | H | 5-EtEtIMD | H |
| 2-156 | Me, CF3CH2 | H, H | H | 5,6-F2 | H |
| 2-157 | Me, CF3CH2 | H, H | H | 5,6-Cl2 | H |
| 2-158 | Me, Ph | H, H | H | H | H |
| 2-159 | Me, Ph | H, H | H | 5-F | H |
| 2-160 | Me, Ph | H, H | H | 5-Cl | H |
| 2-161 | Me, Ph | H, H | H | 5-Br | H |
| 2-162 | Me, Ph | H, H | H | 5-I | H |
| 2-163 | Me, Ph | H, H | H | 5-MeMeIMD | H |

TABLE 2-continued (Ib)

| Compound No. | R1, R2 | R3, R4 | R5 | Xn | Ym |
|---|---|---|---|---|---|
| 2-164 | Me, Ph | H, H | H | 5-MeEtIMD | H |
| 2-165 | Me, Ph | H, H | H | 5-EtEtIMD | H |
| 2-166 | Me, Ph | H, H | H | 5,6-F2 | H |
| 2-167 | Me, Ph | H, H | H | 5,6-Cl2 | H |
| 2-168 | Me, FPh | H, H | H | H | H |
| 2-169 | Me, FPh | H, H | H | 5-F | H |
| 2-170 | Me, FPh | H, H | H | 5-Cl | H |
| 2-171 | Me, FPh | H, H | H | 5-Br | H |
| 2-172 | Me, FPh | H, H | H | 5-I | H |
| 2-173 | Me, FPh | H, H | H | 5-MeMeIMD | H |
| 2-174 | Me, FPh | H, H | H | 5-MeEtIMD | H |
| 2-175 | Me, FPh | H, H | H | 5-EtEtIMD | H |
| 2-176 | Me, FPh | H, H | H | 5,6-F2 | H |
| 2-177 | Me, FPh | H, H | H | 5,6-Cl2 | H |
| 2-178 | Me, ClPh | H, H | H | H | H |
| 2-179 | Me, ClPh | H, H | H | 5-F | H |
| 2-180 | Me, ClPh | H, H | H | 5-Cl | H |
| 2-181 | Me, ClPh | H, H | H | 5-Br | H |
| 2-182 | Me, ClPh | H, H | H | 5-I | H |
| 2-183 | Me, ClPh | H, H | H | 5-MeMeIMD | H |
| 2-184 | Me, ClPh | H, H | H | 5-MeEtIMD | H |
| 2-185 | Me, ClPh | H, H | H | 5-EtEtIMD | H |
| 2-186 | Me, ClPh | H, H | H | 5,6-F2 | H |
| 2-187 | Me, ClPh | H, H | H | 5,6-Cl2 | H |
| 2-188 | Ph, CF3 | H, H | H | H | H |
| 2-189 | Ph, CF3 | H, H | H | 5-F | H |
| 2-190 | Ph, CF3 | H, H | H | 5-Cl | H |
| 2-191 | Ph, CF3 | H, H | H | 5-Br | H |
| 2-192 | Ph, CF3 | H, H | H | 5-MeEtIMD | H |
| 2-193 | Ph, CF3 | H, H | H | 5-EtEtIMD | H |
| 2-194 | ClCH2, FPh | H, H | H | H | H |
| 2-195 | ClCH2, FPh | H, H | H | 5-F | H |
| 2-196 | ClCH2, FPh | H, H | H | 5-Cl | H |
| 2-197 | ClCH2, FPh | H, H | H | 5-Br | H |
| 2-198 | ClCH2, FPh | H, H | H | 5-I | H |
| 2-199 | ClCH2, FPh | H, H | H | 5-MeMeIMD | H |
| 2-200 | ClCH2, FPh | H, H | H | 5-MeEtIMD | H |
| 2-201 | ClCH2, FPh | H, H | H | 5-EtEtIMD | H |
| 2-202 | ClCH2, FPh | H, H | H | 5,6-F2 | H |
| 2-203 | ClCH2, FPh | H, H | H | 5,6-Cl2 | H |
| 2-204 | ClCH2, ClPh | H, H | H | H | H |
| 2-205 | ClCH2, ClPh | H, H | H | 5-F | H |
| 2-206 | ClCH2, ClPh | H, H | H | 5-Cl | H |
| 2-207 | ClCH2, ClPh | H, H | H | 5-Br | H |
| 2-208 | ClCH2, ClPh | H, H | H | 5-I | H |
| 2-209 | ClCH2, ClPh | H, H | H | 5-MeMeIMD | H |
| 2-210 | ClCH2, ClPh | H, H | H | 5-MeEtIMD | H |
| 2-211 | ClCH2, ClPh | H, H | H | 5-EtEtIMD | H |
| 2-212 | ClCH2, ClPh | H, H | H | 5,6-F2 | H |
| 2-213 | ClCH2, ClPh | H, H | H | 5,6-Cl2 | H |
| 2-214 | Me, Bn | H, H | H | 5-F | H |
| 2-215 | Me, Bn | H, H | H | 5-Cl | H |
| 2-216 | Me, Bn | H, H | H | 5-Br | H |
| 2-217 | Me, Bn | H, H | H | 5-I | H |
| 2-218 | Me, Bn | H, H | H | 5-MeMeIMD | H |
| 2-219 | Me, Bn | H, H | H | 5-MeEtIMD | H |
| 2-220 | Me, Bn | H, H | H | 5-EtEtIMD | H |
| 2-221 | Me, Bn | H, H | H | 5,6-F2 | H |
| 2-222 | Me, Bn | H, H | H | 5,6-Cl2 | H |
| 2-223 | cPen | H, H | H | 5-F | H |
| 2-224 | cPen | H, H | H | 5-Cl | H |
| 2-225 | cPen | H, H | H | 5-Br | H |
| 2-226 | cPen | H, H | H | 5-I | H |
| 2-227 | cPen | H, H | H | 5-MeMeIMD | H |

TABLE 2-continued

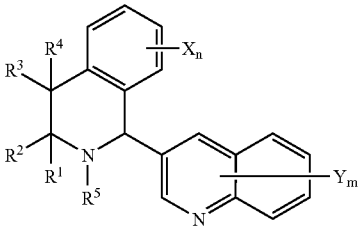

(Ib)

| Compound No. | R1, R2 | R3, R4 | R5 | Xn | Ym | |
|---|---|---|---|---|---|---|
| 2-228 | cPen | H, H | H | 5-MeEtIMD | H | |
| 2-229 | cPen | H, H | H | 5-EtEtIMD | H | |
| 2-230 | cPen | H, H | H | 5,6-F2 | H | |
| 2-231 | cPen | H, H | H | 5,6-Cl2 | H | |
| 2-232 | cHex | H, H | H | 5-F | H | |
| 2-233 | cHex | H, H | H | 5-Cl | H | |
| 2-234 | cHex | H, H | H | 5-Br | H | |
| 2-235 | cHex | H, H | H | 5-I | H | |
| 2-236 | cHex | H, H | H | 5-MeMeIMD | H | |
| 2-237 | cHex | H, H | H | 5-MeEtIMD | H | |
| 2-238 | cHex | H, H | H | 5-EtEtIMD | H | |
| 2-239 | cHex | H, H | H | 5,6-F2 | H | |
| 2-240 | cHex | H, H | H | 5,6-Cl2 | H | |
| 2-241 | Me, Me | H, H | H | H | H | HCl Salt |
| 2-242 | Me, Me | H, H | H | 5-Cl | H | HCl Salt |
| 2-243 | Me, Me | H, H | H | 5-F | H | HCl Salt |
| 2-244 | Me, Et | H, H | H | H | H | HCl Salt |
| 2-245 | Me, Et | H, H | H | 5-Cl | H | HCl Salt |
| 2-246 | Me, Et | H, H | H | 5-F | H | HCl Salt |
| 2-247 | Me, Pr | H, H | H | H | H | HCl Salt |
| 2-248 | Me, Pr | H, H | H | 5-Cl | H | HCl Salt |
| 2-249 | Me, Pr | H, H | H | 5-F | H | HCl Salt |
| 2-250 | Me, Ph | H, H | H | H | H | HCl Salt |
| 2-251 | Me, Ph | H, H | H | 5-Cl | H | HCl Salt |
| 2-252 | Me, Ph | H, H | H | 5-F | H | HCl Salt |
| 2-253 | Me, Me | H, Me | H | H | H | |
| 2-254 | Me, Me | H, Me | H | 5-Cl | H | |
| 2-255 | Me, Me | H, Me | H | 5-F | H | |
| 2-256 | Me, Me | H, Et | H | H | H | |
| 2-257 | Me, Me | H, Et | H | 5-Cl | H | |
| 2-258 | Me, Me | H, Et | H | 5-F | H | |
| 2-259 | Me, Me | H, Pr | H | H | H | |
| 2-260 | Me, Me | H, Pr | H | 5-Cl | H | |
| 2-261 | Me, Me | H, Pr | H | 5-F | H | |
| 2-262 | Me, Me | Me, Me | H | H | H | |
| 2-263 | Me, Me | Me, Me | H | 5-Cl | H | |
| 2-264 | Me, Me | Me, Me | H | 5-F | H | |
| 2-265 | Me, Et | H, Me | H | H | H | |
| 2-266 | Me, Et | H, Me | H | 5-Cl | H | |
| 2-267 | Me, Et | H, Me | H | 5-F | H | |
| 2-268 | Me, Pr | H, Me | H | H | H | |
| 2-269 | Me, Pr | H, Me | H | 5-Cl | H | |
| 2-270 | Me, Pr | H, Me | H | 5-F | H | |
| 2-271 | Me, Ph | H, Me | H | H | H | |
| 2-272 | Me, Ph | H, Me | H | 5-Cl | H | |
| 2-273 | Me, Ph | H, Me | H | 5-F | H | |
| 2-274 | Me, Me | H, H | H | 5-CH$_2$OH | H | |
| 2-275 | Me, Me | H, H | Ac | 5-F | H | |
| 2-276 | Me, Me | H, H | COCH$_2$OMe | 5-F | H | |
| 2-277 | Me, Me | H, H | CH$_2$CH=CHPh | 5-F | H | |
| 2-278 | Me, Me | Me, Me | Me | 5-F | H | |
| 2-279 | Me, Me | O= | H | 5-F | H | |

TABLE 3

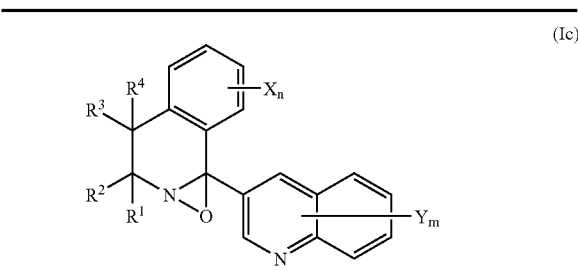

(Ic)

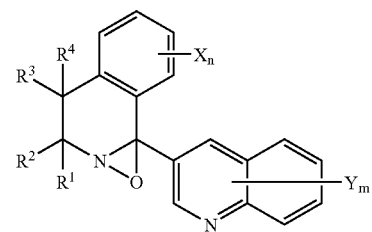

(Ic)

| Compound No. | R1, R2 | R3, R4 | Xn | Ym |
|---|---|---|---|---|
| 3-1 | Me, Me | H, H | H | H |
| 3-2 | Me, Me | H, H | H | 5-F |
| 3-3 | Me, Me | H, H | H | 6-F |
| 3-4 | Me, Me | H, H | H | 7-F |
| 3-5 | Me, Me | H, H | H | 8-F |
| 3-6 | Me, Me | H, H | H | 5-Cl |
| 3-7 | Me, Me | H, H | H | 6-Cl |
| 3-8 | Me, Me | H, H | H | 7-Cl |
| 3-9 | Me, Me | H, H | H | 8-Cl |
| 3-10 | Me, Me | H, H | H | 2-Me |
| 3-11 | Me, Me | H, H | H | 4-Me |
| 3-12 | Me, Me | H, H | H | 5-Me |
| 3-13 | Me, Me | H, H | H | 6-Me |
| 3-14 | Me, Me | H, H | H | 7-Me |
| 3-15 | Me, Me | H, H | H | 8-Me |
| 3-16 | Me, Me | H, H | H | 8-MeO |
| 3-17 | Me, Me | H, H | H | 2-OH |
| 3-18 | Me, Me | H, H | H | 4-OH |
| 3-19 | Me, Me | H, H | H | 8-OH |
| 3-20 | Me, Me | H, H | 5-F | H |
| 3-21 | Me, Me | H, H | 5-F | 5-F |
| 3-22 | Me, Me | H, H | 5-F | 6-F |
| 3-23 | Me, Me | H, H | 5-F | 7-F |
| 3-24 | Me, Me | H, H | 5-F | 8-F |
| 3-25 | Me, Me | H, H | 5-F | 5-Cl |
| 3-26 | Me, Me | H, H | 5-F | 6-Cl |
| 3-27 | Me, Me | H, H | 5-F | 7-Cl |
| 3-28 | Me, Me | H, H | 5-F | 8-Cl |
| 3-29 | Me, Me | H, H | 5-F | 2-Me |
| 3-30 | Me, Me | H, H | 5-F | 4-Me |
| 3-31 | Me, Me | H, H | 5-F | 5-Me |
| 3-32 | Me, Me | H, H | 5-F | 6-Me |
| 3-33 | Me, Me | H, H | 5-F | 7-Me |
| 3-34 | Me, Me | H, H | 5-F | 8-Me |
| 3-35 | Me, Me | H, H | 5-F | 8-MeO |
| 3-36 | Me, Me | H, H | 5-F | 2-OH |
| 3-37 | Me, Me | H, H | 5-F | 4-OH |
| 3-38 | Me, Me | H, H | 5-F | 1-OH |
| 3-39 | Me, Me | H, H | 6-F | H |
| 3-40 | Me, Me | H, H | 7-F | H |
| 3-41 | Me, Me | H, H | 8-F | H |
| 3-42 | Me, Me | H, H | 5-Cl | H |
| 3-43 | Me, Me | H, H | 6-Cl | H |
| 3-44 | Me, Me | H, H | 7-Cl | H |
| 3-40 | Me, Me | H, H | 8-Cl | H |
| 3-41 | Me, Me | H, H | 5-Br | H |
| 3-42 | Me, Me | H, H | 5-I | H |
| 3-43 | Me, Me | H, H | 5-Me | H |
| 3-44 | Me, Me | H, H | 6-Me | H |
| 3-45 | Me, Me | H, H | 7-Me | H |
| 3-46 | Me, Me | H, H | 8-Me | H |
| 3-47 | Me, Me | H, H | 5-Et | H |
| 3-48 | Me, Me | H, H | 5-MeO | H |
| 3-49 | Me, Me | H, H | 6-MeO | H |
| 3-50 | Me, Me | H, H | 7-MeO | H |
| 3-51 | Me, Me | H, H | 8-MeO | H |
| 3-52 | Me, Me | H, H | 5-EtO | H |
| 3-53 | Me, Me | H, H | 5,6-F$_2$ | H |
| 3-54 | Me, Me | H, H | 6-F, 7-Me | H |
| 3-55 | Me, Me | H, H | H | H |
| 3-56 | Me, Me | H, Me | H | H |
| 3-57 | Me, Me | H, Me | H | 5-F |
| 3-58 | Me, Me | H, Me | H | 6-F |
| 3-59 | Me, Me | H, Me | H | 7-F |
| 3-60 | Me, Me | H, Me | H | 8-F |
| 3-61 | Me, Me | H, Me | H | 2-Me |
| 3-62 | Me, Me | H, Me | H | 4-Me |
| 3-63 | Me, Me | H, Me | H | 8-Me |
| 3-64 | Me, Me | H, Me | H | 8-MeO |
| 3-65 | Me, Me | H, Me | 5-F | H |
| 3-66 | Me, Me | H, Me | 5-F | 5-F |
| 3-67 | Me, Me | H, Me | 5-F | 6-F |
| 3-68 | Me, Me | H, Me | 5-F | 7-F |
| 3-69 | Me, Me | H, Me | 5-F | 8-F |
| 3-70 | Me, Me | H, Me | 5-F | 2-Me |
| 3-71 | Me, Me | H, Me | 5-F | 4-Me |
| 3-72 | Me, Me | H, Me | 5-F | 8-Me |
| 3-73 | Me, Me | H, Me | 5-F | 8-MeO |
| 3-74 | Me, Me | H, Me | 6-F | H |
| 3-75 | Me, Me | H, Me | 7-F | H |
| 3-76 | Me, Me | H, Me | 8-F | H |
| 3-77 | Me, Me | H, Me | 5-Cl | H |
| 3-78 | Me, Me | H, Me | 6-Cl | H |
| 3-79 | Me, Me | H, Me | 7-Cl | H |
| 3-80 | Me, Me | H, Me | 8-Cl | H |
| 3-81 | Me, Me | H, Me | 5-Me | H |
| 3-82 | Me, Me | H, Me | 6-Me | H |
| 3-83 | Me, Me | H, Me | 7-Me | H |
| 3-84 | Me, Me | H, Me | 8-Me | H |
| 3-85 | Me, Me | H, Me | 5-MeO | H |
| 3-86 | Me, Me | H, Me | 6-MeO | H |
| 3-87 | Me, Me | H, Me | 7-MeO | H |
| 3-88 | Me, Me | H, Me | 8-MeO | H |
| 3-89 | Me, Me | H, Me | 5,6-F$_2$ | H |
| 3-90 | Me, Me | H, Me | 6-F, 7-Me | H |
| 3-91 | Me, Me | Me, Me | H | H |
| 3-92 | Me, Me | Me, Me | H | 5-F |
| 3-93 | Me, Me | Me, Me | H | 6-F |
| 3-94 | Me, Me | Me, Me | H | 7-F |
| 3-95 | Me, Me | Me, Me | H | 8-F |
| 3-96 | Me, Me | Me, Me | H | 2-Me |
| 3-97 | Me, Me | Me, Me | H | 4-Me |
| 3-98 | Me, Me | Me, Me | H | 8-Me |
| 3-99 | Me, Me | Me, Me | H | 8-MeO |
| 3-100 | Me, Me | Me, Me | 5-F | H |
| 3-101 | Me, Me | Me, Me | 5-F | 5-F |
| 3-102 | Me, Me | Me, Me | 5-F | 6-F |
| 3-103 | Me, Me | Me, Me | 5-F | 7-F |
| 3-104 | Me, Me | Me, Me | 5-F | 8-F |
| 3-105 | Me, Me | Me, Me | 5-F | 2-Me |
| 3-106 | Me, Me | Me, Me | 5-F | 4-Me |
| 3-107 | Me, Me | Me, Me | 5-F | 8-Me |
| 3-108 | Me, Me | Me, Me | 5-F | 8-OH |
| 3-109 | Me, Me | Me, Me | 6-F | H |
| 3-110 | Me, Me | Me, Me | 7-F | H |
| 3-111 | Me, Me | Me, Me | 8-F | H |
| 3-112 | Me, Me | Me, Me | 5-Cl | H |
| 3-113 | Me, Me | Me, Me | 6-Cl | H |
| 3-114 | Me, Me | Me, Me | 7-Cl | H |
| 3-115 | Me, Me | Me, Me | 8-Cl | H |
| 3-116 | Me, Me | Me, Me | 5-Me | H |
| 3-117 | Me, Me | Me, Me | 6-Me | H |
| 3-118 | Me, Me | Me, Me | 7-Me | H |
| 3-119 | Me, Me | Me, Me | 8-Me | H |
| 3-120 | Me, Me | Me, Me | 5-MeO | H |
| 3-121 | Me, Me | Me, Me | 6-MeO | H |
| 3-122 | Me, Me | Me, Me | 7-MeO | H |
| 3-123 | Me, Me | Me, Me | 8-MeO | H |

TABLE 3-continued

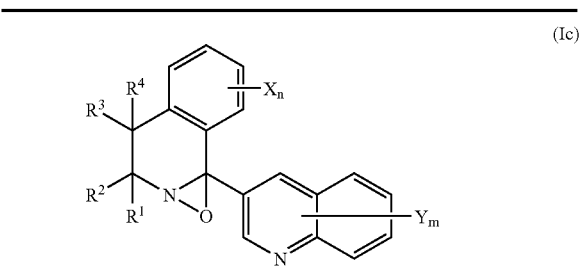

(Ic)

| Compound No. | R1, R2 | R3, R4 | Xn | Ym |
|---|---|---|---|---|
| 3-124 | Me, Me | Me, Me | 5,6-F$_2$ | H |
| 3-125 | Me, Me | Me, Me | 6-F, 7-Me | H |
| 3-126 | Me, Me | cPen | H | H |
| 3-127 | cPen | Me, Me | H | H |
| 3-128 | Me, Me | cHex | H | H |
| 3-129 | cHex | Me, Me | H | H |
| 3-130 | Me, Et | H, H | 5-F | H |
| 3-131 | Me, Me | CH$_2$= | 5-F | H |
| 3-132 | Me, Me | H, F | 5-F | H |
| 3-133 | Me, Me | H, Cl | 5-F | H |
| 3-134 | Me, Me | F, F | H | H |
| 3-135 | Me, Me | F, F | 5-F | H |
| 3-136 | Me, Me | H, OH | 5-F | H |
| 3-137 | Me, Me | H, OMe | 5-F | H |
| 3-138 | Me, Me | O= | H | H |
| 3-139 | Me, Me | O= | 5-F | H |
| 3-140 | Me, Me | Me, OH | 5-F | H |
| 3-141 | Me, Me | Et, OH | 5-F | H |
| 3-142 | Me, Me | Me, OMe | 5-F | H |
| 3-143 | Me, Me | Me, OEt | 5-F | H |
| 3-144 | Me, Me | Et, OMe | 5-F | H |

TABLE 4

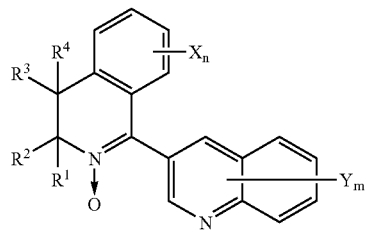

(Id)

| Compound No. | R1, R2 | R3, R4 | Xn | Ym |
|---|---|---|---|---|
| 4-1 | Me, Me | H, H | H | H |
| 4-2 | Me, Me | H, H | H | 5-F |
| 4-3 | Me, Me | H, H | H | 6-F |
| 4-4 | Me, Me | H, H | H | 7-F |
| 4-5 | Me, Me | H, H | H | 8-F |
| 4-6 | Me, Me | H, H | H | 5-Cl |
| 4-7 | Me, Me | H, H | H | 6-Cl |
| 4-8 | Me, Me | H, H | H | 7-Cl |
| 4-9 | Me, Me | H, H | H | 8-Cl |
| 4-10 | Me, Me | H, H | H | 2-Me |
| 4-11 | Me, Me | H, H | H | 4-Me |
| 4-12 | Me, Me | H, H | H | 5-Me |
| 4-13 | Me, Me | H, H | H | 6-Me |
| 4-14 | Me, Me | H, H | H | 7-Me |
| 4-15 | Me, Me | H, H | H | 8-Me |
| 4-16 | Me, Me | H, H | H | 8-MeO |
| 4-17 | Me, Me | H, H | H | 2-OH |
| 4-18 | Me, Me | H, H | H | 4-OH |
| 4-19 | Me, Me | H, H | H | 8-OH |
| 4-20 | Me, Me | H, H | 5-F | H |
| 4-21 | Me, Me | H, H | 5-F | 5-F |
| 4-22 | Me, Me | H, H | 5-F | 6-F |
| 4-23 | Me, Me | H, H | 5-F | 7-F |
| 4-24 | Me, Me | H, H | 5-F | 8-F |

TABLE 4-continued (Id)

| Compound No. | R1, R2 | R3, R4 | Xn | Ym |
|---|---|---|---|---|
| 4-25 | Me, Me | H, H | 5-F | 5-Cl |
| 4-26 | Me, Me | H, H | 5-F | 6-Cl |
| 4-27 | Me, Me | H, H | 5-F | 7-Cl |
| 4-28 | Me, Me | H, H | 5-F | 8-Cl |
| 4-29 | Me, Me | H, H | 5-F | 2-Me |
| 4-30 | Me, Me | H, H | 5-F | 4-Me |
| 4-31 | Me, Me | H, H | 5-F | 5-Me |
| 4-32 | Me, Me | H, H | 5-F | 6-Me |
| 4-33 | Me, Me | H, H | 5-F | 7-Me |
| 4-34 | Me, Me | H, H | 5-F | 8-Me |
| 4-35 | Me, Me | H, H | 5-F | 8-MeO |
| 4-36 | Me, Me | H, H | 5-F | 2-OH |
| 4-37 | Me, Me | H, H | 5-F | 4-OH |
| 4-38 | Me, Me | H, H | 5-F | 1-OH |
| 4-39 | Me, Me | H, H | 6-F | H |
| 4-40 | Me, Me | H, H | 7-F | H |
| 4-41 | Me, Me | H, H | 8-F | H |
| 4-42 | Me, Me | H, H | 5-Cl | H |
| 4-43 | Me, Me | H, H | 6-Cl | H |
| 4-44 | Me, Me | H, H | 7-Cl | H |
| 4-40 | Me, Me | H, H | 8-Cl | H |
| 4-41 | Me, Me | H, H | 5-Br | H |
| 4-42 | Me, Me | H, H | 5-I | H |
| 4-43 | Me, Me | H, H | 5-Me | H |
| 4-44 | Me, Me | H, H | 6-Me | H |
| 4-45 | Me, Me | H, H | 7-Me | H |
| 4-46 | Me, Me | H, H | 8-Me | H |
| 4-47 | Me, Me | H, H | 5-Et | H |
| 4-48 | Me, Me | H, H | 5-MeO | H |
| 4-49 | Me, Me | H, H | 6-MeO | H |
| 4-50 | Me, Me | H, H | 7-MeO | H |
| 4-51 | Me, Me | H, H | 8-MeO | H |
| 4-52 | Me, Me | H, H | 5-EtO | H |
| 4-53 | Me, Me | H, H | 5,6-F$_2$ | H |
| 4-54 | Me, Me | H, H | 6-F, 7-Me | H |
| 4-55 | Me, Me | H, H | H | H |
| 4-56 | Me, Me | H, Me | H | H |
| 4-57 | Me, Me | H, Me | H | 5-F |
| 4-58 | Me, Me | H, Me | H | 6-F |
| 4-59 | Me, Me | H, Me | H | 7-F |
| 4-60 | Me, Me | H, Me | H | 8-F |
| 4-61 | Me, Me | H, Me | H | 2-Me |
| 4-62 | Me, Me | H, Me | H | 4-Me |
| 4-63 | Me, Me | H, Me | H | 8-Me |
| 4-64 | Me, Me | H, Me | H | 8-MeO |
| 4-65 | Me, Me | H, Me | 5-F | H |
| 4-66 | Me, Me | H, Me | 5-F | 5-F |
| 4-67 | Me, Me | H, Me | 5-F | 6-F |
| 4-68 | Me, Me | H, Me | 5-F | 7-F |
| 4-69 | Me, Me | H, Me | 5-F | 8-F |
| 4-70 | Me, Me | H, Me | 5-F | 2-Me |
| 4-71 | Me, Me | H, Me | 5-F | 4-Me |
| 4-72 | Me, Me | H, Me | 5-F | 8-Me |
| 4-73 | Me, Me | H, Me | 5-F | 8-MeO |
| 4-74 | Me, Me | H, Me | 6-F | H |
| 4-75 | Me, Me | H, Me | 7-F | H |
| 4-76 | Me, Me | H, Me | 8-F | H |
| 4-77 | Me, Me | H, Me | 5-Cl | H |
| 4-78 | Me, Me | H, Me | 6-Cl | H |

TABLE 4-continued (Id)

| Compound No. | R1, R2 | R3, R4 | Xn | Ym |
|---|---|---|---|---|
| 4-79 | Me, Me | H, Me | 7-Cl | H |
| 4-80 | Me, Me | H, Me | 8-Cl | H |
| 4-81 | Me, Me | H, Me | 5-Me | H |
| 4-82 | Me, Me | H, Me | 6-Me | H |
| 4-83 | Me, Me | H, Me | 7-Me | H |
| 4-84 | Me, Me | H, Me | 8-Me | H |
| 4-85 | Me, Me | H, Me | 5-MeO | H |
| 4-86 | Me, Me | H, Me | 6-MeO | H |
| 4-87 | Me, Me | H, Me | 7-MeO | H |
| 4-88 | Me, Me | H, Me | 8-MeO | H |
| 4-89 | Me, Me | H, Me | 5,6-F$_2$ | H |
| 4-90 | Me, Me | H, Me | 6-F, 7-Me | H |
| 4-91 | Me, Me | Me, Me | H | H |
| 4-92 | Me, Me | Me, Me | H | 5-F |
| 4-93 | Me, Me | Me, Me | H | 6-F |
| 4-94 | Me, Me | Me, Me | H | 7-F |
| 4-95 | Me, Me | Me, Me | H | 8-F |
| 4-96 | Me, Me | Me, Me | H | 2-Me |
| 4-97 | Me, Me | Me, Me | H | 4-Me |
| 4-98 | Me, Me | Me, Me | H | 8-Me |
| 4-99 | Me, Me | Me, Me | H | 8-MeO |
| 4-100 | Me, Me | Me, Me | 5-F | H |
| 4-101 | Me, Me | Me, Me | 5-F | 5-F |
| 4-102 | Me, Me | Me, Me | 5-F | 6-F |
| 4-103 | Me, Me | Me, Me | 5-F | 7-F |
| 4-104 | Me, Me | Me, Me | 5-F | 8-F |
| 4-105 | Me, Me | Me, Me | 5-F | 2-Me |
| 4-106 | Me, Me | Me, Me | 5-F | 4-Me |
| 4-107 | Me, Me | Me, Me | 5-F | 8-Me |
| 4-108 | Me, Me | Me, Me | 5-F | 8-MeO |
| 4-109 | Me, Me | Me, Me | 6-F | H |
| 4-110 | Me, Me | Me, Me | 7-F | H |
| 4-111 | Me, Me | Me, Me | 8-F | H |
| 4-112 | Me, Me | Me, Me | 5-Cl | H |
| 4-113 | Me, Me | Me, Me | 6-Cl | H |
| 4-114 | Me, Me | Me, Me | 7-Cl | H |
| 4-115 | Me, Me | Me, Me | 8-Cl | H |
| 4-116 | Me, Me | Me, Me | 5-Me | H |
| 4-117 | Me, Me | Me, Me | 6-Me | H |
| 4-118 | Me, Me | Me, Me | 7-Me | H |
| 4-119 | Me, Me | Me, Me | 8-Me | H |
| 4-120 | Me, Me | Me, Me | 5-MeO | H |
| 4-121 | Me, Me | Me, Me | 6-MeO | H |
| 4-122 | Me, Me | Me, Me | 7-MeO | H |
| 4-123 | Me, Me | Me, Me | 8-MeO | H |
| 4-124 | Me, Me | Me, Me | 5,6-F$_2$ | H |
| 4-125 | Me, Me | Me, Me | 6-F, 7-Me | H |
| 4-126 | Me, Me | cPen | H | H |
| 4-127 | cPen | Me, Me | H | H |
| 4-128 | Me, Me | cHex | H | H |
| 4-129 | cHex | Me, Me | H | H |
| 4-130 | Me, Et | H, H | 5-F | H |
| 4-131 | Me, Me | CH$_2$= | 5-F | H |
| 4-132 | Me, Me | H, F | 5-F | H |
| 4-133 | Me, Me | H, Cl | 5-F | H |
| 4-134 | Me, Me | F, F | H | H |
| 4-135 | Me, Me | F, F | 5-F | H |
| 4-136 | Me, Me | H, OH | 5-F | H |
| 4-137 | Me, Me | H, OMe | 5-F | H |
| 4-138 | Me, Me | O= | H | H |
| 4-139 | Me, Me | O= | 5-F | H |
| 4-140 | Me, Me | Me, OH | 5-F | H |
| 4-141 | Me, Me | Et, OH | 5-F | H |
| 4-142 | Me, Me | Me, OMe | 5-F | H |
| 4-143 | Me, Me | Me, OEt | 5-F | H |
| 4-144 | Me, Me | Et, OMe | 5-F | H |

Preferable compounds among the aforementioned compounds consist of compound nos. 1-001, 1-007, 1-019, 1-032, 1-038, 1-041, 1-044, 1-053, 1-054, 1-056, 1-065, 1-069, 1-085, 1-094, 1-095, 1-100, 1-101, 1-106, 1-116, 1-117, 1-126, 1-137, 1-147, 1-175, 1-185, 1-213, 1-251, 1-307, 1-345, 1-385, 1-387, 1-424, 1-464, 1-502, 1-540, 1-578, 1-594, 1-672, 1-710, 1-720, 1-721, 1-764, 1-790, 1-793, 1-796, 1-799, 1-802, 1-804, 1-806, 1-807, 1-866, 2-001, 1-099, 1-856, 1-857, 1-858, 1-867, 1-886, 1-904, 1-908, 1-910, 1-912, 1-913, 1-914, 1-917, 1-918, 1-919, 1-925, 1-926, 1-927, 1-929, 1-930, 1-935, 1-937, 1-938, 1-939, 2-255, 2-264, 2-278, 3-020, 3-091, 3-100, 3-108, 3-110, 3-126, 3-135, 4-020, 4-065, 4-091, 4-100, 4-109, 4-110, 4-113, 4-129, 4-134, 4-135, 2-036 or 2-040, more preferable compounds consist of compound nos. 1-032, 1-038, 1-044, 1-054, 1-056, 1-085, 1-116, 1-117, 1-147, 1-185, 1-385, 1-387, 1-424, 1-464, 1-502, 1-540, 1-594, 1-672, 1-793, 1-804, 1-806, 1-807, 1-866, 1-910, 1-912, 1-917, 1-918, 1-919, 1-927, 1-929, 1-930, 2-036, 2-040, 3-020, 3-091, 3-100, 3-110, 3-126, 3-135, 4-091, 4-100, 4-109, 4-113, 4-129, 4-134, or 4-135, and even more preferable compounds consist of compound nos. 1-032, 1-044, 1-056, 1-085, 1-117, 1-147, 1-185, 1-387, 1-424, 1-464, 1-502, 1-540, 1-866, 1-910, 1-912, 1-917, 1-918, 1-919, 1-927, 1-929, 1-930, 3-020, 3-091, 3-100, 3-110, 3-126, 3-135, 4-091, 4-100, 4-109, 4-113, 4-129, 4-134, or 4-135.

A compound of general formula (Ia) of the present invention can be produced according to the following method A or B, a compound of general formula (Ib) can be produced according to the following method C or D, a compound of the present invention having a keto group, hydroxyl group, alkoxy group or halogen atom at position 4 can be produced according to the following method E, F or G, a compound of general formula (Ic) can be produced according to the following method H, and a compound of general formula (Id) can be produced according to the following Method I.

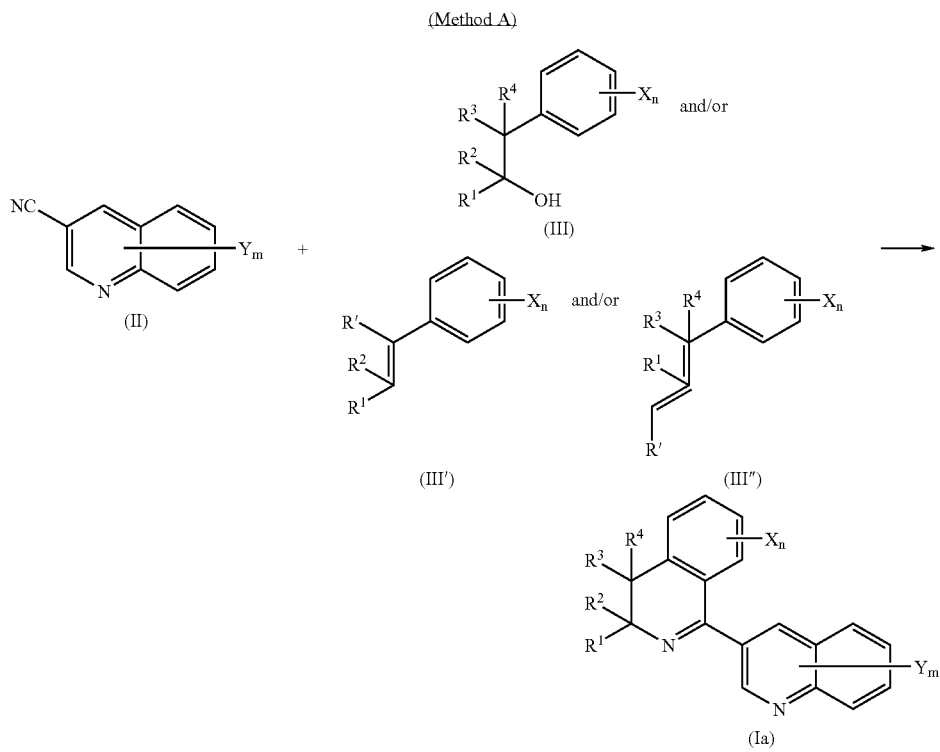

In the above formula, $R^1$, $R^2$, $R^3$, $R^4$, X, n, Y and m are the same as previously defined, and R' represents a hydrogen atom or alkyl group.

Method A is a method for producing compound (Ia) of the present invention by reacting a nitrile (II), an alcohol (III) and/or an olefin (III') and/or an olefin (III").

(Process A)

Process A is a process for producing compound (Ia) of the present invention by reacting compound (II) with one type of compound (III), compound (III') or compound (III"), or a mixture thereof, in the presence or absence of solvent and in the presence of acid.

The total amount of compound (III), compound (III') and compound (III") used is normally 1 to 6 moles and preferably 1.1 to 3.0 moles based on 1 mole of compound (II).

In the case of using a solvent in this process, there are no particular limitations on the solvent used provided it does not inhibit the reaction, examples of which include hydrocarbons such as hexane, cyclohexane, benzene, toluene or xylene; halogenated hydrocarbons such as dichloromethane, dichloroethane, chloroform or carbon tetrachloride; and, ethers such as dioxane, diethyl ether, tetrahydrofuran (THF) or dibutyl ether, preferably hydrocarbons or halogenated hydrocarbons, and more preferably benzene or dichloroethane.

There are no particular limitations on the acid used in the present process provided it is that used as an acid in ordinary ritter reactions, examples of which include inorganic acids such as sulfuric acid, formic acid, phosphoric acid or perchloric acid; sulfonic acids such as benzene sulfonic acid, toluene sulfonic acid or trifluoromethane sulfonic acid; and, Lewis acids such as tin tetrachloride or trifluoroboron, preferably inorganic acids or sulfonic acids, and more preferably sulfuric acid or trifluoromethane sulfonic acid.

The amount of acid used is normally 1 to 20 moles, and preferably 1.1 to 15 moles, based on 1 mole of compound (II).

Although varying according to the raw material compounds, reaction reagents, solvent and so forth, the reaction temperature is normally −20° C. to 100° C., and preferably 0° C. to 80° C.

Although varying according to the raw material compounds, reaction reagents, solvent, reaction temperature and so forth, the reaction time is normally 15 minutes to 120 hours, and preferably 30 minutes to 72 hours.

The raw material compound of the aforementioned method A in the form of 3-quinoline carbonitrile compound (II) is a known compound, or can be produced in compliance with a known method (such as the method described in J. Med. Chem., Vol. 22, p. 816 (1979)).

Alcohol compound (III) used in the present process is a known compound, or can be produced in compliance with a known method (such as the method described in Tetrahedron, Vol. 55, p. 4595 (1999)).

Olefin compound (III') and olefin compound (III") used in the present process are known compounds, or can be produced in compliance with a known method (such as a method involving dehydration of alcohol with acid as described in Bull. Chim. Fr., Vol. 2, p. 633 (1935), or a method involving dehydration by attaching a leaving group to an alcohol as described in Tetrahedron Lett., Vol. 35, p. 4129 (1994), or J. Org. Chem., Vol. 47, p. 2928 (1982)).

(Method B)

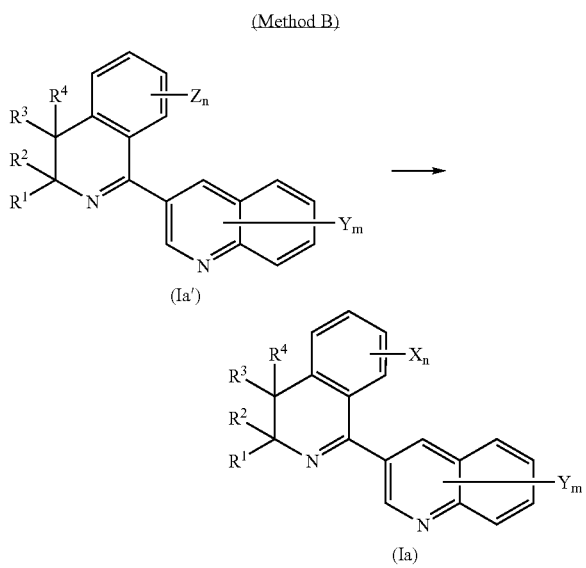

In the above formula, $R^1$, $R^2$, $R^3$, $R^4$, X, n, Y and m are the same as previously defined, and Z represents bromine or iodine.

Method B is a method for producing compound (Ia) of the present invention by carrying out a coupling reaction with compound (Ia') of the present invention (X=Z).

(Process B)

Process B is a process for producing compound (Ia) of the present invention by reacting compound (Ia') in a solvent, in the presence or absence of base, and in the presence of a coupling agent and a metal catalyst.

There are no particular limitations on the coupling agent used in the present process provided it is used in ordinary coupling reactions, examples of which include an organic metal such as organic magnesium, organic zinc, organic aluminum, organic zirconium, organic tin, organic boron, organic mercury, organic lithium or organic copper, and preferably organic tin, organic boric acid ester or organic copper.

The amount of coupling agent used is normally 1 to 6 moles, and preferably 1.1 to 3 moles, based on 1 mole of compound (Ia').

There are no particular limitations on the metal catalyst used in the present process provided it is used in ordinary coupling reactions, examples of which include metal salts such as nickel, palladium, copper or chromium salts, and preferably nickel acetyl acetonate, tetraquis triphenyl phosphine palladium or copper iodide.

There are no particular limitations on the solvent used in the present process provided it does not inhibit the reaction, examples of which include hydrocarbons such as hexane, cyclohexane, benzene, toluene or xylene; halogenated hydrocarbons such as dichloromethane, chloroform or carbon tetrachloride; ethers such as dioxane, diethyl ether, tetrahydrofuran (THF) or dibutyl ether; nitriles such as acetonitrile or propionitrile; and, amides such as dimethylformamide or dimethylacetoamide, preferably hydrocarbons, and more preferably toluene.

In the case of using a base in the present process, there are no particular limitations on the base used provided it is used as a base in ordinary reactions, examples of which include alkaline metal carbonates such as sodium carbonate or potassium carbonates; alkaline metal bicarbonates such as sodium bicarbonate or potassium bicarbonate; alkaline metal hydroxides or alkaline earth metal hydroxides such as sodium hydroxide, potassium hydroxide or barium hydroxide; alkaline metal alkoxides such as sodium methoxide, sodium ethoxide or potassium t-butoxide; organic bases such as triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4.3.0]nona-5-ene, 1,4-diazabicyclo[2.2.2]octane (DABCO) or 1,8-diazabicyclo[5.4.0]-7-undecene (DBU), preferably alkaline metal carbonates, organic bases or alkaline metal hydroxides; and more preferably sodium carbonate, pyridine, triethylamine or sodium hydroxide.

The amount of base used is normally 1 to 6 moles, and preferably 1.1 to 3 moles, based on 1 mole of compound (Ia').

Although varying according to the raw material compounds, reaction reagents, solvent and so forth, the reaction temperature is normally 0° C. to 200° C., and preferably 20° C. to 180° C.

Although varying according to the raw material compounds, reaction reagents, solvent, reaction temperature and so forth, the reaction time is normally 1 to 120 hours, and preferably 3 to 72 hours.

The starting raw material of the aforementioned method B in the form of compound (Ia') can be produced with the aforementioned method A.

(Method C)

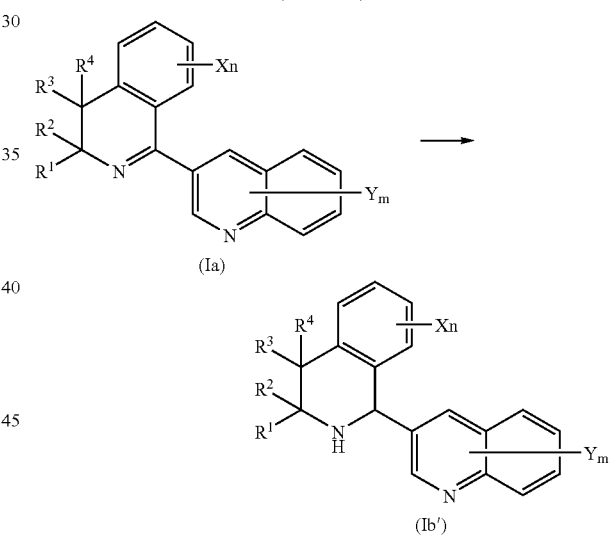

In the above formula, $R^1$, $R^2$, $R^3$, $R^4$, X, n, Y and m are the same as previously defined.

Method C is a method for producing compound (Ib') of the present invention ($R^5$=H) by reducing compound (Ia) of the present invention.

(Process C)

Process C is a process for producing compound (Ib') of the present invention by reducing compound (Ia) in a solvent.

There are no particular limitations on the reducing agent used in the present process provided it is used for reducing imines, examples of which include those used in hydrogenation reactions using a catalyst such as palladium carbon, platinum oxide or Rainey nickel; those used in reactions combining metal and acid such as zinc and acetic acid or tin and hydrochloric acid; and those used in reactions of metal hydrides such as sodium borohydride or sodium cyanoborohydride, preferably those used in reactions of metal hydrides, and more preferably sodium borohydride.

The amount of reducing agent used is normally 0.5 to 20 moles, and preferably 0.5 to 10 moles, based on 1 mole of compound (Ia).

In the case of using a solvent in the present process, there are no particular limitations on the solvent used provided it does not inhibit the reaction, examples of which include hydrocarbons such as hexane, cyclohexane, benzene, toluene or xylene; halogenated hydrocarbons such as dichloromethane, chloroform or carbon tetrachloride; alcohols such as methanol, ethanol or 2-propanol; acids such as acetic acid, hydrochloric acid or sulfuric acid; and ethers such as dioxane, diethyl ether, tetrahydrofuran (THF) or dibutyl ether, preferably alcohols, and more preferably ethanol.

Although varying according to the raw material compounds, reaction reagents, solvent and so forth, the reaction temperature is normally 0° C. to 200° C., and preferably 20° C. to 180° C.

Although varying according to the raw material compounds, reaction reagents, solvent, reaction temperature and so forth, the reaction time is normally 1 to 120 hours, and preferably 3 to 72 hours.

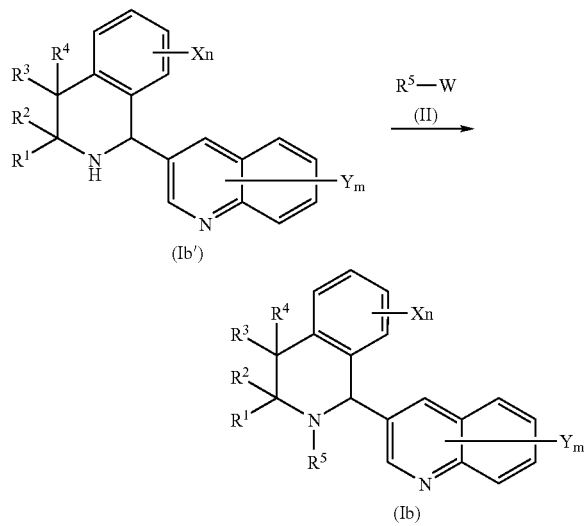

In the above formula, $R^1$, $R^2$, $R^3$, $R^4$, $R^5$, X, n, Y and m are the same as previously defined, and W represents a halogen atom.

Method D is a method for producing compound (Ib) of the present invention by alkylating or acylating compound (Ib') of the present invention ($R^5$=H).

(Process D)

Process D is a process for producing compound (Ib) of the present invention from an alkyl halide or acyl halide (II) of compound (Ib') in a solvent and in the presence of base.

The amount of compound (II) used is normally 1 to 130 moles, and preferably 1.1 to 10 moles, based on 1 mole of compound (Ib').

In the case of using a base in the present process, there are no particular limitations on the base used provided it is used as a base in ordinary reactions, examples of which include alkaline metal carbonates such as sodium carbonate or potassium carbonates; alkaline metal bicarbonates such as sodium bicarbonate or potassium bicarbonate; alkaline metal hydrides such as sodium hydride, lithium hydride or potassium hydride; alkaline metal hydroxides or alkaline earth metal hydroxides such as sodium hydroxide, potassium hydroxide or barium hydroxide; alkaline metal alkoxides such as sodium methoxide, sodium ethoxide or potassium t-butoxide; organic bases such as triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4.3.0]nona-5-ene, 1,4-diazabicyclo[2.2.2]octane (DABCO) or 1,8-diazabicyclo[5.4.0]-7-undecene (DBU); and organic metals such as butyl lithium or lithium diisopropyl amide; preferably alkaline metal carbonates, and more preferably potassium carbonate.

The amount of base used is normally 1 to 30 moles, and preferably 1.1 to 10 moles, based on 1 mole of compound (IV).

There are no particular limitations on the solvent used in the present process provided it does not inhibit the reaction, examples of which include hydrocarbons such as hexane, cyclohexane, benzene, toluene or xylene; halogenated hydrocarbons such as dichloromethane, dichloroethane, chloroform or tetrachloroethane; ethers such as dioxane, diethyl ether, tetrahydrofuran (THF) or ethylene glycol dimethyl ether; amides such as dimethylformamide, dimethylacetoamide or hexamethylene phosphoric triamide (HMPA); ketones such as acetone, methyl ethyl ketone, methyl isobutyl ketone or cyclohexanone; nitriles such as acetonitrile or isobutyronitrile; and esters such as methyl acetate, ethyl acetate or propyl acetate, preferably ketones, and more preferably acetone.

Although varying according to the raw material compounds, reaction reagents, solvent and so forth, the reaction temperature is normally 20° C. to 150° C., and preferably 0° C. to 40° C.

Although varying according to the raw material compounds, reaction reagents, solvent, reaction temperature and so forth, the reaction time is normally 10 minutes to 120 hours, and preferably 30 minutes to 72 hours.

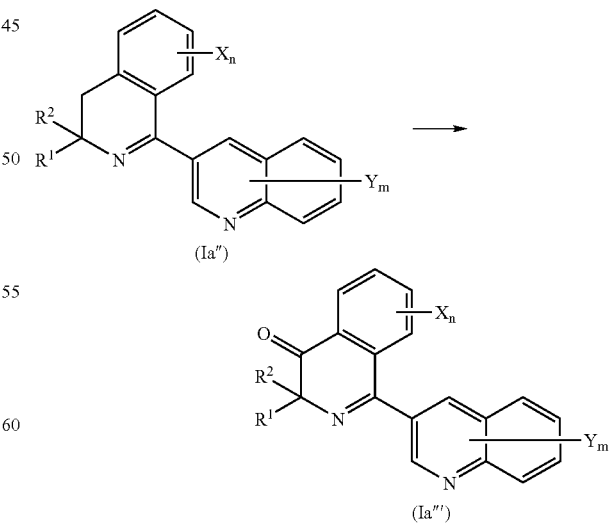

In the above formula, $R^1$, $R^2$, X, n, Y and m are the same as previously defined.

Method E is a method for producing compound (Ia''') of the present invention by oxidizing compound (Ia'') of the present invention.

(Process E)

Process E is a process for producing compound (Ia''') of the present invention by reacting compound (Ia'') with an oxidizing agent in the presence or absence of a solvent.

In the case of using a solvent in the present process, there are no particular limitations on the solvent used provided it does not inhibit the reaction, examples of which include organic acids such as formic acid or acetic acid; hydrocarbons such as hexane, cyclohexane, benzene, toluene or xylene; halogenated hydrocarbons such as dichloromethane, dichloroethane, chloroform or carbon tetrachloride; and ethers such as dioxane, diethyl ether, tetrahydrofuran (THF) or dibutyl ether, preferably organic acids or hydrocarbons, and more preferably acetic acid.

There are no particular limitations on the oxidizing agent used in the present process provided it is used to oxidize an active methylene to a carbonyl group in an ordinary oxidation reaction, examples of which include permanganates such as potassium permanganate or barium permanganate; chromic acids such as chromium oxide, dichromates, chromates, cromyl oxide and chromate esters; and metal oxides such as ruthenium oxide or selenium oxide, preferably chromates, and more preferably chromium oxide.

The amount of oxidizing agent used is normally 1 to 20 moles, and preferably 1.1 to 15 moles, based on 1 mole of compound (II).

Although varying according to the raw material compounds, reaction reagents, solvent and so forth, the reaction temperature is normally 0° C. to 200° C., and preferably 10° C. to 150° C.

Although varying according to the raw material compounds, reaction reagents, solvent, reaction temperature and so forth, the reaction time is normally 15 minutes to 120 hours, and preferably 30 minutes to 72 hours.

The starting raw material of the aforementioned method E in the form of compound (Ia'') can be produced with the aforementioned method A or B.

In the above formula, $R^1$, $R^2$, X, n, Y and m are the same as previously defined, and $R^3$ represents a hydrogen atom or a $C_1$-$C_6$ alkyl group which may be substituted with 1 to 3 same or different substituents selected from the group consisting of a halogen atom, $C_1$-$C_6$ alkoxy group, $C_1$-$C_6$ alkylthio group and phenoxy group.

Method F is a method for producing compound (1a'''') of the present invention by carrying out a nucleophilic reaction on compound (Ia''') of the present invention.

(Process F)

Process F is a process for producing compound (Ia'''') of the present invention by carrying out a nucleophilic reaction on the carbonyl group of compound (Ia''') in a solvent.

There are no particular limitations on the nucleophile used in the present process provided is used in ordinary nucleophilic reactions, examples of which include metal hydrides such as lithium aluminum hydride or sodium borohydride; and organic metal compounds such as Grignard's reagent, Reformatski's reagent, butyl lithium or copper acetylide, and preferably sodium borohydride or chlorinated methyl magnesium.

The amount of nucleophile used is normally 1 to 6 moles, and preferably 1.1 to 3 moles based on 1 mole of compound (Ia''').

There are no particular limitations on the solvent used in the present process provided it does not inhibit the reaction, examples of which include hydrocarbons such as hexane, cyclohexane, benzene, toluene or xylene; halogenated hydrocarbons such as dichloromethane, chloroform or carbon tetrachloride; alcohols such as methanol, ethanol or 2-propanol; acids such as acetic acid, hydrochloric acid or sulfuric acid; and ethers such as dioxane, diethyl ether, tetrahydrofuran (THF) or dibutyl ether, preferably alcohols or ethers, and more preferably methanol or diethyl ether.

Although varying according to the raw material compounds, reaction reagents, solvent and so forth, the reaction temperature is normally −20° C. to 200° C., and preferably 0° C. to 180° C.

Although varying according to the raw material compounds, reaction reagents, solvent, reaction temperature and so forth, the reaction time is normally 0.5 to 120 hours, and preferably 1 to 72 hours.

The starting raw material of the aforementioned method F in the form of compound (Ia''') can be produced with the aforementioned method E.

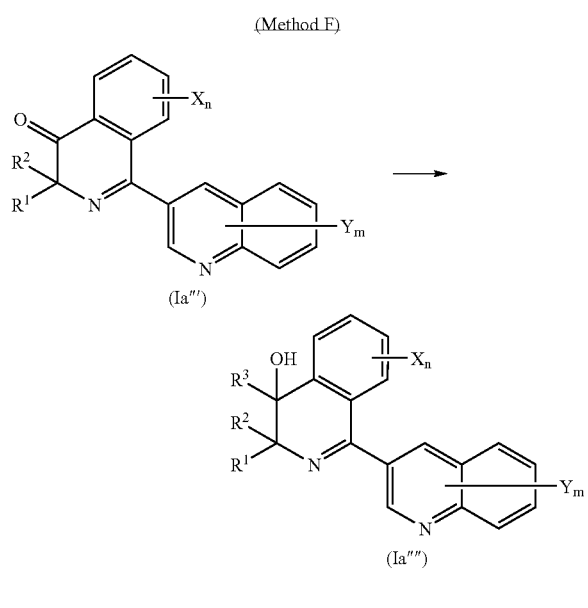

(Method F)

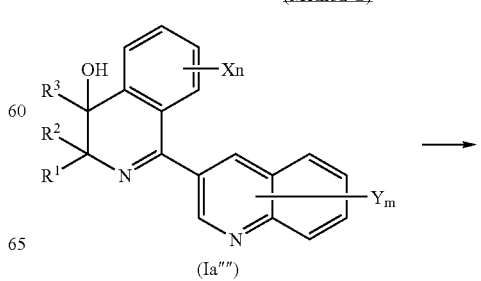

(Method G)

-continued

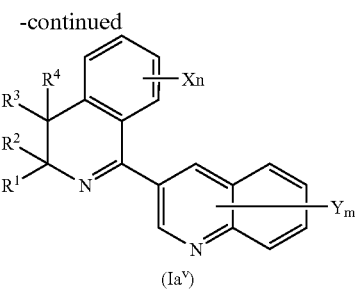

(Ia$^v$)

In the above formula, $R^1$, $R^2$, X, n, Y and m are the same as previously defined, $R^3$ represents a hydrogen atom or a $C_1$-$C_6$ alkyl group which may be substituted with 1 to 3 same or different substituents selected from the group consisting of a halogen atom, $C_1$-$C_6$ alkoxy group, $C_1$-$C_6$ alkylthio group and phenoxy group, and $R^4$ represents a halogen atom.

Method G is a method for producing compound (Ia$^v$) of the present invention by halogenating the hydroxyl group of compound (Ia"") of the present invention.

(Process G)

Process G is a process for producing compound (Ia$^v$) of the present invention by carrying out a halogenation reaction on compound (Ia"") in a solvent.

There are no particular limitations on the halogenating agent used in the present process provided it is used for halogenation. Examples of fluorinating agents include sulfur fluorides such as sulfur tetrafluoride, diethylaminosulfur trifluoride (DAST) or morpholinosulfur trifluoride, examples of chlorinating and brominating agents include hydrogen halides used in the presence of a catalyst such as zinc chloride, sulfuric acid or lithium bromide; phosphorous halide compounds such as phosphorous trihalides, phosphorous pentahalides or phosphorous oxyhalides; phosphine halides such as triphenylphosphine, carbon tetrahalides or triphenylphosphine halides; and thienyl halides, a preferable fluorinating agent is DAST, and a preferable chlorinating or brominating agent is a phosphorous trihalide.

The amount of halogenating agent used is normally 0.5 to 20 moles, and preferably 1 to 10 moles, based on 1 mole of compound (Ia"").

There are no particular limitations on the solvent used in the present process provided it does not inhibit the reaction, examples of which include hydrocarbons such as hexane, cyclohexane, benzene, toluene; halogenated hydrocarbons such as dichloromethane, dichloroethane, chloroform or tetrachloroethane; ethers such as dioxane, diethyl ether, tetrahydrofuran (THF) or ethylene glycol dimethyl ether; amides such as dimethylformamide, dimethylacetoamide or hexamethylene phosphoric triamide (HMPA); ketones such as acetone, methyl ethyl ketone, methyl isobutyl ketone or cyclohexanone; nitriles such as acetonitrile or isobutyronitrile; and esters such as methyl acetate, ethyl acetate or propyl acetate, preferably hydrocarbons or halogenated hydrocarbons, and more preferably toluene or methylene chloride.

Although varying according to the raw material compounds, reaction reagents, solvent and so forth, the reaction temperature is normally –20° C. to 150° C., and preferably 0° C. to 80° C.

Although varying according to the raw material compounds, reaction reagents, solvent, reaction temperature and so forth, the reaction time is normally 10 minutes to 120 hours, and preferably 30 minutes to 72 hours.

The starting raw material of the aforementioned method G in the form of compound (Ia"") can be produced with the aforementioned method F.

(Method H)

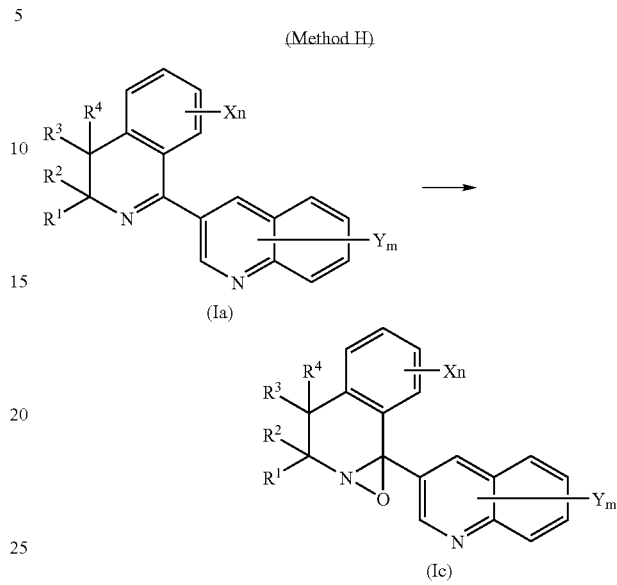

In the above formula, $R^1$, $R^2$, $R^3$, $R^4$, X, n, Y and m are the same as previously defined.

Method H is a method for producing compound (Ic) of the present invention by oxidizing compound (Ia) of the present invention.

(Process H)

Process H is a process for producing compound (Ic) of the present invention by reacting compound (Ia) with an oxidizing agent in the presence or absence of a solvent.

In the case of using a solvent in the present process, there are no particular limitations on the solvent used provided it does not inhibit the reaction, examples of which include organic acids such as formic acid or acetic acid; hydrocarbons such as hexane, cyclohexane, benzene, toluene or xylene; halogenated hydrocarbons such as dichloromethane, dichloroethane, chloroform or carbon tetrachloride; alcohols such as methanol, ethanol or 2-propanol; and ethers such as dioxane, diethyl ether, tetrahydrofuran (THF) or dibutyl ether, preferably alcohols or hydrocarbons, and more preferably methanol.

There are no particular limitations on the oxidizing agent used in the present process provided it is used to oxidize an ordinary imine to an oxazolidine, examples of which include perbenzoic acids such as metachloroperbenzoic acid, paranitroperbenzoic acid or monoperoxyphthalic acid; peracids such as trifluoroperacetic acid, peracetic acid or performic acid; peroxides such as dimethyldioxolan; and hydroperoxides such as t-butyl hydroperoxide, t-amyl hydroperoxide or hydrogen peroxide in the presence of a metal catalyst, preferably perbenzoic acids, peracids or hydroperoxides, and more preferably metachloroperbenzoic acid or peracetic acid.

The amount of oxidizing agent used is normally 1 to 20 moles, and preferably 1.1 to 15 moles, based on 1 mole of compound (Ia).

Although varying according to the raw material compounds, reaction reagents, solvent and so forth, the reaction temperature is normally 0° C. to 200° C., and preferably 10° C. to 150° C.

Although varying according to the raw material compounds, reaction reagents, solvent, reaction temperature and so forth, the reaction time is normally 15 minutes to 120 hours, and preferably 30 minutes to 72 hours.

The starting raw material of the aforementioned method H in the form of compound (Ia) can be produced with the aforementioned method A, B, C, D, E, F or G.

(Method I)

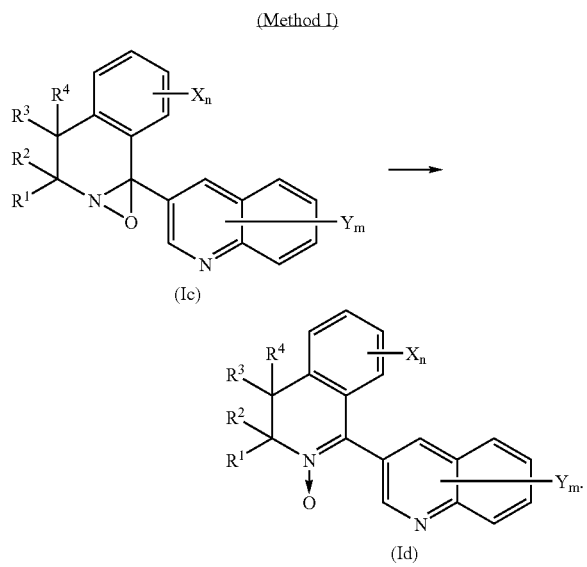

In the above formula, $R^1$, $R^2$, $R^3$, $R^4$, X, n, Y and m are the same as previously defined.

Method I is a method for producing compound (Id) of the present invention by treating compound (Ic) of the present invention with acid.

(Process I)

Process I is a process for producing compound (Id) of the present invention by treating compound (Ic) of the present invention with acid in the presence of absence of solvent.

In the case of using a solvent in the present process, there are no particular limitations on the solvent used provided it does not inhibit the reaction, examples of which include hydrocarbons such as hexane, cyclohexane, benzene, toluene or xylene; halogenated hydrocarbons such as dichloromethane, dichloroethane, chloroform or carbon tetrachloride; and ethers such as dioxane, diethyl ether, tetrahydrofuran (THF) or dibutyl ether, preferably halogenated hydrocarbons, and more preferably chloroform.

There are no particular limitations on the acid used in the present process, examples of which include inorganic acids such as sulfuric acid, formic acid, phosphoric acid or perchloric acid; sulfonic acids such as benzene sulfonic acid, toluene sulfonic acid or trifluoromethane sulfonic acid; and, Lewis acids such as tin tetrachloride or trifluoroboron, preferably inorganic acids or sulfonic acids, and more preferably sulfuric acid or methane sulfonic acid.

The amount of acid used is normally 1 to 20 moles, and preferably 1.1 to 15 moles, based on 1 mole of compound (Ic).

Although varying according to the raw material compounds, reaction reagents, solvent and so forth, the reaction temperature is normally –20° C. to 100° C., and preferably 0° C. to 80° C.

Although varying according to the raw material compounds, reaction reagents, solvent, reaction temperature and so forth, the reaction time is normally 15 minutes to 120 hours, and preferably 30 minutes to 72 hours.

The starting raw material of the aforementioned method I in the form of compound (Ic) can be produced with the aforementioned method H.

Following completion of each of the aforementioned reactions, the target compound of each reaction can be collected from the reaction mixture in accordance with ordinary methods. For example, after suitably neutralizing the reaction mixture, or filtering in the case impurities are present, an immiscible organic solvent in the manner of water and ethyl acetate is added, and after rinsing with water, the organic layer containing the target compound is separated followed by drying with anhydrous magnesium sulfate and so forth and then distilling off the solvent to obtain the target compound.

The resulting target compound can be further purified as necessary using an ordinary method such as recrystallization, re-precipitation or chromatography.

A process for producing a salt of compound (Ia), (Ib), (Ic) or (Id) of the present invention is carried out by adding an acid to an extraction concentrate of a reaction mixture containing compound (Ia), (Ib), (Ic) or (Id) produced in each process, or by adding acid to a solution in which compound (Ia), (Ib, (Ic) or (Id) has been dissolved in a suitable solvent.

Examples of acids used in the reaction include halogenated hydroacids such as hydrofluoric acid, hydrochloric acid, hydrobromic acid or hydroiodic acid; lower alkyl sulfonic acids such as methane sulfonic acid, trifluoromethane sulfonic acid or ethane sulfonic acid; aryl sulfonic acids such as benzene sulfonic acid or p-toluene sulfonic acid; organic acids such as succinic acid or oxalic acid; and, organic acid amide compounds such as saccharin.

The amount of acid used is normally 1 to 10 equivalents, and preferably 1 to 5 equivalents.

Although there are no particular limitations on the solvent used in the reaction provided it does not inhibit the reaction, and preferable examples include ethers such as ether, diisopropyl ether, tetrahydrofuran (THF) or dioxane, and alcohols such as methanol or ethanol.

The reaction temperature is normally –20° C. to 50° C., and preferably –10° C. to 30° C.

Although varying according to the type of solvent used, temperature and so forth, the reaction time is normally 10 minutes to 1 hour.

The resulting salt is isolated according to ordinary methods. Namely, in the case of precipitating as crystals, the salt is isolated by filtration, while in the case of an aqueous salt, the salt is isolated in the form of aqueous solution by separating between an organic solvent and water.

A compound of the present invention is useful as an active ingredient of a pest control agent. For example, a compound of the present invention demonstrates superior control effects as an agrohorticultural antimicrobial agent against diseases caused by various types of plant pathogens. A compound of the present invention demonstrates particularly superior control effects against various types of diseases such as rice blast, rice tip blight, gray mold of adzuki bean, tomato, cucumber and green bean plants, root rot, onion leaf blight, wheat snow mold, powdery mildew, apple Monilinia blossom blight, Alternaria leaf spot, tea anthracnose, pear rust, black blight, grape bird's eye rot and citrus fruit black spot disease. A compound of the present invention can be used to control damage by treating after infection since it has superior therapeutic effects.

When using a compound of the present invention, said compound can be prepared in various forms such as an emulsion, powder, water-dispersible powder, liquid, granules or suspension together with an assistant in the same manner as in the case of conventional agricultural chemical preparations. During actual use of these preparations, they can be used directly or used after diluting to a predetermined concentration with water or other diluent.

Examples of assistants used include carriers, emulsifiers, suspension agents, dispersants, spreading agents, penetrating agents, wetting agents, thickeners and stabilizers, and these assistants can be suitably added as necessary.

Carriers used are divided into solid carriers and liquid carriers. Examples of solid carriers include animal and plant powders such as starch, sugar, powdered cellulose, cyclodextrin, activated charcoal, soybean powder, wheat powder, chaff powder, wood chips, fish meal or powdered milk; and, mineral powders such as talc, kaolin, bentonite, organic bentonite, calcium carbonate, calcium sulfate, sodium bicarbonate, zeolite, diatomaceous earth, white carbon, clay, alumina, silica or sulfur powder, while examples of liquid carriers include water; animal and vegetable oils such as soybean oil, cottonseed oil or corn oil; alcohols such as ethyl alcohol or ethylene glycol; ketones such as acetone or methyl ethyl ketone; ethers such as dioxane or tetrahydrofuran; aliphatic/aromatic hydrocarbons such as kerosene, lamp oil, liquid paraffin, xylene, trimethylbenzene, tetramethylbenzene, cyclohexane or solvent naphtha; halogenated hydrocarbons such as chloroform or chlorobenzene; acid amides such as dimethylformamide; esters such as ethyl acetate ester or glycerin esters of fatty acids; nitriles such as acetonitrile; sulfur-containing compounds such as dimethylsulfoxide; and, N-methylpyrrolidone.

The blending weight ratio of a compound of the present invention and an assistant is normally 0.05:99.95 to 90:10, and preferably 0.2:99.8 to 80:20.

Although varying according to the target crop, usage method, preparation form, applied amount and so forth, the usage concentration and amount used of a compound of the present invention is normally 0.1 to 10000 ppm, and preferably 1 to 1000 ppm, per active ingredient, and in the case of soil treatment, normally 10 to 100000 g/ha, and preferably 100 to 10000 g/ha.

A compound of the present invention can be mixed or used in combination with other agricultural chemicals such as insecticides, miticides, attractants, nematocides, antimicrobial agents, antivirus agents, herbicides or plant growth regulators, and is preferably mixed or used in combination with insecticides, miticides, nematocides or antimicrobial agents.

Examples of insecticides used include organic phosphate ester compounds such as O,O-diethyl-O-(5-phenyl-3-isoxazolyl)phosphorothioate (common name: Isoxathion), O,O-dimethyl-O-(3-methyl-4-nitrophenyl)thiophosphate (common name: Fenitrothion), O,O-diethyl-O-(2-isopropyl-4-methylpyrimidin-6-yl)thiophosphate (common name: Diazinon), O,S-dimethyl-N-acetylphosphoroamide thioate (common name: Acephate) or O,O-dimethyl-S-1,2-diethoxycarbonylethyl dithiophosphate (common name: Malathion);

carbamate compounds such as 2-tert-butylimino-3-isopropyl-5-phenyl-3,4,5,6-tetrahydro-2H-1,3,5-thiadiazin-4-one (common name: Buprofezin), S-methyl-N-(methylcarbamoyloxy)thioacetoimidate (common name: Methyomyl), or N,N-dimethyl-2-methylcarbamoyloxyimino-2-(methylthio) acetoamide (common name: Oxamyl);

pyrethroid compounds such as (RS)-α-cyano-3-phenoxybenzyl=(RS)-2-(4-chlorophenyl)-3-methylbutyrate (common name: Fenvalerate), 3-phenoxybenzyl=(1RS,3RS)-(1RS,3SR)-3-(2,2-dichlorovinyl)-2,2-dimethylcyclopropane carboxylate (common name: Pyrethrum), or (2-(4-ethoxyphenyl)-2-methylpropyl-3-phenoxybenzyl ether (common name: Etofenprox);

benzoylurea compounds such as 1-[3,5-dichloro-4-(3-chloro-5-trifluoromethyl-2-pyridyloxy)phenyl]-3-(2,6-difluorobenzoyl)urea (common name: Chlorfurazuron), or 1-(3,5-dichloro-2,4-difluorophenyl)-3-(2,6-difluorobenzoyl)urea (common name: Teflubenzuron);

neonicotinoid compounds such as 1-(6-chloro-3-pyridylmethyl)-N-nitro-imidazolidine-2-indeneamine (common name: Imidacloprid), or [C(E)]-N-[(2-chloro-5-thiazinyl)methyl]-N'-methyl-nitroguanidine (common name: Clothianidin); and, pyrazole compounds such as 5-amino-1-[2,6-dichloro-4-(trifluoromethyl)phenyl]-4-[(trifluoromethyl)sulfinyl]-1-1H-pyrazole-3-carbonitrile (common name: Fipronil).

Examples of antimicrobial agents used include dithiocarbamate compounds such as manganese ethylene-bis(dithiocarbamate) (common name: Maneb), zinc and manganese ethylene-bis(dithiocarbamate) (common name: Manzeb), or 3,3-ethylene-bis(tetrahydro-4,6-dimethyl-2H-1,3,5-thiadiazine-2-thione (common name: Milneb);

N-halogenoalkylthioimide compounds such as N-(trichloromethylthio)cyclohex-4-ene-1,2-dicarboximide (common name: Captan), or N-(1,1,2,2-tetrachloroethylthio)cyclohex-4-ene-1,2-dicarboximide (common name: Captahol);

halogenoaromatic compounds such as 4,5,6,7-tetrachlorophthalide (common name: Fthalide), or tetrachloroisophthalonitrile (common name: Chlorothalonil);

benzimidazole compounds such as methyl-1-(butylcarbamoyl)-2-benzimidazole carbamate (common name: Benomyl);

azole compounds such as (E)-4-chloro-α,α,α-trifluoro-N-(1-imidazol-1-yl-2-propoxyethylidene)-o-toluidine (common name: Triflumizole), 2-(4-chlorophenyl)-2-(1H-1,2,4-triazol-1-ylmethyl)hexanenitrile (common name: Myclobutanil), N-propyl-N-[2-(2,4,6-trichlorophenoxy) ethyl]imidazole-1-carboxamide (common name: Prochloraz), or 2-(4-fluorophenyl)-1-(1H-1,2,4-triazol-1-yl)-3-trimethylsilylpropan-2-ole (common name: Siomeconazole);

pyridinamine compounds such as 3-chloro-N-(3-chloro-2,6-dinitro-4-α,α,α-trifluorotolyl)-5-trifluoromethyl-2-pyridinamine (common name: Fluazinam);

cyanoacetoamide compounds such as 1-(2-cyano-2-methoxyiminoacetyl)-3-ethyl urea (common name: Cymoxanil);

phenylamide compounds such as methyl-N-(2-methoxyacetyl)-N-(2,6-xylyl)-DL-alaninate (common name: Metalaxyl), 2-methoxy-N-(2-oxo-1,3-oxazolidin-3-yl)aceto-2',6'-xylidide (common name: Oxadixyl), or methyl-N-phenylacetyl-N-(2,6-xylyl)-DL-alaninate (common name: Benalaxyl);

dicarboxyimide compounds such as N-(3,5-dichlorophenyl)-1,2-dimethylcyclopropane-1,2-dicarboxyimide (common name: Procymidone), 3-(3,5-dichlorophenyl)-N-isopropyl-2,4-dioxoimidazoline-1-carboxamide (common name: Iprodione), or 3-(3,5-dichlorophenyl)-5-methyl-5-vinyl-2,4-oxazolidinone (common name: Vinclozolin);

copper compounds such as cupric hydroxide (common name: cupric hydroxide) or kappa-8-quinolinolate (common name: Copper quinolin);

isoxazole compounds such as 3-hydroxy-5-methylisoxazole (common name: Hymexazol);

organic phosphorous compounds such as aluminum tris (ethylphosphonate) (common name: Fosetyl aluminum), O-2,6-dichloro-p-tolyl=O,O-dimethylphosphorothioate, O-ethyl-S,S-diphenylphosphorodithionate, or aluminum ethyl hydrogen phosphonate;

benzanilide compounds such as α,α,α-trifluoro-3'-isopropoxy-o-toluanilide (common name: Flutolanil), or 3'-isopropoxy-o-toluanilide (common name: Mepronil);

morpholine compounds such as (E,Z)4-[3-(4-chlorophenyl)-3-(3,4-dimethoxyphenyl)acryloyl]morpholine (common name: Dimethomorph), (±)-cis-4-[3-(4-t-butylphenyl)-2-methylpropyl]-2,6-dimethylmorpholine (common name: Fenpropimorph), or (±)-cis-4-[3-(4-t-butylphenyl)-2-methylpropyl]-2,6-dimethylmorpholine (common name: Fenpropimorph);

iminoctadine compounds such as 1,1-iminodi(octamethylene) diguanidinium triacetate (common name: Iminoctadine);

melanine biosynthesis inhibitors such as 1,2,5,6-tetrahydro-4H-pyrrolo[3,2,1-ij]quinolin-4-one (common name: Pyroquilon), 4,5,6,7-tetrachlorophthalide (common name: Fthalide), or 2,2-dichloro-N-[1-(4-chlorophenyl)ethyl]-1-ethyl-3-methylcyclopropane carboxamide (common name: Carpropamid);

tolerance inducers such as 1,2,5,6-tetrahydro-3-aryloxy-1,2-benzisothiazole-1,1-dioxide (common name: Probenazole);

sulfur agents, and tin agents.

Although the following provides a detailed explanation of compounds of the present invention using examples, preparation examples and test examples, the present invention is not limited thereto.

Example 1

6'-methyl-1'-quinolin-3-yl-4'H-spiro[cyclohexane-1,3'-isoquinoline (Compound No. 1-772) (Process A)

Sulfuric acid (0.4 mL) and 1-(3-methylbenzyl)cyclohexanol (204 mg, 1.0 mmol) were added while cooling with ice to a benzene (1.0 mL) solution of quinoline-3-carbonitrile (154 mg, 1.0 mmol), and after stirring for 1 hour at 80° C., the solution was poured into water followed by extraction with ethyl acetate and applying the resulting residue to chromatography to obtain 180 mg of the target compound (yield: 73%).

Physical property: oil.

$^1$H-NMR (270 MHz, CDCl$_3$) δ ppm: 1.51-1.85 (10H, m), 2.40 (3H, s), 2.81 (2H, s), 7.02-7.14 (3H, m), 7.57 (1H, t, J=8.4 Hz), 7.75 (1H, t, J=8.4 Hz), 7.86 (1H, d, J=8.4 Hz), 8.15 (1H, d, J=8.4 Hz), 8.36 (1H, s), 9.16 (1H, s). MS m/z: 340 (M$^+$), 325, 311, 297, 284, 244, 142, 128.

Example 2

3-(5-fluoro-3,3-dimethyl-3,4-dihydroisoquinolin-1-yl)quinoline (Compound No. 1-32) (Process A)

Trifluoromethane sulfonic acid (0.52 mL) were added while cooling with ice to a dichloroethane (0.58 mL) solution of an about 4:7 mixture of 1-fluoro-(2-methylpropen-1-yl)benzene and 1-fluoro-(2-methylpropen-2-yl)benzene (87.3 mg, 0.58 mmol) and quinoline-3-carbonitrile (89.6 mg, 0.58 mmol), and after stirring for 18 hours at room temperature, the solution was poured into water followed by extraction with ethyl acetate and applying the resulting residue to chromatography to obtain 82.2 mg of the target compound (yield: 47%).

Melting point: 97-100° C.

$^1$H-NMR (500 MHz, CDCl$_3$) δ ppm: 1.36 (6H, s), 2.89 (2H, s), 7.03 (1H, dd, J=1.4, 6.9 Hz) 7.18-7.24 (2H, m), 7.60 (1H, t, J=8.2 Hz), 7.77 (1H, ddd, J=1.3, 6.9, 8.2 Hz), 7.88 (1H, d, J=8.2 Hz), 8.16 (1H, d, J=8.2 Hz), 8.36 (1H, d, J=2.1 Hz), 9.09 (1H, d, J=2.1 Hz).

MS m/z: 304 (M$^+$), 303, 289, 248, 156.

Example 3

3-(5-acetyl-3,3-dimethyl-3,4-dihydroisoquinolin-1-yl)quinoline (Compound No. 1-114) (Process B)

Tributyl (1-ethoxyvinyl) tin (0.85 mL, 2.4 mmol) and dichlorobis(triphenylphosphine)palladium (15.8 mg, 0.022 mmol) were added to a toluene solution (0.9 mL) of 3-(5-bromo-3,3-dimethyl-3,4-dihydroisoquinolin-1-yl)quinoline (806 mg, 2.2 mmol), and after stirring for 3 hours at 100° C., dilute hydrochloric acid was added to temporarily acidify followed by basifying with ammonium water, filtering, concentrating the filtrate and applying the resulting residue to chromatography to obtain 647 mg of the target compound (yield: 89%).

Physical property: oil.

$^1$H-NMR (500 MHz, CDCl$_3$) δ ppm: 1.31 (6H, s), 2.67 (3H, s), 3.13 (2H, s), 7.32 (1H, t, J=7.6 Hz), 7.37 (1H, dd, J=1.4, 7.6 Hz), 7.60 (1H, ddd, J=1.4, 6.9, 8.2 Hz), 7.78 (1H, ddd, J=1.4, 6.9, 8.2 Hz), 7.82 (1H, dd, J=1.4, 7.6 Hz), 7.87 (1H, d, J=8.2 Hz), 8.16 (1H, d, J=8.2 Hz), 8.35 (1H, d, J=2.1 Hz), 9.06 (1H, d, J=2.1 Hz).

MS m/z: 328 (M$^+$), 313, 285.

Example 4

3-(3,3-dimethyl-1,2,3,4-tetrahydroisoquinolin-1-yl)quinoline (Compound No. 2-1) (Process C)

Sodium borohydride (370 mg, 1.0 mmol) was added to an ethanol (30 mL) solution of 3-(3,3-dimethyl-3,4-dihydroisoquinolin-1-yl)quinoline (650 mg, 2.7 mmol) followed by heating and refluxing for 3 hours, pouring this reaction solution into ice water, extracting with ethyl acetate, and applying the resulting residue to chromatography to obtain 420 mg of the target compound (yield: 54%).

Melting point: 117-122° C.

$^1$H-NMR (270 MHz, CDCl$_3$) δ ppm: 1.24 (3H, s), 1.29 (3H, s), 2.65 (1H, d, J=15.8 Hz), 2.98 (1H, d, J=15.8 Hz), 5.33 (1H, s), 6.70 (1H, d, J=7.7 Hz), 6.99-7.03 (1H, m), 7.12 (2H, s), 7.49 (1H, t, J=8.2 Hz), 7.65 (1H, t, J=8.2 Hz), 7.74 (1H, d, J=8.2 Hz), 8.08 (1H, d, J=2.1 Hz), 8.09 (1H, d, J=8.2 Hz), 8.85 (1H, d, J=2.1 Hz).

MS m/z: 288 (M$^+$), 273, 230, 202, 160, 144, 128, 155.

Example 5

3-(2,3,3-trimethyl-1,2,3,4-tetrahydroisoquinolin-1-yl)quinoline (Compound No. 2-33) (Process D)

Potassium carbonate (500 mg, 3.6 mmol) and methyl iodide (0.33 mL, 5.0 mmol) were added to an acetone (2 mL) solution of 3-(3,3-dimethyl-1,2,3,4-tetrahydroisoquinolin-1-yl) quinoline (144 mg, 0.5 mmol) followed by stirring for 3 hours at room temperature, filtering, concentrating the filtrate and applying the resulting residue to chromatography to obtain 60 mg of the target compound (yield: 40%).

Melting point: 116-118° C.

$^1$H-NMR (270 MHz, CDCl$_3$) δ ppm: 1.00 (3H, s), 1.35 (3H, s), 2.15 (3H, s), 2.61 (1H, d, J=15.6 Hz), 3.23 (1H, d, J=15.6 Hz), 4.58 (1H, s), 6.64 (1H, d, J=7.9 Hz), 6.93 (1H, t, J=7.9 Hz), 7.06-7.08 (2H, m), 7.51 (1H, t, J=8.2 Hz), 7.65

(1H, t, J=8.2 Hz), 7.78 (1H, d, J=8.2 Hz), 8.07 (1H, d, J=2.1 Hz), 8.08 (1H, d, J=7.9 Hz), 8.84 (1H, d, J=2.1 Hz).

MS m/z: 302 (M⁺), 287, 265, 230, 174, 158, 149, 128, 115.

The following compounds were synthesized in the same manner as Example 1 to 5.

Example 6

3-(3,3-dimethyl-3,4-dihydroisoquinolin-1-yl)quinoline (Compound No. 1-1)

Physical property: oil.

¹H-NMR (270 MHz, CDCl₃) δ ppm: 1.33 (6H, s), 2.86 (2H, s), 7.20-7.27 (3H, m), 7.37-7.40 (1H, m), 7.56 (1H, t, J=8.4 Hz), 7.74 (1H, t, J=8.4 Hz), 7.86 (1H, d, J=8.4 Hz), 8.16 (1H, d, J=8.4 Hz), 8.39 (1H, d, J=2.0 Hz), 9.11 (1H, d, J=2.0 Hz).

MS m/z: 286 (M⁺), 285, 271, 230, 128, 115.

Example 7

3-(3,3-dimethyl-3,4-dihydroisoquinolin-1-yl)-8-fluoroquinoline (Compound No. 1-7)

Physical property: oil.

¹H-NMR (500 MHz, CDCl₃) δ ppm: 1.34 (6H, s), 2.87 (2H, s), 7.16-7.29 (3H, m), 7.42-7.54 (3H, m), 7.68 (1H, d, J=7.6 Hz), 8.42 (1H, s), 9.14 (1H, d, J=1.4 Hz).

MS m/z: 304 (M⁺), 303, 289, 248, 144, 115.

Example 8

3-(3,3-dimethyl-3,4-dihydroisoquinolin-1-yl)-6-chloroquinoline (Compound No. 1-11)

Physical property: oil.

¹H-NMR (500 MHz, CDCl₃) δ ppm: 1.33 (6H, s), 2.87 (2H, s), 7.17 (1H, d, J=7.7 Hz), 7.25 (1H, t, J=7.7 Hz), 7.28 (1H, d, J=7.7 Hz), 7.43 (1H, t, J=7.7 Hz), 7.69 (1H, dd, J=1.9, 8.8 Hz), 7.85 (1H, d, J=1.9 Hz), 8.10 (1H, d, J=8.8 Hz), 8.28 (1H, d, J=1.7 Hz), 9.10 (1H, d, J=1.7 Hz).

MS m/z: 320 (M⁺), 319, 305, 264, 229, 152, 116.

Example 9

3-(3,3-dimethyl-3,4-dihydroisoquinolin-1-yl)-8-methylquinoline (Compound No. 1-19)

Physical property: oil.

¹H-NMR (500 MHz, CDCl₃) δ ppm: 1.33 (6H, s), 2.85 (3H, s), 2.87 (2H, s), 7.21-7.28 (3H, m), 7.40-7.43 (1H, m), 7.47 (1H, t, J=7.6 Hz), 7.60 (1H, d, J=7.6 Hz), 7.72 (1H, d, J=7.6 Hz), 8.36 (1H, d, J=2.1 Hz), 9.11 (1H, d, J=2.1 Hz).

MS m/z: 300 (M⁺), 299, 285, 244, 149, 115.

Example 10

3-(3,3-dimethyl-3,4-dihydroisoquinolin-1-yl)-8-methoxyquinoline (Compound No. 1-25)

Physical property: oil.

¹H-NMR (500 MHz, CDCl₃) δ ppm: 1.33 (6H, s), 2.87 (2H, s), 4.12 (3H, s), 7.10 (1H, d, J=7.6 Hz), 7.17 (1H, d, J=7.6 Hz), 7.21 (1H, t, J=7.6 Hz), 7.27 (1H, d, J=7.6 Hz), 7.41 (1H, t, J=7.6 Hz), 7.46 (1H, t, J=7.6 Hz), 7.51 (1H, d, J=7.6 Hz), 8.39 (1H, d, J=1.4 Hz), 9.06 (1H, d, J=1.4 Hz).

MS m/z: 316 (M⁺), 315, 301, 286, 260, 230, 149, 128, 115.

Example 11

3-(3,3-dimethyl-3,4-dihydroisoquinolin-1-yl)-8-hydroxyquinoline (Compound No. 1-31)

Physical property: oil.

¹H-NMR (500 MHz, CDCl₃) δ ppm: 1.32 (6H, s), 2.86 (2H, s), 5.33 (1H, s), 7.18-7.47 (7H, m), 8.35 (1H, s), 8.98 (1H, s).

MS m/z: 303, 302 (M⁺), 288, 245, 164, 149, 129, 115.

Example 12

3-(5-fluoro-3,3-dimethyl-3,4-dihydroisoquinolin-1-yl)-4-chloroquinoline (Compound No. 1-35)

Physical property: oil.

¹H-NMR (500 MHz, CDCl₃) δ ppm: 1.35 (3H, s), 1.47 (3H, s), 2.91 (1H, d, J=15.8 Hz), 2.98 (1H, d, J=15.8 Hz), 6.71 (1H, dd, J=1.4, 7.6 Hz), 7.11-7.17 (2H, m), 7.70 (1H, ddd, J=1.4, 6.9, 8.2 Hz), 7.82 (1H, ddd, J=1.4, 6.9, 8.2 Hz), 8.18 (1H, d, J=8.2 Hz), 8.30 (1H, d, J=8.2 Hz), 8.81 (1H, s).

MS m/z: 338 (M⁺), 323 303, 287, 247.

Example 13

3-(5-fluoro-3,3-dimethyl-3,4-dihydroisoquinolin-1-yl)-4-methoxyquinoline (Compound No. 1-37)

Physical property: amorphous.

¹H-NMR (500 MHz, CDCl₃) δ ppm: 1.40 (6H, brs), 2.42 (2H, brs), 3.90 (3H, s), 6.82-6.86 (1H, m), 7.15-7.17 (2H, m), 7.57 (1H, ddd, J=1.4, 6.9, 8.2 Hz), 7.75 (1H, ddd, J=1.4, 6.9, 8.2 Hz), 8.11 (1H, d, J=8.2 Hz), 8.23 (1H, dd, J=1.4, 8.2 Hz), 8.70 (1H, s).

MS m/z: 334 (M⁺), 319, 303, 288, 277, 263.

Example 14

3-(5-fluoro-3,3-dimethyl-3,4-dihydroisoquinolin-1-yl)-8-methylquinoline (Compound No. 1-38)

Physical property: oil.

¹H-NMR (500 MHz, CDCl₃) δ ppm: 1.35 (6H, s), 2.85 (3H, s), 2.89 (2Hs), 7.05 (1H, d, J=6.9 Hz), 7.18-7.22 (2H, m), 7.47 (1H, t, J=7.3 Hz), 7.61 (1H, d, J=6.9 Hz), 7.73 (1H, d, J=7.3 Hz), 8.34 (1H, s), 9.09 (1H, s).

MS m/z: 318 (M⁺), 317, 303, 262, 152, 134, 115.

Example 15

3-(5-fluoro-3,3-dimethyl-3,4-dihydroisoquinolin-1-yl)-8-methoxyquinoline (Compound No. 1-39)

Physical property: oil.

¹H-NMR (500 MHz, CDCl₃) δ ppm: 1.36 (6H, s), 2.89 (2H, s), 4.12 (3H, s), 7.00 (1H, d, J=8.2 Hz), 7.12 (1H, d, J=7.6 Hz), 7.18-7.27 (2H, m), 7.46 (1H, d, J=8.2 Hz), 7.51 (1H, t, J=8.2 Hz), 8.37 (1H, d, J=2.1 Hz), 9.04 (1H, d, J=2.1 Hz).

MS m/z: 334 (M⁺), 333, 319, 278, 248, 167.

Example 16

3-(6-fluoro-3,3-dimethyl-3,4-dihydroisoquinolin-1-yl)quinoline (Compound No. 1-41)

Physical property: oil.
$^1$H-NMR (500 MHz, CDCl$_3$) δ ppm: 1.33 (6H, s), 2.85 (2H, s), 6.91 (1H, td, J=2.1, 8.9 Hz), 6.98 (1H, dd, J=2.1 8.9 Hz), 7.21 (1H, dd, J=5.5, 8.2 Hz), 7.58 (1H, t, J=8.2 Hz), 7.76 (1H, ddd, J=1.4, 6.9, 8.2 Hz), 7.87 (1H, d, J=8.2 Hz), 8.16 (1H, d, J=8.2 Hz), 8.36 (1H, d, J=2.1 Hz), 9.09 (1H, d, J=2.1 Hz).
MS m/z: 304 (M$^+$), 303, 289, 279, 248, 156.

Example 17

3-(7-fluoro-3,3-dimethyl-3,4-dihydroisoquinolin-1-yl)quinoline (Compound No. 1-42)

Physical property: oil.
$^1$H-NMR (500 MHz, CDCl$_3$) δ ppm: 1.33 (6H, s), 2.83 (2H, s), 6.93 (1H, dd, J=2.7, 8.9 Hz), 7.13 (1H, td, J=2.7, 8.2 Hz), 7.25 (1H, dd, J=5.5, 8.2 Hz), 7.60 (1H, t, J=8.2 Hz), 7.78 (1H, ddd, J=1.4, 6.9, 8.2 Hz), 7.88 (1H, d, J=8.2 Hz), 8.17 (1H, d, J=8.9 Hz), 8.30 (1H, d, J=2.1 Hz), 9.11 (1H, d, J=2.1 Hz).
MS m/z: 304 (M$^+$), 303, 289, 248, 156.

Example 18

3-(5-chloro-3,3-dimethyl-3,4-dihydroisoquinolin-1-yl)quinoline (Compound No. 1-44)

Melting point: 85-88° C.
$^1$H-NMR (270 MHz, CDCl$_3$) δ ppm: 1.36 (6H, s), 2.97 (2H, s), 7.11-7.22 (2H, m), 7.49 (1H, dd, J=1.3, 7.6 Hz), 7.58 (1H, ddd, J=1.3, 6.9, 8.2 Hz), 7.76 (1H, ddd, J=1.6, 6.9, 8.2 Hz), 7.87 (1H, d, J=7.9 Hz), 8.16 (1H, d, J=8.2 Hz), 8.34 (1H, d, J=2.0 Hz), 9.06 (1H, d, J=2.0 Hz).
MS m/z: 320 (M$^+$), 319, 305, 285, 264.

Example 19

3-(5-chloro-3,3-dimethyl-3,4-dihydroisoquinolin-1-yl)-4-methylquinoline (Compound No. 1-49)

Physical property: oil.
$^1$H-NMR (500 MHz, CDCl$_3$) δ ppm: 1.41 (6H, s), 2.54 (3H, s), 3.03 (2H, s), 6.78 (1H, d, J=7.6 Hz), 7.09 (1H, t, J=7.6 Hz), 7.45 (1H, d, J=7.6 Hz), 7.61 (1H, t, J=8.2 Hz), 7.75 (1H, t, J=8.2 Hz), 8.06 (1H, d, J=8.2 Hz), 8.14 (1H, d, J=8.2 Hz), 8.71 (1H, s).
MS m/z: 334 (M$^+$), 333, 319, 194, 149, 115.

Example 20

3-(6-chloro-3,3-dimethyl-3,4-dihydroisoquinolin-1-yl)quinoline (Compound No. 1-53)

Physical property: oil.
$^1$H-NMR (270 MHz, CDCl$_3$) δ ppm: 1.33 (6H, s), 2.84 (2H, s), 7.13-7.27 (3H, m), 7.59 (1H, t, J=7.9 Hz), 7.77 (1H, ddd, J=1.3, 6.9, 8.2 Hz), 7.87 (1H, d, J=7.9 Hz), 8.16 (1H, d, J=8.2 Hz), 8.34 (1H, d, J=2.0 Hz), 9.08 (1H, d, J=2.0 Hz).
MS m/z: 320 (M$^+$), 319, 305, 285, 264.

Example 21

3-(7-chloro-3,3-dimethyl-3,4-dihydroisoquinolin-1-yl)quinoline (Compound No. 1-54)

Physical property: amorphous.
$^1$H-NMR (270 MHz, CDCl$_3$) δ ppm: 1.33 (6H, s), 2.82 (2H, s), 7.16-7.26 (2H, m), 7.34 (1H, dd, J=2.3, 8.2 Hz), 7.60 (1H, t, J=7.9 Hz), 7.77 (1H, ddd, J=1.3, 6.9, 8.2 Hz), 7.88 (1H, d, J=7.9 Hz), 8.17 (1H, d, J=8.6 Hz), 8.36 (1H, d, J=2.0 Hz), 9.09 (1H, d, J=2.0 Hz).
MS m/z: 320 (M$^+$), 319, 305, 285, 264.

Example 22

3-(5-bromo-3,3-dimethyl-3,4-dihydroisoquinolin-1-yl)quinoline (Compound No. 1-56)

Physical property: amorphous.
$^1$H-NMR (500 MHz, CDCl$_3$) δ ppm: 1.33 (6H, s), 2.84 (2H, s), 7.09 (1H, d, J=8.2 Hz), 7.39 (1H, dd, J=1.6, 8.2 Hz), 7.44 (1H, d, J=1.6 Hz), 7.59 (1H, ddd, J=1.1, 6.6, 8.2 Hz), 7.77 (1H, ddd, J=1.1, 6.6, 8.2 Hz), 7.87 (1H, d, J=8.2 Hz), 8.16 (1H, d, J=8.2 Hz), 8.35 (1H, d, J=2.2 Hz), 9.08 (1H, d, J=2.2 Hz).
MS m/z: 365 (M$^+$), 349, 309, 285, 269.

Example 23

3-(6-bromo-3,3-dimethyl-3,4-dihydroisoquinolin-1-yl)quinoline (Compound No. 1-65)

Physical property: oil.
$^1$H-NMR (500 MHz, CDCl$_3$) δ ppm: 1.33 (6H, s), 2.84 (2H, s), 7.09 (1H, d, J=8.2 Hz), 7.39 (1H, dd, J=1.6, 8.2 Hz), 7.44 (1H, d, J=1.6 Hz), 7.59 (1H, ddd, J=1.1, 6.6, 8.2 Hz), 7.77 (1H, ddd, J=1.1, 6.6, 8.2 Hz), 7.87 (1H, d, J=8.2 Hz), 8.16 (1H, d, J=8.2 Hz), 8.35 (1H, d, J=2.2 Hz), 9.08 (1H, d, J=2.2 Hz).
MS m/z: 365 (M$^+$), 349, 309, 285, 269.

Example 24

3-(7-bromo-3,3-dimethyl-3,4-dihydroisoquinolin-1-yl)quinoline (Compound No. 1-66)

Physical property: amorphous.
$^1$H-NMR (500 MHz, CDCl$_3$) δ ppm: 1.33 (6H, s), 2.81 (2H, s), 7.17 (1H, d, J=7.7 Hz), 7.34 (1H, d, J=1.6 Hz), 7.55 (1H, dd, J=1.6, 7.7 Hz), 7.61 (1H, ddd, J=1.1, 7.1, 8.2 Hz), 7.78 (1H, ddd, J=1.6, 7.1, 8.2 Hz), 7.90 (1H, d, J=8.2 Hz), 8.18 (1H, d, J=8.2 Hz), 8.36 (1H, d, J=2.2 Hz), 9.09 (1H, d, J=2.2 Hz).
MS m/z: 365 (M$^+$), 349, 309, 285, 229.

Example 25

3-(5-iodo-3,3-dimethyl-3,4-dihydroisoquinolin-1-yl)quinoline (Compound No. 1-68)

Physical property: oil.
$^1$H-NMR (500 MHz, CDCl$_3$) δ ppm: 1.35 (6H, s), 2.92 (2H, s), 6.99 (1H, t, J=8.2 Hz), 7.19 (1H, d, J=8.2 Hz), 7.59 (1H, t, J=8.2 Hz), 7.77 (1H, ddd, J=1.4, 6.9, 8.2 Hz), 7.87 (1H, d, J=8.2 Hz), 7.92 (1H, d, J=8.2 Hz), 8.16 (1H, d, J=8.2 Hz), 8.34 (1H, d, J=2.1 Hz), 9.06 (1H, d, J=2.1 Hz).
MS m/z: 412 (M$^+$), 397, 355, 285, 243, 229.

Example 26

3-(3,3,5-trimethyl-3,4-dihydroisoquinolin-1-yl)quinoline (Compound No. 1-69)

Physical property: oil.
$^1$H-NMR (500 MHz, CDCl$_3$) δ ppm: 1.34 (6H, s), 2.37 (3H, s), 2.81 (2H, s), 7.04 (1H, d, J=7.6 Hz) 7.13 (1H, t, J=7.6 Hz), 7.30 (1H, d, J=7.6 Hz), 7.58 (1H, ddd, J=1.4, 6.9, 7.6 Hz), 7.75 (1H, ddd, J=1.4, 6.9, 8.2 Hz), 7.86 (1H, d, J=7.6 Hz), 8.15 (1H, d, J=7.6 Hz), 8.35 (1H, d, J=2.1 Hz), 9.07 (1H, d, J=2.1 Hz).
MS m/z: 300 (M$^+$), 299, 285, 269, 258, 244.

Example 27

3-(3,3,6-trimethyl-3,4-dihydroisoquinolin-1-yl)quinoline (Compound No. 1-70)

Physical property: oil.
$^1$H-NMR (500 MHz, CDCl$_3$) δ ppm: 1.33 (6H, s), 2.39 (3H, s), 2.82 (2H, s), 7.04-7.09 (3H, d, m), 7.57 (1H, t, J=8.2 Hz), 7.75 (1H, ddd, J=1.4, 6.9, 8.2 Hz), 7.86 (1H, d, J=8.2 Hz), 8.16 (1H, d, J=8.2 Hz), 8.36 (1H, d, J=2.1 Hz), 9.10 (1H, d, J=2.1 Hz).
MS m/z: 300 (M$^+$), 299, 285, 269, 258, 244.

Example 28

3-(3,3,7-trimethyl-3,4-dihydroisoquinolin-1-yl)quinoline (Compound No. 1-71)

Physical property: oil.
$^1$H-NMR (270 MHz, CDCl$_3$) δ ppm: 1.32 (6H, s), 2.26 (3H, s), 2.82 (2H, s), 6.99 (1H, s), 7.14-7.24 (2H, m), 7.58 (1H, ddd, J=1.3, 6.9, 8.2 Hz), 7.76 (1H, ddd, J=1.3, 6.9, 8.2 Hz), 7.89 (1H, d, J=8.2 Hz), 8.16 (1H, d, J=8.2 Hz), 8.38 (1H, d, J=2.0 Hz), 9.09 (1H, d, J=2.0 Hz).
MS m/z: 300 (M$^+$), 299, 285, 269, 258, 244, 156.

Example 29

3-(5-vinyl-3,3-dimethyl-3,4-dihydroisoquinolin-1-yl)quinoline (Compound No. 1-81)

Physical property: oil.
$^1$H-NMR (500 MHz, CDCl$_3$) δ ppm: 1.34 (6H, s), 2.91 (2H, s), 5.45 (1H, d, J=11.0 Hz), 5.72 (1H, t, J=17.2 Hz), 7.02 (1H, dd, J=11.0, 17.2 Hz), 7.13 (1H, d, J=7.6 Hz), 7.23 (1H, t, J=7.6 Hz), 7.58 (1H, t, J=8.2 Hz), 7.62 (1H, d, J=7.6 Hz), 7.76 (1H, t, J=8.2 Hz), 7.87 (1H, d, J=7.6 Hz), 8.16 (1H, d, J=8.2 Hz), 8.36 (1H, d, J=2.1 Hz), 9.08 (1H, d, J=2.1 Hz)
MS m/z: 312 (M$^+$), 311 297, 285, 269, 256.

Example 30

3-(5-ethynyl-3,3-dimethyl-3,4-dihydroisoquinolin-1-yl)quinoline (Compound No. 1-85)

Physical property: amorphous.
$^1$H-NMR (500 MHz, CDCl$_3$) δ ppm: 1.35 (6H, s), 3.06 (2H, s), 3.36 (1H, s), 7.21 (2H, d, J=4.4 Hz), 7.58-7.62 (2H, m), 7.77 (1H, ddd, J=1.6, 7.1, 7.7 Hz), 7.88 (1H, d, J=8.2 Hz), 8.16 (1H, d, J=8.2 Hz), 8.35 (1H, d, J=2.2 Hz), 9.07 (1H, d, J=2.2 Hz).
MS m/z: 310 (M$^+$), 295, 268, 254.

Example 31

3-(5-phenyl-3,3-dimethyl-3,4-dihydroisoquinolin-1-yl)quinoline (Compound No. 1-89)

Physical property: oil.
$^1$H-NMR (270 MHz, CDCl$_3$) δ ppm: 1.25 (6H, s), 2.81 (2H, s), 7.21-7.32 (2H, m), 7.36-7.51 (6H, m), 7.58 (1H, ddd, J=1.4, 6.9, 7.9 Hz), 7.58 (1H, ddd, J=1.4, 6.9, 8.5 Hz), 7.89 (1H, d, J=7.9 Hz), 8.17 (1H, d, J=8.5 Hz), 8.42 (1H, d, J=2.1 Hz), 9.15 (1H, d, J=2.1 Hz).
MS m/z: 362 (M$^+$), 347 306.

Example 32

3-[5-(2-thienyl)-3,3-dimethyl-3,4-dihydroisoquinolin-1-yl]quinoline (Compound No. 1-94)

Physical property: amorphous.
$^1$H-NMR (500 MHz, CDCl$_3$) δ ppm: 1.29 (6H, s), 2.96 (2H, s), 7.10 (1H, dd, J=1.1, 3.8 Hz), 7.17 (1H, dd, J=3.8, 4.9 Hz), 7.22 (1H, dd, J=1.1, 7.7 Hz), 7.26-7.29 (1H, m), 7.43 (1H, dd, J=1.1, 4.9 Hz), 7.57-7.61 (2H, m), 7.77 (1H, ddd, J=1.6, 7.1, 8.2 Hz), 7.89 (1H, d, J=7.6 Hz), 8.17 (1H, d, J=8.2 Hz), 8.40 (1H, d, J=2.2 Hz), 9.13 (1H, d, J=2.2 Hz).
MS m/z: 368 (M$^+$), 353, 326, 312, 299, 285, 271.

Example 33

3-[5-(3-thienyl)-3,3-dimethyl-3,4-dihydroisoquinolin-1-yl]quinoline (Compound No. 1-95)

Physical property: amorphous.
$^1$H-NMR (500 MHz, CDCl$_3$) δ ppm: 1.28 (6H, s), 2.88 (2H, s), 7.19-7.21 (2H, m), 7.26-7.27 (1H, m), 7.30 (1H, dd, J=1.1, 2.7 Hz), 7.46 (1H, dd, J=2.7, 4.9 Hz), 7.50 (1H, dd, J=1.1, 7.7 Hz), 7.60 (1H, ddd, J=1.1, 7.1, 8.2 Hz), 7.77 (1H, ddd, J=1.1, 7.1, 8.2 Hz), 7.86 (1H, d, J=8.2 Hz), 8.17 (1H, d, J=8.2 Hz), 8.41 (1H, d, J=2.2 Hz), 9.13 (1H, d, J=2.2 Hz).
MS m/z: 368 (M$^+$), 353, 326, 312, 285, 271.

Example 34

3-[5-(5-oxazolyl)-3,3-dimethyl-3,4-dihydroisoquinolin-1-yl]quinoline (Compound No. 1-97)

Melting point: 175-179° C.
$^1$H-NMR (500 MHz, CDCl$_3$) δ ppm: 1.33 (6H, s), 3.00 (2H, s), 7.26-7.31 (2H, m), 7.35 (1H, t, J=7.7 Hz), 7.60 (1H, ddd, J=1.1, 7.1, 8.2 Hz), 7.76-7.80 (2H, m), 7.88 (1H, d, J=8.2 Hz), 8.05 (1H, s), 8.17 (1H, d, J=8.2 Hz), 8.38 (1H, d, J=2.2 Hz), 9.10 (1H, d, J=2.2 Hz).
MS m/z: 353 (M$^+$), 338, 311, 297, 269.

Example 35

1-(3,3-dimethyl-1-quinolin-3-yl-3,4-dihydroiso-quinolin-5-yl)ethanone=oxime (Compound No. 1-98)

Melting point: 187-190° C.
$^1$H-NMR (500 MHz, CDCl$_3$) δ ppm: 1.31 (6H, s), 2.29 (3H, s), 2.89 (2H, s), 7.21 (1H, dd, J=1.4, 7.6 Hz), 7.25 (1H, t, J=7.6 Hz), 7.41 (1H, dd, J=1.4, 7.6 Hz), 7.59 (1H, ddd, J=1.4, 6.9, 8.2 Hz), 7.77 (1H, ddd, J=1.4, 6.9, 8.2 Hz), 7.87 (1H, d, J=8.2 Hz), 8.19 (1H, d, J=8.2 Hz), 8.39 (1H, d, J=2.1 Hz), 9.11 (1H, d, J=2.1 Hz), 9.39 (1H, brs).
MS m/z: 343 (M$^+$), 326, 310, 296, 285, 269.

Example 36

1-(3,3-dimethyl-1-quinolin-3-yl-3,4-dihydroiso-quinolin-5-yl)ethanone=O-methyloxime (Compound No. 1-100)

Stereoisomer of Compound of Example 37
Physical property: oil.
$^1$H-NMR (500 MHz, CDCl$_3$) δ ppm: 1.31 (6H, s), 2.24 (3H, s), 2.89 (2H, s), 4.03 (3H, s), 7.21 (1H, dd, J=1.4, 7.6 Hz), 7.25-7.28 (1H, m), 7.42 (1H, dd, J=1.4, 7.6 Hz), 7.59 (1H, t, J=8.2 Hz), 7.76 (1H, ddd, J=1.4, 6.9, 8.2 Hz), 7.87 (1H, d, J=8.2 Hz), 8.16 (1H, d, J=8.2 Hz), 8.36 (1H, d, J=2.1 Hz), 9.08 (1H, d, J=2.1 Hz).
MS m/z: 357 (M$^+$), 342, 326, 310, 285, 269.

Example 37

1-(3,3-dimethyl-1-quinolin-3-yl-3,4-dihydroiso-quinolin-5-yl)ethanone=O-methyloxime (Compound No. 1-100)

Stereoisomer of Compound of Example 36
Physical property: oil.
$^1$H-NMR (500 MHz, CDCl$_3$) δ ppm: 1.32 (6H, s), 2.20 (3H, s), 2.69 (2H, brs), 3.85 (3H, s), 7.21 (1H, d, J=7.6 Hz), 7.22 (1H, d, J=7.6 Hz), 7.29 (1H, t, J=7.6 Hz), 7.59 (1H, t, J=8.2 Hz), 7.77 (1H, ddd, J=1.4, 6.9, 8.2 Hz), 7.87 (1H, d, J=8.2 Hz), 8.16 (1H, d, J=8.2 Hz), 8.39 (1H, d, J=2.1 Hz), 9.12 (1H, d, J=2.1 Hz).
MS m/z: 357 (M$^+$), 342, 326, 310, 285, 269.

Example 38

1-(3,3-dimethyl-1-quinolin-3-yl-3,4-dihydroiso-quinolin-5-yl)ethanone=O-ethyloxime (Compound No. 1-101)

Stereoisomer of Compound of Example 39
Physical property: amorphous.
$^1$H-NMR (500 MHz, CDCl$_3$) δ ppm: 1.31 (6H, s), 1.37 (3H, t, J=6.9 Hz), 2.26 (3H, s), 2.90 (2H, s), 4.27 (2H, q, J=6.9 Hz), 7.20 (1H, dd, J=1.4, 7.6 Hz), 7.26 (1H, t, J=7.6 Hz), 7.43 (1H, dd, J=1.4, 7.6 Hz), 7.59 (1H, t, J=8.2 Hz), 7.76 (1H, ddd, J=1.4, 6.9, 8.2 Hz), 7.87 (1H, d, J=8.2 Hz), 8.16 (1H, d, J=8.2 Hz), 8.36 (1H, d, J=2.1 Hz), 9.08 (1H, d, J=2.1 Hz).
MS m/z: 371 (M$^+$), 356, 326, 310, 285, 269.

Example 39

1-(3,3-dimethyl-1-quinolin-3-yl-3,4-dihydroiso-quinolin-5-yl)ethanone=O-ethyloxime (Compound No. 1-101)

Stereoisomer of Compound of Example 38
Physical property: amorphous.
$^1$H-NMR (500 MHz, CDCl$_3$) δ ppm: 1.23 (3H, t, J=6.9 Hz), 1.32 (6H, s), 2.19 (3H, s), 2.69 (2H, brs), 4.10 (2H, q, J=6.9 Hz), 7.19-7.23 (2H, m), 7.59 (1H, t, J=8.2 Hz), 7.77 (1H, ddd, J=1.4, 6.9, 8.2 Hz), 7.88 (1H, d, J=8.2 Hz), 8.17 (1H, d, J=8.2 Hz), 8.39 (1H, d, J=2.1 Hz), 9.12 (1H, d, J=2.1 Hz).
MS m/z: 371 (M$^+$), 356, 326, 310, 285, 269.

Example 40

1-(3,3-dimethyl-1-quinolin-3-yl-3,4-dihydroiso-quinolin-5-yl)ethanone=O-t-butyloxime (Compound No. 1-103)

Physical property: amorphous.
$^1$H-NMR (500 MHz, CDCl$_3$) δ ppm: 1.30 (6H, s), 1.37 (9H, s), 2.24 (3H, s), 2.95 (2H, s), 7.18 (1H, d, J=7.6 Hz), 7.26 (1H, t, J=7.6 Hz) 7.44 (1H, dd, J=1.4, 7.6 Hz), 7.59 (1H, ddd, J=1.4, 6.9, 8.2 Hz), 7.76 (1H, ddd, J=1.4, 6.9, 8.2 Hz), 7.87 (1H, d, J=8.2 Hz), 8.16 (1H, d, J=8.2 Hz), 8.37 (1H, d, J=2.1 Hz), 9.10 (1H, d, J=2.1 Hz).
MS m/z: 399 (M$^+$), 384, 342, 326, 310, 285, 269.

Example 41

1-(3,3-dimethyl-1-quinolin-3-yl-3,4-dihydroiso-quinolin-5-yl)ethanone=O-allyloxime (Compound No. 1-104)

Stereoisomer of Compound of Example 42
Physical property: oil.
$^1$H-NMR (500 MHz, CDCl$_3$) δ ppm: 1.31 (6H, s), 2.20 (3H, s), 2.70 (2H, brs), 4.55 (2H, d, J=6.2 Hz), 5.19 (1H, ddd, J=1.4, 2.7, 11.7 Hz), 5.23 (1H, ddd, J=1.4, 2.7, 17.2 Hz), 5.94-5.99 (1H, m), 7.21-7.23 (2H, m), 7.28 (1H, t, J=7.6 Hz), 7.59 (1H, ddd, J=1.4, 6.9, 8.2 Hz), 7.77 (1H, ddd, J=1.4, 6.9, 8.2 Hz), 7.88 (1H, d, J=8.2 Hz), 8.16 (1H, d, J=8.2 Hz), 8.36 (1H, d, J=2.1 Hz), 9.11 (1H, d, J=2.1 Hz).

Example 42

1-(3,3-dimethyl-1-quinolin-3-yl-3,4-dihydroiso-quinolin-5-yl)ethanone=O-allyloxime (Compound No. 1-104)

Stereoisomer of Compound of Example 41
Physical property: 128-131° C.
$^1$H-NMR (500 MHz, CDCl$_3$) δ ppm: 1.31 (6H, s), 2.28 (3H, s), 2.90 (2H, s), 4.73 (2H, d, J=5.5 Hz), 5.28 (1H, ddd, J=1.4, 2.7, 10.3 Hz), 5.38 (1H, ddd, J=1.4, 2.7, 17.2 Hz), 6.05-6.13 (1H, m), 7.21 (1H, d, J=7.6 Hz), 7.24-7.28 (1H, m), 7.42 (1H, dd, J=1.4, 7.6 Hz), 7.59 (1H, t, J=8.2 Hz), 7.78 (1H, ddd, J=1.4, 6.9, 8.2 Hz), 7.87 (1H, d, J=8.2 Hz), 8.16 (1H, d, J=8.2 Hz), 8.36 (1H, d, J=2.1 Hz), 9.08 (1H, d, J=2.1 Hz).
MS m/z: 383 (M$^+$), 368, 326, 310, 285, 269.

Example 43

1-(3,3-dimethyl-1-quinolin-3-yl-3,4-dihydroisoquinolin-5-yl)ethanone=O-benzyloxime (Compound No. 1-105)

Physical property: oil.
$^1$H-NMR (500 MHz, CDCl$_3$) δ ppm: 1.21 (6H, s), 2.29 (3H, s), 2.72 (2H, s), 5.25 (2H, s), 7.18-7.45 (8H, m), 7.58 (1H, t, J=7.6 Hz), 7.76 (1H, ddd, J=1.4, 6.9, 8.2 Hz), 7.86 (1H, d, J=7.6 Hz), 8.15 (1H, d, J=8.2 Hz), 8.39 (1H, d, J=2.1 Hz), 9.06 (1H, d, J=2.1 Hz).
MS m/z: 433 (M$^+$), 418, 326, 310, 285, 269.

Example 44

1-(3,3-dimethyl-1-quinolin-3-yl-3,4-dihydroisoquinolin-5-yl)ethanone=O-phenyloxime (Compound No. 1-106)

Stereoisomer mixture (1:2)
Physical property: amorphous.
$^1$H-NMR (500 MHz, CDCl$_3$) δ ppm: 1.28 (12H×⅓, s), 1.33 (12H×⅔, s), 2.35 (6H×⅓, s), 2.48 (6H×⅔, s), 2.74 (4H×⅓, brs), 2.99 (4H×⅔, s), 7.00-7.53 (16H, m), 7.58-7.62 (2H, m), 7.76-7.79 (2H, m), 7.88-7.89 (2H, m), 8.16-8.18 (2H, m), 8.39 (2H×⅔, d, J=2.1 Hz), 8.41 (2H×⅓, d, J=2.1 Hz), 9.11 (2H×⅔, d, J=2.1 Hz), 9.13 (2H×⅓, d, J=2.1 Hz).
MS m/z: 419 (M$^+$), 404, 326, 310, 269, 255.

Example 45

3-(6-methoxy-3,3-dimethyl-3,4-dihydroisoquinolin-1-yl)quinoline (Compound No. 1-108)

Physical property: oil.
$^1$H-NMR (500 MHz, CDCl$_3$) δ ppm: 1.33 (6H, s), 2.83 (2H, s), 3.86 (3H, s), 6.71 (1H, dd, J=2.8, 8.2 Hz) 6.80 (1H, d, J=2.8 Hz), 7.14 (1H, d, J=8.2 Hz), 7.58 (1H, t, J=8.2 Hz), 7.75 (1H, ddd, J=1.4, 6.9, 8.2 Hz), 7.87 (1H, d, J=7.6 Hz), 8.15 (1H, d, J=8.2 Hz), 8.36 (1H, d, J=2.1 Hz), 9.09 (1H, d, J=2.1 Hz).
MS m/z: 316 (M$^+$), 315, 301, 285, 260.

Example 46

3-(8-methoxy-3,3-dimethyl-3,4-dihydroisoquinolin-1-yl)quinoline (Compound No. 1-110)

Physical property: oil.
$^1$H-NMR (500 MHz, CDCl$_3$) δ ppm: 1.30 (6H, s), 2.79 (2H, s), 3.40 (3H, s), 6.82 (1H, d, J=8.9 Hz) 6.89 (1H, d, J=7.6 Hz), 7.39 (1H, t, J=7.6 Hz), 7.53 (1H, t, J=8.2 Hz), 7.69 (1H, t, J=8.2 Hz), 7.80 (1H, d, J=8.2 Hz), 8.10 (1H, d, J=8.9 Hz), 8.83 (1H, d, J=2.1 Hz), 8.85 (1H, d, J=2.1 Hz).
MS m/z: 316 (M$^+$), 315, 301, 285, 260.

Example 47

3-(5-amino-3,3-dimethyl-3,4-dihydroisoquinolin-1-yl)quinoline (Compound No. 1-111)

Melting point: 181-184° C.
$^1$H-NMR (270 MHz, CDCl$_3$) δ ppm: 1.37 (6H, s), 2.63 (2H, s), 3.76 (2H, brs), 6.65 (1H, dd, J=1.1, 7.7 Hz), 6.84 (1H, dd, J=1.1, 7.7 Hz), 7.05 (1H, t, J=7.7 Hz), 7.57 (1H, ddd, J=1.3, 6.9, 8.2 Hz), 7.74 (1H, ddd, J=1.3, 6.9, 8.5 Hz), 7.86 (1H, dd, J=1.3, 8.2 Hz), 8.15 (1H, d, J=8.5 Hz), 8.34 (1H, d, J=2.3 Hz), 9.07 (1H, d, J=2.3 Hz).
MS m/z: 401 (M$^+$), 286, 270, 259, 245.

Example 48

3-(5-acetylamino-3,3-dimethyl-3,4-dihydroisoquinolin-1-yl)quinoline (Compound No. 1-112)

Physical property: amorphous.
$^1$H-NMR (270 MHz, CDCl$_3$) δ ppm: 1.32 (6H, s), 2.27 (3H, s), 2.72 (2H, s), 7.08 (1H, d, J=7.7 Hz), 7.20-7.26 (1H, m), 7.43 (1H, brs), 7.58 (1H, ddd, J=1.1, 6.9, 7.9 Hz), 7.71-7.79 (2H, m), 7.86 (1H, d, J=7.9 Hz), 8.15 (1H, d, J=8.5 Hz), 8.35 (1H, d, J=2.1 Hz), 9.08 (1H, d, J=2.1 Hz).
MS m/z: 343 (M$^+$), 328, 300, 285, 269, 245.

Example 49

3-(5-Formyl-3,3-dimethyl-3,4-dihydroisoquinolin-1-yl)quinoline

Physical property: oil.
$^1$H-NMR (500 MHz, CDCl$_3$) δ ppm: 1.36 (6H, s), 3.37 (2H, s), 7.43 (1H, t, J=7.7 Hz), 7.49 (1H, dd, J=1.1, 7.7 Hz), 7.60 (1H, ddd, J=1.1, 7.1, 8.2 Hz), 7.78 (1H, ddd, J=1.1, 7.1, 8.2 Hz), 7.88 (1H, d, J=8.2 Hz), 7.97 (1H, dd, J=1.1, 7.7 Hz), 8.17 (1H, d, J=8.2 Hz), 8.35 (1H, d, J=2.2 Hz), 9.07 (1H, d, J=2.2 Hz), 10.4 (1H, s).
MS m/z: 314 (M$^+$), 299, 285, 269, 258, 244.

Example 50

3-(5-methylaminocarbonyl-3,3-dimethyl-3,4-dihydroisoquinolin-1-yl)quinoline (Compound No. 1-115)

Physical property: amorphous.
$^1$H-NMR (500 MHz, CDCl$_3$) δ ppm: 1.31 (3H, brs), 1.43 (3H, s), 2.19 (3H, s), 2.75 (2H, brs), 7.22 (1H, dd, J=1.6, 7.7 Hz), 7.25 (1H, dd, J=1.6, 7.7 Hz), 7.30 (1H, t, J=7.7 Hz), 7.59 (1H, ddd, J=1.1, 6.6, 7.7 Hz), 7.77 (1H, ddd, J=1.1, 6.6, 8.2 Hz), 7.87 (1H, d, J=7.7 Hz), 8.19 (1H, d, J=8.2 Hz), 8.41 (1H, d, J=2.2 Hz), 8.94 (1H, brs), 9.12 (1H, d, J=2.2 Hz).
MS m/z: 343 (M$^+$), 326, 310, 285, 269.

Example 51

3-(5-cyano-3,3-dimethyl-3,4-dihydroisoquinolin-1-yl)quinoline (Compound No. 1-116)

Physical property: amorphous.
$^1$H-NMR (270 MHz, CDCl$_3$) δ ppm: 1.37 (6H, s), 3.10 (2H, s), 7.37 (1H, t, J=7.9 Hz), 7.48 (1H, dd, J=0.8, 7.9 Hz), 7.61 (1H, ddd, J=1.2, 6.9, 8.2 Hz), 7.73-7.82 (2H, m), 7.88 (1H, d, J=7.9 Hz), 8.17 (1H, d, J=8.5 Hz), 8.35 (1H, d, J=2.1 Hz), 9.06 (1H, d, J=2.1 Hz).
MS m/z: 311 (M$^+$), 310, 296, 269, 255

Example 52

3-(5,6-difluoro-3,3-dimethyl-3,4-dihydroisoquinolin-1-yl)quinoline (Compound No. 1-117)

Physical property: gum.
$^1$H-NMR (270 MHz, CDCl$_3$) δ ppm: 1.36 (6H, s), 2.91 (2H, s), 7.01-7.08 (2H, m), 7.57-7.62 (1H, m) 7.74-7.80 (1H, m), 7.87 (1H, d, J=8.2 Hz), 8.16 (1H, d, J=8.5 Hz), 8.33 (1H, d, J=2.1 Hz), 9.06 (1H, d, J=2.1 Hz).
MS m/z: 322 (M$^+$), 321, 307, 266.

Example 53

3-(5,6-dichloro-3,3-dimethyl-3,4-dihydroisoquinolin-1-yl)quinoline (Compound No. 1-126)

Physical property: oil.
$^1$H-NMR (500 MHz, CDCl$_3$) δ ppm: 1.36 (6H, s), 3.02 (2H, s), 7.10 (1H, d, J=8.2 Hz) 7.37 (1H, d, J=8.2 Hz), 7.60 (1H, t, J=8.2 Hz), 7.78 (1H, ddd, J=1.4, 6.9, 8.2 Hz), 7.87 (1H, d, J=8.2 Hz), 8.16 (1H, d, J=8.2 Hz), 8.33 (1H, d, J=2.1 Hz), 9.05 (1H, d, J=2.1 Hz).
MS m/z: 355 (M$^+$), 354, 353, 319, 298, 263.

Example 54

3-(6-fluoro-3,3,7-trimethyl-3,4-dihydroisoquinolin-1-yl)quinoline (Compound No. 1-136)

Physical property: oil.
$^1$H-NMR (270 MHz, CDCl$_3$) δ ppm: 1.32 (6H, s), 2.18 (3H, s), 2.81 (2H, s), 6.93 (1H, d, J=9.5 Hz), 7.02 (1H, d, J=7.4 Hz), 7.59 (1H, ddd, J=1.1, 6.9, 8.2 Hz), 7.77 (1H, ddd, J=1.4, 6.9, 8.2 Hz), 7.89 (1H, dd, J=1.1, 8.2 Hz), 8.16 (1H, d, J=8.2 Hz), 8.36 (1H, d, J=2.1 Hz), 9.06 (1H, d, J=2.1 Hz).
MS m/z: 318 (M$^+$), 317, 303, 262.

Example 55

3-(3-ethyl-3-methyl-3,4-dihydroisoquinolin-1-yl)quinoline (Compound No. 1-137)

Physical property: gum.
$^1$H-NMR (270 MHz, CDCl$_3$) δ ppm: 1.01 (3H, t, J=7.4 Hz), 1.25 (3H, s), 1.63 (1H, qd, J=13.0 Hz, 7.4 Hz), 1.73 (1H, qd, J=13.0 Hz, 7.4 Hz), 2.78 (1H, d, J=15.8 Hz), 2.90 (1H, d, J=15.8 Hz), 7.19-7.28 (3H, m), 7.38-7.43 (1H, m), 7.58 (1H, dd, J=7.9 Hz, 7.1 Hz), 7.76 (1H, dd, J=8.5 Hz, 7.1 Hz), 7.87 (1H, d, J=7.9 Hz), 8.16 (1H, d, J=8.5 Hz), 8.37 (1H, d, J=2.1 Hz), 9.12 (1H, d, J=2.1 Hz).
MS m/z: 300 (M$^+$), 285, 271, 255, 245, 230, 202, 128.

Example 56

3-(3-ethyl-5-fluoro-3-methyl-3,4-dihydroisoquinolin-1-yl)quinoline (Compound No. 1-147)

Physical property: gum.
$^1$H-NMR (270 MHz, CDCl$_3$) δ ppm: 1.03 (3H, t, J=7.4 Hz), 1.26 (3H, s), 1.65 (1H, qd, J=14.0 Hz, 7.4 Hz), 1.74 (1H, qd, J=14.0 Hz, 7.4 Hz), 2.82 (1H, d, J=16.4 Hz), 2.88 (1H, d, J=16.4 Hz), 7.04 (1H, dd, J=6.6 Hz, 2.1 Hz), 7.14-7.23 (2H, m), 7.61 (1H, ddd, J=8.2 Hz, 6.9 Hz, 1.3 Hz), 7.77 (1H, ddd, J=8.2 Hz, 6.9 Hz, 1.3 Hz), 7.87 (1H, d, J=8.2 Hz), 8.15 (1H, d, J=8.2 Hz), 8.35 (1H, d, J=2.1 Hz), 9.10 (1H, d, J=2.1 Hz).
MS m/z: 318 (M$^+$), 303, 289, 263, 248, 220, 134.

Example 57

3-(3-methyl-3-propyl-3,4-dihydroisoquinolin-1-yl)quinoline (Compound No. 1-175)

Physical property: gum.
$^1$H-NMR (270 MHz, CDCl$_3$) δ ppm 0.92 (3H, t, J=7.5 Hz), 1.26 (3H, s), 1.43-1.70 (4H, m), 2.78 (1H, d, J=15.8 Hz), 2.92 (1H, d, J=15.8 Hz), 7.19-7.27 (3H, m), 7.37-7.44 (1H, m), 7.58 (1H, ddd, J=8.2 Hz, 7.1 Hz, 1.3 Hz), 7.76 (1H, ddd, J=8.2 Hz, 7.1 Hz, 1.3 Hz), 7.87 (1H, d, J=8.2 Hz), 8.16 (1H, d, J=8.2 Hz), 8.36 (1H, d, J=2.1 Hz), 9.11 (1H, d, J=2.1 Hz).
MS m/z: 314 (M$^+$), 313, 299, 285, 271, 255, 230, 202, 128.

Example 58

3-(5-fluoro-3-methyl-3-propyl-3,4-dihydroisoquinolin-1-yl)quinoline (Compound No. 1-185)

Physical property: oil.
$^1$H-NMR (270 MHz, CDCl$_3$) δ ppm: 0.93 (3H, t, J=6.3 Hz), 1.28 (3H, s), 1.46-1.72 (4H, m), 2.82 (1H, d, J=16.4 Hz), 2.89 (1H, d, J=16.4 Hz), 7.03 (1H, dd, J=6.5 Hz, 2.1 Hz), 7.14-7.22 (2H, m), 7.59 (1H, ddd, J=8.2 Hz, 6.9 Hz, 1.3 Hz), 7.77 (1H, ddd, J=8.2 Hz, 6.9 Hz, 1.3 Hz), 7.87 (1H, dd, J=8.2 Hz, 1.3 Hz), 8.15 (1H, d, J=8.2 Hz), 8.35 (1H, d, J=2.1 Hz), 9.10 (1H, d, J=2.1 Hz).
MS m/z: 331 (M−1), 315, 303, 289, 275, 263, 248, 149.

Example 59

3-(3-isopropyl-3-methyl-3,4-dihydroisoquinolin-1-yl)quinoline (Compound No. 1-213)

Physical property: gum.
$^1$H-NMR (270 MHz, CDCl$_3$) δ ppm: 0.98 (3H, d, J=6.8 Hz), 1.11 (3H, d, J=6.8 Hz), 1.13 (3H, s), 1.94 (1H, hept, J=6.8 Hz), 2.74 (1H, d, J=15.8 Hz), 2.95 (1H, d, J=15.8 Hz), 7.21-7.28 (3H, m), 7.37-7.44 (1H, m), 7.58 (1H, t, J=8.2 Hz), 7.76 (1H, t, J=8.2 Hz), 7.87 (1H, d, J=8.2 Hz), 8.16 (1H, d, J=8.2 Hz), 8.36 (1H, d, J=2.1 Hz), 9.15 (1H, d, J=2.1 Hz).
MS m/z: 314 (M$^+$), 299, 271, 255, 230.

Example 60

3-(3-isobutyl-3-methyl-3,4-dihydroisoquinolin-1-yl)quinoline (Compound No. 1-251)

Physical property: gum.
$^1$H-NMR (270 MHz, CDCl$_3$) δ ppm: 0.93 (3H, d, J=6.6 Hz), 1.01 (3H, d, J=6.6 Hz), 1.34 (3H, s), 1.40-1.62 (2H, m), 1.96 (1H, bhept, J=6.6 Hz), 2.81 (1H, d, J=15.8 Hz), 2.89 (1H, d, J=15.8 Hz), 7.22-7.27 (3H, m), 7.37-7.44 (1H, m), 7.57 (1H, ddd, J=8.2 Hz, 6.9 Hz, 1.3 Hz), 7.75 (1H, ddd, J=8.2 Hz, 6.9 Hz, 1.3 Hz), 7.86 (1H, d, J=8.2 Hz), 8.16 (1H, d, J=8.2 Hz), 8.36 (1H, d, J=2.1 Hz), 9.15 (1H, d, J=2.1 Hz).
MS m/z: 328 (M$^+$), 313, 285, 271, 257, 245, 230, 128.

Example 61

3-(3-t-butyl-3-methyl-3,4-dihydroisoquinolin-1-yl)quinoline (Compound No. 1-289)

Physical property: oil.
$^1$H-NMR (270 MHz, CDCl$_3$) δ ppm: 0.97 (3H, s), 1.10 (9H, s), 2.67 (1H, d, J=15.6 Hz), 3.14 (1H, d, J=15.6 Hz), 7.20-7.30 (3H, m), 7.37-7.42 (1H, m), 7.58 (1H, t, J=8.4 Hz), 7.75 (1H, t, J=8.4 Hz), 7.87 (1H, d, J=8.4 Hz), 8.17 (1H, d, J=8.4 Hz), 8.36 (1H, s), 9.23 (1H, s).
MS m/z: 328 (M$^+$), 313, 271, 255, 230, 142, 128, 115.

Example 62

3-(3-isopentyl-3-methyl-3,4-dihydroisoquinolin-1-yl)quinoline (Compound No. 1-307)

Physical property: gum.
$^1$H-NMR (270 MHz, CDCl$_3$) δ ppm: 0.86 (3H, d, J=6.6 Hz), 0.89 (3H, d, J=6.6 Hz), 1.25 (3H, s), 1.25-1.75 (5H, m), 2.79 (1H, d, J=15.8 Hz), 2.88 (1H, d, J=15.8 Hz), 7.21-7.27 (3H, m), 7.37-7.43 (1H, m), 7.58 (1H, ddd, J=7.9 Hz, 6.9 Hz, 1.3 Hz), 7.76 (1H, ddd, J=8.5 Hz, 6.9 Hz, 1.3 Hz), 7.87 (1H, d, J=7.9 Hz), 8.16 (1H, d, J=8.5 Hz), 8.36 (1H, d, J=2.1 Hz), 9.12 (1H, d, J=2.1 Hz).
MS m/z: 342 (M$^+$), 341, 327, 285, 271, 257, 245, 230, 202, 128.

Example 63

3-(3,3-diethyl-3,4-dihydroisoquinolin-1-yl)quinoline (Compound No. 1-345)

Physical property: oil.
$^1$H-NMR (270 MHz, CDCl$_3$) δ ppm: 0.96 (6H, t, J=7.4 Hz), 1.53-1.74 (4H, m), 2.82 (2H, s), 7.20-7.25 (3H, m), 7.35-7.41 (1H, m), 7.56 (1H, t, J=8.3 Hz), 7.73 (1H, t, J=8.3 Hz), 7.85 (1H, d, J=8.3 Hz), 8.16 (1H, d, J=8.3 Hz), 8.35 (1H, s), 9.16 (1H, s).
MS m/z: 314 (M$^+$), 285, 255, 230, 128, 116.

Example 64

3-(3-ethyl-3-isobutyl-3,4-dihydroisoquinolin-1-yl)quinoline (Compound No. 1-383)

Physical property: gum.
$^1$H-NMR (270 MHz, CDCl$_3$) δ ppm: 0.90 (3H, d, J=6.0 Hz), 0.98 (3H, t, J=7.4 Hz), 1.00 (3H, d, J=6.0 Hz), 1.44 (1H, dd, J=14.0 Hz, 6.0 Hz), 1.53 (1H, dd, J=14.0 Hz, 6.0 Hz), 1.64-1.97 (3H, m), 2.82 (1H, d, J=15.8 Hz), 2.85 (1H, d, J=15.8 Hz), 7.22-7.26 (3H, m), 7.37-7.44 (1H, m), 7.58 (1H, dd, J=8.2 Hz, 7.1 Hz), 7.76 (1H, dd, J=8.2 Hz, 7.1 Hz), 7.86 (1H, d, J=8.2 Hz), 8.16 (1H, d, J=8.2 Hz), 8.35 (1H, s), 9.16 (1H, s).
MS m/z: 342 (M$^+$), 341, 327, 313, 299, 285, 271, 257, 245, 230, 202, 128.

Example 65

3-(3,3-dipropyl-3,4-dihydroisoquinolin-1-yl)quinoline (Compound No. 1-384)

Physical property: gum.
$^1$H-NMR (270 MHz, CDCl$_3$) δ ppm: 1.26 (6H, d, J=7.1 Hz), 1.31-1.67 (8H, m), 2.83 (2H, s), 7.20-7.26 (3H, m), 7.36-7.43 (1H, m), 7.58 (1H, ddd, J=8.2 Hz, 6.9 Hz, 1.3 Hz), 7.76 (1H, ddd, J=8.2 Hz, 6.9 Hz, 1.3 Hz), 7.87 (1H, d, J=8.2 Hz), 8.15 (1H, d, J=8.2 Hz), 8.34 (1H, d, J=2.1 Hz), 9.12 (1H, d, J=2.1 Hz).
MS m/z: 342 (M$^+$), 341, 313, 299, 285, 271, 257, 230, 149, 128.

Example 66

3-(3-chloromethyl-3-methyl-3,4-dihydroisoquinolin-1-yl)quinoline (Compound No. 1-385)

Physical property: amorphous.
$^1$H-NMR (270 MHz, CDCl$_3$) δ ppm: 1.33 (3H, s), 2.91 (1H, d, J=16.1 Hz), 3.14 (1H, d, J=16.1 Hz), 3.65 (1H, d, J=10.8 Hz), 3.76 (1H, d, J=10.8 Hz), 7.23-7.34 (3H, m), 7.43-7.49 (1H, m), 7.60 (1H, ddd, J=8.5 Hz, 7.1 Hz, 1.3 Hz), 7.78 (1H, ddd, J=8.5 Hz, 7.1 Hz, 1.3 Hz), 7.88 (1H, d, J=8.5 Hz), 8.17 (1H, d, J=8.5 Hz), 8.38 (1H, d, J=2.1 Hz), 9.11 (1H, d, J=2.1 Hz).
MS m/z: 340 (M$^+$), 311, 269, 255, 242, 230, 149.

Example 67

3-(3-dichloromethyl-3-methyl-3,4-dihydroisoquinolin-1-yl)quinoline (Compound No. 1-386)

Physical property: gum.
$^1$H-NMR (270 MHz, CDCl$_3$) δ ppm: 1.37 (3H, s), 3.02 (1H, d, J=15.8 Hz), 3.41 (1H, d, J=15.8 Hz), 6.01 (1H, s), 7.28-7.37 (3H, m), 7.44-7.51 (1H, m), 7.60 (1H, dd, J=8.2 Hz, 6.9 Hz), 7.78 (1H, dd, J=8.2 Hz, 6.9 Hz), 7.89 (1H, d, J=8.2 Hz), 8.17 (1H, d, J=8.2 Hz), 8.39 (1H, d, J=2.1 Hz), 9.14 (1H, d, J=2.1 Hz).
MS m/z: 354 (M$^+$), 319, 283, 271, 255, 149.

Example 68

3-(3-trifluoromethyl-3-methyl-3,4-dihydroisoquinolin-1-yl)quinoline (Compound No. 1-387)

Physical property: gum.
$^1$H-NMR (270 MHz, CDCl$_3$) δ ppm: 1.63 (3H, s), 3.78 (1H, d, J=16.9 Hz), 4.50 (1H, d, J=16.9 Hz), 7.33-7.44 (2H, m), 7.55-7.65 (3H, m), 7.79 (1H ddd, J=8.2 Hz, 7.1 Hz, 1.3 Hz), 7.87 (1H, d, J=8.2 Hz), 8.18 (1H, d, J=8.2 Hz), 8.35 (1H, d, J=2.1 Hz), 9.12 (1H, d, J=2.1 Hz).
MS m/z: 340 (M$^+$), 311, 269, 255, 242, 230, 149.

Example 69

3-(3-trifluoroethyl-3-methyl-3,4-dihydroisoquinolin-1-yl)quinoline (Compound No. 1-424)

Physical property: gum.
$^1$H-NMR (270 MHz, CDCl$_3$) δ ppm: 1.44 (3H, s), 2.41 (1H, qd, J=15.1 Hz, 11.6 Hz), 2.60 (1H, qd, J=15.1 Hz, 11.6 Hz), 2.98 (1H, d, J=15.0 Hz), 3.06 (1H, d, J=15.0 Hz), 7.24-7.32 (3H, m), 7.43-7.49 (1H, m), 7.59 (1H, dd, J=8.2 Hz, 6.9 Hz), 7.78 (1H, dd, J=8.2 Hz, 6.9 Hz), 7.88 (1H, d, J=8.2 Hz), 8.17 (1H, d, J=8.2 Hz), 8.38 (1H, d, J=1.8 Hz), 9.13 (1H, d, J=1.8 Hz).
MS m/z: 354 (M$^+$), 340, 286, 272, 256, 231, 136.

Example 70

3-[3,3-di(chloromethyl)-3,4-dihydroisoquinolin-1-yl]quinoline (Compound No. 1-212)

Physical property: gum.
$^1$H-NMR (270 MHz, CDCl$_3$) δ ppm: 3.15 (2H, s), 3.68 (2H, d, J=11.1 Hz), 3.87 (2H, d, J=11.1 Hz), 7.30-7.38 (3H, m), 7.45-7.53 (1H, m), 7.61 (1H, ddd, J=8.2 Hz, 6.9 Hz, 1.3 Hz), 7.79 (1H, ddd, J=8.2 Hz, 6.9 Hz, 1.3 Hz), 7.90 (1H, dd, J=8.2 Hz, 1.3 Hz), 8.17 (1H, d, J=8.2 Hz), 8.41 (1H, d, J=2.1 Hz), 9.14 (1H, d, J=2.1 Hz).
MS m/z: 354 (M$^+$), 319, 305, 283, 269, 255, 229.

Example 71

3-(3-methyl-3-phenyl-3,4-dihydroisoquinolin-1-yl)quinoline (Compound No. 1-464)

Physical property: amorphous.
$^1$H-NMR (270 MHz, CDCl$_3$) δ ppm: 1.60 (3H, s), 3.18 (1H, d, J=15.8 Hz), 3.30 (1H, d, J=15.8 Hz), 7.17-7.44 (7H, m), 7.57-7.63 (3H, m), 7.78 (1H, ddd, J=1.3, 6.9, 8.2 Hz), 7.90 (1H, dd, J=1.1, 7.9 Hz), 8.18 (1H, d, J=8.2 Hz), 8.47 (1H, d, J=2.1 Hz), 9.26 (1H, d, J=2.1 Hz).
MS m/z: 348 (M$^+$), 333 271, 245, 230.

Example 72

3-[3-(4-fluorophenyl)-3-methyl-3,4-dihydroisoquinolin-1-yl]quinoline (Compound No. 1-502)

Physical property: gum.
$^1$H-NMR (270 MHz, CDCl$_3$) δ ppm: 1.57 (3H, s), 3.17 (1H, d, J=15.8 Hz), 3.24 (1H, d, J=15.8 Hz), 6.99 (2H, t, J=8.7 Hz), 7.21-7.45 (4H, m), 7.56-7.63 (3H, m), 7.78 (1H, ddd, J=8.2 Hz, 6.9 Hz, 1.0 Hz), 7.90 (1H, d, J=8.2 Hz), 8.19 (1H, d, J=8.2 Hz), 8.46 (1H, d, J=2.1 Hz), 9.25 (1H, d, J=2.1 Hz).
MS m/z: 367 (M+1), 352, 272, 246, 231, 184.

Example 73

3-[3-(4-chlorophenyl)-3-methyl-3,4-dihydroisoquinolin-1-yl]quinoline (Compound No. 1-540)

Physical property: gum.
$^1$H-NMR (270 MHz, CDCl$_3$) δ ppm: 1.56 (3H, s), 3.15 (1H, d, J=15.8 Hz), 3.25 (1H, d, J=15.8 Hz), 7.26-7.45 (6H, m), 7.56 (2H, d, J=8.7 Hz), 7.60 (1H, ddd, J=8.2 Hz, 6.9 Hz, 1.0 Hz), 7.78 (1H, ddd, J=8.2 Hz, 6.9 Hz, 1.0 Hz), 7.90 (1H, d, J=8.2 Hz), 8.19 (1H, d, J=8.2 Hz), 8.46 (1H, d, J=2.1 Hz), 9.25 (1H, d, J=2.1 Hz).
MS m/z: 383 (M+1), 368, 272, 246, 231, 150.

Example 74

3-(3-trifluoromethyl-3-phenyl-3,4-dihydroisoquinolin-1-yl)quinoline (Compound No. 1-578)

Physical property: amorphous.
$^1$H-NMR (270 MHz, CDCl$_3$) δ ppm: 3.57 (1H, d, J=15.8 Hz), 3.64 (1H, d, J=15.8 Hz), 7.18-7.30 (5H, m), 7.34-7.42 (2H, m), 7.56 (2H, d, J=7.1 Hz), 7.63 (1H, ddd, J=8.2 Hz, 6.9 Hz, 1.3 Hz), 7.79 (1H, ddd, J=8.2 Hz, 6.9 Hz, 1.3 Hz), 7.94 (1H, d, J=8.2 Hz), 8.19 (1H, d, J=8.2 Hz), 8.54 (1H, d, J=2.1 Hz), 9.29 (1H, d, J=2.1 Hz).
MS m/z: 402 (M$^+$), 361, 333, 325, 255, 230, 166, 128.

Example 75

3-[3-chloromethyl-3-(4-fluorophenyl)-3,4-dihydroisoquinolin-1-yl]quinoline (Compound No. 1-594)

Physical property: gum.
$^1$H-NMR (270 MHz, CDCl$_3$) δ ppm: 3.46 (1H, d, J=16.1 Hz), 3.52 (1H, d, J=16.1 Hz), 3.94 (2H, s), 6.98 (2H, t, J=8.7 Hz), 7.21-7.26 (2H, m), 7.36-7.47 (2H, m), 7.52-7.65 (3H, m), 7.80 (1H, ddd, J=8.5 Hz, 7.1 Hz, 1.3 Hz), 7.91 (1H, d, J=8.5 Hz), 8.18 (1H, d, J=8.5 Hz), 8.44 (1H, d, J=1.8 Hz), 9.24 (1H, d, J=1.8 Hz).
MS m/z: 400 (M$^+$), 365, 351, 245, 230, 175, 128.

Example 76

3-[3-chloromethyl-3-(4-chlorophenyl)-3,4-dihydroisoquinolin-1-yl]quinoline (Compound No. 1-632)

Physical property: gum.
$^1$H-NMR (270 MHz, CDCl$_3$) δ ppm: 3.46 (1H, d, J=16.1 Hz), 3.51 (1H, d, J=16.1 Hz), 3.93 (2H, s), 7.22-7.28 (4H, m), 7.36-7.53 (4H, m), 7.62 (1H, ddd, J=8.2 Hz, 6.9 Hz, 1.3 Hz), 7.80 (1H, ddd, J=8.2 Hz, 6.9 Hz, 1.3 Hz), 7.91 (1H, d, J=8.2 Hz), 8.18 (1H, d, J=8.2 Hz), 8.44 (1H, d, J=2.1 Hz), 9.24 (1H, d, J=2.1 Hz).
MS m/z: 416 (M$^+$), 381, 367, 255, 245, 230, 165, 128.

Example 77

3-[3-methyl-3-(3-pyridyl)-3,4-dihydroisoquinolin-1-yl]quinoline (Compound No. 1-670)

Physical property: gum.
$^1$H-NMR (270 MHz, CDCl$_3$) δ ppm: 1.61 (3H, s), 3.23 (1H, d, J=15.6 Hz), 3.28 (1H, d, J=15.6 Hz), 7.22-7.47 (5H, m), 7.61 (1H, ddd, J=8.2 Hz, 6.9 Hz, 1.3 Hz), 7.79 (1H, ddd, J=8.2 Hz, 6.9 Hz, 1.3 Hz), 7.90 (1H, dd, J=8.2 Hz, 1.3 Hz), 7.99 (1H, dd, J=8.2 Hz, 2.4 Hz, 1.6 Hz), 8.19 (1H, d, J=8.2 Hz), 8.45 (1H, d, J=1.6 Hz), 8.47 (1H, dd, J=2.4 Hz, 1.6 Hz), 8.85 (1H, d, J=2.1 Hz), 9.25 (1H, d, J=2.1 Hz).
MS m/z: 349 (M$^+$), 334, 305, 271, 245, 230, 195.

Example 78

3-[3-methyl-3-(4-pyridyl)-3,4-dihydroisoquinolin-1-yl]quinoline (Compound No. 1-671)

Physical property: gum.
$^1$H-NMR (500 MHz, CDCl$_3$) δ ppm: 1.55 (3H, s), 3.03 (1H, d, J=13.8 Hz), 3.18 (1H, d, J=13.8 Hz), 7.27-7.46 (4H, m), 7.55 (2H, d, J=6.3 Hz), 7.61 (1H, ddd, J=8.2 Hz, 6.9 Hz, 1.3 Hz), 7.79 (1H, ddd, J=8.2 Hz, 6.9 Hz, 1.3 Hz), 7.91 (1H, d, J=8.2 Hz), 8.19 (1H, d, J=8.2 Hz), 8.46 (1H, d, J=2.1 Hz), 8.55 (2H, d, J=6.3 Hz), 9.26 (1H, d, J=2.1 Hz).
MS m/z: 349 (M$^+$), 334, 271, 245, 230, 175.

Example 79

3-(3-Benzyl-3-methyl-3,4-dihydroisoquinolin-1-yl)quinoline (Compound No. 1-672)

Physical property: gum.
$^1$H-NMR (270 MHz, CDCl$_3$) δ ppm: 1.32 (3H, s), 2.74 (1H, d, J=15.8 Hz), 2.84 (1H, d, J=13.0 Hz), 2.87 (1H, d, J=15.8 Hz), 2.93 (1H, d, J=13.0 Hz), 7.18-7.31 (8H, m), 7.41-7.47 (1H, m), 7.59 (1H, dd, J=8.2 Hz, 6.9 Hz), 7.77 (1H, dd, J=8.2 Hz, 6.9 Hz), 7.88 (1H, d, J=8.2 Hz), 8.17 (1H, d, J=8.2 Hz), 8.39 (1H, d, J=2.1 Hz), 9.16 (1H, d, J=2.1 Hz).
MS m/z: 362 (M$^+$), 361, 341, 313, 299, 271, 255, 230.

Example 80

1'-quinolin-3-yl-4'H-spiro[cyclopentane-1,3'-isoquinoline] (Compound No. 1-710)

Physical property: oil.
$^1$H-NMR (270 MHz, CDCl$_3$) δ ppm: 1.55-1.96 (8H, m), 2.91 (2H, s), 7.19-7.26 (3H, m), 7.29-7.38 (1H, m), 7.58 (1H, t, J=8.5 Hz), 7.76 (1H, t, J=8.5 Hz), 7.87 (1H, d, J=8.5 Hz), 8.15 (1H, d, J=8.5 Hz), 8.37 (1H, d, J=2.3 Hz), 9.13 (1H, d, J=2.3 Hz).
MS m/z: 312 (M$^+$), 311, 283, 270, 230, 149, 128, 115.

Example 81

5'-fluoro-1'-quinolin-3-yl-4'H-spiro[cyclopentane-1,3'-isoquinoline] (Compound No. 1-720)

Physical property: oil.
$^1$H-NMR (500 MHz, CDCl$_3$) δ ppm: 1.74-1.98 (8H, m), 2.93 (2H, s), 7.04 (1H, d, J=7.6 Hz), 7.17-7.23 (2H, m), 7.59 (1H, t, J=8.2 Hz) 7.77 (1H, ddd, J=1.4, 6.9, 8.2 Hz), 7.87 (1H, d, J=8.2 Hz), 8.16 (1H, d, J=8.2 Hz), 8.35 (1H, d, J=2.1 Hz), 9.12 (1H, d, J=2.1 Hz).
MS m/z: 330 (M$^+$), 301, 288, 273, 248, 149.

Example 82

6'-fluoro-1'-quinolin-3-yl-4'H-spiro[cyclopentane-1,3'-isoquinoline] (Compound No. 1-721)

Physical property: oil.
$^1$H-NMR (270 MHz, CDCl$_3$) δ ppm: 1.70-1.99 (8H, m), 2.89 (2H, s), 6.91 (1H, td, J=2.6, 8.6 Hz), 6.99 (1H, dd, J=2.3, 8.6 Hz), 7.21 (1H, dd, J=5.6, 8.6 Hz), 7.58 (1H, t, J=7.9 Hz) 7.75 (1H, t, J=8.2 Hz), 7.86 (1H, d, J=7.9 Hz), 8.15 (1H, d, J=8.2 Hz), 8.34 (1H, d, J=2.0 Hz), 9.11 (1H, d, J=2.0 Hz).
MS m/z: 330 (M$^+$), 301, 288, 273, 248, 149.

Example 83

7'-fluoro-1'-quinolin-3-yl-4'H-spiro[cyclopentane-1,3'-isoquinoline] (Compound No. 1-722)

Physical property: oil.
$^1$H-NMR (500 MHz, CDCl$_3$) δ ppm: 1.70-1.98 (8H, m), 2.87 (2H, s), 6.94 (1H, dd, J=2.7, 8.9 Hz), 7.12 (1H, td, J=2.7, 8.2 Hz), 7.24-7.26 (1H, m), 7.60 (1H, t, J=8.2 Hz), 7.78 (1H, t, J=8.2 Hz), 7.89 (1H, d, J=8.2 Hz), 8.17 (1H, d, J=8.2 Hz), 8.35 (1H, d, J=2.1 Hz), 9.13 (1H, d, J=2.1 Hz).
MS m/z: 330 (M$^+$), 301, 288, 273, 248.

Example 84

6'-fluoro-1'-(4-methylquinoline)-3-yl-4'H-spiro[cyclopentane-1,3'-isoquinoline] (Compound No. 1-723)

Physical property: oil.
$^1$H-NMR (500 MHz, CDCl$_3$) δ ppm: 1.77-1.96 (8H, m), 2.56 (3H, s), 2.96 (2H, s), 6.69-6.85 (2H, m), 6.98 (1H, dd, J=2.1, 8.9 Hz), 7.61 (1H, ddd, J=1.4, 6.9, 7.6 Hz) 7.75 (1H, ddd, J=1.4, 6.9, 8.2 Hz), 8.07 (1H, d, J=7.6 Hz), 8.14 (1H, d, J=8.2 Hz), 8.73 (1H, s).
MS m/z: 344 (M$^+$), 343, 329, 170, 156, 128.

Example 85

5'-chloro-1'-quinolin-3-yl-4'H-spiro[cyclopentane-1,3'-isoquinoline] (Compound No. 1-724)

Physical property: oil.
$^1$H-NMR (270 MHz, CDCl$_3$) δ ppm: 1.69-2.00 (8H, m), 3.02 (2H, s), 7.12-7.22 (2H, m), 7.48 (1H, dd, J=1.3, 7.7 Hz) 7.59 (1H, ddd, J=1.3, 6.9, 7.9 Hz) 7.77 (1H, ddd, J=1.3, 6.9, 8.2 Hz), 7.87 (1H, d, J=7.9 Hz), 8.16 (1H, d, J=8.2 Hz), 8.34 (1H, d, J=2.1 Hz), 9.09 (1H, d, J=2.1 Hz).
MS m/z: 346 (M$^+$), 311, 304, 279, 264, 231.

Example 86

1'-quinolin-3-yl-4'H-spiro[cyclohexane-1,3'-isoquinoline] (Compound No. 1-749)

Physical property: oil.
$^1$H-NMR (270 MHz, CDCl$_3$) δ ppm: 1.51-1.54 (6H, m), 1.74-1.81 (4H, m), 2.85 (2H, s), 7.23-7.28 (3H, m), 7.37-7.42 (1H, m), 7.56 (1H, t, J=8.0 Hz), 7.75 (1H, t, J=8.0 Hz), 7.86 (1H, d, J=8.0 Hz), 8.15 (1H, d, J=8.0 Hz), 8.36 (1H, d, J=2.0 Hz), 9.18 (1H, d, J=2.0 Hz).
MS m/z: 326 (M$^+$), 283, 230, 128, 115.

Example 87

1'-(4-methylquinoline)-3-yl-4'H-spiro[cyclohexane-1,3'-isoquinoline] (Compound No. 1-755)

Physical property: oil.
$^1$H-NMR (270 MHz, CDCl$_3$) δ ppm: 1.54-1.80 (10H, m), 2.61 (3H, s), 2.95 (2H, s), 6.84 (1H, d, J=7.6 Hz), 7.10-7.36 (3H, m), 7.60 (1H, t, J=8.0 Hz), 7.73 (1H, t, J=8.0 Hz), 8.06 (1H, d, J=8.0 Hz), 8.14 (1H, d, J=8.0 Hz), 8.77 (1H, s).
MS m/z: 340 (M$^+$), 339, 325, 311, 297, 285, 257, 244.

Example 88

5'-fluoro-1'-quinolin-3-yl-4'H-spiro[cyclohexane-1,3'-isoquinoline] (Compound No. 1-759)

Physical property: oil.
$^1$H-NMR (270 MHz, CDCl$_3$) δ ppm: 1.55-1.83 (10H, m), 2.88 (2H, s), 7.07 (1H, d, J=6.6 Hz), 7.19-7.27 (2H, m), 7.60 (1H, t, J=8.0 Hz), 7.78 (1H, t, J=8.0 Hz), 7.88 (1H, d, J=8.0 Hz), 8.17 (1H, d, J=8.0 Hz), 8.36 (1H, d, J=2.0 Hz), 9.16 (1H, d, J=2.0 Hz).
MS m/z: 344 (M$^+$), 301, 288, 275, 263, 248, 220.

Example 89

6'-fluoro-1'-quinolin-3-yl-4'H-spiro[cyclohexane-1,3'-isoquinoline] (Compound No. 1-760)

Physical property: oil.
$^1$H-NMR (270 MHz, CDCl$_3$) δ ppm: 1.51-1.85 (10H, m), 2.84 (2H, s), 6.88-7.00 (2H, m), 7.21-7.26 (1H, m), 7.59 (1H, t, J=8.4 Hz), 7.76 (1H, t, J=8.4 Hz), 7.87 (1H, d, J=8.4 Hz), 8.16 (1H, d, J=8.4 Hz), 8.35 (1H, s), 9.14 (1H, s).
MS m/z: 344 (M$^+$), 315, 301, 288, 248, 220.

Example 90

7'-fluoro-1'-quinolin-3-yl-4'H-spiro[cyclohexane-1,3'-isoquinoline] (Compound No. 1-761)

Physical property: oil.
$^1$H-NMR (270 MHz, CDCl$_3$) δ ppm: 1.55-1.81 (10H, m), 2.81 (2H, s), 6.95-7.26 (3H, m), 7.60 (1H, t, J=8.0 Hz), 7.77 (1H, t, J=8.0 Hz), 7.88 (1H, d, J=8.0 Hz), 8.17 (1H, d, J=8.0 Hz), 8.36 (1Hs), 9.17 (1H, s).
MS m/z: 344 (M$^+$), 315, 301, 288, 275, 262, 248, 220, 156, 128.

Example 91

6'-fluoro-1'-(4-methylquinoline)-3-yl-4'H-spiro[cyclohexane-1,3'-isoquinoline] (Compound No. 1-762)

Physical property: oil.
$^1$H-NMR (270 MHz, CDCl$_3$) δ ppm: 1.55-1.80 (10H, m), 2.55 (3H, s), 2.92 (2H, s), 6.80-6.84 (2H, m), 6.97 (1H, d, J=7.3 Hz), 7.60 (1H, t, J=8.2 Hz), 7.74 (1H, t, J=8.2 Hz), 8.06 (1H, d, J=8.2 Hz), 8.13 (1H, d, J=8.2 Hz), 8.74 (1H, s).
MS m/z: 358 (M$^+$), 357, 343, 315, 168, 140, 129, 114.

Example 92

6'-chloro-1'-quinolin-3-yl-4'H-spiro[cyclohexane-1,3'-isoquinoline] (Compound No. 1-764)

Physical property: oil.
$^1$H-NMR (270 MHz, CDCl$_3$) δ ppm: 1.47-1.85 (10H, m), 2.83 (2H, s), 7.16-7.27 (3H, m), 7.59 (1H, t, J=8.3 Hz), 7.76 (1H, t, J=8.3 Hz), 7.87 (1H, d, J=8.3 Hz), 8.16 (1H, d, J=8.3 Hz), 8.34 (1H, d, J=2.0 Hz), 9.14 (1H, d, J=2.0 Hz).
MS m/z: 362 (M$^+$+2), 360 (M$^+$), 317, 304, 264, 141, 128, 115.

Example 93

7'-chloro-1'-quinolin-3-yl-4'H-spiro[cyclohexane-1,3'-isoquinoline] (Compound No. 1-765)

Physical property: oil.
$^1$H-NMR (270 MHz, CDCl$_3$) δ ppm: 1.55-1.87 (12H, m), 2.85 (2H, s), 7.20-7.26 (3H, m), 7.37-7.39 (1H, m), 7.58 (1H, t, J=8.6 Hz), 7.75 (1H, t, J=8.6 Hz), 7.87 (1H, d, J=8.6 Hz), 8.15 (1H, d, J=8.6 Hz), 8.36 (1H, d, J=2.0 Hz), 9.14 (1H, d, J=2.0 Hz).
MS m/z: 362 (M$^+$+2), 360 (M$^+$), 317, 304, 264, 229, 128, 115.

Example 94

6'-chloro-1'-(4-methylquinoline)-3-yl-4'H-spiro[cyclohexane-1,3'-isoquinoline] (Compound No. 1-766)

Physical property: oil.
$^1$H-NMR (270 MHz, CDCl$_3$) δ ppm: 1.55-1.81 (10H, m), 2.54 (3H, s), 2.91 (2H, s), 6.78 (1H, d, J=8.2 Hz), 7.10-7.29 (2H, m), 7.61 (1H, t, J=8.2 Hz), 7.74 (1H, t, J=8.2 Hz), 8.07 (1H, d, J=8.2 Hz), 8.14 (1H, d, J=8.2 Hz), 8.74 (1H, s).
MS m/z: 376 (M$^+$+2), 374 (M$^+$), 373, 357, 331, 170, 141, 115.

Example 95

6'-bromo-1'-quinolin-3-yl-4'H-spiro[cyclohexane-1,3'-isoquinoline] (Compound No. 1-764)

Physical property: oil.
$^1$H-NMR (270 MHz, CDCl$_3$) δ ppm: 1.50-1.84 (10H, m), 2.81 (2H, s), 7.11 (1H, d, J=8.1 Hz), 7.38 (1H, d, J=8.1 Hz), 7.42 (1H, s), 7.57 (1H, t, J=8.3 Hz), 7.75 (1H, t, J=8.3 Hz), 7.85 (1H, d, J=8.3 Hz), 8.15 (1H, d, J=8.3 Hz), 8.33 (1H, d, J=2.0 Hz), 9.15 (1H, d, J=2.0 Hz).
MS m/z: 406 (M$^+$+2), 404 (M$^+$), 375, 361, 349, 325, 268, 229, 141, 128, 115.

Example 96

5'-methyl-1'-quinolin-3-yl-4'H-spiro[cyclohexane-1,3'-isoquinoline] (Compound No. 1-771)

Physical property: oil.
$^1$H-NMR (270 MHz, CDCl$_3$) δ ppm: 1.52-1.86 (10H, m), 2.39 (3H, s), 2.80 (2H, s), 7.06-7.16 (2H, m), 7.26-7.30 (1H, m), 7.57 (1H, t, J=8.0 Hz), 7.75 (1H, t, J=8.0 Hz), 7.86 (1H, d, J=8.0 Hz), 8.15 (1H, d, J=8.0 Hz), 8.35 (1H, s), 9.14 (1H, s).
MS m/z: 340 (M$^+$), 297, 284, 244, 149, 128, 115.

Example 97

7'-methyl-1'-quinolin-3-yl-4'H-spiro[cyclohexane-1,3'-isoquinoline] (Compound No. 1-773)

Physical property: oil.
$^1$H-NMR (270 MHz, CDCl$_3$) δ ppm: 1.51-1.84 (10H, m), 2.27 (3H, s), 2.81 (2H, s), 7.03 (1H, s), 7.16 (1H, d, J=7.6 Hz), 7.26 (1H, d, J=7.6 Hz), 7.58 (1H, t, J=8.0 Hz), 7.76 (1H, t, J=8.0 Hz), 7.89 (1H, d, J=8.0 Hz), 8.16 (1H, d, J=8.0 Hz), 8.38 (1H, s), 9.15 (1H, s).
MS m/z: 340 (M$^+$), 325, 311, 297, 284, 271, 258, 244, 142, 128.

Example 98

6'-methyl-1'-(4-methylquinoline)-3-yl-4'H-spiro[cyclohexane-1,3'-isoquinoline] (Compound No. 1-774)

Physical property: oil.
$^1$H-NMR (270 MHz, CDCl$_3$) δ ppm: 1.53-1.80 (10H, m), 2.35 (3H, s), 2.55 (3H, s), 2.88 (2H, s), 6.72 (1H, d, J=7.9 Hz), 6.92 (1H, d, J=7.9 Hz), 7.06 (1H, s), 7.58 (1H, t, J=8.2 Hz), 7.71 (1H, t, J=8.2 Hz), 8.05 (1H, d, J=8.2 Hz), 8.13 (1H, d, J=8.2 Hz), 8.76 (1H, s).
MS m/z: 354 (M$^+$), 353, 339, 311, 298, 168, 149, 115.

Example 99

6'-cyano-1'-quinolin-3-yl-4'H-spiro[cyclohexane-1,3'-isoquinoline] (Compound No. 1-786)

Physical property: oil.
$^1$H-NMR (270 MHz, CDCl$_3$) δ ppm: 1.47-1.84 (10H, m), 2.88 (2H, s), 7.37 (1H, d, J=8.2 Hz), 7.55-7.78 (3H, m), 7.81 (1H, t, J=8.0 Hz), 7.88 (1H, d, J=8.0 Hz), 8.16 (1H, d, J=8.0 Hz), 8.33 (1H, d, J=2.0 Hz), 9.14 (1H, d, J=2.0 Hz).
MS m/z: 351 (M$^+$), 322, 308, 295, 270, 255, 227.

Example 100

1'-quinolin-3-yl-4'H-spiro[cycloheptane-1,3'-isoquinoline] (Compound No. 1-789)

Physical property: oil.

$^1$H-NMR (270 MHz, CDCl$_3$) δ ppm: 1.55-1.87 (12H, m), 2.85 (2H, s), 7.20-7.26 (3H, m), 7.37-7.39 (1H, m), 7.58 (1H, t, J=8.6 Hz), 7.75 (1H, t, J=8.6 Hz), 7.87 (1H, d, J=8.6 Hz), 8.15 (1H, d, J=8.6 Hz), 8.36 (1H, d, J=2.0 Hz), 9.14 (1H, d, J=2.0 Hz).

MS m/z: 340 (M$^+$), 283, 271, 230, 149, 128, 115.

Example 101

1'-quinolin-3-yl-4'H-spiro[(3-methylcyclopentane)-1,3'-isoquinoline] (Compound No. 1-774)

Physical property: oil.

$^1$H-NMR (270 MHz, CDCl$_3$) δ ppm: 1.06-2.89 (10H, s), 2.93 (2H, s), 7.19-7.307 (3H, m), 7.38-7.44 (1H, m), 7.58 (1H, t, J=8.3 Hz), 7.76 (1H, t, J=8.3 Hz), 7.88 (1H, d, J=8.3 Hz), 8.17 (1H, d, J=8.3 Hz), 8.37 (1H, s), 9.14 (1H, s).

MS m/z: 326 (M$^+$), 325, 311, 297, 283, 271, 230, 128, 115.

Example 102

1-quinolin-3-yl-2',3',5',6'-tetrahydro-4H-spiro[isoquinoline-3,4'-pyran] (Compound No. 1-791)

Physical property: oil.

$^1$H-NMR (270 MHz, CDCl$_3$) δ ppm: 1.72-1.76 (4H, m), 2.84 (2H, s), 3.76-3.83 (2H, m), 4.05-4.14 (2H, m), 7.19-7.30 (3H, m), 7.40-7.45 (1H, m), 7.58 (1H, t, J=8.2 Hz), 7.76 (1H, t, J=8.2 Hz), 7.87 (1H, d, J=8.2 Hz), 8.15 (1H, d, J=8.2 Hz), 8.38 (1H, s), 9.20 (1H, s).

MS m/z: 328 (M$^+$), 299, 283, 271, 255, 230, 128, 115.

Example 103

3-(5-fluoro-3,3-dimethyl-3,4-dihydroisoquinolin-1-yl)quinoline hydrochloride (Compound No. 1-793)

Physical property: amorphous.

$^1$H-NMR (500 MHz, CDCl$_3$) δ ppm: 1.78 (6H, s), 3.31 (2H, brs), 7.26-7.47 (1H, m) 7.54 (2H, brs), 7.91 (1H, brs), 8.12 (1H, brs), 8.37 (1H, brs), 8.62 (1H, brs), 9.41 (1H, brs), 9.87 (1H, brs).

Example 104

3-(5-fluoro-3,3-dimethyl-3,4-dihydroisoquinolin-1-yl)quinoline sulfate (Compound No. 1-796)

Physical property: amorphous.

$^1$H-NMR (500 MHz, D$_2$O) δ ppm: 1.51 (6H, s), 3.26 (2H, s), 7.25 (1H, d, J=7.6 Hz) 7.42 (1H, td, J=5.5, 7.6 Hz), 7.58 (1H, t, J=8.2 Hz), 7.95 (1H, t, J=8.2 Hz), 8.19 (1H, ddd, J=1.4, 6.9, 8.2 Hz), 8.25 (1H, d, J=8.9 Hz), 8.26 (1H, d, J=8.9 Hz), 9.27 (1H, d, J=2.1 Hz), 9.29 (1H, d, J=2.1 Hz)

Example 105

3-(5-fluoro-3,3-dimethyl-3,4-dihydroisoquinolin-1-yl)quinoline nitrate (Compound No. 1-799)

Melting point: 190-193° C.

$^1$H-NMR (500 MHz, CDCl$_3$) δ ppm: 1.63 (6H, s), 3.18 (2H, s), 7.29 (1H, d, J=7.6 Hz) 7.45-7.53 (2H, m), 7.75-7.78 (1H, m), 7.96-7.99 (1H, m), 8.10 (1H, d, J=8.2 Hz), 8.26 (1H, d, J=8.9 Hz), 9.06-9.07 (2H, m).

Example 106

3-(5-fluoro-3,3-dimethyl-3,4-dihydroisoquinolin-1-yl)quinoline oxalate (Compound No. 1-802)

Physical property: amorphous.

$^1$H-NMR (500 MHz, CDCl3) δ ppm: 1.48 (6H, s), 3.03 (2H, s), 7.14 (1H, dd, J=3.4, 5.5 Hz), 7.33-7.35 (2H, m), 7.70 (1H, t, J=8.2 Hz), 7.89 (1H, t, J=8.2 Hz), 7.96 (1H, t, J=8.2 Hz), 8.28 (1H, d, J=8.2 Hz), 8.68 (1H, s), 9.12 (1H, d, J=1.4 Hz)

Example 107

3-(5-fluoro-3,3-dimethyl-3,4-dihydroisoquinolin-1-yl)quinoline methanesulfonate (Compound No. 1-804)

Melting point: 227-230° C.

$^1$H-NMR (500 MHz, CDCl$_3$) δ ppm: 1.77 (6H, s), 2.76 (6H, s), 3.31 (2H, s), 7.26-7.27 (1H, m) 7.51-7.59 (2H, m), 7.95 (1H, t, J=8.2 Hz), 8.16 (1H, ddd, J=1.4, 6.9, 8.2 Hz), 8.42 (1H, d, J=8.2 Hz), 8.55 (1H, d, J=8.2 Hz), 9.40 (1H, s), 9.91 (1H, s).

Example 108

3-(5-fluoro-3,3-dimethyl-3,4-dihydroisoquinolin-1-yl)quinoline salicylate (Compound No. 1-806)

Physical property: oil.

$^1$H-NMR (500 MHz, CDCl3) δ ppm: 1.42 (6H, s), 2.93 (2H, s), 6.83-6.86 (1H, m) 6.94 (1H, d, J=8.2 Hz), 7.05 (1H, d, J=6.9 Hz), 7.22-7.29 (2H, m), 7.39-7.45 (1H, m), 7.64 (1H, dd, J=6.9, 8.2 Hz), 7.83 (1H, ddd, J=1.4, 6.9, 8.9 Hz), 7.88-7.90 (1H, m), 7.91 (1H, d, J=8.2 Hz), 8.29 (1H, d, J=8.2 Hz), 8.54 (1H, d, J=2.1 Hz), 9.18 (1H, d, J=2.1 Hz).

Example 109

3-(5-fluoro-3,3-dimethyl-3,4-dihydroisoquinolin-1-yl)quinoline fumarate (Compound No. 1-807)

Melting point: 146-149° C.

$^1$H-NMR (500 MHz, CDCl$_3$) δ ppm: 1.26 (6H, s), 2.84 (2H, s), 6.63 (4H, s), 7.14 (1H, dd, J=1.4, 7.6 Hz), 7.35-7.43 (2H, m), 7.68 (1H, t, J=8.2 Hz), 7.84 (1H, ddd, J=1.4, 6.9, 8.2 Hz), 8.09-8.12 (2H, m), 8.50 (1H, d, J=2.1 Hz), 9.04 (1H, d, J=2.1 Hz), 13.13 (2H, br s)

Example 110

3-(5-fluoro-3,3-dimethyl-1,2,3,4-tetrahydroisoquinoline-1-yl)quinoline (Compound No. 2-36)

Melting point: 142-144° C.
$^1$H-NMR (270 MHz, CDCl$_3$) δ ppm: 1.27 (3H, s), 1.35 (3H, s), 2.74 (1H, d, J=16.5 Hz), 2.86 (1H, d, J=16.5 Hz), 5.35 (1H, s), 6.51 (1H, d, J=7.9 Hz), 6.87-7.03 (2H, m), 7.54 (1H, t, J=7.9 Hz), 7.70 (1H, t, J=7.9 Hz), 7.79 (1H, d, J=7.9 Hz), 8.09 (1H, d, J=2.1 Hz), 8.10 (1H, d, J=7.9 Hz), 8.84 (1H, d, J=2.1 Hz).
MS m/z: 306 (M$^+$), 291, 248, 220, 178, 162.

Example 111

3-(5-fluoro-1,3,3-trimethyl-1,2,3,4-tetrahydroisoquinoline-1-yl)quinoline (Compound No. 2-37)

Melting point: 148-150° C.
$^1$H-NMR (270 MHz, CDCl$_3$) δ ppm: 1.01 (3H, s), 1.39 (3H, s), 2.15 (3H, s), 2.84 (1H, d, J=16.3 Hz), 2.86 (1H, d, J=16.3 Hz), 4.59 (1H, s), 6.43 (1H, d, J=7.7 Hz), 6.78-6.91 (2H, m), 7.53 (1H, t, J=8.2 Hz), 7.68 (1H, t, J=8.2 Hz), 7.80 (1H, d, J=8.2 Hz), 8.06 (1H, d, J=1.8 Hz), 8.08 (1H, d, J=8.2 Hz), 8.81 (1H, d, J=1.8 Hz).
MS m/z: 320 (M$^+$), 305, 248, 192, 176, 161.

Example 112

3-(5-chloro-3,3-dimethyl-1,2,3,4-tetrahydroisoquinoline-1-yl)quinoline (Compound No. 2-40)

Melting point: 129-131° C.
$^1$H-NMR (270 MHz, CDCl$_3$) δ ppm: 1.26 (3H, s), 1.35 (3H, s), 2.78 (1H, d, J=16.5 Hz), 2.92 (1H, d, J=16.5 Hz), 5.34 (1H, s), 6.63 (1H, d, J=8.2 Hz), 6.94 (1H, t, J=8.2 Hz), 7.25 (1H, d, J=8.2 Hz), 7.52 (1H, t, J=7.6 Hz), 7.69 (1H, t, J=7.6 Hz), 7.77 (1H, d, J=7.6 Hz), 8.08 (1H, d, J=2.1 Hz), 8.10 (1H, d, J=8.2 Hz), 8.83 (1H, d, J=2.1 Hz).
MS m/z: 322 (M$^+$), 307, 264, 230, 194, 178, 130, 115.

Example 113

3-(5-chloro-1,3,3-trimethyl-1,2,3,4-tetrahydroisoquinoline-1-yl)quinoline (Compound No. 2-41)

Melting point: 142-144° C.
$^1$H-NMR (270 MHz, CDCl$_3$) δ ppm: 1.00 (3H, s), 1.40 (3H, s), 2.14 (3H, s), 2.95 (1H, d, J=15.8 Hz), 2.97 (1H, d, J=15.8 Hz), 4.60 (1H, s), 6.56 (1H, d, J=7.9 Hz), 6.88 (1H, t, J=7.9 Hz), 7.11 (1H, d, J=7.9 Hz), 7.53 (1H, t, J=8.2 Hz), 7.68 (1H, t, J=8.2 Hz), 7.79 (1H, d, J=8.2 Hz), 8.05 (1H, d, J=2.0 Hz), 8.08 (1H, d, J=8.2 Hz), 8.79 (1H, d, J=2.0 Hz).
MS m/z: 336 (M$^+$), 323, 321, 264, 230, 208, 192, 142.

Example 114

3-(5-fluoro-3,3,4,4-tetramethyl-3,4-dihydroisoquinolin-1-yl)quinoline (Compound No. 1-866)

Physical property: amorphous.
$^1$H-NMR (270 MHz, CDCl$_3$) δ ppm: 1.33 (6H, s), 1.46 (6H, d, J=3.4 Hz), 6.96 (1H, dd, J=6.6, 2.1 Hz), 7.15-7.20 (2H, m), 7.59 (1H, t, 7.5 Hz), 7.76 (1H, dt, J=11.0, 3.8 Hz), 7.87 (1H, d, J=7.9 Hz), 8.16 (1H, d, J=8.5 Hz), 8.31 (1H, d, J=2.1 Hz), 9.03 (1H, d, J=1.8 Hz).
MS m/z: 332 (M$^+$), 317, 289, 275, 260, 233, 146.

Example 115

3-(3,3-dimethyl-3,4-dihydroisoquinolin-1-yl)-2-methylquinoline (Compound No. 1-14)

Physical property: oil.
$^1$H-NMR (500 MHz, CDCl$_3$) δ ppm: 1.37 (6H, s), 2.58 (3H, s), 2.91 (2H, s), 6.85 (1H, d, J=7.4 Hz), 7.14 (1H, t, J=7.4 Hz), 7.26 (1H, d, J=7.4 Hz), 7.38 (1H, t, J=7.4 Hz), 7.51 (1H, t, J=7.7 Hz), 7.71 (1H, t, J=7.7 Hz), 7.80 (1H, d, J=7.7 Hz), 8.06 (1H, s), 8.07 (1H, d, J=7.7 Hz).
MS m/z: 300 (M$^+$), 299, 285, 269, 257, 244, 229.

Example 116

3-(5-ethyl-3,3-dimethyl-3,4-dihydroisoquinolin-1-yl)quinoline (Compound No. 1-73)

Physical property: oil.
$^1$H-NMR (500 MHz, CDCl$_3$) δ ppm: 1.25 (3H, t, J=7.7 Hz), 1.34 (6H, s), 2.77 (2H, q, J=7.7 Hz), 2.83 (2H, s), 7.05 (1H, d, J=7.7 Hz), 7.16 (1H, t, J=7.7 Hz), 7.32 (1H, d, J=7.7 Hz), 7.57 (1H, ddd, J=1.1, 6.6, 8.2 Hz), 7.77 (1H, ddd, J=1.1, 6.6, 8.2 Hz), 7.86 (1H, d, J=8.2 Hz), 8.15 (1H, d, J=8.2 Hz), 8.36 (1H, d, J=2.2 Hz), 9.08 (1H, d, J=2.2 Hz)
MS m/z: 314 (M$^+$), 313, 299, 285, 269, 242, 229, 128.

Example 117

1-(3,3-dimethyl-1-quinolin-3-yl-3,4-dihydroisoquinolin-5-yl)methanone=O-methyloxime (Compound No. 1-99)

Stereoisomer of Compound of Example 118
Physical property: oil.
$^1$H-NMR (500 MHz, CDCl$_3$) δ ppm: 1.34 (6H, s), 2.96 (2H, s), 4.03 (3H, s), 7.23-7.27 (2H, m), 7.59 (1H, ddd, J=1.1, 7.1, 8.2 Hz), 7.77 (1H, ddd, J=1.6, 6.6, 8.2 Hz), 7.85-7.88 (2H, m), 8.16 (1H, d, J=8.2 Hz), 8.35 (1H, d, J=2.2 Hz), 8.42 (1H, s), 9.07 (1H, d, J=2.2 Hz).
MS m/z: 343 (M$^+$), 328, 312, 296, 285, 269, 255, 128.

Example 118

1-(3,3-dimethyl-1-quinolin-3-yl-3,4-dihydroisoquinolin-5-yl)methanone=O-methyloxime (Compound No. 1-99)

Stereoisomer of Compound of Example 117
Physical property: oil.
$^1$H-NMR (500 MHz, CDCl$_3$) δ ppm: 1.33 (6H, s), 2.84 (2H, s), 4.00 (3H, s), 7.23-7.29 (2H, m), 7.59 (1H, ddd, J=1.1, 7.1, 8.2 Hz), 7.63 (1H, s), 7.75-7.78 (2H, s), 7.87 (1H, d, J=8.2 Hz), 8.16 (1H, d, J=8.8 Hz), 8.37 (1H, d, J=2.2 Hz), 9.09 (1H, d, J=2.2 Hz).
MS m/z: 343 (M$^+$), 328, 312, 296, 285, 269, 255, 128.

Example 119

3-(3,3,4-trimethyl-3,4-dihydroisoquinolin-1-yl)quinoline (Compound No. 1-856)

Physical property: oil.
¹H-NMR (270 MHz, CDCl₃) δ ppm: 1.29 (3H, s), 1.31 (6H, s), 2.86 (1H, q, J=7.0 Hz), 7.15-7.28 (2H, m), 7.33 (1H, d, J=7.4 Hz), 7.42 (1H, t, J=6.4 Hz), 7.58 (1H, t, J=7.5 Hz), 7.75 (1H, t, J=7.3 Hz), 7.87 (1H, d, J=7.9 Hz), 8.16 (1H, d, J=8.5 Hz), 8.38 (1H, d, J=2.0 Hz), 9.11 (1H, d, J=1.6 Hz).
MS m/z: 300 (M⁺), 285, 269, 244, 230, 215, 135, 115.

Example 120

3-(5-fluoro-3,3,4-trimethyl-3,4-dihydroisoquinolin-1-yl)quinoline (Compound No. 1-857)

Physical property: oil.
¹H-NMR (270 MHz, CDCl₃) δ ppm: 1.09 (3H, s), 1.20 (3H, d, J=7.1 Hz), 1.62 (3H, s), 3.17 (1H, q, J=7.1), 7.00-7.06 (1H, m), 7.15-7.24 (2H, m), 7.59 (1H, t, J=7.5), 7.79 (1H, t, J=7.6 Hz), 7.88 (1H, d, J=7.7 Hz), 8.17 (1H, d, J=8.5 Hz), 8.36 (1H, d, J=1.8 Hz), 9.09 (1H, d, J=2.1 Hz).
MS m/z: 318 (M⁺), 317, 303, 287, 265, 247, 233, 144, 133, 101, 84.

Example 121

3-(5-chloro-3,3,4-trimethyl-3,4-dihydroisoquinolin-1-yl)quinoline (Compound No. 1-858)

Physical property: oil.
¹H-NMR (270 MHz, CDCl₃) δ ppm: 1.07 (3H, s), 1.18 (3H, d, J=6.9 Hz), 1.63 (3H, s), 3.23 (1H, q, J=7.1 Hz), 7.10-7.20 (2H, m), 7.49 (1H, d, J=7.4 Hz), 7.59 (1H, t, J=7.5 Hz), 7.76 (1H, t, J=7.7 Hz), 7.87 (1H, d, J=7.9 Hz), 8.16 (1H, d, J=8.5 Hz), 8.35 (1H, d, J=1.8), 9.08 (1H, d, J=1.6 Hz).
MS m/z: 334 (M⁺), 319, 303, 278, 263, 242, 152, 128, 101.

Example 122

3-(3,3,4,4-tetramethyl-3,4-dihydroisoquinolin-1-yl)quinoline (Compound No. 1-865)

Physical property: oil.
¹H-NMR (270 MHz, CDCl₃) δ ppm: 1.28 (6H, s), 1.35 (6H, s), 2.04 (2H, s), 7.15-7.26 (2H, m), 7.48 (2H, d, J=3.2 Hz), 7.58 (1H, t, J=7.5 Hz), 7.76 (1H, t, J=7.4 Hz), 7.87 (1H, d, J=7.7 Hz), 8.16 (1H, d, J=8.4 Hz), 8.36 (1H, d, J=2.1 Hz), 9.10 (1H, d, J=1.6 Hz).
MS m/z: 314 (M⁺), 299, 257, 242, 142, 128, 115.

Example 123

3-(5-chloro-3,3,4,4-tetramethyl-3,4-dihydroisoquinolin-1-yl)quinoline (Compound No. 1-867)

Physical property: amorphous.
¹H-NMR (500 MHz, CDCl₃) δ ppm: 1.33 (6H, br s), 1.59 (6H, s), 7.07 (1H, dd, J=1.6, 7.7 Hz), 7.13 (1H, t, J=7.7 Hz), 7.48 (1H, dd, J=1.6, 7.7 Hz), 7.59 (1H, ddd, J=1.1, 6.6, 8.2 Hz), 7.76 (1H, ddd, J=1.1, 6.6, 8.2 Hz), 7.86 (1H, d, J=8.2 Hz), 8.15 (1H, d, J=8.2 Hz), 8.28 (1H, d, J=2.2 Hz), 8.99 (1H, d, J=2.2 Hz).
MS m/z: 348 (M⁺), 347, 333, 305, 276, 256, 128.

Example 124

3-(5-fluoro-3,3,4-trimethyl-1,2,3,4-tetrahydroisoquinoline-1-yl)quinoline (Compound No. 2-255)

Physical property: Melting point 133-134° C.
¹H-NMR (270 MHz, CDCl₃) δ ppm: 1.22 (3H, s), 1.26 (3H, s), 1.40 (3H, d, J=6.9 Hz), 2.92 (1H, q, J=6.6 Hz), 5.31 (1H, s), 6.50 (1H, d, J=7.7 Hz), 6.85-7.03 (2H, m), 7.54 (1H, t, J=7.5 Hz), 7.70 (1H, t, J=7.4 Hz), 7.80 (1H, d, J=7.9 Hz), 8.09 (1H, d, J=2.1), 8.01 (1H, d, J=7.7 Hz), 8.86 (1H, d, J=1.8 Hz).
MS m/z: 320 (M⁺), 305, 263, 248, 162.

Example 125

3-(5-fluoro-3,3,4,4-tetramethyl-1,2,3,4-tetrahydroisoquinoline-1-yl)quinoline (Compound No. 2-264)

Physical property: Melting point 179-181° C.
¹H-NMR (270 MHz, CDCl₃) δ ppm: 1.19 (3H, s), 1.31 (3H, s), 1.46 (3H, d, J=4.8 Hz), 1.55 (3H, s), 5.38 (1H, s), 6.45 (1H, d, J=7.4 Hz), 6.82-6.98 (2H, m), 7.53 (1H, t, J=7.9 Hz), 7.69 (1H, t, J=8.4 Hz), 7.79 (1H, d, J=8.2 Hz), 8.05 (1H, d, J=2.1 Hz), 8.08 (1H, d, J=8.7 Hz), 8.78 (1H, d, J=2.1 Hz).
MS m/z: 334 (M⁺), 332, 319, 277, 262, 248, 149, 133.

Example 126

3-(5-isopropyl-3,3-dimethyl-3,4-dihydroisoquinolin-1-yl)quinoline (Compound No. 1-880)

Physical property: oil.
¹H-NMR (500 MHz, CDCl₃) δ ppm: 1.30 (6H, d, J=6.6 Hz), 1.34 (6H, s), 2.87 (2H, s), 3.27 (1H, sep, J=6.6 Hz), 7.05 (1H, d, J=7.7 Hz), 7.20 (1H, t, J=7.7 Hz), 7.43 (1H, d, J=7.7 Hz), 7.58 (1H, ddd, J=1.1, 6.6, 8.2 Hz), 7.76 (1H, ddd, J=1.1, 6.6, 8.2 Hz), 7.87 (1H, d, J=8.2 Hz), 8.16 (1H, d, J=8.2 Hz), 8.36 (1H, d, J=2.2 Hz), 9.08 (1H, d, J=2.2 Hz).
MS m/z: 328 (M⁺), 327, 313, 297, 285, 271, 256, 128.

Example 127

3-{5-(1-methylpropyl)-3,3-dimethyl-3,4-dihydroisoquinolin-1-yl}quinoline (Compound No. 1-881)

Physical property: oil.
¹H-NMR (500 MHz, CDCl₃) δ ppm: 0.90 (3H, t, J=7.1 Hz), 1.27 (3H, d, J=7.1 Hz), 1.33 (3H, s), 1.35 (3H, s), 1.62-1.72 (2H, m), 2.84 (1H, d, J=15.4 Hz), 2.88 (1H, d, J=15.4Hz), 3.02 (1H, sep, J=7.1 Hz), 7.04 (1H, d, J=7.7 Hz), 7.20 (1H, t, J=7.7 Hz), 7.37 (1H, d, J=7.7 Hz), 7.57 (1H, t, J=7.7 Hz), 7.59 (1H, ddd, J=1.1, 7.1, 8.2 Hz), 7.87 (1H, d, J=7.7 Hz), 8.16 (1H, d, J=8.2 Hz), 8.36 (1H, d, J=2.2 Hz), 9.09 (1H, d, J=2.2 Hz).
MS m/z: 342 (M⁺), 341, 327, 313, 297, 285, 271, 128.

Example 128

3-{5-(1-methylvinyl)-3,3-dimethyl-3,4-dihydroisoquinolin-1-yl}quinoline (Compound No. 1-882)

Physical property: oil.
¹H-NMR (500 MHz, CDCl₃) δ ppm: 1.30 (6H, s), 2.09 (3H, s), 2.85 (2H, s), 4.91-4.92 (1H, m), 5.31-5.32 (1H, m), 7.11 (1H, dd, J=1.1, 7.7 Hz), 7.19 (1H, t, J=7.7 Hz), 7.30 (1H, dd, J=1.1, 7.7 Hz), 7.58 (1H, ddd, J=1.1, 6.6, 8.2 Hz), 7.76

(1H, ddd, J=1.1, 6.6, 8.2 Hz), 7.87 (1H, d, J=8.2 Hz), 8.16 (1H, d, J=8.2 Hz), 8.39 (1H, d, J=2.2 Hz), 9.11 (1H, d, J=2.2 Hz).

MS m/z: 326 (M$^+$), 311, 295, 285, 270, 254, 128.

Example 129

3-{5-(2-methoxycarbonylvinyl)-3,3-dimethyl-3,4-dihydroisoquinolin-1-yl}quinoline (Compound No. 1-883)

Physical property: oil.
$^1$H-NMR (500 MHz, CDCl$_3$) δ ppm: 1.35 (6H, s), 2.98 (2H, s), 3.86 (3H, s), 6.45 (1H, d, J=15.9 Hz), 7.25-7.29 (2H, m), 7.59 (1H, ddd, J=1.1, 7.1, 8.2 Hz), 7.70 (1H, dd, J=1.6, 7.1 Hz), 7.77 (1H, ddd, J=1.1, 6.6, 7.7 Hz), 7.88 (1H, d, J=8.2 Hz), 8.06 (1H, d, J=15.9 Hz), 8.16 (1H, d, J=8.8 Hz), 8.36 (1H, d, J=2.2 Hz), 9.07 (1H, d, J=2.2 Hz).

MS m/z: 370 (M$^+$), 355, 339, 320, 305, 295, 254, 127.

Example 130

3-(5-fluoromethyl-3,3-dimethyl-3,4-dihydroisoquinolin-1-yl)quinoline (Compound No. 1-884)

Physical property: oil.
$^1$H-NMR (500 MHz, CDCl$_3$) δ ppm: 1.36 (6H, s), 2.91 (2H, s), 5.52 (2H, d, J=47.8 Hz), 7.25-7.29 (2H, m), 7.49-7.51 (1H, m), 7.59 (1H, ddd, J=1.1, 6.6, 8.2 Hz), 7.77 (1H, ddd, J=1.1, 6.6, 8.2 Hz), 7.88 (1H, d, J=8.2 Hz), 8.16 (1H, d, J=8.2 Hz), 8.37 (1H, d, J=2.2 Hz), 9.08 (1H, d, J=2.2 Hz).

MS m/z: 318 (M$^+$), 303, 285, 269, 262, 242, 128.

Example 131

3-(5-chloromethyl-3,3-dimethyl-3,4-dihydroisoquinolin-1-yl)quinoline (Compound No. 1-885)

Physical property: oil.
$^1$H-NMR (500 MHz, CDCl$_3$) δ ppm: 1.37 (6H, s), 2.95 (2H, s), 4.69 (2H, s), 7.21-7.26 (2H, m), 7.47 (1H, dd, J=2.2, 7.1 Hz), 7.59 (1H, ddd, J=1.1, 7.1, 8.2 Hz), 7.77 (1H, ddd, J=1.1, 7.1, 8.2 Hz), 7.87 (1H, d, J=8.2 Hz), 8.16 (1H, d, J=8.2 Hz), 8.36 (1H, d, J=2.2 Hz), 9.08 (1H, d, J=2.2 Hz).

MS m/z: 334 (M$^+$), 319, 299, 285, 269, 262, 242, 128.

Example 132

3-(5-difluoromethyl-3,3-dimethyl-3,4-dihydroisoquinolin-1-yl)quinoline (Compound No. 1-886)

Physical property: oil.
$^1$H-NMR (500 MHz, CDCl$_3$) δ ppm: 1.36 (6H, s), 2.98 (2H, s), 6.86 (1H, t, J=55.5 Hz), 7.32-7.36 (2H, m), 7.60 (1H, ddd, J=1.1, 6.6, 8.2 Hz), 7.65 (1H, dd, J=2.2, 6.6 Hz), 7.76 (1H, ddd, J=1.1, 6.6, 8.2 Hz), 7.88 (1H, d, J=8.2 Hz), 8.17 (1H, d, J=8.2 Hz), 8.36 (1H, d, J=2.2 Hz), 9.08 (1H, d, J=2.2 Hz).

MS m/z: 336 (M$^+$), 321, 285, 255, 229.

Example 133

3-(5-hydroxymethyl-3,3-dimethyl-3,4-dihydroisoquinolin-1-yl)quinoline (Compound No. 1-887)

Physical property: amorphous.
$^1$H-NMR (500 MHz, CDCl$_3$) δ ppm: 1.35 (6H, s), 2.92 (2H, s), 4.82 (2H, s), 7.17 (1H, d, J=7.1 Hz), 7.24 (1H, t, J=7.1 Hz), 7.51 (1H, d, J=7.1 Hz), 7.59 (1H, ddd, J=1.1, 6.6, 8.2 Hz), 7.77 (1H, ddd, J=1.1, 6.6, 8.2 Hz), 7.87 (1H, d, J=8.2 Hz), 8.16 (1H, d, J=8.2 Hz), 8.36 (1H, d, J=2.2 Hz), 9.05 (1H, d, J=2.2 Hz).

MS m/z: 316 (M$^+$), 297, 285, 269, 255, 242, 128.

Example 134

3-{5-(1-hydroxy-1-methylethyl)-3,3-dimethyl-3,4-dihydroisoquinolin-1-yl}quinoline (Compound No. 1-888)

Physical property: oil.
$^1$H-NMR (500 MHz, CDCl$_3$) δ ppm: 1.32 (6H, s), 1.73 (6H, s), 3.10 (1H, br s), 3.29 (2H, s), 7.02 (1H, dd, J=1.1, 7.7 Hz), 7.15 (1H, t, J=7.7 Hz), 7.57-7.60 (2H, m), 7.76 (1H, ddd, J=1.1, 7.1, 8.2 Hz), 7.87 (1H, d, J=8.2 Hz), 8.16 (1H, d, J=8.2 Hz), 8.38 (1H, d, J=1.6 Hz), 8.78 (1H, br s).

MS m/z: 344 (M$^+$), 325, 311, 285, 270, 254.

Example 135

3-(5-methoxymethyl-3,3-dimethyl-3,4-dihydroisoquinolin-1-yl)quinoline (Compound No. 1-889)

Physical property: amorphous.
$^1$H-NMR (500 MHz, CDCl$_3$) δ ppm: 1.34 (6H, s), 2.88 (2H, s), 3.45 (3H, s), 4.56 (2H, s), 7.17 (1H, d, J=7.1 Hz), 7.22 (1H, t, J=7.1 Hz), 7.47 (1H, d, J=7.1 Hz), 7.58 (1H, ddd, J=1.1, 7.1, 8.2 Hz), 7.76 (1H, ddd, J=1.1, 7.1, 8.2 Hz), 7.87 (1H, d, J=8.2 Hz), 8.16 (1H, d, J=8.2 Hz), 8.35 (1H, d, J=2.2 Hz), 9.08 (1H, d, J=2.2 Hz).

MS m/z: 330 (M$^+$), 315, 297, 285, 268, 256, 242, 128.

Example 136

3-(5-methoxycarbonylmethyl-3,3-dimethyl-3,4-dihydroisoquinolin-1-yl)quinoline (Compound No. 1-890)

Physical property: oil.
$^1$H-NMR (500 MHz, CDCl$_3$) δ ppm: 1.34 (6H, s), 2.83 (2H, s), 3.73 (3H, s), 3.76 (2H, s), 7.16 (1H, d, J=7.7 Hz), 7.21 (1H, t, J=7.7 Hz), 7.36 (1H, d, J=7.7 Hz), 7.59 (1H, ddd, J=1.1, 7.1, 8.2 Hz), 7.76 (1H, ddd, J=1.1, 7.1, 8.2 Hz), 7.87 (1H, d, J=8.2 Hz), 8.16 (1H, d, J=8.2 Hz), 8.36 (1H, d, J=2.2 Hz), 9.09 (1H, d, J=2.2 Hz).

MS m/z: 358 (M$^+$), 357, 343, 285, 269, 242, 128.

Example 137

3-(5-benzoylamino-3,3-dimethyl-3,4-dihydroisoquinolin-1-yl)quinoline (Compound No. 1-891)

Physical property: oil.
$^1$H-NMR (500 MHz, CDCl$_3$) δ ppm: 1.35 (6H, s), 2.79 (2H, s), 7.14 (1H, d, J=7.7 Hz), 7.31 (1H, t, J=7.7 Hz), 7.54-7.64 (4H, m), 7.77 (1H, ddd, J=1.1, 6.6, 8.2 Hz), 7.86-7.89 (3H, m), 7.96 (2H, d, J=7.1 Hz), 8.16 (1H, d, J=8.8 Hz), 8.38 (1H, d, J=2.2 Hz), 9.11 (1H, d, J=2.2 Hz).

MS m/z: 405 (M$^+$), 390, 349, 299, 285, 269.

Example 138

3-{5-(2-fluorobenzoylamino)-3,3-dimethyl-3,4-dihydroisoquinolin-1-yl}quinoline (Compound No. 1-892)

Physical property: amorphous.
$^1$H-NMR (500 MHz, CDCl$_3$) δ ppm: 1.36 (6H, s), 2.81 (2H, s), 7.13 (1H, d, J=7.7 Hz), 7.24-7.28 (1H, m), 7.32 (1H, t, J=7.7 Hz), 7.38 (1H, d, J=7.7 Hz), 7.57-7.61 (2H, m), 7.77 (1H, ddd, J=1.1, 6.6, 8.2 Hz), 7.88 (1H, d, J=7.7 Hz), 8.06 (1H, d, J=8.2 Hz), 8.17 (1H, d, J=8.2 Hz), 8.25 (1H, td, J=2.2, 7.7 Hz), 8.38 (1H, d, J=2.2 Hz), 8.50 (1H, d, J=6.5 Hz), 9.11 (1H, d, J=2.2 Hz).
MS m/z: 423 (M$^+$), 408, 367, 328, 313, 300, 285, 269.

Example 139

3-{5-(3-fluorobenzoylamino)-3,3-dimethyl-3,4-dihydroisoquinolin-1-yl}quinoline (Compound No. 1-893)

Physical property: oil.
$^1$H-NMR (500 MHz, CDCl$_3$) δ ppm: 1.34 (6H, s), 2.77 (2H, s), 7.15 (1H, d, J=7.7 Hz), 7.28-7.32 (2H, m), 7.49-7.54 (1H, m), 7.60 (1H, ddd, J=1.1, 6.6, 8.2 Hz), 7.64-7.68 (1H, m), 7.73 (1H, d, J=7.7 Hz), 7.75-7.77 (2H, m), 7.88 (1H, d, J=8.2 Hz), 8.05 (1H, br s), 8.16 (1H, d, J=8.2 Hz), 8.38 (1H, d, J=1.6 Hz), 9.10 (1H, d, J=1.6 Hz).
MS m/z: 423 (M$^+$), 408, 367, 328, 313, 300, 285, 269.

Example 140

3-{5-(4-fluorobenzoylamino)-3,3-dimethyl-3,4-dihydroisoquinolin-1-yl}quinoline (Compound No. 1-894)

Physical property: amorphous.
$^1$H-NMR (500 MHz, CDCl$_3$) δ ppm: 1.34 (6H, s), 2.77 (2H, s), 7.14 (1H, d, J=7.7 Hz), 7.21 (2H, t, J=8.2 Hz), 7.29 (1H, t, J=7.7 Hz), 7.60 (1H, d, J=7.7 Hz), 7.75-7.79 (2H, m), 7.88 (1H, d, J=8.2 Hz), 7.94-7.99 (3H, m), 8.15 (1H, d, J=8.8 Hz), 8.38 (1H, d, J=1.6 Hz), 9.09 (1H, d, J=1.6 Hz).
MS m/z: 423 (M$^+$), 408, 300, 285, 269.

Example 141

3-(5-carboxy-3,3-dimethyl-3,4-dihydroisoquinolin-1-yl)quinoline (Compound No. 1-895)

Physical property: amorphous.
$^1$H-NMR (500 MHz, CDCl$_3$) δ ppm: 1.36 (6H, s), 3.34 (2H, s), 7.34 (1H, t, J=7.7 Hz), 7.41 (1H, dd, J=1.1, 7.7 Hz), 7.63 (1H, ddd, J=1.6, 7.1, 8.2 Hz), 7.81 (1H, ddd, J=1.1, 7.1, 8.2 Hz), 7.91 (1H, d, J=7.7 Hz), 8.15 (1H, dd, J=1.6, 8.2 Hz), 8.25 (1H, d, J=8.2 Hz), 8.44 (1H, d, J=2.2 Hz), 9.11 (1H, d, J=2.2 Hz).
MS m/z: 330 (M$^+$), 315, 297, 285, 269, 243, 128.

Example 142

3-(5-methoxycarbonyl-3,3-dimethyl-3,4-dihydroisoquinolin-1-yl)-8-methoxyquinoline (Compound No. 1-896)

Physical property: oil.
$^1$H-NMR (500 MHz, CDCl$_3$) δ ppm: 1.33 (6H, s), 3.27 (2H, s), 3.97 (3H, s), 7.30 (1H, t, J=7.7 Hz), 7.39 (1H, dd, J=1.1, 7.7 Hz), 7.59 (1H, ddd, J=1.1, 6.6, 8.2 Hz), 7.77 (1H, ddd, J=1.6, 6.6, 8.2 Hz), 7.87 (1H, dd, J=1.1, 8.2 Hz), 8.03 (1H, dd J=1.1, 7.7 Hz), 8.16 (1H, d, J=8.2 Hz), 8.35 (1H, d, J=2.2 Hz), 9.06 (1H, d, J=2.2 Hz).
MS m/z: 344 (M$^+$), 343, 329, 313, 297, 285, 128.

Example 143

3-(5-ethoxycarbonyl-3,3-dimethyl-3,4-dihydroisoquinolin-1-yl)-8-methoxyquinoline (Compound No. 1-897)

Physical property: oil.
$^1$H-NMR (500 MHz, CDCl$_3$) δ ppm: 1.33 (6H, s), 1.44 (3H, t, J=7.1 Hz), 3.27 (2H, s), 4.43 (2H, q, J=7.1 Hz), 7.30 (1H, t, J=7.7 Hz), 7.38 (1H, d, J=7.7 Hz), 7.59 (1H, ddd, J=1.1, 6.6, 8.2 Hz), 7.77 (1H, ddd, J=1.1, 6.6, 8.2 Hz), 7.87 (1H, d, J=8.2 Hz), 8.02 (1H, d, J=7.7 Hz), 8.16 (1H, d, J=8.2 Hz), 8.35 (1H, d, J=2.2 Hz), 9.05 (1H, d, J=2.2 Hz).
MS m/z: 358 (M$^+$), 357, 343, 329, 313, 297, 285, 128.

Example 144

3-(5-aminocarbonyl-3,3-dimethyl-3,4-dihydroisoquinolin-1-yl)quinoline (Compound No. 1-898)

Physical property: Melting point 236-240° C.
$^1$H-NMR (500 MHz, CDCl$_3$) δ ppm: 1.34 (6H, s), 3.09 (2H, s), 5.84 (2H, br s), 7.28-7.34 (2H, m), 7.60 (1H, ddd, J=1.1, 7.1, 8.2 Hz), 7.64 (1H, dd, J=1.6, 7.1 Hz), 7.78 (1H, ddd, J=1.6, 7.1, 8.2 Hz), 7.88 (1H, d, J=8.2 Hz), 8.16 (1H, d, J=8.2 Hz), 8.36 (1H, d, J=2.2 Hz), 9.06 (1H, d, J=2.2 Hz).
MS m/z: 329 (M$^+$), 314, 297, 285, 269, 242, 128.

Example 145

3-(5-fluoro-3,3-dimethyl-3,4-dihydroisoquinolin-1-yl)-2-methylquinoline (Compound No. 1-899)

Physical property: oil.
$^1$H-NMR (500 MHz, CDCl$_3$) δ ppm: 1.39 (6H, s), 2.57 (3H, s), 2.92 (2H, s), 6.68 (1H, d, J=7.1 Hz), 7.11-7.15 (2H, m), 7.52 (1H, t, J=7.7 Hz), 7.72 (1H, t, J=7.7 Hz), 7.80 (1H, d, J=7.7 Hz), 8.05 (1H, s), 8.06 (1H, d, J=7.7 Hz).
MS m/z: 318 (M$^+$), 317, 303, 262.

Example 146

3-(5-fluoro-3,3-dimethyl-3,4-dihydroisoquinolin-1-yl)-4-methylquinoline (Compound No. 1-900)

Physical property: amorphous.
$^1$H-NMR (270 MHz, CDCl$_3$) δ ppm: 1.42 (6H, s), 2.56 (3H, s), 2.95 (2H, s), 6.69 (1H, d, J=7.1 Hz), 7.11-7.15 (2H, m), 7.62 (1H, t, J=8.2 Hz), 7.75 (1H, t, J=8.2 Hz), 8.07 (1H, d, J=8.2 Hz), 8.15 (1H, d, J=8.2 Hz), 8.74 (1H, s).
MS m/z: 318 (M$^+$), 317, 303, 287, 262, 247.

Example 147

3-(5-fluoro-3,3,4-trimethyl-3,4-dihydroisoquinolin-1-yl)-2-methylquinoline (Compound No. 1-901)

Physical property: oil.
$^1$H-NMR (500 MHz, CDCl$_3$) δ ppm: 1.17 (3H, s), 1.25 (3H, d, J=7.1 Hz), 1.59 (3H, s), 2.58 (3H, s), 3.21 (1H, q, J=7.1 Hz), 6.67 (1H, d, J=7.1 Hz), 7.09-7.17 (2H, m), 7.52 (1H, t, J=7.7 Hz), 7.73 (1H, t, J=7.7 Hz), 7.81 (1H, d, J=7.7 Hz), 8.07 (2H, d, J=7.7 Hz).
MS m/z: 332 (M$^+$), 331, 317, 301, 287, 274.

Example 148

3-(5-fluoro-3,3,4-trimethyl-3,4-dihydroisoquinolin-1-yl)-8-methylquinoline (Compound No. 1-902)

Physical property: oil.
$^1$H-NMR (500 MHz, CDCl$_3$) δ ppm: 1.09 (3H, s), 1.20 (3H, d, J=7.1 Hz), 1.61 (3H, s), 2.85 (3H, s), 3.17 (1H, q, J=7.1 Hz), 7.04 (1H, dd, J=1.6, 6.0 Hz), 7.18-7.21 (2H, m), 7.48 (1H, t, J=7.7 Hz), 7.61 (1H, d, J=7.7 Hz), 7.73 (1H, d, J=7.7 Hz), 8.35 (1H, d, J=2.2 Hz), 9.10 (1H, d, J=2.2 Hz).
MS m/z: 332 (M$^+$), 317, 301, 289, 276, 261.

Example 149

3-(5-fluoro-3,3,4-trimethyl-3,4-dihydroisoquinolin-1-yl)-8-methoxyquinoline (Compound No. 1-903)

Physical property: oil.
$^1$H-NMR (500 MHz, CDCl$_3$) δ ppm: 1.09 (3H, s), 1.20 (3H, d, J=7.1 Hz), 1.61 (3H, s), 3.17 (1H, q, J=7.1 Hz), 4.12 (3H, s), 6.98 (1H, t, J=4.4 Hz), 7.11 (1H, d, J=7.1 Hz), 7.17-7.19 (2H, m), 7.46 (1H, d, J=7.7 Hz), 7.51 (1H, t, J=7.7 Hz), 8.37 (1H, d, J=1.6 Hz), 9.04 (1H, d, J=1.6 Hz).
MS m/z: 348 (M$^+$), 333, 317, 305, 292, 277, 262, 248.

Example 150

3-(6-fluoro-3,3,4,4-tetramethyl-3,4-dihydroisoquinolin-1-yl)quinoline (Compound No. 1-904)

Physical property: oil.
$^1$H-NMR (500 MHz, CDCl$_3$) δ ppm: 1.29 (6H, br s), 1.34 (6H, s), 6.88 (1H, td, J=2.2, 8.2 Hz), 7.17-7.20 (2H, m), 7.59 (1H, ddd, J=1.1, 7.1, 8.2 Hz), 7.77 (1H, ddd, J=1.6, 7.1, 8.2 Hz), 7.88 (1H, d, J=8.2 Hz), 8.16 (1H, d, J=8.2 Hz), 8.35 (1H, d, J=2.2 Hz), 9.08 (1H, d, J=2.2 Hz).
MS m/z: 332 (M$^+$), 317, 289, 275, 260.

Example 151

3-(7-fluoro-3,3,4,4-tetramethyl-3,4-dihydroisoquinolin-1-yl)quinoline (Compound No. 1-905)

Physical property: amorphous.
$^1$H-NMR (500 MHz, CDCl$_3$) δ ppm: 1.29 (6H, br s), 1.34 (6H, s), 6.88 (1H, dd, J=2.7, 8.8 Hz), 7.17 (1H, ddd, J=2.7, 8.2, 8.8 Hz), 7.45 (1H, dd, J=4.9, 8.2 Hz), 7.60 (1H, ddd, J=1.1, 7.1, 8.2 Hz), 7.78 (1H, ddd, J=1.6, 7.1, 8.2 Hz), 7.89 (1H, d, J=8.2 Hz), 8.17 (1H, d, J=8.2 Hz), 8.35 (1H, d, J=2.2 Hz), 9.11 (1H, d, J=2.2 Hz).
MS m/z: 332 (M$^+$), 317, 301, 289, 275, 260.

Example 152

3-(5-fluoro-3,3,4,4-tetramethyl-3,4-dihydroisoquinolin-1-yl)-2-methylquinoline (Compound No. 1-906)

Physical property: oil.
$^1$H-NMR (500 MHz, CDCl$_3$) δ ppm: 1.35 (6H, s), 1.50 (6H, s), 2.56 (3H, s), 6.65 (1H, dd, J=1.6, 7.1 Hz), 7.08-7.14 (2H, m), 7.51 (1H, t, J=8.2 Hz), 7.71 (1H, t, J=8.2 Hz), 7.80 (1H, d, J=8.2 Hz), 8.03 (1H, s), 8.06 (1H, d, J=8.2 Hz).
MS m/z: 346 (M$^+$), 331, 316, 303, 290, 274.

Example 153

3-(5-fluoro-3,3,4,4-tetramethyl-3,4-dihydroisoquinolin-1-yl)-4-methylquinoline (Compound No. 1-907)

Physical property: oil.
$^1$H-NMR (500 MHz, CDCl$_3$) δ ppm: 1.27-1.33 (6H, m), 1.50 (6H, s), 2.54 (3H, s), 6.65 (1H, dd, J=1.6, 7.1 Hz), 7.08-7.13 (2H, m), 7.61 (1H, t, J=8.2 Hz), 7.74 (1H, t, J=8.2 Hz), 8.06 (1H, d, J=8.2 Hz), 8.14 (1H, d, J=8.2 Hz), 8.70 (1H, s).
MS m/z: 346 (M$^+$), 331, 316, 303, 290, 274.

Example 154

3-(6-chloro-3,3,4,4-tetramethyl-3,4-dihydroisoquinolin-1-yl)quinoline (Compound No. 1-908)

Physical property: oil.
$^1$H-NMR (500 MHz, CDCl$_3$) δ ppm: 1.29 (6H, br s), 1.34 (6H, s), 7.13 (1H, d, J=8.2 Hz), 7.20 (1H, dd, J=2.2, 8.2 Hz), 7.47 (1H, d, J=2.2 Hz), 7.60 (1H, ddd, J=1.1, 6.6, 8.2 Hz), 7.77 (1H, ddd, J=1.1, 6.6, 8.2 Hz), 7.88 (1H, d, J=8.2 Hz), 8.17 (1H, d, J=8.2 Hz), 8.34 (1H, d, J=2.2 Hz), 9.08 (1H, d, J=2.2 Hz).
MS m/z: 348 (M$^+$), 333, 317, 305, 292, 277, 256, 128.

Example 155

3-(7-chloro-3,3,4,4-tetramethyl-3,4-dihydroisoquinolin-1-yl)quinoline (Compound No. 1-909)

Physical property: oil.
$^1$H-NMR (500 MHz, CDCl$_3$) δ ppm: 1.28 (6H, br s), 1.34 (6H, s), 7.15 (1H, d, J=1.6 Hz), 7.42-7.46 (2H, m), 7.61 (1H, t, J=8.2 Hz), 7.78 (1H, t, J=8.2 Hz), 7.90 (1H, d, J=8.2 Hz), 8.18 (1H, d, J=8.2 Hz), 8.35 (1H, d, J=2.2 Hz), 9.09 (1H, d, J=2.2 Hz).
MS m/z: 348 (M$^+$), 333, 317, 305, 292, 277, 256, 128.

Example 156

3-(5-fluoro-3,3,4,4-tetramethyl-3,4-dihydroisoquinolin-1-yl)quinoline hydrochloride (Compound No. 1-910)

Physical property: Melting point 123-135° C.
$^1$H-NMR (500 MHz, DMSO-d$_6$) δ ppm: 1.46 (12H, s), 7.37-7.43 (1H, m), 7.53-7.57 (1H, m), 7.74-7.78 (1H, m), 7.81 (1H, t, J=8.2 Hz), 8.02 (1H, t, J=8.2 Hz), 8.21-8.22 (2H, m), 8.90 (1H, s), 9.17 (1H, s).

Example 157

3-(5-fluoro-3,3,4,4-tetramethyl-3,4-dihydroisoquinolin-1-yl)quinoline sulfate (Compound No. 1-911)

Physical property: amorphous.
$^1$H-NMR (500 MHz, DMSO-$d_6$) δ ppm: 1.46 (12H, s), 7.37-7.43 (1H, m), 7.53-7.57 (1H, m), 7.74-7.78 (1H, m), 7.81 (1H, t, J=8.2 Hz), 8.01 (1H, t, J=8.2 Hz), 8.21 (2H, d, J=8.2 Hz), 8.86 (1H, s), 9.16 (1H, s).

Example 158

3-(5-fluoro-3,3,4,4-tetramethyl-3,4-dihydroisoquinolin-1-yl)quinoline nitrate (Compound No. 1-912)

Physical property: Melting point 165-170° C.
$^1$H-NMR (500 MHz, DMSO-$d_6$) δ ppm: 1.41 (6H, s), 1.45 (6H, s), 7.31-7.38 (1H, m), 7.48-7.55 (1H, m), 7.60-7.77 (1H, m), 7.79 (1H, t, J=8.2 Hz), 7.98 (1H, t, J=8.2 Hz), 8.19 (2H, d, J=8.2 Hz), 8.78 (1H, s), 9.13 (1H, s).

Example 159

3-(5-fluoro-3,3,4,4-tetramethyl-3,4-dihydroisoquinolin-1-yl)quinoline methanesulfonate (Compound No. 1-913)

Physical property: Melting point 185-190° C.
$^1$H-NMR (500 MHz, DMSO-$d_6$) δ ppm: 1.47 (12H, s), 2.32 (3H, s), 7.41-7.43 (1H, m), 7.55-7.59 (1H, m), 7.74-7.78 (1H, m), 7.82 (1H, t, J=8.2 Hz), 8.03 (1H, t, J=8.2 Hz), 8.22 (2H, d, J=8.2 Hz), 8.90 (1H, s), 9.17 (1H, s).

Example 160

3-(3,3,4,4,5-pentamethyl-3,4-dihydroisoquinolin-1-yl)quinoline (Compound No. 1-914)

Physical property: amorphous.
$^1$H-NMR (500 MHz, CDCl$_3$) δ ppm: 1.05 (3H, br s), 1.30 (3H, br s), 1.62 (6H, br s), 2.60 (3H, s), 6.99 (1H, dd, J=1.1, 7.7 Hz), 7.09 (1H, t, J=7.7 Hz), 7.25 (1H, d, J=7.7 Hz), 7.58 (1H, ddd, J=1.1, 6.6, 8.2 Hz), 7.75 (1H, ddd, J=1.1, 6.6, 8.2 Hz), 7.86 (1H, d, J=8.2 Hz), 8.15 (1H, d, J=8.2 Hz), 8.30 (1H, d, J=2.2 Hz), 9.00 (1H, d, J=2.2 Hz).
MS m/z: 328 (M$^+$), 313, 285, 271, 256, 241, 128.

Example 161

3-(3,3,4,4,6-pentamethyl-3,4-dihydroisoquinolin-1-yl)quinoline (Compound No. 1-915)

Physical property: oil.
$^1$H-NMR (500 MHz, CDCl$_3$) δ ppm: 1.28 (6H, br s), 1.34 (6H, s), 2.42 (3H, s), 7.01 (1H, d, J=7.7 Hz), 7.05 (1H, d, J=7.7 Hz), 7.20 (1H, s), 7.58 (1H, ddd, J=1.1, 6.6, 8.2 Hz), 7.75 (1H, ddd, J=1.1, 6.6, 8.2 Hz), 7.87 (1H, d, J=8.2 Hz), 8.16 (1H, d, J=8.2 Hz), 8.35 (1H, d, J=2.2 Hz), 9.09 (1H, d, J=2.2 Hz).
MS m/z: 328 (M$^+$), 313, 297, 285, 256, 241, 128.

Example 162

3-(3,3,4,4,7-pentamethyl-3,4-dihydroisoquinolin-1-yl)quinoline (Compound No. 1-916)

Physical property: oil.
$^1$H-NMR (500 MHz, CDCl$_3$) δ ppm: 1.28 (6H, br s), 1.36 (6H, s), 2.25 (3H, s), 6.96 (1H, s), 7.29 (1H, d, J=7.7 Hz), 7.37 (1H, d, J=7.7 Hz), 7.59 (1H, ddd, J=1.1, 6.6, 8.2 Hz), 7.77 (1H, ddd, J=1.1, 6.6, 8.2 Hz), 7.89 (1H, d, J=8.2 Hz), 8.16 (1H, d, J=8.2 Hz), 8.38 (1H, d, J=2.2 Hz), 9.09 (1H, d, J=2.2 Hz).
MS m/z: 328 (M$^+$), 313, 297, 285, 256, 241, 128.

Example 163

3-(5-fluoro-3,3,4,4-tetramethyl-3,4-dihydroisoquinolin-1-yl)-6-fluoroquinoline (Compound No. 1-917)

Physical property: oil.
$^1$H-NMR (500 MHz, CDCl$_3$) δ ppm: 1.33 (6H, s), 1.46 (6H, s), 6.95 (1H, dd, J=1.6, 7.5 Hz), 7.15-7.21 (2H, m), 7.46-7.55 (2H, m), 8.16 (1H, dd, J=4.9, 8.8 Hz), 8.27 (1H, d, J=2.2 Hz), 9.00 (1H, d, J=2.2 Hz).
MS m/z: 350 (M$^+$), 335, 319, 307, 293, 278.

Example 164

3-(5-fluoro-3,3,4,4-tetramethyl-3,4-dihydroisoquinolin-1-yl)-8-fluoroquinoline (Compound No. 1-918)

Physical property: oil.
$^1$H-NMR (500 MHz, CDCl$_3$) δ ppm: 1.33 (6H, s), 1.46 (6H, s), 6.97 (1H, d, J=7.1 Hz), 7.15-7.21 (2H, m), 7.42-7.54 (2H, m), 7.67 (1H, d, J=8.2 Hz), 8.37 (1H, s), 9.09 (1H, s).
MS m/z: 350 (M$^+$), 335, 319, 307, 293, 278.

Example 165

3-(5-fluoro-3,3,4,4-tetramethyl-3,4-dihydroisoquinolin-1-yl)-8-methylquinoline (Compound No. 1-919)

Physical property: oil.
$^1$H-NMR (500 MHz, CDCl$_3$) δ ppm: 1.32 (6H, s), 1.46 (6H, s), 2.84 (3H, s), 6.99 (1H, d, J=6.6 Hz), 7.11-7.17 (2H, m), 7.45 (1H, t, J=7.7 Hz), 7.58 (1H, d, J=7.6 Hz), 7.70 (1H, d, J=7.6 Hz), 8.30 (1H, d, J=1.6 Hz), 9.06 (1H, d, J=1.6 Hz).
MS m/z: 346 (M$^+$), 331, 315, 303, 289, 274.

Example 166

3-(5-fluoro-3,3,4,4-tetramethyl-3,4-dihydroisoquinolin-1-yl)-8-methoxyquinoline (Compound No. 1-920)

Physical property: oil.
$^1$H-NMR (500 MHz, CDCl$_3$) δ ppm: 1.32 (6H, s), 1.46 (6H, s), 4.12 (3H, s), 6.93 (1H, d, J=7.1 Hz), 7.11 (1H, d, J=7.1 Hz), 7.14-7.17 (2H, m), 7.45 (1H, d, J=7.7 Hz), 7.51 (1H, t, J=7.7 Hz), 8.33 (1H, d, J=2.2 Hz), 8.98 (1H, d, J=2.2 Hz).
MS m/z: 362 (M$^+$), 347, 331, 319, 306, 290, 276, 260.

Example 167

3',3'-dimethyl-1'-quinolin-3-yl-3'H-spiro[cyclopentane-1,4'-isoquinoline] (Compound No. 1-921)

Physical property: oil.
$^1$H-NMR (500 MHz, CDCl$_3$) δ ppm: 0.65 (3H, s), 1.26 (3H, s), 1.34-1.96 (6H, m), 2.35-2.37 (1H, m), 2.78-2.80 (1H, m), 7.23-7.49 (4H, m), 7.57 (1H, t, J=7.6 Hz), 7.75 (1H, t, J=7.6 Hz), 7.87 (1H, d, J=7.6 Hz), 8.16 (1H, d, J=7.6 Hz), 8.39 (1H, d, J=2.2 Hz), 9.22 (1H, d, J=2.2 Hz).
MS m/z: 340 (M$^+$), 325, 311, 283, 271, 257.

Example 168

4',4'-dimethyl-1'-quinolin-3-yl-4'H-spiro[cyclopentane-1,4'-isoquinoline] (Compound No. 1-922)

Physical property: oil.
$^1$H-NMR (500 MHz, CDCl$_3$) δ ppm: 0.94-1.90 (14H, m), 7.18 (2H, d, J=3.3 Hz), 7.46 (2H, d, J=3.3 Hz), 7.56 (1H, t, J=7.6 Hz), 7.73 (1H, t, J=7.6 Hz), 7.86 (1H, d, J=7.6 Hz), 8.18 (1H, d, J=7.6 Hz), 8.35 (1H, d, J=2.2 Hz), 9.11 (1H, d, J=2.2 Hz).
MS m/z: 340 (M$^+$), 325, 311, 285, 271, 257.

Example 169

3',3'-dimethyl-1'-quinolin-3-yl-3'H-spiro[cyclohexane-1,4'-isoquinoline] (Compound No. 1-923)

Physical property: oil.
$^1$H-NMR (500 MHz, CDCl$_3$) δ ppm: 0.86-1.90 (16H, m), 7.17 (1H, d, J=7.3 Hz), 7.22 (1H, t, J=7.3 Hz), 7.45 (1H, t, J=8.2 Hz), 7.59 (1H, t, J=8.2 Hz), 7.73-7.78 (2H, m), 7.89 (1H, d, J=8.2 Hz), 8.19 (1H, d, J=8.2 Hz), 8.42 (1H, d, J=2.2 Hz), 9.18 (1H, d, J=2.2 Hz).
MS m/z: 354 (M$^+$), 339, 325, 311, 297, 268, 257.

Example 170

4',4'-dimethyl-1'-quinolin-3-yl-4'H-spiro[cyclohexane-1,4'-isoquinoline] (Compound No. 1-924)

Physical property: oil.
$^1$H-NMR (500 MHz, CDCl$_3$) δ ppm: 1.24-1.85 (16H, m), 7.22 (1H, t, J=7.1 Hz), 7.27 (1H, d, J=7.1 Hz), 7.44-7.48 (2H, m), 7.56 (1H, t, J=8.2 Hz), 7.74 (1H, t, J=8.2 Hz), 7.87 (1H, d, J=8.2 Hz), 8.18 (1H, d, J=8.2 Hz), 8.40 (1H, d, J=2.2 Hz), 9.28 (1H, d, J=2.2 Hz).
MS m/z: 354 (M$^+$), 339, 311, 273, 257, 242.

Example 171

1'-quinolin-3-yl-4'H-spiro[cyclobutane-1,4'-isoquinoline] (Compound No. 1-925)

Physical property: oil.
$^1$H-NMR (270 MHz, CDCl$_3$) δ ppm: 1.88-2.20 (4H, m), 2.32-2.46 (2H, m), 3.08 (2H, s), 7.04 (1H, d, J=6.6 Hz), 7.17-7.25 (2H, m), 7.59 (1H, t, J=7.5 Hz), 7.77 (1H, t, J=10.7 Hz), 7.88 (1H, d, J=7.9 Hz), 8.16 (1H, d, J=8.5 Hz), 8.39 (1H, d, J=2.1 Hz), 9.14 (1H, d, J=2.1 Hz).
MS m/z: 316 (M$^+$), 315, 287, 273, 247, 144.

Example 172

3-(5-fluoro-4-keto-3,3-dimethyl-3,4-dihydroisoquinolin-1-yl)quinoline (Compound No. 1-934)(Process E)

Chromic acid (4.9 g) was added to an acetic acid (50 mL) solution of 3-(5-fluoro-3,3-dimethyl-3,4-dihydroisoquinolin-1-yl)quinoline (5.0 g, 16.4 mmol), followed by heating and refluxing for 14 hours, pouring water, aqueous sodium sulfite solution and aqueous sodium hydrogencarbonate solution. After stirring for 30 minutes, extracting with ethyl acetate, and applying the resulting residue to chromatography to obtain 0.3 g (yield 6%) of the target compound.
Physical property: Melting point 151-152° C.
$^1$H-NMR (270 MHz, CDCl$_3$) δ ppm: 1.61 (6H, s), 7.19 (1H, d, J=7.7 Hz), 7.37 (1H, t, J=9.2 Hz), 7.60-7.74 (2H, m), 7.81 (1H, t, J=6.6 Hz), 7.91 (1H, d, J=7.9 Hz), 8.19 (1H, d, J=8.5 Hz), 8.37 (1H, d, J=2.4 Hz), 9.09 (1H, d, J=2.4 Hz)

Example 173

3-(5-fluoro-4-hydroxy-3,3-dimethyl-3,4-dihydroisoquinolin-1-yl)quinoline (Compound No. 1-935)(Process F)

Sodium borohydride (103 mg) was added to a methanol (8 mL) solution of 3-(5-fluoro-4-keto-3,3-dimethyl-3,4-dihydroisoquinolin-1-yl)quinoline (300 mg, 0.9 mmol) followed by stirring for 2.5 hours at room temperature, pouring water, extracting with ethyl acetate, and applying the resulting residue to chromatography to obtain 215 mg (yield 74%) of the target compound.
Physical property: Melting point 225-226° C.
$^1$H-NMR (270 MHz, CDCl$_3$) δ ppm: 1.06 (3H, s), 1.75 (3H, s), 2.42 (1H, s), 4.89 (1H, s), 7.09 (1H, d, J=7.7 Hz), 7.20-7.38 (2H, m), 7.59 (1H, t, J=7.0 Hz), 7.77 (1H, t, J=7.0 Hz), 7.86 (1H, d, J=8.2 Hz), 8.15 (1H, d, J=8.5 Hz), 8.36 (1H, d, J=2.1 Hz), 9.07 (1H, d, J=2.1 Hz).
MS m/z: 320 (M$^+$), 277, 263, 235, 214, 207.

Example 174

3-(4,5-difluoro-3,3-dimethyl-3,4-dihydroisoquinolin-1-yl)quinoline (Compound No. 1-927) (Process G)

Diethylaminosulphur trifluoride (76 mg) was added to an methylene chloride (20 mL) solution of 3-(5-fluoro-4-hydroxy-3,3-dimethyl-3,4-dihydroisoquinolin-1-yl)quinoline (50 mg, 0.16 mmol), followed by stirring for 1 hour under ice cooling, pouring water, extracting with ethyl acetate, and applying the resulting residue to chromatography to obtain 45 mg (yield 90%) of the target compound.
Physical property: oil.
$^1$H-NMR (270 MHz, CDCl$_3$) δ ppm: 1.07 (3H, s), 1.78 (3H, d, J=1.6 Hz), 5.65 (1H, d, J=49.4 Hz), 7.17 (1H, d, J=7.7 Hz), 7.30 (1H, t, J=8.0 Hz), 7.42-7.54 (1H, m), 7.59 (1H, t, J=7.6 Hz), 7.78 (1H, t, J=7.7 Hz), 7.88 (1H, d, J=8.2 Hz), 8.17 (1H, d, J=8.5 Hz), 8.37 (1H, s), 9.13 (1H, d, J=1.6 Hz).
MS m/z: 322 (M$^+$), 301, 287, 266, 248, 151, 119, 84.
The following compounds were synthesized in the same manner as Example 172 to 174.

Example 175

3-(5-fluoro-3,3-dimethyl-4-methylene-3,4-dihydroisoquinolin-1-yl)quinoline (Compound No. 1-926)

Physical property: oil.
$^1$H-NMR (270 MHz, CDCl$_3$) δ ppm: 1.53 (6H, s), 5.80 (2H, dd, J=17.4, 1.8 Hz), 7.02 (1H, dt, J=9.5, 4.2 Hz), 7.22-7.30 (2H, m), 7.59 (1H, t, J=7.4 Hz), 7.77 (1H, t, J=7.7 Hz), 7.87 (1H, d, J=8.5 Hz), 8.16 (1H, d, J=8.2 Hz), 8.34 (1H, d, J=2.1 Hz), 9.07 (1H, d, J=1.8 Hz).
MS m/z: 316 (M$^+$), 301, 275, 259, 119, 84.

Example 176

3-(4-chloro-5-fluoro-3,3-dimethyl-3,4-dihydroiso-quinolin-1-yl)quinoline (Compound No. 1-928)

Physical property: amorphous.
$^1$H-NMR (270 MHz, CDCl$_3$) δ ppm: 1.15 (3H, s), 1.85 (3H, s), 5.35 (1H, s), 7.14 (1H, d, J=7.7 Hz), 7.23-7.43 (2H, m), 7.60 (1H, t, J=7.7 Hz), 7.78 (1H, t, J=7.7 Hz), 7.88 (1H, d, J=5.5 Hz), 8.18 (1H, d, J=8.5 Hz), 8.39 (1H, d, J=2.1 Hz), 9.14 (1H, d, J=2.1 Hz).
MS m/z: 338 (M$^+$), 303, 287, 262, 247, 151, 144, 134, 110.

Example 177

3-(4,4-difluoro-3,3-dimethyl-3,4-dihydroisoquinolin-1-yl)quinoline (Compound No. 1-929)

Physical property: oil.
$^1$H-NMR (500 MHz, CDCl$_3$) δ ppm: 1.46 (6H, s), 7.34 (1H, d, J=7.7 Hz), 7.55 (1H, t, J=7.7 Hz), 7.61 (1H, ddd, J=1.1, 7.1, 8.2 Hz), 7.67 (1H, td, J=1.1, 7.7 Hz), 7.80 (1H, ddd, J=1.6, 7.1, 8.2 Hz), 7.87-7.90 (2H, m), 8.18 (1H, d, J=8.2 Hz), 8.40 (1H, d, J=2.2 Hz), 9.14 (1H, d, J=2.2 Hz).
MS m/z: 322 (M$^+$), 307, 287, 266, 230.

Example 178

3-(4,4,5-trifluoro-3,3-dimethyl-3,4-dihydroisoquino-lin-1-yl)quinoline (Compound No. 1-930)

Physical property: Melting point 126-127° C.
$^1$H-NMR (270 MHz, CDCl$_3$) δ ppm: 1.50 (6H, s), 7.13 (1H, d, J=7.7 Hz), 7.35 (1H, t, J=9.2 Hz), 7.48-7.64 (2H, m), 7.80 (1H, t, J=8.5 Hz), 7.88 (1H, d, J=8.2 Hz), 8.18 (1H, d, J=1.5 Hz), 8.35 (1H, d, J=2.1 Hz), 9.08 (1H, d, J=2.4 Hz).
MS m/z: 340 (M$^+$), 325, 305, 284, 248, 149, 128.

Example 179

3-(5-fluoro-4-methoxy-3,3-dimethyl-3,4-dihydroiso-quinolin-1-yl)quinoline (Compound No. 1-932)

Physical property: amorphous.
$^1$H-NMR (270 MHz, CDCl$_3$) δ ppm: 1.00 (3H, s), 1.75 (3H, s), 3.38 (3H, s), 4.39 (1H, s), 7.13 (1H, d, J=7.4 Hz), 7.22-7.42 (2H, m), 7.58 (1H, t, J=7.4 Hz), 7.76 (1H, t, J=7.4 Hz), 7.87 (1H, d, J=8.2 Hz), 8.16 (1H, d, J=8.2 Hz), 8.39 (1H, s), 9.14 (1H, s).
MS m/z: 334 (M$^+$), 319, 303, 287, 262, 234, 207, 190, 151, 130, 104.

Example 180

3-(4-keto-3,3-dimethyl-3,4-dihydroisoquinolin-1-yl)quinoline (Compound No. 1-933)

Physical property: Melting point 137° C.
$^1$H-NMR (270 MHz, CDCl$_3$) δ ppm: 1.62 (6H, s), 7.38-7.43 (1H, m), 7.58-7.68 (2H, m), 7.81 (1H, t, J=8.2 Hz), 7.91 (1H, d, J=7.9 Hz), 8.20 (1H, d, J=7.1 Hz), 8.37 (1H, d, J=2.1 Hz), 9.11 (1H, d, J=2.1 Hz).
MS m/z: 300 (M$^+$), 285, 271, 257, 244, 231, 216, 189, 149, 128, 107, 94.

Example 181

3-(5-fluoro-4-hydroxy-3,3,4-trimethyl-3,4-dihy-droisoquinolin-1-yl)quinoline (Compound No. 1-935)

Physical property: amorphous.
$^1$H-NMR (270 MHz, CDCl$_3$) δ ppm: 1.25 (6H, s), 1.58 (3H, s), 1.63 (3H, s), 2.95 (1H, d, J=10.0 Hz), 6.99 (1H, d, J=7.1 Hz), 7.18-7.33 (2H, m), 7.59 (1H, t, J=8.1 Hz), 7.77 (1H, t, J=8.1 Hz), 7.87 (1H, d, J=8.2 Hz), 8.16 (1H, d, J=8.5 Hz), 8.32 (1H, d, J=2.1 Hz), 9.03 (1H, d, J=2.1 Hz).
MS m/z: 334 (M$^+$), 277, 248, 234, 220, 207, 138, 128, 101.

Example 182

3-(4-ethyl-5-fluoro-4-hydroxy-3,3-dimethyl-3,4-dihydroisoquinolin-1-yl)quinoline (Compound No. 1-936)

Physical property: amorphous.
$^1$H-NMR (270 MHz, CDCl$_3$) δ ppm: 0.91 (3H, td, J=7.5, 1.5 Hz), 1.17 (3H, s), 1.63 (3H, s), 1.95 (2H, q, J=7.5 Hz), 3.14 (1H, d, J=12.4 Hz), 7.00 (1H, d, J=4.0 Hz), 7.18-7.33 (2H, m), 7.60 (1H, t, J=7.5 Hz), 7.77 (1H, t, J=7.7 Hz), 7.87 (1H, d, J=8.2 Hz), 8.16 (1H, d, J=8.5 Hz), 8.32 (1H, d, J=2.1 Hz), 9.04 (1H, d, J=1.8 Hz).
MS m/z: 348 (M$^+$), 291, 276, 248, 234.

Example 183

3-(5-fluoro-4-methoxy-3,3,4-trimethyl-3,4-dihy-droisoquinolin-1-yl)quinoline (Compound No. 1-937)

Physical property: oil.
$^1$H-NMR (270 MHz, CDCl$_3$) δ ppm: 1.05 (3H, s), 1.69 (3H, s), 1.80 (3H, d, J=6.1 Hz), 3.13 (3H, s), 7.07 (1H, d, 7.5 Hz), 7.17-7.37 (2H, m), 7.58 (1H, t, J=8.2 Hz), 7.76 (1H, t, J=8.5 Hz), 7.86 (1H, d, J=8.2 Hz), 8.15 (1H, d, J=8.5 Hz), 8.34 (1H, d, J=2.1 Hz), 9.08 (1H, d, J=2.1 Hz).
MS m/z: 348 (M$^+$), 333, 317, 301, 292, 277, 192, 149, 136, 108, 83.

Example 184

3-(4-ethoxy-5-fluoro-3,3,4-trimethyl-3,4-dihydroiso-quinolin-1-yl)quinoline (Compound No. 1-938)

Physical property: Melting point 118-119° C.
$^1$H-NMR (270 MHz, CDCl$_3$) δ ppm: 1.01 (3H, t, J=6.9 Hz), 1.03 (3H, s), 1.69 (3H, s), 1.79 (3H, d, J=6.1 Hz), 3.09 (1H, m), 3.54 (1H, m), 7.04 (1H, d, J=7.5 Hz), 7.15-7.35 (2H, m), 7.58 (1H, t, J=8.0 Hz), 7.76 (1H, t, J=8.5 Hz), 7.87 (1H, d, J=8.2 Hz), 8.15 (1H, d, J=8.5 Hz), 8.33 (1H, d, J=2.1 Hz), 9.04 (1H, d, J=2.1 Hz).
MS m/z: 362 (M$^+$), 333, 306, 277, 248, 234, 128, 101.

Example 185

3-(4-ethyl-5-fluoro-4-methoxy-3,3-dimethyl-3,4-dihydroisoquinolin-1-yl)quinoline (Compound No. 1-939)

Physical property: Melting point 145-147° C.
$^1$H-NMR (270 MHz, CDCl$_3$) δ ppm: 0.95 (3H, td, J=7.5, 1.9 Hz), 1.31 (3H, s), 1.49 (3H, s), 1.96-2.11 (1H, m), 2.20-

2.36 (1H, m), 3.49 (3H, s), 6.98 (1H, dd, J=7.3, 1.5 Hz), 7.17-7.33 (2H, m), 7.59 (1H, t, J=8.0 Hz), 7.76 (1H, t, J=8.6 Hz), 7.86 (1H, d, J=8.5 Hz), 8.15 (1H, d, J=8.7 Hz), 8.29 (1H, d, J=2.1 Hz), 9.01 (1H, d, J=2.1 Hz).

MS m/z: 362 (M$^+$), 347, 330, 315, 305, 290, 277, 234, 192, 149, 128, 101.

Example 186

3-(5-hydroxymethyl-3,3-dimethyl-1,2,3,4-tetrahydroisoquinoline-1-yl)quinoline (Compound No. 2-274)

Physical property: amorphous.
$^1$H-NMR (500 MHz, CDCl$_3$) δ ppm: 1.27 (3H, s), 1.34 (3H, s), 1.84-1.87 (1H, m), 2.81 (1H, d, J=16.5 Hz), 2.88 (1H, d, J=16.5 Hz), 3.73-3.76 (1H, m), 4.75 (2H, s), 5.39 (1H, s), 6.70 (1H, d, J=7.7 Hz), 7.04 (1H, t, J=7.7 Hz), 7.25-7.27 (1H, m), 7.53 (1H, ddd, J=1.1, 7.1, 8.2 Hz), 7.70 (1H, ddd, J=1.6, 7.1, 8.2 Hz), 7.78 (1H, dd, J=1.1, 8.2 Hz), 8.08-8.11 (2H, m), 8.83 (1H, d, J=2.2 Hz).

MS m/z: 318 (M$^+$), 303, 285, 243, 230, 128.

Example 187

3-(2-acetyl-5-fluoro-3,3-dimethyl-1,2,3,4-tetrahydroisoquinoline-1-yl)quinoline (Compound No. 2-275)

Physical property: amorphous.
$^1$H-NMR (500 MHz, CDCl$_3$) δ ppm: 1.29 (3H, s), 1.89 (3H, s), 2.31 (3H, s), 2.35 (1H, d, J=15.4 Hz), 2.81 (1H, d, J=15.4 Hz), 6.10-6.20 (1H, m), 7.12 (1H, t, J=8.5 Hz), 7.33 (1H, d, J=8.5 Hz), 7.37-7.39 (1H, m), 7.56 (1H, t, J=8.2 Hz), 7.71 (1H, t, J=8.2 Hz), 7.77 (1H, d, J=8.2 Hz), 7.94 (1H, s), 8.08 (1H, d, J=8.2 Hz), 8.75 (1H, s).

MS m/z: 348 (M$^+$), 305, 291, 274, 263, 248.

Example 188

3-(2-methoxyacetyl-5-fluoro-3,3-dimethyl-1,2,3,4-tetrahydroisoquinoline-1-yl)quinoline (Compound No. 2-276)

Stereoisomer of Compound of Example 189
Physical property: oil.
$^1$H-NMR (500 MHz, CDCl$_3$) δ ppm: 1.31 (3H, s), 1.89 (3H, s), 2.31 (1H, d, J=15.4 Hz), 2.82 (1H, d, J=15.4 Hz), 3.41 (3H, s), 4.08 (1H, d, J=13.2 Hz), 4.37 (1H, d, J=13.2 Hz), 6.29 (1H, s), 7.14 (1H, t, J=8.2 Hz), 7.33 (1H, d, J=8.2 Hz), 7.39-7.40 (1H, m), 7.56 (1H, t, J=8.2 Hz), 7.70-7.75 (2H, m), 7.92 (1H, s), 8.08 (1H, d, J=8.2 Hz), 8.75 (1H, s).

MS m/z: 378 (M$^+$), 347, 333, 305, 290, 274, 262, 248.

Example 189

3-(2-methoxyacetyl-5-fluoro-3,3-dimethyl-1,2,3,4-tetrahydroisoquinoline-1-yl)quinoline (Compound No. 2-276)

Stereoisomer of Compound of Example 188
Physical property: oil.
$^1$H-NMR (500 MHz, CDCl$_3$) δ ppm: 0.58 (3H, s), 1.21 (3H, s), 2.68 (1H, d, J=17.0 Hz), 2.91 (1H, d, J=17.0 Hz), 3.26 (3H, s), 3.89 (2H, s), 5.59 (1H, s), 6.48 (1H, d, J=7.7 Hz), 6.93 (1H, t, J=7.7 Hz), 7.02 (1H, q, J=7.7 Hz), 7.57 (1H, t, J=8.2 Hz), 7.74 (1H, t, J=8.2 Hz), 7.79 (1H, d, J=8.2 Hz), 8.12 (1H, d, J=8.2 Hz), 8.31 (1H, s), 8.91 (1H, s).

MS m/z: 378 (M$^+$), 306, 291, 248.

Example 190

3-(2-cinnamyl-5-fluoro-3,3-dimethyl-1,2,3,4-tetrahydroisoquinoline-1-yl)quinoline (Compound No. 2-277)

Physical property: oil.
$^1$H-NMR (500 MHz, CDCl$_3$) δ ppm: 1.14 (3H, s), 1.47 (3H, s), 3.38 (1H, dd, J=6.6, 16.5 Hz), 3.52 (1H, dd, J=6.6, 16.5 Hz), 3.74 (2H, s), 5.08 (1H, s), 5.98-6.02 (1H, m), 6.14 (1H, d, J=15.9 Hz), 6.51 (1H, d, J=7.7 Hz), 6.82 (1H, t, J=7.7 Hz), 6.91-6.93 (1H, m), 7.08 (2H, d, J=7.1 Hz), 7.13-7.17 (1H, m), 7.18 (2H, d, J=7.1 Hz), 7.51 (1H, t, J=8.2 Hz), 7.66 (1H, t, J=8.2 Hz), 7.78 (1H, d, J=8.2 Hz), 8.04 (1H, d, J=8.2 Hz), 8.09 (1H, s), 8.87 (1H, s).

MS m/z: 422 (M$^+$), 407, 303, 265, 248.

Example 191

3-(5-fluoro-2,3,3,4,4-pentamethyl-1,2,3,4-tetrahydroisoquinoline-1-yl)quinoline (Compound No. 2-278)

Physical property: amorphous.
$^1$H-NMR (270 MHz, CDCl$_3$) δ ppm: 1.02 (3H, s), 1.24 (3H, s), 1.48 (3H, d, J=4.5 Hz), 1.61 (3H, s), 2.12 (3H, s), 4.66 (1H, s), 6.38 (1H, d, J=7.9 Hz), 6.72-6.90 (2H, m), 7.54 (1H, t, J=7.4 Hz), 7.68 (1H, t, J=7.7 Hz), 7.80 (1H, d, J=8.2 Hz), 8.01 (1H, d, J=1.8 Hz), 8.07 (1H, d, J=8.5 Hz), 8.73 (1H, d, J=2.1 Hz).

MS m/z: 348 (M$^+$), 333, 277, 262, 190, 167, 149, 133.

Example 192

3-(5-fluoro-4-keto-3,3-dimethyl-1,2,3,4-tetrahydroisoquinoline-1-yl)quinoline (Compound No. 2-279)

Physical property: Melting point 228-229° C.
$^1$H-NMR (270 MHz, CDCl$_3$) δ ppm: 1.06 (3H, s), 1.75 (3H, s), 4.89 (1H, s), 7.09 (1H, d, J=7.4 Hz), 7.20-7.38 (2H, m), 7.59 (1H, t, J=7.0 Hz), 7.76 (1H, t, J=8.4 Hz), 7.86 (1H, d, J=8.2 Hz), 8.15 (1H, d, J=8.5 Hz), 8.36 (1H, d, J=1.8 Hz), 9.07 (1H, d, J=2.1 Hz).

MS m/z: 320 (M$^+$), 287, 277, 263, 235, 207.

Example 193

5-fluoro-3,3,4,4-tetramethyl-8b-quinolin-3-yl-4,8b-dihydro-3H-oxazileno[3,2-a]isoquinoline (Compound No. 3-100) (Process H)

M-chloroperbenzoic acid (9.0 g) was added to a methanol (250 mL) solution of 3-(5-fluoro-3,3,4,4-tetramethyl-3,4-dihydroisoquinolin-1-yl)quinoline (12.0 g, 36.0 mmol), followed by stirring for 5 hours at room temperature, pouring aqueous sodium sulfite solution and aqueous sodium hydrogencarbonate solution. After stirring for 30 minutes, extracting with ethyl acetate, and applying the resulting residue to chromatography to obtain 6.8 g (yield 54%) of the target compound.

Physical property: Melting point 120-121° C.
¹H-NMR (270 MHz, CDCl₃) δ ppm: 1.30 (3H, s), 1.53 (3H, s), 1.54 (3H, s), 1.56 (3H, s), 6.82-6.86 (1H, m), 7.05-7.15 (2H, m), 7.60 (1H, t, J=7.0 Hz), 7.77 (1H, t, J=8.4 Hz), 7.86 (1H, d, J=8.2 Hz), 8.16 (1H, d, J=8.5 Hz), 8.21 (1H, d, J=2.1 Hz), 8.94 (1H, d, J=2.1 Hz).
MS m/z: 348 (M⁺), 331, 317, 292, 275, 260, 248, 177, 128, 101.

The following compounds were synthesized in the same manner as Example 192.

Example 194

5-fluoro-3,3-dimethyl-8b-(1-oxidequinoline-3-yl)-4,8b-dihydro-3H-oxazileno[3,2-a]isoquinoline (Compound No. 3-38)

Physical property: Melting point 164-166° C.
¹H-NMR (270 MHz, CDCl₃) δ ppm: 1.15 (3H, s), 1.57 (3H, s), 2.58 (1H, d, J=16.1 Hz), 2.93 (1H, d, J=16.1 Hz), 6.94 (1H, t, J=4.7 Hz), 7.11-7.23 (2H, m), 7.70 (1H, t, J=7.6 Hz), 7.82 (1H, t, J=7.5 Hz), 7.86 (1H, s), 7.91 (1H, d, J=8.2 Hz), 8.57 (1H, d, J=1.3 Hz), 8.77 (1H, d, J=9.0 Hz).
MS m/z: 336 (M⁺), 320, 303, 288, 261, 235, 202, 162, 134, 101.

Example 195

3,3,4-trimethyl-8b-quinolin-3-yl-4,8b-dihydro-3H-oxazileno[3,2-a]isoquinoline (Compound No. 3-56)

Physical property: oil.
¹H-NMR (500 MHz, CDCl₃) δ ppm: 0.99 (3H, s), 1.42 (3H, d, J=7.1 Hz), 1.61 (3H, s), 3.00 (1H, q, J=7.1 Hz), 7.01 (1H, d, J=7.7 Hz), 7.13 (1H, t, J=7.7 Hz), 7.38-7.41 (2H, m), 7.58 (1H, t, J=8.2 Hz), 7.75 (1H, t, J=8.2 Hz), 7.86 (1H, d, J=8.2 Hz), 8.17 (1H, d, J=8.2 Hz), 8.28 (1H, s), 8.95 (1H, s).
MS m/z: 316 (M⁺), 299, 285, 271, 257, 243.

Example 196

3,3,4,4-tetramethyl-8b-quinolin-3-yl-4,8b-dihydro-3H-oxazileno[3,2-a]isoquinoline (Compound No. 3-91)

Physical property: oil.
¹H-NMR (500 MHz, CDCl₃) δ ppm: 1.25 (3H, s), 1.44 (3H, s), 1.45 (3H, s), 1.49 (3H, s), 7.06 (1H, d, J=7.4 Hz), 7.14 (1H, t, J=7.4 Hz), 7.42 (1H, t, J=7.4 Hz), 7.50 (1H, d, J=7.4 Hz), 7.59 (1H, t, J=7.6 Hz), 7.76 (1H, t, J=7.6 Hz), 7.85 (1H, d, J=7.6 Hz), 8.16 (1H, d, J=7.6 Hz), 8.28 (1H, s), 8.93 (1H, s).
MS m/z: 330 (M⁺), 313, 299, 273, 257, 242.

Example 197

5-fluoro-3,3-dimethyl-8b-quinolin-3-yl-4,8b-dihydro-3H-oxazileno[3,2-a]isoquinoline (Compound No. 3-20)

Physical property: amorphous.
¹H-NMR (270 MHz, CDCl₃) δ ppm: 1.19 (3H, s), 1.59 (3H, s), 2.62 (1H, d, J=16.1 Hz), 2.95 (1H, d, J=16.1 Hz), 6.84 (1H, d, J=6.5 Hz), 7.06-7.16 (2H, m), 7.60 (1H, t, J=7.5 Hz), 7.78 (1H, t, J=10.5 Hz), 7.87 (1H, d, J=8.2 Hz), 8.17 (1H, d, J=8.5 Hz), 8.28 (1H, d, J=2.1 Hz), 8.95 (1H, d, J=2.1 Hz).
MS m/z: 320 (M⁺), 303, 289, 261, 248, 254, 238, 201, 84.

Example 198

5-fluoro-3,3,4,4-tetramethyl-8b-(1-oxidequinoline-3-yl)-4,8b-dihydro-3H-oxazileno[3,2-a]isoquinoline (Compound No. 3-108)

Physical property: Melting point 173-175° C.
¹H-NMR (500 MHz, CDCl₃) δ ppm: 1.29 (6H, s), 1.43 (6H, d, J=3.2 Hz), 7.04 (1H, d, J=6.7 Hz), 7.12-7.27 (2H, m), 7.68 (1H, t, J=7.5 Hz), 7.80 (1H, t, J=7.4 Hz), 7.90 (2H, d, J=8.2 Hz), 8.77 (2H, d, J=9.8 Hz).
MS m/z: 354 (M⁺), 348, 331, 307, 275, 260, 229, 214, 164, 146, 101.

Example 199

6-fluoro-3,3,4,4-tetramethyl-8b-quinolin-3-yl-4,8b-dihydro-3H-oxazileno[3,2-a]isoquinoline (Compound No. 3-110)

Physical property: oil.
¹H-NMR (500 MHz, CDCl₃) δ ppm: 1.24 (3H, s), 1.41 (3H, s), 1.44 (3H, s), 1.49 (3H, s), 6.82 (1H, dt, J=2.2, 8.8 Hz), 7.04 (1H, dd, J=6.0, 8.8 Hz), 7.19 (1H, dd, J=2.2, 10.4 Hz), 7.59 (1H, t, J=8.2 Hz), 7.76 (1H, t, J=8.2 Hz), 7.85 (1H, d, J=8.2 Hz), 8.15 (1H, d, J=8.2 Hz), 8.26 (1H, s), 8.90 (1H, s).
MS m/z: 348 (M⁺), 331, 317, 291, 275, 260.

Example 200

6-chloro-3,3,4,4-tetramethyl-8b-quinolin-3-yl-4,8b-dihydro-3H-oxazileno[3,2-a]isoquinoline (Compound No. 3-113)

Physical property: oil.
¹H-NMR (500 MHz, CDCl₃) δ ppm: 1.24 (3H, s), 1.42 (3H, s), 1.45 (3H, s), 1.49 (3H, s), 7.01 (1H, d, J=8.2 Hz), 7.12 (1H, d, J=8.2 Hz), 7.47 (1H, s), 7.60 (1H, t, J=7.6 Hz), 7.77 (1H, t, J=7.6 Hz), 7.86 (1H, d, J=7.6 Hz), 8.16 (1H, d, J=7.6 Hz), 8.26 (1H, s), 8.90 (1H, s).
MS m/z: 364 (M⁺), 347, 291, 256.

Example 201

7-methyl-3,3,4,4-tetramethyl-8b-quinolin-3-yl-4,8b-dihydro-3H-oxazileno[3,2-a]isoquinoline (Compound No. 3-118)

Physical property: oil.
¹H-NMR (500 MHz, CDCl₃) δ ppm: 1.25 (3H, s), 1.42 (3H, s), 1.43 (3H, s), 1.48 (3H, s), 2.19 (3H, s), 6.84 (1H, s), 7.24 (1H, d, J=8.2 Hz), 7.39 (1H, d, J=8.2 Hz), 7.60 (1H, t, J=7.6 Hz), 7.77 (1H, t, J=7.6 Hz), 7.87 (1H, d, J=7.6 Hz), 8.17 (1H, d, J=7.6 Hz), 8.28 (1H, s), 8.93 (1H, s).
MS m/z: 344 (M⁺), 327, 313, 288, 271, 256.

Example 202

4',4'-dimethyl-8b'-quinolin-3-yl-4',8b'-dihydrospiro[cyclopentane-1,3'-oxazileno[3,2-a]isoquinoline] (Compound No. 3-126)

Physical property: oil.
¹H-NMR (500 MHz, CDCl₃) δ ppm: 1.25-1.67 (14H, m), 7.05-7.59 (4H, m), 7.59-7.61 (1H, m), 7.76 (1H, t, J=7.7 Hz), 7.85-7.87 (1H, m), 8.17 (1H, d, J=8.2 Hz), 8.29 (1H, s), 8.96 (1H, s).
MS m/z: 356 (M⁺), 339, 301, 287, 271, 257, 213.

Example 203

4,4,5-trifluoro-3,3-dimethyl-8b-quinolin-3-yl-4,8b-dihydro-3H-oxazileno[3,2-a]isoquinoline (Compound No. 3-135)

Physical property: oil.
$^1$H-NMR (500 MHz, CDCl$_3$) δ ppm: 1.41 (3H, d, J=2.7 Hz), 1.73 (3H, d, J=2.2 Hz), 6.96 (1H, d, J=8.7 Hz), 7.29 (1H, t, J=8.7 Hz), 7.37-7.40 (1H, m), 7.64 (1H, t, J=8.2 Hz), 7.81 (1H, t, J=8.2 Hz), 7.89 (1H, d, J=8.2 Hz), 8.19 (1H, d, J=8.2 Hz), 8.29 (1H, d, J=2.2 Hz), 8.94 (1H, d, J=2.2 Hz).
MS m/z: 356 (M$^+$), 339, 319, 283.

Example 204

3-(5-fluoro-3,3,4,4-tetramethyl-2-oxide-3,4-dihydroisoquinolin-1-yl)quinoline (Compound No. 4-100)

(Process I)

Methanesulfonic acid (3.5 mL) was added to a chloroform (60 mL) solution of 5-fluoro-3,3,4,4-tetramethyl-8b-quinolin-3-yl-4,8b-dihydro-3H-oxazileno[3,2-a]isoquinoline (6.8 g, 19.5 mmol), followed by stirring for 4 hours at room temperature, pouring aqueous sodium hydrogencarbonate solution, extracting with ethyl acetate, washing with water, concentrating and applying the resulting residue to chromatography to obtain 5.7 g (yield 84%) of the target compound.
Physical property: Melting point 165-168° C.
$^1$H-NMR (270 MHz, CDCl$_3$) δ ppm: 1.56 (12H, s), 6.65 (1H, dd, J=7.5, 1.5 Hz), 6.98-7.16 (2H, m), 7.57 (1H, t, J=7.5 Hz), 7.73-7.88 (2H, m), 8.14 (1H, d, J=8.5 Hz), 8.40 (1H, s), 8.92 (1H, s).
MS m/z: 348 (M$^+$), 331, 317, 291, 275, 260, 234, 177, 128, 101, 83.

The following compounds were synthesized in the same manner as Example 204.

Example 205

3-(5-fluoro-3,3-dimethyl-2-oxide-3,4-dihydroisoquinolin-1-yl)quinoline 1-oxide (Compound No. 4-38)

Physical property: Melting point 130-135° C.
$^1$H-NMR (270 MHz, CDCl$_3$) δ ppm: 1.20 (3H, s), 1.34 (3H, s), 2.04 (2H, s), 7.25-7.55 (5H, m), 7.69 (1H, d, J=7.7 Hz), 7.95 (1H, d, J=7.4 Hz), 8.02 (1H, d, J=7.4 Hz), 8.61 (1H, s).
MS m/z: 336 (M$^+$), 321, 204, 177, 160, 149, 133, 109, 89.

Example 206

3-(3,3,4-trimethyl-2-oxide-3,4-dihydroisoquinolin-1-yl)quinoline (Compound No. 4-65)

Physical property: oil.
$^1$H-NMR (500 MHz, CDCl$_3$) δ ppm: 1.38 (3H, d, J=7.2 Hz), 1.52 (3H, s), 1.54 (3H, s), 3.08 (1H, q, J=7.2 Hz), 6.88 (1H, d, J=7.4 Hz), 7.16 (1H, t, J=7.4 Hz), 7.28-7.34 (2H, m), 7.57 (1H, t, J=7.6 Hz), 7.77 (1H, t, J=7.6 Hz), 7.85 (1H, d, J=7.6 Hz), 8.15 (1H, d, J=7.6 Hz), 8.52 (1H, s), 9.02 (1H, s).
MS m/z: 316 (M$^+$), 299, 257, 243, 256.

Example 207

3-(3,3,4,4-tetramethyl-2-oxide-3,4-dihydroisoquinolin-1-yl)quinoline (Compound No. 4-91)

Physical property: oil.
$^1$H-NMR (500 MHz, CDCl$_3$) δ ppm: 1.38-1.75 (12H, m), 6.88 (1H, d, J=7.7 Hz), 7.16 (1H, t, J=7.7 Hz), 7.36 (1H, t, J=7.7 Hz), 7.45 (1H, d, J=7.7 Hz), 7.58 (1H, t, J=7.7 Hz), 7.77 (1H, t, J=7.7 Hz), 7.85 (1H, d, J=7.7 Hz), 8.16 (1H, d, J=7.7 Hz), 8.49 (1H, s), 9.00 (1H, s).
MS m/z: 330 (M$^+$), 313, 271, 257, 242.

Example 208

3-(5-fluoro-3,3-dimethyl-2-oxide-3,4-dihydroisoquinolin-1-yl)quinoline (Compound No. 4-20)

Physical property: oil.
$^1$H-NMR (270 MHz, CDCl$_3$) δ ppm: 1.59 (6H, d, J=2.4 Hz), 3.26 (2H, s), 6.68 (1H, d, J=7.7 Hz), 7.02-7.19 (2H, m), 7.58 (1H, t, J=7.5 Hz), 7.78 (1H, t, J=7.1 Hz), 7.84 (1H, d, J=7.9 Hz), 8.15 (1H, d, J=8.7 Hz), 8.48 (1H, d, J=1.8 Hz), 8.97 (1H, d, J=2.1 Hz).
MS m/z: 320 (M$^+$), 303, 288, 261, 248, 173, 156, 128, 101, 84.

Example 209

3-(6-fluoro-3,3,4,4-tetramethyl-2-oxide-3,4-dihydroisoquinolin-1-yl)quinoline (Compound No. 4-109)

Physical property: oil.
$^1$H-NMR (500 MHz, CDCl$_3$) δ ppm: 1.42-1.80 (12H, m), 6.85-6.88 (2H, m), 7.16 (1H, dd, J=1.6, 9.9 Hz), 7.58 (1H, t, J=7.6 Hz), 7.78 (1H, t, J=7.6 Hz), 7.85 (1H, d, J=7.6 Hz), 8.15 (1H, d, J=7.6 Hz), 8.48 (1H, s), 8.98 (1H, s).
MS m/z: 348 (M$^+$), 331, 317, 289, 275, 260.

Example 210

3-(7-fluoro-3,3,4,4-tetramethyl-2-oxide-3,4-dihydroisoquinolin-1-yl)quinoline (Compound No. 4-110)

Physical property: oil.
$^1$H-NMR (500 MHz, CDCl$_3$) δ ppm: 1.43-1.60 (12H, m), 6.59 (1H, dd, J=2.7, 9.3 Hz), 7.04 (1H, dt, J=2.7, 8.2 Hz), 7.40 (1H, dd, J=5.5, 8.2 Hz), 7.59 (1H, t, J=7.6 Hz), 7.79 (1H, t, J=7.6 Hz), 7.86 (1H, d, J=7.6 Hz), 8.17 (1H, d, J=7.6 Hz), 8.44 (1H, s), 8.98 (1H, s).
MS m/z: 348 (M$^+$), 331, 275, 260.

Example 211

3-(6-chloro-3,3,4,4-tetramethyl-2-oxide-3,4-dihydroisoquinolin-1-yl)quinoline (Compound No. 4-113)

Physical property: oil.
$^1$H-NMR (500 MHz, CDCl$_3$) δ ppm: 1.43-1.45 (12H, m), 6.83 (1H, d, J=8.2 Hz), 7.14 (1H, dd, J=2.2, 8.2 Hz), 7.41 (1H,

Example 212

3-(7-chloro-3,3,4,4-tetramethyl-2-oxide-3,4-dihydroisoquinolin-1-yl)quinoline (Compound No. 4-114)

Physical property: oil.

$^1$H-NMR (500 MHz, CDCl$_3$) δ ppm: 1.44-1.65 (12H, m), 6.86 (1H, d, J=1.6 Hz), 7.33 (1H, dd, J=1.6, 8.2 Hz), 7.38 (1H, d, J=8.2 Hz), 7.61 (1H, t, J=8.0 Hz), 7.81 (1H, t, J=8.0 Hz), 7.88 (1H, d, J=8.0 Hz), 8.18 (1H, d, J=8.0 Hz), 8.46 (1H, s), 8.97 (1H, s).

MS m/z: 364 (M$^+$), 347, 291, 256.

Example 213

3-(6-methyl-3,3,4,4-tetramethyl-2-oxide-3,4-dihydroisoquinolin-1-yl)quinoline (Compound No. 4-117)

Physical property: oil.

$^1$H-NMR (500 MHz, CDCl$_3$) δ ppm: 1.43-1.76 (12H, m), 2.39 (3H, s), 6.77 (1H, d, J=7.8 Hz), 6.97 (1H, d, J=7.8 Hz), 7.24 (1H, s), 7.57 (1H, t, J=7.6 Hz), 7.76 (1H, t, J=7.6 Hz), 7.84 (1H, d, J=7.6 Hz), 8.15 (1H, d, J=7.6 Hz), 8.50 (1H, s), 9.00 (1H, s).

MS m/z: 344 (M$^+$), 327, 313, 285, 271, 256.

Example 214

3-(7-methyl-3,3,4,4-tetramethyl-2-oxide-3,4-dihydroisoquinolin-1-yl)quinoline (Compound No. 4-118)

Physical property: oil.

$^1$H-NMR (500 MHz, CDCl$_3$) δ ppm: 1.36-1.52 (12H, m), 2.20 (3H, s), 6.67 (1H, s), 7.17 (1H, d, J=8.2 Hz), 7.32 (1H, d, J=8.2 Hz), 7.59 (1H, t, J=7.6 Hz), 7.78 (1H, t, J=7.6 Hz), 7.86 (1H, d, J=7.6 Hz), 8.16 (1H, d, J=7.6 Hz), 8.50 (1H, s), 8.98 (1H, s).

MS m/z: 344 (M$^+$), 327, 313, 271, 256.

Example 215

3',3'-dimethyl-1'-(1-oxide-quinolin-3-yl)-3'H-spiro[cyclopentane-1,4'-isoquinoline] 2'-oxide (Compound No. 4-126)

Physical property: oil.

$^1$H-NMR (500 MHz, CDCl$_3$) δ ppm: 0.79 (3H, s), 1.18 (3H, d, J=6.6 Hz), 1.24-1.91 (6H, m), 2.43-2.48 (1H, m), 2.85-2.90 (1H, m), 7.08 (1H, d, J=7.7 Hz), 7.16 (1H, t, J=7.7 Hz), 7.31 (1H, d, J=7.7 Hz), 7.42 (1H, t, J=7.7 Hz), 7.70 (1H, t, J=8.2 Hz), 7.82 (1H, t, J=8.2 Hz), 7.87 (1H, s), 7.93 (1H, d, J=8.2 Hz), 8.58 (1H, s), 8.79 (1H, d, J=8.2 Hz).

MS m/z: 372 (M$^+$), 356, 339, 287, 269, 257.

Example 216

4',4'-dimethyl-1'-quinolin-3-yl-4'H-spiro[cyclopentane-1,4'-isoquinoline] 2'-oxide (Compound No. 4-127)

Physical property: oil.

$^1$H-NMR (500 MHz, CDCl$_3$) δ ppm: 1.24-2.04 (14H, m), 6.86 (1H, d, J=7.6 Hz), 7.14 (1H, t, J=7.6 Hz), 7.36 (1H, t, J=7.6 Hz), 7.43 (1H, d, J=7.6 Hz), 7.58 (1H, t, J=7.6 Hz), 7.77 (1H, t, J=7.6 Hz), 7.85 (1H, d, J=7.6 Hz), 8.16 (1H, d, J=7.6 Hz), 8.48 (1H, s), 8.99 (1H, s).

MS m/z: 356 (M$^+$), 339, 301, 283, 257.

Example 217

4',4'-dimethyl-1'-quinolin-3-yl-4'H-spiro[cyclohexane-1,4'-isoquinoline] 2'-oxide (Compound No. 4-126)

Physical property: oil.

$^1$H-NMR (500 MHz, CDCl$_3$) δ ppm: 1.30 (3H, s), 1.42-1.90 (8H, m), 1.58 (3H, s), 2.37-2.40 (1H, m), 2.47-2.50 (1H, m), 6.87 (1H, d, J=7.8 Hz), 7.14 (1H, t, J=7.8 Hz), 7.33 (1H, t, J=7.8 Hz), 7.41 (1H, d, J=8.2 Hz), 7.57 (1H, t, J=7.8 Hz), 7.76 (1H, t, J=7.8 Hz), 7.84 (1H, d, J=7.8 Hz), 8.15 (1H, d, J=7.8 Hz), 8.35 (1H, s), 8.99 (1H, s).

MS m/z: 370 (M$^+$), 353, 285, 257, 242.

Example 218

3-(4,4-difluoro-3,3-dimethyl-2-oxide-3,4-dihydroisoquinolin-1-yl)quinoline (Compound No. 4-218)

Physical property: oil.

$^1$H-NMR (270 MHz, CDCl$_3$) δ ppm: 1.68 (6H, s), 7.03 (1H, d, J=7.7 Hz), 7.40-7.63 (3H, m), 7.78-7.88 (3H, m), 8.17 (1H, d, J=8.2 Hz), 8.47 (1H, d, J=2.1 Hz), 9.00 (1H, d, J=2.1 Hz).

MS m/z: 338 (M$^+$), 321, 301, 294, 265, 246, 128, 119, 101, 84.

Example 219

3-(4,4,5-trifluoro-3,3-dimethyl-2-oxide-3,4-dihydroisoquinolin-1-yl)quinoline (Compound No. 4-219)

Physical property: oil.

$^1$H-NMR (500 MHz, CDCl$_3$) δ ppm: 1.72 (6H, s), 6.80 (1H, d, J=8.2 Hz), 7.19 (1H, t, J=8.2 Hz), 7.37-7.42 (1H, m), 7.61 (1H, t, J=7.6 Hz), 7.81 (1H, t, J=7.6 Hz), 7.86 (1H, d, J=7.6 Hz), 8.17 (1H, d, J=7.6 Hz), 8.40 (1H, s), 8.94 (1H, s).

MS m/z: 356 (M$^+$), 339, 319, 283.

Example 220

3-(4,4,6-trifluoro-3,3-dimethyl-3,4-dihydroisoquinolin-1-yl)quinoline (Compound No. 1-940)

Physical property: oil.

$^1$H-NMR (270 MHz, CDCl$_3$) δ ppm: 1.46 (6H, s), 7.16-7.17 (1H, m), 7.33-7.40 (1H, m), 7.57 (1H, d, J=8.5 Hz), 7.62

(1H, t, J=6.9 Hz), 7.80 (1H, t, J=6.9 Hz), 7.89 (1H, d, J=8.2 Hz), 8.18 (1H, d, J=8.5 Hz), 8.37 (1H, d, J=1.8 Hz), 9.12 (1H, d, J=2.1 Hz).

MS m/z: 340 (M⁺), 325, 305, 284, 248, 170, 128, 101.

Example 221

3-(4,4,7-trifluoro-3,3-dimethyl-3,4-dihydroisoquinolin-1-yl)quinoline (Compound No. 1-941)

Physical property: oil.
¹H-NMR (270 MHz, CDCl₃) δ ppm: 1.46 (6H, s), 7.04 (1H, d, J=8.9 Hz), 7.35 (1H, td, J=8.4 Hz, 2.3 Hz), 7.63 (1H, t, J=7.2 Hz), 7.81 (1H, t, J=8.9 Hz), 7.86-7.87 (1H, m), 7.90 (1H, d, J=8.2 Hz), 8.19 (1H, d, J=8.9 Hz), 8.38 (1H, d, J=1.4 Hz), 9.14 (1H, d, J=2.7 Hz).

MS m/z: 340 (M⁺), 325, 305, 284, 248, 160, 149, 128, 101.

Example 222

3-(6-chloro-4,4-difluoro-3,3-dimethyl-3,4-dihydroisoquinolin-1-yl)quinoline (Compound No. 1-943)

Physical property: oil.
¹H-NMR (500 MHz, CDCl₃) δ ppm: 1.46 (6H, s), 7.30 (1H, d, J=8.2 Hz), 7.52 (1H, d, J=6.9 Hz), 7.63 (1H, t, J=7.6 Hz), 7.81 (1H, t, J=7.6 Hz), 7.86 (1H, s), 7.89 (1H, d, J=8.2 Hz), 8.19 (1H, d, J=8.2 Hz), 8.37 (1H, d, J=2.1 Hz), 9.12 (1H, d, J=2.1 Hz).

MS m/z: 356 (M⁺), 321, 300, 265, 149, 101.

Example 223

3-(7-chloro-4,4-difluoro-3,3-dimethyl-3,4-dihydroisoquinolin-1-yl)quinoline (Compound No. 1-944)

Physical property: oil.
¹H-NMR (270 MHz, CDCl₃) δ ppm: 1.45 (6H, s), 7.31 (1H, s), 7.58-7.67 (2H, m), 7.80 (2H, t, J=8.2 Hz), 7.91 (1H, d, J=7.7 Hz), 8.19 (1H, d, J=8.5 Hz), 8.38 (1H, s), 9.12 (1H, s).

MS m/z: 356 (M⁺), 341, 321, 300, 265, 168, 119, 101.

Example 224

3-(6-bromo-4,4-difluoro-3,3-dimethyl-3,4-dihydroisoquinolin-1-yl)quinoline (Compound No. 1-946)

Physical property: oil.
¹H-NMR (500 MHz, CDCl₃) δ ppm: 1.46 (6H, s), 7.28-7.70 (1H, m), 7.61 (1H, t, J=7.4 Hz), 7.67 (1H, d, J=8.2 Hz), 7.80 (1H, t, J=7.7 Hz), 7.89 (1H, d, j=8.2 Hz), 8.00 (1H, s), 8.19 (1H, d, J=8.8 Hz), 8.19 (1H, s), 9.13 (1H, d, J=2.2 Hz).

MS m/z: 400 (M⁺), 385, 353, 321, 297, 265.

Example 225

3-(7-bromo-4,4-difluoro-3,3-dimethyl-3,4-dihydroisoquinolin-1-yl)quinoline (Compound No. 1-947)

Physical property: Melting point 123-125° C.
¹H-NMR (500 MHz, CDCl₃) δ ppm: 1.45 (6H, s), 7.47 (1H, s), 7.63 (1H, t, J=7.7 Hz), 7.75 (1H, d, J=8.2 Hz), 7.78-7.83 (2H, m), 7.92 (1H, d, J=7.7 Hz), 8.20 (1H, d, J=8.2 Hz), 8.39 (1H, d, J=2.2 Hz), 9.13 (1H, d, J=2.2 Hz).

MS m/z: 400 (M⁺), 385, 265, 346, 321, 265, 245, 149, 119, 101.

Example 226

3-(6-methyl-4,4-difluoro-3,3-dimethyl-3,4-dihydroisoquinolin-1-yl)quinoline (Compound No. 1-949)

Physical property: oil.
¹H-NMR (500 MHz, CDCl₃) δ ppm: 1.45 (6H, s), 2.50 (3H, s), 7.21 (1H., d, J=8.2 Hz), 7.33 (1H, d, J=7.7 Hz), 7.61 (1H, t, J=7.7 Hz), 7.68 (1H, s), 7.79 (1H, t, J=7.7 Hz), 7.89 (1H, d, 7.7 Hz), 8.18 (1H, d, J=8.2 Hz), 8.39 (1H, s), 9.13 (1H, d, J=1.6 Hz).

MS m/z: 336 (M⁺), 335, 321, 301, 280, 265, 239, 158, 101.

Example 227

3-(4,4-difluoro-6-methoxy-3,3-dimethyl-3,4-dihydroisoquinolin-1-yl)quinoline (Compound No. 1-950)

Physical property: oil.
¹H-NMR (270 MHz, CDCl₃) δ ppm: 1.45 (6H s), 3.93 (3H, s), 6.98 (1H, dd, J=8.6, 2.4 Hz), 7.24-7.27 (1H, m), 7.37 (1H, d, J=2.1 Hz), 7.61 (1H, t, J=6.9 Hz), 7.78 (1H, t, J=7.6 Hz), 7.88 (1H, d, J=8.2 Hz), 8.17 (1H, d, J=8.2 Hz), 8.38 (1H, d, J=1.4 Hz), 9.12 (1H, d, J=2.1 Hz).

MS m/z: 352 (M⁺), 337, 321, 296, 265, 196, 167, 149, 101, 88, 59.

Example 228

3-(5,7-dichloro-4,4-difluoro-3,3-dimethyl-3,4-dihydroisoquinolin-1-yl)quinoline (Compound No. 1-951)

Physical property: oil.
¹H-NMR (500 MHz, CDCl₃) δ ppm: 1.49 (6H, s), 7.21 (1H, d, J=1.4 Hz), 7.63 (1H, d, J=7.6 Hz), 7.66 (1H, d, J=2.1 Hz), 7.82 (1H, t, J=7.9 Hz), 7.91 (1H, d, J=7.6 Hz), 8.19 (1H, d, J=8.2 Hz), 8.32 (1H, d, J=2.1 Hz), 9.05 (1H, d, J=2.1 Hz).

MS m/z: 390 (M⁺), 355, 334, 299, 178, 149, 126, 101, 72.

Example 229

3-(4,4,6-trifluoro-3,3,7-trimethyl-3,4-dihydroisoquinolin-1-yl)quinoline (Compound No. 1-952)

Physical property: oil.
¹H-NMR (500 MHz, CDCl₃) δ ppm: 1.44 (6H, s), 2.27 (3H, s), 7.16 (1H, d, J=7.6 Hz), 7.50 (1H, d, J=7.6 Hz), 7.63 (1H, t, J=7.6 Hz), 7.81 (1H, td, J=7.9, 1.6 Hz), 7.91 (1H, d, J=8.2 Hz), 8.19 (1H, d, J=8.2 Hz), 8.39 (1H, d, J=2.1 Hz), 9.10 (1H, J=2.1 Hz).

MS m/z: 353 (M⁺−1), 339, 298, 149, 126, 118, 100.

Example 230

3-(6-fluoro-4-keto-3,3-dimethyl-3,4-dihydroiso-quinolin-1-yl)quinoline (Compound No. 1-953)

Physical property: oil.
$^1$H-NMR (270 MHz, CDCl$_3$) δ ppm: 1.62 (6H, s), 7.33-7.48 (3H, m), 7.64 (1H, t, J=8.1 Hz), 7.78-7.87 (2H, m), 7.91 (1H, d, J=8.2 Hz), 8.20 (1H, d, J=8.7 Hz), 8.36 (1H, d, J=2.1 Hz), 9.09 (1H, d, J=2.1 Hz).
MS m/z: 318 (M$^+$), 303, 289, 275, 262, 248, 234, 207, 159, 128, 117, 104.

Example 231

3-(7-fluoro-4-keto-3,3-dimethyl-3,4-dihydroiso-quinolin-1-yl)quinoline (Compound No. 1-954)

Physical property: oil.
$^1$H-NMR (270 MHz, CDCl$_3$) δ ppm: 1.46 (6H, s), 7.04 (1H, d, J=8.9 Hz), 7.35 (1H, td, J=8.4 Hz, 2.3 Hz), 7.63 (1H, br.t, J=7.2 Hz), 7.81 (1H, br.t, J=8.9 Hz), 7.86-7.87 (1H, m), 7.90 (1H, d, J=8.2 Hz), 8.19 (1H, d, J=8.9 Hz), 8.38 (1H, d, J=1.4 Hz), 9.14 (1H, d, J=2.7 Hz).
MS m/z: 340 (M$^+$), 325, 305, 284, 248, 160, 149, 128, 101.

Example 232

3-(5-chloro-4-keto-3,3-dimethyl-3,4-dihydroiso-quinolin-1-yl)quinoline (Compound No. 1-955)

Physical property: oil.
$^1$H-NMR (270 MHz, CDCl$_3$) δ ppm: 1.60 (6H, s), 7.27 (1H, d, J=6.9 Hz), 7.52-7.70 (3H, m), 7.80 (1H, t, J=8.2 Hz), 7.90 (1H, d, J=7.9 Hz), 8.19 (1H, d, J=7.9 Hz), 8.35 (1H, d, J=2.1 Hz), 9.07 (1H, d, J=2.1 Hz).
MS m/z: 334 (M$^+$), 319, 305, 291, 271, 250, 214, 187, 128, 101.

Example 233

3-(7-chloro-4-keto-3,3-dimethyl-3,4-dihydroiso-quinolin-1-yl)quinoline (Compound No. 1-957)

Physical property: oil.
$^1$H-NMR (270 MHz, CDCl$_3$) δ ppm: 1.61 (6H, s), 7.37 (1H, d, J=2.1 Hz), 7.62-7.68 (2H, m), 7.82 (1H, t, J=8.7 Hz), 7.93 (1H, d, J=8.1 Hz), 8.13 (1H, d, J=8.5 Hz), 8.21 (1H, d, J=8.7 Hz), 8.37 (1H, d, J=2.1 Hz), 9.09 (1H, d, J=2.4 Hz).
MS m/z: 334 (M$^+$), 319, 305, 291, 271, 250, 214, 187, 128, 101.

Example 234

3-(5-bromo-4-keto-3,3-dimethyl-3,4-dihydroiso-quinolin-1-yl)quinoline (Compound No. 1-958)

Physical property: oil.
$^1$H-NMR (270 MHz, CDCl$_3$) δ ppm: 1.60 (6H, s), 7.31 (1H, dd, J=7.9, 1.1 Hz), 7.47 (1H, t, J=7.9 Hz), 7.63 (1H, t, J=8.2 Hz), 7.80 (1H, t, J=8.5 Hz), 7.87-7.93 (2H, m), 8.18 (1H, d, J=8.2 Hz), 8.35 (1H, d, J=1.6 Hz), 9.07 (1H, d, J=2.1 Hz).

Example 235

3-(6-bromo-4-keto-3,3-dimethyl-3,4-dihydroiso-quinolin-1-yl)quinoline (Compound No. 1-959)

Physical property: oil.
$^1$H-NMR (270 MHz, CDCl$_3$) δ ppm: 1.61 (6H, s), 7.29 (1H, d, J=8.2 Hz), 7.55-7.67 (1H, m), 7.75-7.88 (2H, m), 7.90 (1H, d, J=9.0 Hz), 8.19 (1H, d, J=8.5 Hz), 8.19 (1H, d, J=1.8 Hz), 8.35 (1H, d, J=1.8 Hz), 9.08 (1H, d, J=1.6 Hz).
MS m/z: 378 (M$^+$), 365, 349, 337, 294, 285, 271, 229, 214, 128, 101.

Example 236

3-(7-bromo-4-keto-3,3-dimethyl-3,4-dihydroiso-quinolin-1-yl)quinoline (Compound No. 1-960)

Physical property: oil.
$^1$H-NMR (500 MHz, CDCl$_3$) δ ppm: 1.61 (6H, s), 7.54 (1H, d, J=1.6 Hz), 7.65 (1H, t, J=7.4 Hz), 7.80-7.89 (2H, m), 7.94 (1H, d, J=7.7 Hz), 8.04 (1H, d, J=8.2 Hz), 8.21 (1H, d, J=8.8 Hz), 8.37 (1H, d, J=2.2 Hz), 9.09 (1H, d, J=2.2 Hz).
MS m/z: 378 (M$^+$), 363, 351, 337, 322, 296, 271, 255, 229, 214, 187, 167, 149, 128, 107, 75, 57.

Example 237

4,4-difluoro-3,3-dimethyl-8b-quinolin-3-yl-4,8b-dihydro-3H-oxazileno[3,2-a]isoquinoline (Compound No. 3-134)

Physical property: oil.
$^1$H-NMR (270 MHz, CDCl$_3$) δ ppm: 1.32 (3H, d, J=2.6 Hz), 1.73 (3H, d, J=2.4 Hz), 7.16 (1H, d, J=7.7 Hz), 7.42 (1H, t, J=7.7 Hz), 7.56-7.66 (2H, m), 7.76-7.83 (1H, m), 7.87-7.93 (2H, m), 8.18 (1H, d, J=9.0 Hz), 8.31 (1H, d, J=2.1 Hz), 8.94 (1H, d, J=2.1 Hz).
MS m/z: 338 (M$^+$), 322, 301, 287, 266, 230, 154, 128, 101, 85.

Preparation Example 1

Powder

After mixing the compound of Example 1 (1.0 parts by weight), Dryless A?? (alkyl ether phosphoric acid ester, Nippon Kayaku, 0.4 parts by weight), Carprex #80-D (white carbon, Shionogi & Co., Ltd., 1.5 parts by weight), calcium carbonate (Ashidachi Lime Co., Ltd., 0.5 parts by weight) and Keiwa Clay (Keiwa Rozai Co., Ltd., 32.1 parts by weight), the mixture was crushed with an Example Model KII-1 (hammer mill, Fuji Paudal Co., Ltd.), and 1.5 times the weight of the resulting powder of DL Clay Keiwa (Keiwa Rozai Co., Ltd.) were added and mixed to obtain a powder DL.

Preparation Example 2

Emulsion

The compound of Example 2 (10 parts by weight) was dissolved in a mixed solution of xylene (Wako Pure Chemical Industries, Ltd., 40 parts by weight) and DMSO (Wako Pure Chemical Industries, Ltd., 35 parts by weight), followed by the addition and mixing of Parakol KPS (anionic surfactant and nonionic surfactant mixture, Nippon Nyukazai Co., Ltd., 25 parts by weight) to this solution to obtain an emulsion.

Preparation Example 3

Water-Dispersible Powder

The compound of Example 3 (1 part by weight), Carprex #80-D (10 parts by weight), Gohsenol GL05 (polyvinyl alcohol, Nippon Synthetic Chemical Industry Co., Ltd., 2 parts by weight), Nyucol 291PG (sodium dioctylsulfosuccinate, Nippon Nyukazai Co., Ltd., 0.5 parts by weight), Neogen Powder (linear sodium alkylbenzenesulfonate, Dai-Ichi Kogyo Seiyaku Co., Ltd., 5 parts by weight), Radiolite #200 (baked diatomaceous earth, Showa Chemical Industry Co., Ltd., 10 parts by weight) and H Bibun (kaolinite clay, Keiwa Rozai Co., Ltd., 71.5 parts by weight) were mixed well and crushed with an Example Model KII-1 to obtain a water-dispersible powder.

Preparation Example 4

Granules

The compound of Example 4 (2 parts by weight), sodium tripolyphosphate (Mitsui Chemicals, Inc., 2 parts by weight), Amycol No. 1 (dextrin, Nippon Starch Chemical Co., Ltd., 1.5 parts by weight) and Carhin 600 (calcium carbonate, Ashidachi Lime Co., Ltd., 69.5 parts by weight) were mixed followed by granulation by extruding using a domed granulator (Fuji Paudal Co., Ltd., screen diameter: 0.9 mm). The resulting granules were dried with a shelf dryer (Tabai Co., Ltd., Perfect Oven Model PS-222, 60° C.) followed by grading to a size of 600 to 1180 μm to obtain granules.

Test Example 1

Rice Blast Control Test

Curative Effects

A suspension of pathogen spores were inoculated by spraying onto potted test plants (rice variety: Karakaze) in the third to fourth leaf stage, and onset of disease was promoted by placing the pots in an inoculation room at a room temperature of 20 to 23° C. Compounds of the present invention were dissolved in a mixed solution of dimethylsulfoxide and methanol (volume ratio: 7/3), spraying liquids containing 300 ppm of the compounds of the present invention were prepared and uniformly sprayed onto the pots. The degree of disease onset of the test plants was observed 7 days after the inoculation. The test was carried out in duplicate.

Furthermore, the degree of disease onset was evaluated to one of four levels from 0 to 3 according to the criteria below by macroscopically observing the degree of disease onset of the test plants.

Degree of disease onset:

0: No onset of disease

1: Degree of disease onset less than 40% of the untreated area

2: Degree of disease onset 40% to less than 80% of the untreated area

3: Degree of disease onset 80% or more

As a result of this test, Example 2 (Compound No. 1-32), Example 4 (Compound No. 2-1), Example. 6 (Compound No. 1-1), Example 7 (Compound No. 1-7), Example 9 (Compound No. 1-19), Example 14 (Compound No. 1-38), Example 16 (Compound No. 1-41), Example 18 (Compound No. 1-44), Example 21 (Compound No. 1-54), Example 22 (Compound No. 1-56), Example 26 (Compound No. 1-69), Example 30 (Compound No. 1-85), Example 32 (Compound No. 1-94), Example 33 (Compound No. 1-95), Example 36 (Compound No. 1-100), Example 38 (Compound No. 1-101), Example 39 (Compound No. 1-101), Example 51 (Compound No. 1-116), Example 52 (Compound No. 1-117), Example 55 (Compound No. 1-137), Example 56 (Compound No. 1-147), Example 57 (Compound No. 1-175), Example 58 (Compound No. 1-185), Example 59 (Compound No. 1-213), Example 60 (Compound No. 1-251), Example 62 (Compound No. 1-307), Example 63 (Compound No. 1-345), Example 66 (Compound No. 1-385), Example 68 (Compound No. 1-387), Example 69 (Compound No. 1-424), Example 71 (Compound No. 1-464), Example 72 (Compound No. 1-502), Example 73 (Compound No. 1-540), Example 74 (Compound No. 1-578), Example 75 (Compound No. 1-594), Example 79 (Compound No. 1-672), Example 80 (Compound No. 1-710), Example 81 (Compound No. 1-720), Example 82 (Compound No. 1-721), Example 101 (Compound No. 1-790), Example 103 (Compound No. 1-793), Example 104 (Compound No. 1-796), Example 105 (Compound No. 1-799), Example 106 (Compound No. 1-802), Example 107 (Compound No. 1-804), Example 108 (Compound No. 1-806), Example 109 (Compound No. 1-807), Example 110 (Compound No. 2-36), Example 112 (Compound No. 2-40), Example 114 (Compound No. 1-866), Example 117 (Compound No. 1-99), Example 118 (Compound No. 1-99), Example 119 (Compound No. 1-856), Example 124 (Compound No. 2-255), Example 125 (Compound No. 2-264), Example 132 (Compound No. 1-886), Example 150 (Compound No. 1-904), Example 156 (Compound No. 1-910), Example 158 (Compound No. 1-912), Example 160 (Compound No. 1-914), Example 163 (Compound No. 1-917), Example 164 (Compound No. 1-918), Example 165 (Compound No. 1-919), Example 171 (Compound No. 1-925), Example 174 (Compound No. 1-927), Example 177 (Compound No. 1-929), Example 178 (Compound No. 1-930), Example 181 (Compound No. 1-935), Example 183 (Compound No. 1-937), Example 184 (Compound No. 1-938), Example 185 (Compound No. 1-939), Example 193 (Compound No. 3-100), Example 196 (Compound No. 3-91), Example 197 (Compound No. 3-20), Example 198 (Compound No. 3-108), Example 199 (Compound No. 3-110), Example 202 (Compound No. 3-126), Example 203 (Compound No. 3-135), Example 204 (Compound No. 4-100), Example 206 (Compound No. 4-65), Example 207 (Compound No. 4-91), Example 208 (Compound No. 4-20), Example 209 (Compound No. 4-109), Example 210 (Compound No. 4-110), Example 211 (Compound No. 4-113), Example 217 (Compound No. 4-129), Example 218 (Compound No. 4-134) and Example 219 (Compound No. 4-135) demonstrated a degree of disease onset of 0.

Test Example 2

Tomato Gray Mold Control Test

Preventive Effects

Bulk drug was dissolved in a mixed solution of dimethylsulfoxide and methanol (volume ratio: 7/3), and spraying liquids containing 300 ppm of compounds of the present invention were uniformly sprayed onto potted test plants (tomato: giant Fukuju variety) in the second to third leaf stage. One day after planting, a suspension of pathogen spores were inoculated by spraying onto the pots in an inoculation room at a room temperature of 20 to 23° C. to promote the onset of disease. The degree of disease onset was investigated 2 days after inoculation. The test was carried out in duplicate.

Furthermore, the degree of disease onset was evaluated to one of four levels from 0 to 3 according to the criteria below by macroscopically observing the degree of disease onset of the test plants.

Degree of disease onset:

0: No onset of disease

1: Degree of disease onset less than 40% of the untreated area

2: Degree of disease onset 40% to less than 80% of the untreated area

3: Degree of disease onset 80% or more

As a result of this test, Example 2 (Compound No. 1-32), Example 14 (Compound No. 1-38), Example 18 (Compound No. 1-44), Example 20 (Compound No. 1-53), Example 21 (Compound No. 1-54), Example 22 (Compound No. 1-56), Example 23 (Compound No. 1-65), Example 30 (Compound No. 1-85), Example 44 (Compound No. 1-106), Example 51 (Compound No. 1-116), Example 52 (Compound No. 1-117), Example 53 (Compound No. 1-126), Example 56 (Compound No. 1-147), Example 58 (Compound No. 1-185), Example 66 (Compound No. 1-385), Example 68 (Compound No. 1-387), Example 69 (Compound No. 1-424), Example 71 (Compound No. 1-464), Example 72 (Compound No. 1-502), Example 73 (Compound No. 1-540), Example 75 (Compound No. 1-594), Example 79 (Compound No. 1-672), Example 92 (Compound No. 1-764), Example 103 (Compound No. 1-793), Example 107 (Compound No. 1-804), Example 108 (Compound No. 1-806), Example 109 (Compound No. 1-807), Example 110 (Compound No. 2-36), Example 112 (Compound No. 2-40), Example 114 (Compound No. 1-866), Example 120 (Compound No. 1-857), Example 121 (Compound No. 1-858), Example 123 (Compound No. 1-867), Example 154 (Compound No. 1-908), Example 156 (Compound No. 1-910), Example 158 (Compound No. 1-912), Example 159 (Compound No. 1-913), Example 163 (Compound No. 1-917), Example 164 (Compound No. 1-918), Example 165 (Compound No. 1-919), Example 174 (Compound No. 1-927), Example 175 (Compound No. 1-926), Example 177 (Compound No. 1-929), Example 178 (Compound No. 1-930), Example 191 (Compound No. 2-278), Example 193 (Compound No. 3-100), Example 196 (Compound No. 3-91), Example 197 (Compound No. 3-20), Example 199 (Compound No. 3-110), Example 202 (Compound No. 3-126), Example 203 (Compound No. 3-135), Example 204 (Compound No. 4-100), Example 207 (Compound No. 4-91), Example 209 (Compound No. 4-109), Example 211 (Compound No. 4-113), Example 217 (Compound No. 4-129), Example 218 (Compound No. 4-134) and Example 219 (Compound No. 4-135) demonstrated a degree of disease onset of 0.

INDUSTRIAL APPLICABILITY

Compounds of the present invention can be used as agro-horticultural antimicrobial agents, and are superior as agri-horticultural antimicrobial agents since they demonstrate outstanding effects against various plant pathogens, and particularly rice blast, without causing damage to the host plant.

Although examples of plant diseases against which compounds of the present invention demonstrate superior effects include rice blast (*Pyricularia oryzae*) and gray mold (*Botrytis cinerea*) in tomatoes, cucumbers and green beans, the antimicrobial spectrum of compounds of the present invention is not limited thereto.

The invention claimed is:

1. A compound, or salt thereof, represented by general formula (Ia), (Ib), (Ic) or (Id):

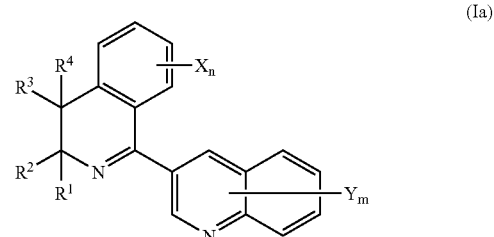

(Ia)

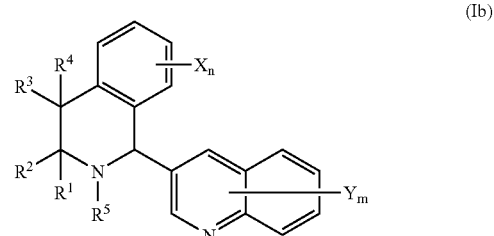

(Ib)

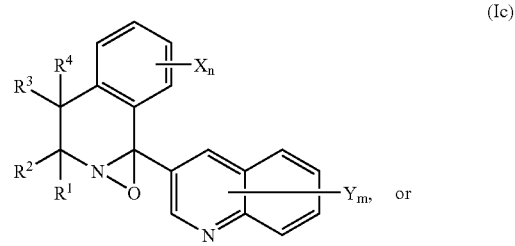

(Ic)

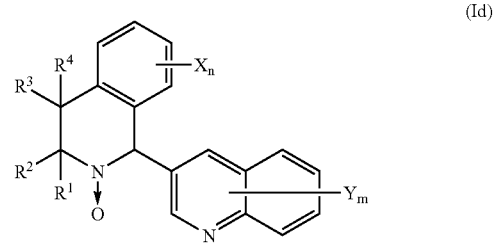

(Id)

(wherein, $R^1$ and $R^2$ may be the same or different, and represent a $C_1$-$C_6$ alkyl group which may be substituted with 1 to 3 substituents, which may be the same or different, selected from the group consisting of a halogen atom, $C_1$-$C_6$ alkoxy group, $C_1$-$C_6$ alkylthio group and phenoxy group;

an aryl group which may be substituted with 1 to 6 substituents, which may be the same or different, selected from the group consisting of a halogen atom, $C_1$-$C_6$ alkyl group which may be substituted with 1 to 3 same or different halogen atoms, $C_1$-$C_6$ alkoxy group, amino group which may be substituted with 1 to 2 same or different $C_1$-$C_6$ alkyl groups or acyl groups, nitro group, cyano group, hydroxyl group mercapto group, and $C_1$-$C_6$ alkylthio group;

a heteroaryl group which may be substituted with 1 to 6 substituents, which may be the same or different, selected from the group consisting of a halogen atom, $C_1$-$C_6$ alkyl group which may be substituted with 1 to 3 same or different halogen atoms, and $C_1$-$C_6$ alkoxy group;

an aralkyl group which may be substituted with 1 to 6 substituents, which may be the same or different, selected from the group consisting of a halogen atom, $C_1$-$C_6$ alkyl group which may be substituted with 1 to 3 same or different halogen atoms, $C_1$-$C_6$ alkoxy group, amino group which may be substituted with 1 to 2 same or different $C_1$-$C_6$ alkyl groups or acyl groups, nitro group, cyano group, hydroxyl group, mercapto group and $C_1$-$C_6$ alkylthio group; or $R^1$ and $R^2$ together represent a $C_3$-$C_{10}$ cycloalkyl group, which may be substituted with 1 to 3 substituents, which may be the same or different, selected from the group consisting of a halogen atom, $C_1$-$C_6$ alkyl group, $C_1$-$C_6$ alkoxy group and phenoxy group;

$R^3$ and $R^4$ may be the same or different, and represent a hydrogen atom;

a $C_1$-$C_6$ alkyl group which may be substituted with 1 to 3 substituents, which may be the same or different, selected from the group consisting of a halogen atom, $C_1$-$C_6$ alkoxy group, $C_1$-$C_6$ alkylthio group and phenoxy group;

a halogen atom;

a $C_1$-$C_6$ alkylene group;

a $C_1$-$C_6$ alkoxy group;

a hydroxyl group;

a keto group; or, $R^3$ and $R^4$ together represent a $C_3$-$C_{10}$ cycloalkyl group which may be substituted with 1 to 3 substituents, which may the same or different, selected from the group consisting of a halogen atom, $C_1$-$C_6$ alkyl group, $C_1$-$C_6$ alkoxy group and phenoxy group;

$R^5$ represents a hydrogen atom, acyl group; or a $C_1$-$C_6$ alkyl group which may be substituted with 1 to 3 substituents, which may be the same or different, selected from the group consisting of a halogen atom, $C_1$-$C_6$ alkoxy group, $C_1$-$C_6$ alkylthio group and phenoxy group;

X represents a halogen atom;

a $C_1$-$C_6$ alkyl group which may be substituted with 1 to 3 substituents, which may be the same or different, selected from the group consisting of a halogen atom, $C_1$-$C_6$ alkoxy group, hydroxyl group, $C_1$-$C_6$ alkoxycarbonyl group and phenoxy group;

a $C_2$-$C_6$ alkenyl group which may be substituted with 1 to 3 substituents, which may be the same or different, selected from the group consisting of a halogen atom, $C_1$-$C_6$ alkoxy group, $C_1$-$C_6$ alkoxycarbonyl group and phenoxy group;

a $C_2$-$C_6$ alkynyl group which may be substituted with 1 to 3 substituents, which may be the same or different, selected from the group consisting of a halogen atom, $C_1$-$C_6$ alkoxy group and phenoxy group;

an aryl group which may be substituted with 1 to 6 substituents, which may be the same or different, selected from the group consisting of a halogen atom, $C_1$-$C_6$ alkyl group which may be substituted with 1 to 3 same or different halogen atoms, $C_1$-$C_6$ alkoxy group, amino group which may be substituted with 1 to 2 same or different $C_1$-$C_6$ alkyl groups or acyl groups, nitro group, cyano group, hydroxyl group, mercapto group and $C_1$-$C_6$ alkylthio group;

a heteroaryl group which may be substituted with 1 to 6 substituents, which may be the same or different, selected from the group consisting of a halogen atom, $C_1$-$C_6$ alkyl group which may be substituted with 1 to 3 same or different halogen atoms, and $C_1$-$C_6$ alkoxy group;

a $C_1$-$C_6$ alkoxy group;

an amino group which may be substituted with 1 to 2 $C_1$-$C_6$ alkyl groups or acyl groups, which may be the same or different;

an acyl group;

a cyano group; or an N-hydroxyalkaneimidoyl group in which a hydrogen atom of the hydroxyl group may be substituted with a substituent selected from the group consisting of a $C_1$-$C_6$ alkyl group, $C_2$-$C_6$ alkenyl group, $C_2$-$C_6$ alkynyl group, aralkyl group, aryl group and heteroaryl group;

Y represents a substituent selected from the group consisting of a halogen atom, $C_1$-$C_6$ alkyl group, $C_1$-$C_6$ alkoxy group and hydroxyl group;

n represents an integer of 0 to 4; and, m represents an integer of 0 to 6).

2. The compound or salt thereof according to claim 1 wherein $R^1$ and $R^2$ represent a $C_1$-$C_6$ alkyl group which may be substituted with 1 to 3 substituents, which may be the same or different, selected from the group consisting of a halogen atom, $C_1$-$C_6$ alkoxy group, and phenoxy group, or an aryl group which may be substituted with 1 to 6 substituents, which may the same or different, selected from the group consisting of a halogen atom, $C_1$-$C_6$ alkyl group, $C_1$-$C_6$ alkoxy group and hydroxyl group.

3. The compound or salt thereof according to claim 1 wherein $R^1$ and $R^2$ represent a $C_1$-$C_6$ alkyl group which may be substituted with 1 to 3 substituents, which may be the same or different, or a phenyl group which may be substituted with 1 to 6 halogen atoms, which may be the same or different.

4. The compound or salt thereof according to claim 1 wherein $R^1$ and $R^2$ represent a methyl group, ethyl group, propyl group, trifluoromethyl group, trifluoroethyl group, phenyl group, fluorophenyl group or chlorophenyl group.

5. The compound or salt thereof according to claim 1 wherein $R^3$ and $R_4$ represent a hydrogen atom, halogen atom or $C_1$-$C_6$ alkyl group.

6. The compound or salt thereof according to claim 1 wherein X represents a halogen atom; a $C_1$-$C_6$ alkyl group; a $C_1$-$C_6$ alkynyl group; an aryl group which may be substituted with 1 to 6 substituents, which may be the same or different, selected from the group consisting of a halogen atom, $C_1$-$C_6$ alkyl group which may be substituted with 1 to 3 same or different halogen atoms, and a $C_1$-$C_6$ alkoxy group; a heteroaryl group which may be substituted with 1 to 6 substituents, which may be the same or different, selected from the group consisting of a halogen atom, $C_1$-$C_6$ alkyl group which may be substituted with 1 to 3 same or different halogen atoms, and $C_1$-$C_6$ alkoxy group; a cyano group; or, an N-hydroxyalkaneimidoyl group in which a hydrogen atom of the hydroxyl group may be substituted with a substituent selected from the group consisting of a $C_1$-$C_6$ alkyl group and a phenyl group, and n represents an integer of 0 to 2.

7. The compound or salt thereof according to claim 1 wherein X represents a halogen atom; a $C_1$-$C_6$ alkyl group; a $C_1$-$C_6$ alkynyl group; a heteroaryl group which may be substituted with 1 to 6 substituents, which may be the same or different, selected from the group consisting of a halogen atom, $C_1$-$C_6$ alkyl group which may be substituted with 1 to 3 same or different halogen atoms, and $C_1$-$C_6$ alkoxy group; a cyano group; or, an N-hydroxyalkaneimidoyl group in which a hydrogen atom of the hydroxyl group may be substituted with a substituent selected from the group consisting of a $C_1$-$C_6$ alkyl group and a phenyl group, and n represents an integer of 0 to 2.

8. The compound or salt thereof according to claim 1 wherein X represents a fluorine atom, chlorine atom, bromine atom, methyl group, ethynyl group, furyl group, thienyl group, cyano group, methoxyethaneimidoyl group, ethoxyethaneimidoyl group or phenoxyethaneimidoyl group, and n represents an integer of 0 or 1.

9. The compound or salt thereof according to claim 1 wherein Y represents a fluorine atom, chlorine atom or methyl group, and m represents an integer of 0 or 1.

10. The compound of salt thereof according to claim 1 wherein Y represents a methyl group, and m represents an integer of 0 or 1.

11. The compound or salt according to claim 1 which is
3-(5-fluoro-3,3-dimethyl-3,4-dihydroisoquinolin-1-yl) quinoline,
3-(5-chloro-3,3-dimethyl-3,4-dihydroisoquinolin-1-yl) quinoline,
3-(5-bromo-3,3-dimethyl-3,4-dihydroisoquinolin-1-yl) quinoline,
3-(5-ethynyl-3,3-dimethyl-3,4-dihydroisoquinolin-1-yl) quinoline,
3-(5,6-difluoro-3,3-dimethyl-3,4-dihydroisoquinolin-1-yl)quinoline,
3-(3-ethyl-5-fluoro-3-methyl-3,4-dihydroisoquinolin-1-yl)quinoline,
3-(5-fluoro-3-methyl-3-propyl-3,4-dihydroisoquinolin-1-yl)quinoline,
3-(3-methyl-3-trifluoromethyl-3,4-dihydroisoquinolin-1-yl)quinoline,
3-[3-methyl-3-(2,2,2-trifluoroethyl)-3,4-dihydroisoquinolin-1-yl]quinoline,
3-(3-methyl-3-phenyl-3,4-dihydroisoquinolin-1-yl) quinoline,
3-[3-methyl-3-(4-fluorophenyl)-3,4-dihydroisoquinolin-1-yl]quinoline,
3-[3-methyl-3-(4-chlorophenyl)-3,4-dihydroisoquinolin-1-yl]quinoline,
3-(5-fluoro-3,3,4,4-tetramethyl-3,4-dihydroisoquinolin-1-yl)-6-fluoroquinoline,
3-(5-fluoro-3,3,4,4-tetramethyl-3,4-dihydroisoquinolin-1-yl)-8-fluoroquinoline,
3-(5-fluoro-3,3,4,4-tetramethyl-3,4-dihydroisoquinolin-1-yl)-8-methylquinoline,
3-(4,5-difluoro-3,3-dimethyl-3,4-dihydroisoquinolin-1-yl)quinoline,
3-(4,4-difluoro-3,3-dimethyl-3,4-dihydroisoquinolin-1-yl)quinoline,
3-(4,4,5-trifluoro-3,3-dimethyl-3,4-dihydroisoquinolin-1-yl)quinoline,
5-fluoro-3,3,4,4-tetramethyl-8b-quinolin-3-yl-4,8b-dihydro-3H-oxazileno[3,2-a]isoquinoline,
3,3,4,4-tetramethyl-8b-quinolin-3-yl-4,8b-dihydro-3H-oxazileno[3,2-a]isoquinoline,
5-fluoro-3,3-dimethyl-8b-quinolin-3-yl-4,8b-dihydro-3H-oxazileno[3,2-a]isoquinoline,
6-fluoro-3,3,4,4-tetramethyl-8b-quinolin-3-yl-4,8b-dihydro-3H-oxazileno[3,2-a]isoquinoline,
4',4'-dimethyl-8b'-quinolin-3-yl-4',8b'-dihydrospiro[cyclopentane-1,3'-oxazileno[3,2-a]isoquinoline],
4,4,5-trifluoro-3,3-dimethyl-8b-quinolin-3-yl-4,8b-dihydro-3H-oxazileno[3,2-a]isoquinoline,
3-(5-fluoro-3,3,4,4-tetramethyl-2-oxide-3,4-dihydroisoquinolin-1-yl)quinoline,
3-(3,3,4,4-tetramethyl-2-oxide-3,4-dihydroisoquinolin-1-yl)quinoline,
3-(6-fluoro-3,3,4,4-tetramethyl-2-oxide-3,4-dihydroisoquinolin-1-yl)quinoline,
3-(6-chloro-3,3,4,4-tetramethyl-2-oxide-3,4-dihydroisoquinolin-1-yl)quinoline,
3-(4,4-difluoro-3,3-dimethyl-2-oxide-3,4-dihydroisoquinolin-1-yl)quinoline,
3-(4,4,5-trifluoro-3,3-dimethyl-2-oxide-3,4-dihydroisoquinolin-1-yl)quinoline or
3-(5-fluoro-3,3,4,4-tetramethyl-3,4-dihydroisoquinolin-1-yl)quinoline or salt thereof.

12. An agricultural chemical containing a compound or salt thereof according to claim 1 as an active ingredient.

* * * * *

UNITED STATES PATENT AND TRADEMARK OFFICE
CERTIFICATE OF CORRECTION

PATENT NO. : 7,632,783 B2  Page 1 of 1
APPLICATION NO. : 10/587100
DATED : December 15, 2009
INVENTOR(S) : Ito et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 816 days.

Signed and Sealed this

Second Day of November, 2010

David J. Kappos
*Director of the United States Patent and Trademark Office*